(12) United States Patent
Van Dijk et al.

(10) Patent No.: US 11,993,653 B2
(45) Date of Patent: May 28, 2024

(54) ANTIBODIES AND METHODS OF USE THEREOF

(71) Applicants: AGENUS INC., Lexington, MA (US); Ludwig Institute for Cancer Research Ltd., Zurich (CH); Memorial Sloan Kettering Cancer Center, New York, NY (US)

(72) Inventors: Marc Van Dijk, Bosch en Duin (NL); Cornelia Anne Mundt, Lörrach (DE); Gerd Ritter, New York, NY (US); David Schaer, Mamaroneck, NY (US); Jedd David Wolchok, New York, NY (US); Taha Merghoub, Jersey City, NJ (US); Nicholas Stuart Wilson, San Carlos, CA (US); David Adam Savitsky, Boxford, MA (US); Mark Arthur Findeis, Belmont, MA (US); Roberta Zappasodi, New York, NY (US); Rikke Baek Holmgaard, New York, NY (US); Jean-Marie Cuillerot, Somerville, MA (US); Igor Proscurshim, Carlisle, MA (US); Olga Shebanova, Somerville, MA (US)

(73) Assignees: AGENUS INC., Lexington, MA (US); Ludwig Institute for Cancer Research Ltd., Zurich (CH); Memorial Sloan Kettering Cancer Center, New York, NY (US)

( * ) Notice: Subject to any disclaimer, the term of this patent is extended or adjusted under 35 U.S.C. 154(b) by 298 days.

(21) Appl. No.: 16/435,175

(22) Filed: Jun. 7, 2019

(65) Prior Publication Data
US 2020/0024350 A1 Jan. 23, 2020

Related U.S. Application Data

(63) Continuation of application No. PCT/US2017/065014, filed on Dec. 7, 2017.

(60) Provisional application No. 62/586,605, filed on Nov. 15, 2017, provisional application No. 62/582,814, filed on Nov. 7, 2017, provisional application No. 62/570,451, filed on Oct. 10, 2017, provisional application No. 62/431,279, filed on Dec. 7, 2016.

(51) Int. Cl.
*C07K 16/28* (2006.01)
*A61K 39/00* (2006.01)

(52) U.S. Cl.
CPC .... *C07K 16/2818* (2013.01); *A61K 2039/507* (2013.01); *C07K 2317/31* (2013.01); *C07K 2317/33* (2013.01); *C07K 2317/34* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 5,897,862 A | 4/1999 | Hardy et al. |
| 6,808,710 B1 | 10/2004 | Wood et al. |
| 7,029,674 B2 | 4/2006 | Carreno et al. |
| 7,332,582 B2 | 2/2008 | Hardy et al. |
| 7,521,051 B2 | 4/2009 | Collins et al. |
| 7,595,048 B2 | 9/2009 | Honjo et al. |
| 7,851,598 B2 | 12/2010 | Davis |
| 7,858,746 B2 | 12/2010 | Honjo et al. |
| 8,008,449 B2 | 8/2011 | Korman et al. |
| 8,168,757 B2 | 5/2012 | Finnefrock et al. |
| 8,354,509 B2 | 1/2013 | Carven et al. |
| 8,617,546 B2 | 12/2013 | Kang et al. |
| 8,735,553 B1 | 5/2014 | Li et al. |
| 8,741,295 B2 | 6/2014 | Olive |
| 8,927,697 B2 | 1/2015 | Davis et al. |
| 8,993,731 B2 | 3/2015 | Tyson |
| 9,067,998 B1 | 6/2015 | Clube |
| 9,084,776 B2 | 7/2015 | Korman et al. |
| 9,102,727 B2 | 8/2015 | Freeman et al. |
| 9,132,281 B2 | 9/2015 | Zeng et al. |
| 9,163,087 B2 | 10/2015 | Kuchroo et al. |
| 9,181,342 B2 | 11/2015 | Davis |
| 9,220,776 B2 | 12/2015 | Sharma et al. |
| 9,243,052 B2 | 1/2016 | Olive et al. |
| 9,358,289 B2 | 6/2016 | Korman et al. |
| 9,381,244 B2 | 7/2016 | Noelle |

(Continued)

FOREIGN PATENT DOCUMENTS

| | | |
|---|---|---|
| CN | 102134276 A | 7/2011 |
| CN | 101074264 B | 8/2011 |

(Continued)

OTHER PUBLICATIONS

"A comprehensive immune-oncology Ecosystem" Cowen and Company 36th Annual Health Care Conference Mar. 2016.

(Continued)

*Primary Examiner* — Marianne P Allen
(74) *Attorney, Agent, or Firm* — Dechert LLP; Andrew T. Wilkins

(57) ABSTRACT

Provided are antibodies that specifically bind to CTLA-4 and/or PD-1 and antagonize CTLA-4 and/or PD-1 function. Also provided are pharmaceutical compositions and kits comprising these antibodies, nucleic acids encoding these antibodies, expression vectors and host cells for making these antibodies, and methods of treating a subject using these antibodies either alone or in combination.

Figure 1A:
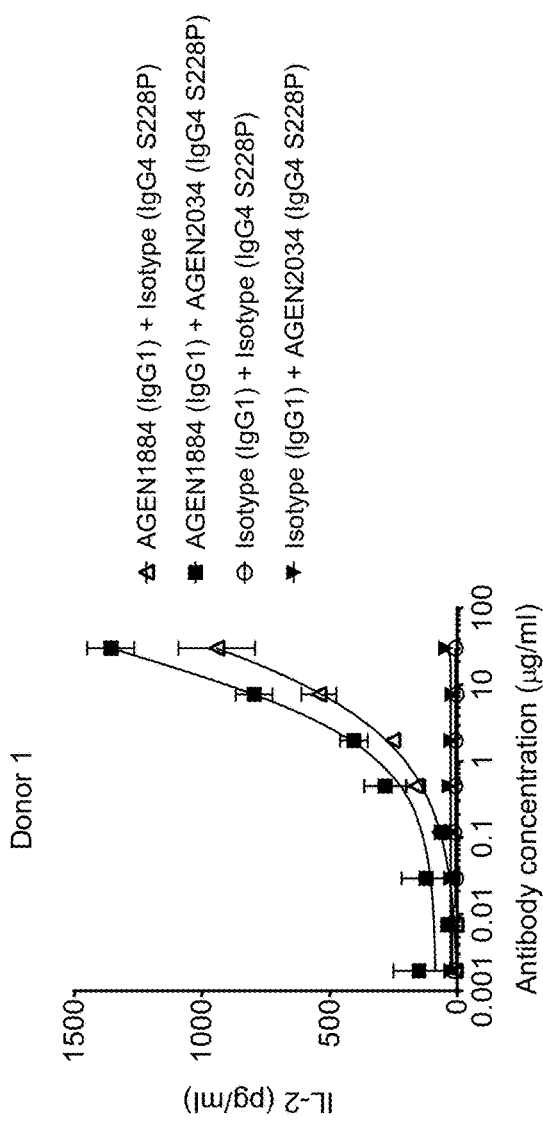

19 Claims, 9 Drawing Sheets
Specification includes a Sequence Listing.

(56) References Cited

U.S. PATENT DOCUMENTS

| | | | |
|---|---|---|---|
| 9,394,365 | B1 | 7/2016 | Eisenbach-Schwartz et al. |
| 9,499,603 | B2 | 11/2016 | Tyson |
| 9,580,504 | B1 | 2/2017 | Rotem-Yehudar et al. |
| 9,605,070 | B2 | 3/2017 | Sabatos-Peyton et al. |
| 9,676,853 | B2 | 6/2017 | Zhou et al. |
| 9,683,048 | B2 | 6/2017 | Freeman et al. |
| 9,701,749 | B2 | 7/2017 | Shibayama et al. |
| 9,771,425 | B2 | 9/2017 | Wang et al. |
| 9,815,898 | B2 | 11/2017 | Freeman et al. |
| 10,323,091 | B2 | 6/2019 | van Dijk et al. |
| 10,703,971 | B2 | 7/2020 | De Silva et al. |
| 10,912,831 | B1 | 2/2021 | van Dijk et al. |
| 11,013,802 | B2 | 5/2021 | van Dijk et al. |
| 11,345,755 | B2 * | 5/2022 | Van Dijk ................ A61P 35/00 |
| 11,638,755 | B2 * | 5/2023 | van Dijk ................ A61P 11/00 424/136.1 |
| 2003/0059937 | A1 | 3/2003 | Ruben et al. |
| 2006/0246071 | A1 | 11/2006 | Green et al. |
| 2007/0009536 | A1 | 1/2007 | Pullen |
| 2008/0152587 | A1 | 6/2008 | Zhou et al. |
| 2009/0155164 | A1 | 6/2009 | Brasel et al. |
| 2011/0110956 | A1 | 5/2011 | Rothe et al. |
| 2011/0177070 | A1 | 7/2011 | Lofquist et al. |
| 2012/0121591 | A1 | 5/2012 | Sullivan et al. |
| 2012/0195879 | A1 | 8/2012 | Walker et al. |
| 2014/0234331 | A1 | 8/2014 | Korman et al. |
| 2014/0302070 | A1 | 10/2014 | Chen et al. |
| 2014/0356363 | A1 | 12/2014 | Zhou et al. |
| 2015/0125463 | A1 | 5/2015 | Cogswell et al. |
| 2015/0190506 | A1 | 7/2015 | Cheung et al. |
| 2015/0202291 | A1 | 7/2015 | Bosch et al. |
| 2015/0203579 | A1 | 7/2015 | Papadopoulos et al. |
| 2015/0210769 | A1 | 7/2015 | Freeman et al. |
| 2015/0216970 | A1 | 8/2015 | Grogan et al. |
| 2015/0344577 | A1 | 12/2015 | Fu |
| 2016/0032014 | A1 | 2/2016 | Michaels et al. |
| 2016/0051672 | A1 | 2/2016 | Stewart et al. |
| 2016/0075783 | A1 | 3/2016 | King et al. |
| 2016/0090417 | A1 | 3/2016 | Cogswell et al. |
| 2016/0108123 | A1 | 4/2016 | Freeman et al. |
| 2016/0130345 | A1 | 5/2016 | Fotin-Mleczek et al. |
| 2016/0130348 | A1 | 5/2016 | Langermann et al. |
| 2016/0159905 | A1 | 6/2016 | Abdiche et al. |
| 2016/0176963 | A1 | 6/2016 | Maurer et al. |
| 2016/0208000 | A1 | 7/2016 | Smytbe |
| 2016/0222113 | A1 | 8/2016 | Buchanan et al. |
| 2016/0222121 | A1 | 8/2016 | Johnson et al. |
| 2016/0264667 | A1 | 9/2016 | Chen et al. |
| 2016/0272708 | A1 | 9/2016 | Chen |
| 2016/0280786 | A1 | 9/2016 | Hermans et al. |
| 2016/0311904 | A1 | 10/2016 | Haas et al. |
| 2016/0319018 | A1 | 11/2016 | Morsey et al. |
| 2016/0319019 | A1 | 11/2016 | Amirina et al. |
| 2016/0339090 | A1 | 11/2016 | Hacohen et al. |
| 2016/0340428 | A1 | 11/2016 | Yang |
| 2016/0347836 | A1 | 12/2016 | Grosso |
| 2016/0355589 | A1 | 12/2016 | Williams et al. |
| 2016/0362489 | A1 | 12/2016 | Yang |
| 2016/0362492 | A1 | 12/2016 | Freeman et al. |
| 2016/0376367 | A1 | 12/2016 | Yuan et al. |
| 2017/0007693 | A1 | 1/2017 | Weiner et al. |
| 2017/0037127 | A1 | 2/2017 | Grogan et al. |
| 2017/0037132 | A1 | 2/2017 | Manekas et al. |
| 2017/0044256 | A1 | 2/2017 | Grogan et al. |
| 2017/0044259 | A1 | 2/2017 | Tipton et al. |
| 2017/0044260 | A1 | 2/2017 | Baruah et al. |
| 2017/0088613 | A1 | 3/2017 | Grogan et al. |
| 2017/0088618 | A1 | 3/2017 | Bennett et al. |
| 2017/0088626 | A1 | 3/2017 | Jure-Kunkel et al. |
| 2017/0130271 | A1 | 5/2017 | Wong |
| 2017/0158776 | A1 | 6/2017 | Feltquate et al. |
| 2017/0165325 | A1 | 6/2017 | Sharpe et al. |
| 2017/0166637 | A1 | 6/2017 | Ben-Moshe et al. |
| 2017/0166642 | A1 | 6/2017 | Pantaleo et al. |
| 2017/0174774 | A1 | 6/2017 | Coric et al. |
| 2017/0198039 | A1 | 7/2017 | Wong |
| 2017/0209574 | A1 | 7/2017 | Cao et al. |
| 2017/0210806 | A1 | 7/2017 | Liu |
| 2017/0218068 | A1 | 8/2017 | Lesterhuis et al. |
| 2017/0239351 | A1 | 8/2017 | Hamdy et al. |
| 2017/0240644 | A1 | 8/2017 | Zhou et al. |
| 2017/0247454 | A1 | 8/2017 | Benz et al. |
| 2017/0247455 | A1 | 8/2017 | Jure-Kunkel et al. |
| 2017/0267760 | A1 | 9/2017 | Diaz et al. |
| 2017/0267762 | A1 | 9/2017 | Qiu et al. |
| 2020/0024350 | A1 | 1/2020 | Van Dijk et al. |
| 2021/0205451 | A1 | 7/2021 | van Dijk et al. |

FOREIGN PATENT DOCUMENTS

| | | |
|---|---|---|
| CN | 105754990 A | 7/2016 |
| EP | 1262193 A1 | 12/2002 |
| EP | 1165616 B1 | 11/2004 |
| EP | 1137436 B1 | 6/2008 |
| EP | 2905030 A1 | 8/2015 |
| EP | 2906241 A1 | 8/2015 |
| EP | 2911669 A1 | 9/2015 |
| EP | 2931738 A1 | 10/2015 |
| EP | 2100615 B1 | 2/2016 |
| EP | 3036256 A1 | 6/2016 |
| EP | 3064220 A2 | 9/2016 |
| EP | 2133365 B1 | 5/2017 |
| EP | 3160505 A1 | 5/2017 |
| EP | 2958588 B1 | 8/2017 |
| EP | 3206711 A1 | 8/2017 |
| EP | 3218004 A1 | 9/2017 |
| EP | 3218408 A1 | 9/2017 |
| EP | 3233123 A2 | 10/2017 |
| EP | 3240551 A1 | 11/2017 |
| JP | 2006327937 A | 12/2006 |
| WO | WO-2004072286 A1 | 8/2004 |
| WO | WO-2006121168 A1 | 11/2006 |
| WO | WO-2008083174 A2 | 7/2008 |
| WO | WO-2008156712 A1 | 12/2008 |
| WO | WO-2014179664 A2 | 11/2014 |
| WO | WO-2015176033 A1 | 11/2015 |
| WO | WO-2015181331 A1 | 12/2015 |
| WO | WO-2016077397 A2 | 5/2016 |
| WO | WO-2016100561 A2 | 6/2016 |
| WO | WO-2016127179 A2 | 8/2016 |
| WO | WO-2016137850 A1 | 9/2016 |
| WO | WO-2016137985 A1 | 9/2016 |
| WO | WO-2016149387 A1 | 9/2016 |
| WO | WO-2016168143 A1 | 10/2016 |
| WO | WO-2016172624 A1 | 10/2016 |
| WO | WO-2016179517 A1 | 11/2016 |
| WO | WO-2016183469 A1 | 11/2016 |
| WO | WO-2016196237 A1 | 12/2016 |
| WO | WO-2016196389 A1 | 12/2016 |
| WO | WO-2016205320 A1 | 12/2016 |
| WO | WO-2016210129 A1 | 12/2016 |
| WO | WO-2017016497 A1 | 2/2017 |
| WO | WO-2017019846 A1 | 2/2017 |
| WO | WO-2017024515 A1 | 2/2017 |
| WO | WO-2017040790 A1 | 3/2017 |
| WO | WO-2017054646 A1 | 4/2017 |
| WO | WO-2017055443 A1 | 4/2017 |
| WO | WO-2017055547 A1 | 4/2017 |
| WO | WO-2017058115 A1 | 4/2017 |
| WO | WO-2017059095 A1 | 4/2017 |
| WO | WO-2017079080 A1 | 5/2017 |
| WO | WO-2017079303 A1 | 5/2017 |
| WO | WO-2017087280 A1 | 5/2017 |
| WO | WO-2017087599 A1 | 5/2017 |
| WO | WO-2017096026 A1 | 6/2017 |
| WO | WO-2017103280 A1 | 6/2017 |
| WO | WO-2017107885 A1 | 6/2017 |
| WO | WO-2017124050 A1 | 7/2017 |
| WO | WO-2017125815 A2 | 7/2017 |
| WO | WO-2017129763 A1 | 8/2017 |
| WO | WO-2017129790 A1 | 8/2017 |
| WO | WO-2017132508 A1 | 8/2017 |
| WO | WO-2017132536 A1 | 8/2017 |
| WO | WO-2017133540 A1 | 8/2017 |

(56) References Cited

FOREIGN PATENT DOCUMENTS

| | | |
|---|---|---|
| WO | WO-2017147368 A1 | 8/2017 |
| WO | WO-2017151502 A1 | 9/2017 |
| WO | WO-2017151517 A1 | 9/2017 |
| WO | WO-2017160975 A1 | 9/2017 |
| WO | WO-2018106864 A1 | 6/2018 |

OTHER PUBLICATIONS

"Agenus Announces Clearance of Investigational New Drug Applications by the FDA for anti-CTLA-4 and anti-GITR Antibodies" Jan. 21, 2016 (Business Wire).
"Agenus Announces Combination Clinical Trials of its Anti-CTLA4 (AGEN1884) & Anti-PD1 (AGEN2034)" Jan. 22, 2018 /PRNewswire/.
"Agenus Background Slide Deck" Jan. 2017.
"Agenus Commences Phase I Clinical trials of its CTLA-4 Checkpoint Antibody to Treat Solid Tumors," Apr. 27, 2016 /Business Wire/.
"Agenus Inc. Closes $230 Million Royalty Monetization with HealthCare Royalty Partners" Jan. 22, 2018 /PRNewswire/.
"Agenus Investor Relations Deck" May 15, 2015.
"Agenus IR Deck" Dec. 2016.
"Agenus IR Presentation" Aug. 2016.
"Agenus Presents Clinical Responses of AGEN1884 (anti-CTLA-4) and AGEN2034 (anti-PD-1) at ASCO 2018" Jun. 4, 2018 /PRNewswire/.
"Agenus Presents Posters on Checkpoint Antibody Product Candidates at the American Association for Cancer Research (AACR) 2016 Annual Meeting" Apr. 18, 2016 (Business Wire).
"Agenus R&D Day" Nov. 19, 2015 New York, NY.
"Agenus Roadshow Slide Deck" May 15, 2015.
"Agenus to Present Clinical Data on Lead Programs at ASCO 2018" May 17, 2018 /PRNewswire/.
"Agenus To Present on Lead Antibody Programs AGEN1884 (CTLA-4) and AGEN2034 (PD-1) at SITC 2017" Nov. 9, 2017 /PRNewswire/.
"Agonist Checkpoint Modulators: Challenges and Opportunities" PEGS Boston May 8, 2015.
"Emerging Leader In Immuno-Oncology" Nov. 2015, Lexington, MA.
"Enabling Best-in-Class I-O Combinations" Mar. 2018.
"Guideline on immunogenicity assessment of monoclonal antibodies intended for in vivo clinical use," European Medicines Agency, London, UK, 2012.
"Immuno-Oncology" RBS Immunotherapy Conference Mar. 27, 2014.
"Integrated Approach to Immuno-Oncology" Blair Maidstone I-O Conference NYC Mar. 31, 2016.
"Integrated Approach to Immuno-oncology" Mar. 31, 2016.
"Integrated Immunotherapy: Enabling Best-in-Class I-O combinations" Feb. 2017.
"Integrated Immunotherapy: Enabling Best-in-Class I-O Combinations" Jan. 2018.
"Integrated Immunotherapy: Enabling Best-in-Class I-O Combinations" Jun. 2018.
"Integrated Immunotherapy: Enabling Best-in-Class I-O Combinations" Mar. 2018.
"Integrated Immunotherapy: Enabling Best-in-Class I-O Combinations" Nov. 2017.
"Integrated Solutions in Immuno-Oncology" Apr. 2016.
"Integrated Solutions in Immuno-Oncology" May 2016.
"Phase 1/2 Clinical Trial of Agenus' anti-PD-1 Antibody Begins" Apr. 20, 2017 /PRNewswire/.
"Targeting TNFR Family Members: Therapeutic opportunities in immuno-oncology and immuno-inflammation" PEGS Boston 2016.
2018 "Agenus News", vol. 1, Issue 1.
2018 "Agenus News", vol. 1, Issue 2.
2018 "Agenus News", vol. 1, Issue 3.
2018 "Agenus News, vol. 1, Issue 8".
Apr. 11, 2018 "Three Agenus Abstracts Accepted for Presentation at the American Association for Cancer Research (AACR) 2018 Annual Meeting", PR Newswire.
Apr. 18, 2016 "Agenus Presents Posters on Checkpoint Antibody Product Candidates at the American Association for Cancer Research", Annual Meeting, Business Wire, 2 Pages.
Apr. 20, 2017 "Phase 1/2 Clinical Trial of Agenus' anti-PD-1 Antibody Begins", PR Newswire.
Apr. 2016 "Integrated Solutions in Immuno-Oncology", 32 Pages.
Apr. 27, 2016 "Agenus Commences Phase 1 Clinical trials of its CTLA-4 Checkpoint Antibody to Treat Solid Tumors", Business Wire.
Aug. 3, 2017 "Q2 2017 Results", Earnings Call Transcript.
Aug. 2016 "Agenus Roadshow Slide Deck".
Dec. 2016 "Agenus IR Deck".
Feb. 2017 "Integrated Immunotherapy: Enabling Best-in-Class I-O combinations".
Feb. 28, 2016 "Q4 2015 Results", Earnings Call Transcript.
Jan. 1, 2014 "International Nonproprietary Names for Pharmaceutical Substances (INN)", WHO Drug Information records—World Health Organization, pp. 379-422.
Jan. 2017 "Agenus Background Slide Deck".
Jan. 2018 "Integrated Immunotherapy: Enabling Best-in-Class I-O Combinations".
Jan. 22, 2018 "Agenus Inc. Closes $230 Million Royalty Monetization with HealthCare Royalty Partners", PR Newswire.
Jun. 2018 "Integrated Immunotherapy: Enabling Best-in-Class I-O Combinations".
Jun. 4, 2018 "Agenus Presents Clinical Responses of AGEN1884 (anti-CTLA-4) and AGEN2034 (anti-PD-1) at ASCO 2018", PR Newswire.
Mar. 31, 2016 "Integrated Approach to Immuno-Oncology", Blair Maidstone 1-0 Conference, New York City, 28 Pages.
Mar. 7, 2017 "Four Agenus Abstracts Accepted for Presentation at the American Association for Cancer Research (AACR) 2017 Annual Meeting", PRNewswire, 5 Pages.
May 15, 2015 "Agenus Investor Relations Deck".
May 15, 2015 "Agenus Roadshow Slide Deck".
May 17, 2018 "Agenus to Present Clinical Data on Lead Programs at ASCO 2018", PRNewswire.
May 2016 "Integrated Solutions in Immuno-Oncology", 32 Pages.
Nov. 7, 2017 "Q3 2017 Results", Earnings Call Transcript.
Nov. 19, 2015 "Agenus R&D Day", New York, NY.
Nov. 2015 "Emerging Leader in Immuno-Oncology", Lexington, MA, 34 Pages.
Nov. 9, 2017 "Agenus To Present on Lead Antibody Programs AGEN1884 (CTLA-4) and AGEN2034 (PD-1) at SITC 2017", PR Newswire.
Sep. 2015 "Rodman & Renshaw Annual Global Investment Conference", Agenus Presentation given at Rodman & Renshaw Annual Global Investment Conference.
Abdallah A-O., et al., (2016) "Ipilimumab-induced necrotic myelopathy in a patient with metastatic melanoma: A case report and review of literature" Journal of Oncology Pharmacy Practice 22(3):537-542.
Abdiche, et al. (2016) "Assessing Kinetic and Epitopic Diversity Across Orthogonal Monoclonal Antibody Generation Platforms", mAbs, vol. 8, No. 2, pp. 264-277.
Acuto, O., et al., (2003) "CD28-mediated co-stimulation: a quantitative support for TCR signaling" Nature Reviews Immunology 3:939-951.
Afanasiev, Olga K., et al. (2013) "Merkel Polyomavirus-Specific T Cells Fluctuate with Merkel Cell Carcinoma Burden and Express Therapeutically Targetable PD-1 and Tim-3 Exhaustion Markers", Human Cancer Biology, vol. 19, No. 19, pp. 5351-5360.
Agata, Y. et al., (1996) "Expression of the PD-1 antigen on the surface of stimulated mouse T and B lymphocytes." Int. Immunol 8:765-72.
Agenus (Mar. 2016) "A Comprehensive Immune-Oncology Ecosystem", Cowen and Company 36th Annual Health Care Conference, 27 Pages.
Ahmadzadeh, M., et al., (2009) "Tumor antigen-specific CD8 T cells infiltrating the tumor express high levels of PD-1 and are functionally impaired" Blood 114:1537-1544.

(56) References Cited

OTHER PUBLICATIONS

Alegre, M.L., et al., (2001) "T-cell regulation by CD28 and CTLA-4" Nat Rev Immunol 1(3):220-8.
Allie, S.R., et al., (2011) "Programmed death 1 regulates development of central memory CD8 T cells after acute viral infection" J. Immunol. 186:6280-6286.
Ampie L., et al., (2015) "Heat shock protein vaccines against glioblastoma: from bench to bedside" J. Neurooncol. 123:441-8.
Anonymous (2014) "International Nonproprietary Names for Pharmaceutical Substances (INN)," WHO drug Information Rec. Wld Health Org. Resolution EB15.R7), pp. 1-44. [retrieved on Nov. 7, 2016].
Antonia, S., et al., (2016) "Safety and antitumour activity of durvalumab plus tremelimumab in non-small cell lung cancer: a multicentre, phase 1b study" The Lancet Oncology 17(3):299-308.
Antonia, S.J., et al., (2016) "Nivolumab alone and nivolumab plus ipilimumab in recurrent small-cell lung cancer (CheckMate 032): a multicentre, open-label, phase 1/2 trial" The Lancet Oncology 17(7):883-895.
Arnold, D., et al., (1997) "Influences of Transporter Associated with Antigen Processing (TAP) on the Repertoire of Peptides Associated with the Endoplasmic Reticulum-resident Stress Protein gp96" J. Exp. Med. vol. 186(3):461-466.
Attia, P., et al., (2005) "Autoimmunity Correlates With Tumor Regression in Patients With Metastatic Melanoma Treated With Anti-Cytotoxic T-Lymphocyte Antigen-4" Journal of Clinical Oncology 23:6043-6053.
Azuma, M., et al., (1993) "B70 antigen is a second ligand for CTLA-4 and CD28" Nature 366:76-79.
Bally, A.P., et al., (2015) "NF-KAPPA-B regulates PD-1 expression in macrophages" J. Immunol. 194:4545-4554.
Ban-Hoefen M., et al., (2016) "Ipilimumab-Induced Neutropenia in Melanoma." Journal of Investigative Medicine High Impact Case Reports 4(3):1-5.
Barber, D.L., et al., (2006) "Restoring function in exhausted CD8 T cells during chronic viral infection" Nature 439:682-687.
Bartkowiak, T., et al., (2015) "Unique potential of 4-1BB agonist antibody to promote durable regression of HPV+ tumors when combined with an E6/E7 peptide vaccine" PNAS E5290-E5299.
Baruch, K., et al., (2016) "PD-1 immune checkpoint blockade reduces pathology and improves memory in mouse models of Alzheimer's disease" Nature Med. 22(2):135-7.
Bauml et al (2016) "Preliminary results from Keynote-055: Pembrolizumab after platinum and cetuximab failure in head and neck squamous cell carcinoma (HNSCC)" 2016 ASCO Annual Meeting: J Clin Oncol 34, 2016 (suppl? abstr 6011).
Bennett, F., et al., (2003) "Program death-1 engagement upon TCR activation has distinct effects on costimulation and cytokine-driven proliferation: attenuation of ICOS, IL-4, and IL-21, but not CD28, IL-7, and IL-15 responses" J. Immunol. 170:711-718.
Benson, D M et al. (2010) "The PD-1/PD-L1 axis modulates the natural killer cell versus multiple myeloma affect: a therapeutic target for CT-011, a novel monoclonal anti-PD-1 antibody," Blood, American Society of Hemotology, US 116(13):2286-2294.
Bifulco, C.B., et al., (2016) "Unmasking PD-1 Resistance by Next-Generation Sequencing" N. Engl. J. of Med. 375(9):888-889.
Binder, R.J., (2014) "Functions of heat shock proteins in pathways of the innate and adaptive immune system" J. Immunol. 193:5765-5771.
Binder, R.J., et al., (2005) "Peptides chaperoned by heat-shock proteins are a necessary and sufficient source of antigen in the cross-priming of CD8+ T Cells" Nature Immunology 6(6):593-599.
Blachere, N.E., et al., (1993) "Heat Shock Protein Vaccines Against Cancer" Journal of Immunotherapy 14:352-356.
Blank, C., et al., (2004) "PD-L1/B7H-1 inhibits the effector phase of tumor rejection by T cell receptor (TCR) transgenic CD8+ T cells" Cancer Res. 64:1140-1145.

Blank, C., et al., (2005) "Interaction of PD-L1 on tumor cells with PD-1 on tumor-specific T cells as a mechanism of immune evasion: implications for tumor immunotherapy" Cancer Immunol. Immunother. 54:307-314.
Blank, C., et al., (2007) "Contribution of the PD-L1/PD-1 pathway to T-cell exhaustion: an update on implications for chronic infections and tumor evasion" Cancer Immunol. Immunother. 56:739-745.
Boise, L.H., et al., (1995) "CD28 costimulation can promote T cell survival by enhancing the expression of Bcl-XL" Immunity 3:87-98.
Borcoman, E. et al. (2017) "Pembrolizumab in cervical cancer: latest evidence and clinical usefulness," Ther Adv Med Oncol. 9(6):431-439.
Borradori, L. et al., (2016) "Rescue therapy with anti-programmed cell death protein 1 inhibitors of advanced cutaneous squamous cell carcinoma and basosquamous carcinoma: preliminary experience in five cases" The British Journal of Dermatology, 175(6):1382-1386.
Bouchez, C., et al., (2012) "Development of a Delayed-Type Hypersensitivity (DTH) Model in the Cynomolgus Monkey" J. Toxicol. Pathol. 25:183-188.
Boussiotis, V.A., et al., (2014) "Somatic Mutations and Immunotherapy Outcome with CTLA-4 Blockade in Melanoma" N. Engl. J. Med. 371:2189-2199.
Boussiotis, V.A., et al., (2014) "Molecular and Biochemical Aspects of the PD-1 Checkpoint Pathway" N. Engl. J. Med. 375(18):1767-78.
Boutros, C., et al., (2016) "Safety profiles of anti-CTLA-4 and anti-PD-1 antibodies alone and in combination" Nature Reviews 13:473.
Bowes, J., et al., (2012) "Reducing safety-related drug attrition: the use of in vitro pharmacological profiling" Nature Reviews Drug Discovery 11:909-922.
Boyd, S.D., et al. (2016) "Deep Sequencing and Human Antibody Repertoire Analysis" Current Opinion in Immunology, vol. 40, pp. 103-109.
Brahmer, J.R., et al., (2010) "Phase I Study of Single-Agent Anti-Programmed Death-1 (MDX-1106) in Refractory Solid Tumors: Safety, Clinical Activity, Pharmacodynamics, and Immunologic Correlates" J. Clin. Oncol. 28(19):3167-75.
Brahmer, J.R., et al., (2012) "Safety and activity of anti-PD-L1 antibody in patients with advanced cancer" N. Engl. J. Med. 366:2455-2465.
Brantsch, K.D. et al., (2008) "Analysis of risk factors determining prognosis of cutaneous squamous-cell carcinoma: a prospective study" The Lancet Oncology 9(8):713-720.
Braster, R., et al., (2014) "Myeloid cells as effector cells for monoclonal antibody therapy of cancer" Methods 65:28-37.
Brem, H., et al., (1995) "Placebo-controlled trial of safety and efficacy of intraoperative controlled delivery by biodegradable polymers of chemotherapy for recurrent gliomas" Lancet 345:1008-12.
Brennan, F.R., et al., (2010) "Safety and immunotoxicity assessment of immunomodulatory monoclonal antibodies" MAbs 2:233-255.
Breous-Nystrom, E., et al., (2014) "Retrocyte Display® technology: generation and screening of a high diversity cellular antibody library" Methods 65:57-67.
Bretscher, P.A., (1999) "A two-step, two-signal model for the primary activation of precursor helper T cells" Proc. Natl. Acad. Sci. USA 96:185-90.
Bristol-Myers Squibb USA, 2015. Yervoy® (ipilimumab) package insert.
Bristol-Myers Squibb USA, 2016. Opdivo® (nivolumab) package insert.
Brougham, N.D.L.S., et al., (2012) "The incidence of metastasis from cutaneous squamous cell carcinoma and the impact of its risk factors" Journal of Surgical Oncology 106(7):811-815.
Brown, J.A., et al., (2003) "Blockade of programmed death-1 ligands on dendritic cells enhances T cell activation and cytokine production" J. Immunol. 170:1257-66.

(56) References Cited

OTHER PUBLICATIONS

Brown, S.D., (2014) "Neo-antigens predicted by tumor genome meta-analysis correlate with increased patient survival" Genome Res. 24:743-750.
Bruhns, O., et al., (2009) "Specificity and affinity of human Fcgamma receptors and their polymorphic variants for human IgG subclasses" Blood 113:3716-3752.
Brunet, J.F., et al., (1987) "A new member of the immunoglobulin superfamily—CTLA-4" Nature 328:267-270.
Bryceson, Y.T., et al., (2006) "Activation, coactivation, and costimulation of resting human natural killer cells" Immunol Rev 214:73-91.
Buchbinder, E.I., et al., (2016) "CTLA-4 and PD-1 Pathways: Similarities, Differences, and Implications of Their Inhibition" American Journal of Clinical Oncology, 39(1):98-106.
Bukau, B., et al., (1998) "The HSP70 and HSp60 Chaperone Machines" Cell 92:351-366.
Bulliard, Y, et al., (2014) "OX40 engagement depletes intratumoral Tregs via activating Fc?RS, leading to antitumor efficacy" Immunology and Cell Biology 92:475-480.
Bulliard, Y., et al., (2013) "Activating Fc-GAMMA receptors contribute to the antitumor activities of immunoregulatory receptor-targeting antibodies" The Journal of Experimental Medicine 210(9):1685-1693.
Burova, E. et al. (2017) "Characterization of the anti-PD-1 antibody REGN2810 and its antitumor activity in human PD-1 knock-in mice," Mol. Cancer Ther. 16(5): 861-870.
Butte, M.J., et al., (2007) "Programmed death-1 ligand 1 interacts specifically with the B7-1 costimulatory molecule to inhibit T cell responses" Immunity 27:111-122.
Callahan, M.K., et al., (2010) "Anti-CTLA-4 Antibody Therapy: Immune Monitoring During Clinical Development of a Novel Immunotherapy" Semin. Oncol. October; 37(5):473-484.
Callahan, M.K., et al., (2014) "CTLA-4 and PD-1 Pathway Blockade: Combinations in the Clinic" Front. Oncol. 4(385):1-6.
Camacho, L.H., (2015) "CTLA-4 blockade with ipilimumab: biology, safety, efficacy, and future considerations" Cancer Medicine 4(5):661-672.
Caravella et al. (2010) "Structure-Guided Design of Antibodies," Current Computer-Aided Drug Design. 6(2):128-138.
Carrizosa, et al., (2013) "New targets and new mechanisms in lung cancer." Oncology 27(5).
Carter, L. et al. (2003) "Cytotoxic T-lymphocyte antigen-4 and programmed death-1 function as negative regulators of lymphocyte activation," Immunol Res 28(1):49-59.
Carter, L., et al., (2002) "PD-1:PD-L inhibitory pathway affects both CD4(+) and CD8(+) T cells and is overcome by IL-2" Eur. J. Immunol. 32:634-43.
Carthon, B.C., et al., (2010) "Preoperative CTLA-4 Blockade: Tolerability and Immune Monitoring in the Setting of a Presurgical Clinical Trial" Clinical Cancer Res. 16(10): 2861-71.
Cartron, G., et al., (2002) "Therapeutic activity of humanized anti-CD20 monoclonal antibody and polymorphism in IgG Fc receptor Fc-GAMMA-RIIIa gene" Blood 99:754-758.
Casey, S.C., et al., (2016) "MYC regulates the antitumor immune response through CD47 and PD-L1" Science 352:227-231.
Castle J.C., et al., (2014) "Immunomic, genomic and transcriptomic characterization of CT26 colorectal carcinoma" BMC Genomics 15:190.
Caudill et al. (2001) "HSPPC-96: a personalized cancer vaccine," Exp. Opin. Biol. Ther. 1(3):539-547.
Ceuppens, J.L., et al., (1988) "Human T cell activation with phytohemagglutinin. The function of I-6 as an accessory signal" J. Immunol. 141:3868-3874.
Chaft, J.E., (Mar. 30, 2017) "Immunotherapy for lung cancer and the landscape of combinations" Thoracis Oncology Service Memorial Sloan Kettering Cancer Center.
Chand, D., et al., "AGEN2034, a novel anti-PD-1 antibody that combines effectively with CTLA-4 pathway blockade to enhance T cell activity" Poster #P312 SITC Annual Meeting, Washington, DC, USA Nov. 9-12, 2017.

Chang et al., (2013) "Blockade of the negative co-stimulatory molecules PD-1 and CTLA-4 improves survival in primary and secondary fungal sepsis," Crit Care. 17(3):R85.
Chapman, K., (2007) "Preclinical safety testing of monoclonal antibodies: the significance of species relevance" Nat. Rev. Drug Discov. 6:120-126.
Chapon, M., et al., (2011) "Progressive upregulation of PD-1 in primary and metastatic melanomas associated with blunted TCR signaling in infiltrating T lymphocytes" J. Invest. Dermatol. 131:1300-1307.
Chauvin, J., et al., (2015) "TIGIT and PD-1 impair tumor antigen-specific CD8+ T cells in melanoma patients" J Clin Investigation. 125(5):2046-58.
Chemnitz, J.M., et al., (2004) "SHP-1 and SHP-2 associate with immunoreceptor tyrosine-based switch motif of programmed death 1 upon primary human T cell stimulation, but only receptor ligation prevents T cell activation" J. Immunol. 173:945-954.
Chen, D.S., et al., (2013) "Oncology Meets Immunology: The Cancer-Immunity Cycle" Immunity 39:1-10.
Chen, L., et al., (2015) "Anti-PD-1/PD-L1 therapy of human cancer: past, present, and future" J. Clin. Invest. 125:3384-3391.
Chen, S., et al., (2015) "Combination of 4-1BB agonist and PD-1 antagonist promotes antitumor effector/memory CD8 T cells in a poorly immunogenic tumor model" Cancer Immunol. Res. 3(2):149-160.
Cheng, Z.J., et al., (2014) "Development of a robust reporter-based ADCC assay with frozen, thaw-and-use cells to measure Fc effector function of therapeutic antibodies" Journal of Immunological Methods 414: 69-81.
Choe J.H., et al., (2016) "Autoimmune meningoencephalitis in a melanoma patient treated with ipilimumab." Immunotherapy 8(10):1163-1167.
Choueiri, T.K., et al., (2015) "Abstract 1306: Biomarker results from a clinical trial of nivolumab in patients (pts) with metastatic renal cell carcinoma (mRCC) (CA209009): Gene expression, serum profiling for immune markers, and multiplex tissue immunohistochemistry (IHC)" Cancer Res. 75:1306.
Chu, F., et al., (2014) "Anti-PD-1 antibodies for the treatment of B-cell lymphoma Importance of PD-1+ T-cell subsets" OncoImmunology 3(e28101):1-3.
Chung, C.H., (2008) "Managing Premedications and the Risk for Reactions to Infusional Monoclonal Antibody Therapy" The Oncologist 13:725-732.
Coiffier, B., (2007) "Rituximab therapy in malignant lymphoma" Oncogene 26:3603-3613.
Collins A.V., et al., (2002) "The Interaction Properties of Costimulatory Molecules Revisited" Immunity, 17:201-210.
Collins, M., et al., (2005) "The B7 family of immune-regulatory ligands" Genome Biology 6(6):223.1-223.7.
Conroy, P.J., et al. (2017) "Antibodies: From Novel Repertoires to Defining and Refining the Structure of Biologically Important Targets" Methods, vol. 116, pp. 12-22.
Coyne, G.O., et al., (2014) "Nivolumab: Promising Survival Signal Coupled With Limited Toxicity Raises Expectations" J. Clin. Oncol. 32(10):986-988.
Cross, R.S., et al., (2015) "Therapeutic DNA vaccination against colorectal cancer by targeting the MYB oncoprotein" Clin. Transl. Immunol. 4:e30.
Curran, M.A., et al., (2010) "PD-1 and CTLA-4 combination blockade expands infiltrating T cells and reduces regulatory T and myeloid cells within B16 melanoma tumors" Proc. Natl. Acad. Sci. USA 107:4275-4280.
Currie, A.J., et al., (2009) "Dual Control of Antitumor CD8 T Cells through the Programmed Death-1/Programmed Death-Ligand 1 Pathway and Immunosuppressive CD4 T Cells: Regulation and Counterregulation" J. Immunol. 183:7898-08.
Curti B.D., et al., (2013) "OX40 is a potent immune-stimulating target in late-stage cancer patients" Cancer Res. 73:7189-98.
Da Silva, R M et al. (2014) "Nivolumab: Anti-PD-1 monoclonal antibody cancer immunotherapy," Drugs of the Future, 39(1):15-24.
Dahan, R., (2015) "Fc-GAMMA-Rs Modulate the Anti-tumor Activity of Antibodies Targeting the PD-1/PD-L1 Axis." Cancer Cell 28(3):285-295.

(56) References Cited

OTHER PUBLICATIONS

Dangl, J.L., et al., (1988) "Segmental flexibility and complement fixation of genetically engineered chimeric human, rabbit and mouse antibodies" EMBO J. 7:1989-1994.
Dariavach, P., et al., (1988) "Human Ig superfamily CTLA-4 gene: chromosomal localization and identity of protein sequence between murine and human CTLA-4 cytoplasmic domains" Eur. J. Immunol. 18:1901-1905.
Das, R., et al., (2015) "Combination therapy with anti-CTLA-4 and anti-PD-1 leads to distinct immunologic changes in vivo" J. Immunol. 194:950-959.
Dasanu, C., et al., (2016) "Late-onset pericardial tamponade, bilateral pleural effusions and recurrent immune monoarthritis induced by ipilimumab use for metastatic melanoma" Journal of Oncology Pharmacy Practice 23(3):231-234.
Davis, TA, et al., "MDX-010 (human anti-CTLA4): a phase 1 trial in hormone refractory prostate carcinoma (HRPC)" ASCO 38th Annual Meeting (May 18-21, 2002) Orlando FL.
De Souza, P., et al., "Evaluation of Peripheral T-Cell Subset Proliferation as a Pharmacodynamic Assay to Guide the Development of Anti-CTLA-4 and PD-1 Antibody Combinations in Patients With Solid Tumors" CT104 Presented at the 2018 Annual Meeting of the American Association of Cancer Research, Apr. 14-18, 2018, in Chicago, IL, USA.
Demaria, S., et al., (2005) "Combining radiotherapy and immunotherapy: A revived partnership" International J. of Radiation Oncology Biology Physics 63(3):655-666.
Deng, L., et al., (2014) "Irradiation and anti-PD-L1 treatment synergistically promote antitumor immunity in mice" J. Clin. Invest. 124(2):687-695.
Dick, L.W., et al., (2008) "C-Terminal Lysine Variants in Fully Human Monoclonal Antibodies: Investigation of Test Methods and Possible Causes" Biotechnology and Bioengineering 100(6):1132-1143.
Disis, M.L. (2010) "Immune regulation of cancer" J. Clin. Oncol. 28:4531-4538.
Dolan, D.E., et al., (2014) "PD-1 Pathway Inhibitors: Changing the Landscape of Cancer Immunotherapy" Cancer Control 21(3):231-7.
Dong, H., et al., (2002) "Tumor-associated B7-H1 promotes T-cell apoptosis: a potential mechanism of immune evasion" Nat. Med. 8:787-9.
Dong, H., et al., (2003) "B7-H1 pathway and its role in the evasion of tumor immunity." J. Mol. Med. 81:281-7.
Drescher, C., et al., "Phase 1/2, Open-Label, Multiple Ascending Dose Trial of AGEN2034, an Anti-PD-1 Monoclonal Antibody, in Advanced Solid Malignancies: Results of Dose Escalation in Advanced Cancer and Expansion Cohorts in Subjects With Relapsed/Refractory Cervical Cancer" Poster No. 1158P Presented at European Society for Medical Oncology, Munich, Germany (2018).
Drouin, E., et al., "AGEN1884 and AGEN2041: Two functionally distinct anti-CTLA-4 antagonist antibodies" Poster No. #5005 Presented at the American Association for Cancer Research Annual Meeting 2016 New Orleans, LA, USA, Wednesday, Apr. 20, 2016.
Drouin, E., et al., "AGEN1884, an IgG1 anti-CTLA-4 antibody, combines effectively with PD-1 blockade in primary human T cell assays and in a non-human primate pharmacodynamic (PD) model" Poster: #27 Abstract: #3654 AACR Annual Meeting 2017, Washington, DC, USA Apr. 1-5, 2017.
Dudley, J.C., et al., (2016) "Microsatellite Instability as a Biomarker for PD-1 Blockade" Clin. Cancer Res. 22(4):813-20.
Duraiswamy, J., et al., (2013) "Dual Blockade of PD-1 and CTLA-4 Combined with Tumor Vaccine Effectively Restores T-Cell Rejection Function in Tumors" Cancer Res. 73(12):3591-603.
Duraiswamy, J., et al., (2013) "Therapeutic PD-1 pathway blockade augments with other modalities of immunotherapy T-cell function to prevent immune decline in ovarian cancer" Cancer Res. 73(23):6900-6912.
Dyck, L., et al., (2016) "Anti-PD-1 inhibits Foxp3+ Treg cell conversion and unleashes intratumoural effector T cells thereby enhancing the efficacy of a cancer vaccine in a mouse model" Cancer Immunol. Immunother. 65(12):1491-1498.
Ehrenstein, MR, et al., (2010) "The importance of natural IgM: scavenger, protector and regulator" Nat. Rev. Immunol. 10(11):778-86.
Eisenhauer, E.A., et al., (2009) "New response evaluation criteria in solid tumours: Revised RECIST guideline (version 1.1)" European Journal of Cancer 45:228-247.
Epstein, L.B., et al., (1971) "The interaction of human macrophages and lymphocytes in the phytohemagglutinin-stimulated production of interferon" J. Clin. Invest. 50:744-753.
Evans, T.A., et al., (2010) "Functional diversity of Robo receptor immunoglobulin domains promotes distinct axon guidance decisions" Curr. Biol. 20:567-572.
Falchook, G.S., et al., (2016) "Responses of metastatic basal cell and cutaneous squamous cell carcinomas to anti-PD1 monoclonal antibody REGN2810" Journal for Immunotherapy of Cancer 4(1):70.
Ferrara, F., et al. (2015) "Recombinant Renewable Polyclonal Antibodies", mAbs, vol. 7 No. 1, pp. 32-41.
Ferris, R.K., et al., (2016) "Nivolumab for Recurrent Squamous-Cell Carcinoma of the Head and Neck" N. Engl. J. Med. 375(19):1856-1867.
Finco, D., et al., (2014) "Cytokine release assays: Current practices and future directions" Cytokine 66:143-155.
Foote, M.C. et al., (2014) "Phase II study of single-agent panitumumab in patients with incurable cutaneous squamous cell carcinoma" Annals of Oncology, 25(10):2047-2052.
Four Agenus Abstracts Accepted for Presentation at the American Association for Cancer Research (AACR) 2017 Annual Meeting Mar. 7, 2017 /PRNewswire/.
Francisco, L.M., et al., (2010) "The PD-1 pathway in tolerance and autoimmunity" Immunol. Rev. 236:219-242.
Frazier, K.S., et al., (2015) "Scientific and Regulatory Policy Committee Points-to-consider Paper: Drug-induced Vascular Injury Associated with Nonsmall Molecule Therapeutics in Preclinical Development: Part I. Biotherapeutics" Toxicol. Pathol. 43:915-934.
Freedman, A.S., et al., (1991) "Selective induction of B7/BB-1 on interferon-gamma stimulated monocytes: a potential mechanism for amplification of T cell activation through the CD28 pathway" Cell Immunol 137:429-437.
Freeman, G.J et al. (2000) "Engagement of the PD-1 immunoinhibitory receptor by a novel B7 family member leads to negative regulation of lymphocyte activation" J. Exp. Med. 192:1027-1034.
Freeman, G.J., et al. (2006) "Reinvigorating exhausted HIV-specific T cells via PD-1-PD-1 ligand blockade" J. Exp. Med. 203:2223-2227.
Frenel, J.-S., et al., (2016) "Pembrolizumab in patients with advanced cervical squamous cell cancer: Preliminary results from the phase Ib Keynote-028 study" J. Clin. Oncol. 34 (suppl), Abstract 5515.
Friedman, H.S., et al., (2009) "Bevacizumab Alone and in Combination With Irinotecan in Recurrent Glioblastoma" J Clin Oncol 27(28):4733-40.
Fu, J., et al., (2014) "Preclinical Evidence That PD1 Blockade Cooperates with Cancer Vaccine TEGVAX to Elicit Regression of Established Tumors" Cancer Res; 74(15):4042-52.
Furness, A.J.S., et al., (2014) "Impact of tumour microenvironment and Fc receptors on the activity of immunomodulatory antibodies" Trends in Immunology 35(7):290-298.
Garcia-Sanz, J.A., et al. (1996) "Translational control of interleukin 2 messenger RNA as a molecular mechanism of T cell anergy" J. Exp. Med. 184:159-164.
Gatalica, Z., et al., (2014) "Programmed Cell Death 1 (PD-1) and Its Ligand (PD-L1) in Common Cancers and Their Correlation with Molecular Cancer Type" Cancer Epidemiol Biomarkers Prev. 23(12); 2965-70.
Ge, Y., et al., (2013) "Blockade of PD-1/PD-L1 immune checkpoint during DC vaccination induces potent protective immunity against breast cancer in hu-SCID mice" Cancer Letters 336:253-259.
George, S. et al. (2017) "Loss of PTEN is associated with resistance to anti-PD-1 checkpoint blockade therapy in metastatic uterine leiomyosarcoma," Immunity. 46:197-204.
Ghebeh, H., et al., (2006) "The B7-H1 (PD-L1) T lymphocyte-inhibitory molecule is expressed in breast cancer patients with

(56) References Cited

OTHER PUBLICATIONS infiltrating ductal carcinoma: correlation with important high-risk prognostic factors" Neoplasia 8:190-198.
Ghiotto, M., et al., (2010) "PD-L1 and PD-L2 differ in their molecular mechanisms of interaction with PD-1" International Immunology 22(8):651-60.
Goldman, JW et al. (2017) "Nivolumab (N) plus Ipillimub (I) as first-line (1L) treatment for advanced (adv) NSCLC: 2-yr OS and long-term outcome from CheckMate 012," J Clin Oncol. 35(15): 4 pp.
Gombos, R.B., et al., (2018) "Toxicological and pharmacological assessment of AGEN1884, a novel human IgG1 anti-CTLA-4 antibody" PLoS ONE 13(4): e0191926.
Gonzalez, A., et al., "INCAGN1949, an Anti-OX40 Antibody With an Optimal Agonistic Profile and the Ability to Selectively Deplete Intratumoral Regulatory T Cells" 4703 Presented at the American Association for Cancer Research Annual Meeting 2017; Washington, DC, USA Apr. 1-5, 2017.
Gonzalez, et al., "INCAGN1876, a Unique GITR Agonist Antibody That Facilitates GITR Oligomerization" 3643 Presented at the American Association for Cancer Research Annual Meeting 2017 Washington, DC, USA Apr. 1-5, 2017.
Gooden, M. et al. (2011) "HLA-E expression by gynecological cancers restrains tumor-infiltrating CD8+ T lymphocytes," PNAS 108(26):10656-10661.
Gooden, M.J., et al., (2011) "The prognostic influence of tumour-infiltrating lymphocytes in cancer: a systematic review with meta-analysis" Br. J. Cancer 105:93-103.
Gros, A., et al., (2014) "PD-1 identifies the patient-specific CD8+ tumor-reactive repertoire infiltrating human tumors" Journal of Clinical Investigation 124(5):2246.
Grosso, J.F., et al., (2013) "CTLA-4 blockade in tumor models: an overview of preclinical and translational research" Cancer Immun. 13(5).
Hahn, L., et al., (2016) "Bilateral neuroretinitis and anterior uveitis following ipilimumab treatment for metastatic melanoma" Journal of Ophthalmic Inflammation and Infection 6(14):1-4.
Hall, W., et al., (2008) "Tissue Cross-Reactivity Studies for Monoclonal Antibodies: Predictive Value and Use for Selection of Relevant Animal Species for Toxicity Testing. In Preclinical Safety Evaluation of Biopharmaceuticals: A Science-Based Approach to Facilitating Clinical Trials" J.A.Cavagnaro, ed. (John Wiley & Sons, Inc.) pp. 208-240.
Hamanishi, J., et al., (2007) "Programmed cell death 1 ligand 1 and tumor infiltrating CD8+ T lymphocytes are prognostic factors of human ovarian cancer" Proc. Nat. Acd. Sci. USA 104(9):3360-5.
Hamid, O., et al. (2013) "Safety and tumor responses with lambrolizumab (anti-PD-1) in melanoma" N. Engl. J. Med. 369:134-144.
Hanahan, D., et al., (2011) "Hallmarks of cancer: the next generation" Cell 144:646-674.
Hathcock, K.S., et al., (1993) "Identification of an alternative CTLA-4 ligand costimulatory for T cell activation" Science 262:905-907.
Haymaker, C., et al., (2012) "PD-1 and BTLA and CD8+ T-cell "exhaustion" in cancer "Exercising" an alternative viewpoint" OncoImmunology 1(5):735-8.
Heemskerk, B., et al., (2013) "The cancer antigenome" EMBO J. 32:194-203.
Heinzerling, L., et al., (2016) "Cardiotoxicity associated with CTLA4 and PD1 blocking immunotherapy." Journal for Immuno Therapy of Cancer 4(1):1-11.
Hellmann, M.D., et al., (2016) CheckMate 012: safety and efficacy of first-line nivolumab and ipilimumab in advanced NSCLC In ASCO Annual Meeting. Chicago: Proc Am Soc Clin Oncol.
Hirano, F. et al. (2005) "Blockade of B7-H1 and PD-1 by Monoclonal Antibodies Potentiates Cancer Therapeutic Immunity," Cancer Res 65(3):1089-1096.
Hodi, F.S., et al. (2010) "Improved survival with ipilimumab in patients with metastatic melanoma" N. Engl. J. Med. 363:711-723.

Hodi, F.S., et al., (2014) "Long-term survival of ipilimumab-naive patients (pts) with advanced melanoma (MEL) treated with nivolumab (anti-PD-1, BMS-936558, ONO-4538) in a phase I trial" ASCO.
Hogarth, PM, et al., (2012) "Fc receptor-targeted therapies for the treatment of inflammation, cancer and beyond" Nat. Rev. Drug Discov. 11(4):311-31.
Howard, S.C., et al., (2011) "The Tumor Lysis Syndrome" N. Engl. J. Med. 364(19):1844-1854.
Huang, R., et al., (2015) "LAG3 and PD1 co-inhibitory molecules collaborate to limit CD8+ T cell signaling and dampen antitumor immunity in a murine ovarian cancer model" Oncotarget 6(29):27359-77.
Hurwitz, A.A., et al., (1998) "CTLA-4 blockade synergizes with tumor-derived granulocyte-macrophage colony-stimulating factor for treatment of an experimental mammary carcinoma" Proc. Natl. Acad. Sci. USA 95:10067-10071.
Hurwitz, A.A., et al., (2000) "Combination Immunotherapy of Primary Prostate Cancer in a Transgenic Mouse Model Using CTLA-4 Blockade" Cancer Res. 60:2444-2448.
Ichigotani, Y., et al., (2000) "Molecular cloning of a novel human gene (SIRP-B2) which encodes a new member of the SIRP/SHP S-1 protein family" J. Hum. Genet. 45:378-382.
Idusogie, E.E., et al., (2000) "Mapping of the Cq Binding Site on Rituxan a Chimeric Antibody with a Human IgG1 Fc" J. Immunol. 164:4178-4184.
Ikemizu, S., et al., (2000) "Structure and Dimerization of a Soluble Form of B7-1" Immunity 12:51-60.
International Search Report and Written Opinion corresponding to International Patent Application No. PCT/US2017/065014, dated Feb. 13, 2018.
International Search report for PCT/US2016/049913 dated Jan. 20, 2017.
International Search Report with Written Opinion corresponding to International Patent Application No. PCT/US2016/034508, dated Aug. 5, 2016.
Intlekofer, A., et al., (2013) "At the Bench: preclinical rationale for CTLA-4 and PD-1 blockade as cancer immunotherapy" J. of Leukocyte Biol. 94:25-39.
Ishida M, et al., (2002) "Differential expression of PD-L1 and PD-L2, ligands for an inhibitory receptor PD-1, in the cells of lymphohematopoietic tissues" Immunol. Lett. 84(1):57-62.
Ishida, Y., et al., (1992) "Induced expression of PD-1, a novel member of the immunoglobulin gene superfamily, upon programmed cell death" EMBO J. 11:3887-3895.
Iwai, Y. et al. (2003) "PD-1 inhibits antiviral immunity at the effector phase in the liver," J Exp Med 198(1):39-50.
Iwai, Y., et al. (2002) "Involvement of PD-L1 on tumor cells in the escape from host immune system and tumor immunotherapy by PD-L1 blockade" Proc. Natl. Acad. Sci. USA 99:12293-12297.
Iwai, Y., et al., (2002) "Microanatomical localization of PD-1 in human tonsils" Immunol. Lett. 83:215-220.
Jacobsen, F.W., et al., (2011) "Molecular and functional characterization of cynomolgus monkey lgG subclasses" J. Immunol. 186:341-349.
Jarkowski, A., et al., (2016) "Systemic Therapy in Advanced Cutaneous Squamous Cell Carcinoma (CSCC): The Roswell Park Experience and a Review of the Literature" American Journal of Clinical Oncology, 39(6):545-548.
Jawad, Z., "Targeting the next generation of checkpoint pathways using a disease-centric approach" ICI Europe Meeting Nov. 16-17, 2016.
Jiang, H., et al., (2015) "Elevated chronic inflammatory factors and myeloid-derived suppressor cells indicate poor prognosis in advanced melanoma patients" Int. J. Cancer 136:2352-2360.
Jin, H., et al., (2010) "Role of PD-1 in Regulating T-Cell Immunity" Current Topics in Microbiology and Immunology 350:17-36.
John, L.B., et al., (2013) "Anti-PD-1 Antibody Therapy Potently Enhances the Eradication of Established Tumors By Gene-Modified T Cells" Clin. Cancer Res. 19(20):5636-46.
John, L.B., et al., (2013) "Blockade of PD-1 immunosuppression boosts CAR T-cell therapy" OncoImmunology 2(10):e26286-1-3.
Kamphorst, A.O., et al., (2013) "Manipulating the PD-1 pathway to improve immunity" Current Opinion in Immunology 25:381-388.

(56) References Cited

OTHER PUBLICATIONS

Karia, P.S., et al., (2013) "Cutaneous squamous cell carcinoma: estimated incidence of disease, nodal metastasis, and deaths from disease in the United States, 2012" Journal of the American Academy of Dermatology 68(6):957-966.
Kaufman, H., et al., (2016) "Avelumab (MSB0010718C; anti-{D-1) in patients with metastatic Merkel cell carcinoma previously treated with chemotherapy: results of the phase 2 Javelin Merkel 200 trial" Oral Presentation at the 52nd ASCO Annual Meeting June 307 Chicago, IL Abstract No. 9508.
Keir, M.E., et al., (2005) "Programmed Death-1 (PD-1):PD-Ligand 1 Interactions Inhibit TCR-Mediated Positive Selection of Thymocytes" The Journal of Immunology 175:7372-7379.
Keir, M.E., et al., (2008) "PD-1 and Its Ligands in Tolerance and Immunity" Annu. Rev. Immunol. 26:677-704.
Kelderman, S., et al., (2015) "Mismatch Repair-Deficient Cancers Are Targets for Anti-PD-1 Therapy" Cancer Cell 28:11-13.
Keler, T., (2003) "Activity and safety of CTLA-4 blockade combined with vaccines in cynomolgus macaques" J. Immunol. 171:6251-6259.
Kesari, S., et al., (2007) "Phase II study of metronomic chemotherapy for recurrent malignant gliomas in adults" Neuro-Oncology 9:354-363.
Khan, L., et al. (2017) "Cross-Neutralizing Anti-HIV-1 Human Single Chain Variable Fragments(scFvs) Against CD4 Binding Site and N332 Glycan Identified from A Recombinant Phage Library" Scientific Reports, vol. 7, Article No. 45163, 12 Pages.
Kim, J.M., et al., (2013) "Fc-GAMMA receptors enable anticancer action of proapoptotic and immune-modulatory antibodies" J. of Exp. Med. 210(9):1647-1651.
Kinter, A.L., et al., (2008) "The common gamma-chain cytokines IL-2, IL-7, IL-15, and IL-21 induce the expression of programmed death-1 and its ligands" J. Immunol. 181:6738-6746.
Kirchberger et al., (2016) "Combined low-dose ipilimumab and pembrolizumab after sequential ipilimumab and pembrolizumab failure in advanced melanoma," Eur J Cancer. 65: 182-184.
Kleffel, S., et al., (2015) "Melanoma Cell-Intrinsic PD-1 Receptor Functions Promote Tumor Growth." Cell 162(6): 1242-1256.
Koene, H.R., et al., (1997) "Fc gammaRIIIa-158V/F polymorphism influences the binding of IgG by natural killer cell Fc gammaRIIa, independently of the Fc gammaRIIIa-48L/R/H phenotype" Blood 90:1109-1114.
Konishi, J., et al., (2004) "B7-H1 expression on non-small cell lung cancer cells and its relationship with tumor-infiltrating lymphocytes and their PD-1 expression" Clin. Cancer Res. 10:5094-100.
Konitzer, J.D., et al. (2017) "Generation of A Highly Diverse Panel of Antagonistic Chicken Monoclonal Antibodies Against the GIP Receptor" mAbs, vol. 9, No. 3, pp. 536-549.
Kreisl, T.N., et al., (2009) "Phase II Trial of Single-Agent Bevacizumab Followed by Bevacizumab Plus Irinotecan at Tumor Progression in Recurrent Glioblastoma" J. Clin. Oncol. 27:740-745.
Krummel, M.F., et al., (1995) "CD28 and CTLA-4 have opposing effects on the response of T cells to stimulation" J. Exp. Med. 182:459-465.
Kuehn, H.S., et al., (2014) "Immune dysregulation in human subjects with heterozygous germline mutations in CTLA4" Science 345:1623-1627.
Kuiper, H.M., et al., (1995) "Activated T cells can induce high levels of CTLA-4 expression on B cells" J Immunol 155:1776-1783.
Kumaraguru, U., et al., (2002) "Immunization with Chaperone-Peptide Complex Induces Low-Avidity Cytotoxic T Lymphocytes Providing Transient Protection against Herpes Simplex Virus Infection" Journal of Virology 76(1):136-141.
Lammert, E., et al., (1997) "The endoplasmic reticulum-resident stress protein gp96 binds peptides translocated by TAP" Eur. J. Immunol. 27:923-927.
Langer, C.J., et al., (2016) "Carboplatin and pemetrexed with or without pembrolizumab for advanced, non-squamous non-small-cell lung cancer: a randomised, phase 2 cohort of the open-label Keynote-021 study" The Lancet Oncology, 17(11):1497-1508.
Larkin, J., et al., (2015) "Combined Nivolumab and Ipilimumab or Monotherapy in Untreated Melanoma" New England Journal of Medicine 373(1):23-34.
Latchman, Y., et al., (2001) "PD-L2 is a second ligand for PD-1 and inhibits T cell activation" Nat. Immunol. 2:261-8.
Le Tourneau, C., et al., (2009) "Dose Escalation Methods on Phase I Cancer Clinical Trials" J. Natl. Cancer Inst. 101:708-720.
Le, D.T., et al., (2015) "PD-1 Blockade in Tumors with Mismatch-Repair Deficiency" N. Engl. J. Med. 372:2509-2520.
Leach, D.R., et al., (1996) "Enhancement of Antitumor Immunity by CTLA-4 Blockade" Science 271:1734-36.
Leach, M.W., et al. (2010) "Use of tissue cross-reactivity studies in the development of antibody-based biopharmaceuticals: history, experience, ethodology, and future directions" Toxicol. Pathol. 38:1138-1166.
Leach, M.W., et al., (2014) "Immunogenicity/hypersensitivity of biologics" Toxicol. Pathol. 42:293-300.
Leach, S., "Immune Checkpoint Inhibitors: Response rates in solid tumors" 2018 Gastrointestinal Cancers Symposium.
Lee, J., et al. (2016) "Molecular-Level Analysis of The Serum Antibody Repertoire in Young Adults Before and After Seasonal Influenza Vaccination" Nature Medicine, vol. 22, No. 12, pp. 1456-1464.
Li, B., (2009) "Anti-Programmed Death-1 Synergizes with Granulocyte Macrophage Colony-Stimulating Factor-Secreting Tumor Cell Immunotherapy roviding Therapeutic Benefit to Mice with Established Tumors" Clin Cancer Res 1623 2009;15(5).
Li, Z., et al., (1993) "Tumor rejection antigen gp96/grp94 is an ATPase: implications for protein folding and antigen presentation" EMBO Journal 12(8):3143-3151.
Li-Weber, M., (2003) "Regulation of IL4 Gene Expression by T Cells and Therapeutic Perspectives" Nature Reviews 3:534.
Li-Weber, M., et al., (2003) "Function and regulation of the CD95 (APO-1/Fas) ligand in the immune system" Semin. Immunol. 15:145-157.
Lin, D.Y., et al., (2008) "The PD-1/PD-L1 complex resembles the antigen-binding Fv domains of antibodies and T cell receptors" Proc. Natl. Acad. Sci. USA 105:3011-3016.
Lin, E.I., et al., (2015) "Mutational profiling of colorectal cancers with microsatellite Instability" Oncotarget 6(39):42334-44.
Lin, Y.M., et al., (2015) "High PD-L1 Expression Correlates with Metastasis and Poor Prognosis in Oral Squamous Cell Carcinoma" PLoS One 10:e0142656.
Lindquist, S., (1986) "The heat-shock response" Ann. Rev. Biochem. 55:1151-91.
Linsley, P.S., et al., (1992) "Coexpression and Functional Cooperation of CTLA-4 and CD28 on Activated T Lymphocytes" J Exp Med 176:1595-1604.
Linsley, P.S., et al., (1996) "Intracellular Trafficking of CTLA-4 and Focal Localization Towards Sites of TCR Engagement" Immunity 4:535-543.
Lindsten, T., et al., (1993) "Characterization of CTLA-4 Structure and Expression on Human T Cells" Journal of Immunology 51(7):3489-99.
Liu, L., et al. (2015) "The BRAF and MEK Inhibitors Dabrafenib and Trametinib: Effects on Immune Function and in Combination with Immunomodulatory Antibodies Targeting PD-1, PD-L1, and CTLA-4" Clin. Cancer Res. 21:1639-1651.
Liu, X., et al., (2003) "B7DC/PDL2 Promotes Tumor Immunity by a PD-1-independent Mechanism" J. Exp. Med. 197(12):1721-30.
Loke, P., et al., (2003) "PD-L1 and PD-L2 are differentially regulated by Th1 and Th2 cells" Proc. Natl. Acad. Sci. USA 100(9):5336-5341.
Long, G.V., et al., (2016) "Pembrolizumab (pembro) plus ipilimumab (ipi) for advanced melanoma: Results of the Keynote-029 expansion cohort" Journal of Clinical Oncology, 34(15 suppl.):9506-9506.
Lote, H., et al., (2015) "PD-1 and PD-L1 blockade in gastrointestinal malignancies" Cancer Treatment Reviews 41:893-903.
Lowther, D.E., et al. (2016) "PD-1 marks dysfunctional regulatory T cells in malignant gliomas" 1(5):e85935.

(56) References Cited

OTHER PUBLICATIONS

Luke, J.J., et al., (2015) "PD-1 pathway inhibitors: The next generation of immunotherapy for advanced melanoma" Oncotarget 6(6):3479-92.
MacFarlane, A.W., et al., (2013) "PD-1 Expression on Peripheral Blood Cells Increases with Stage in Renal Cell Carcinoma Patients and Is Rapidly Reduced after Surgical Tumor Resection" Cancer Immunol Res; 2(4):320-31.
Macian, F. (2005) "NFAT proteins: key regulators of T-cell development and function" Nat. Rev. Immunol. 5:472-484.
Mahoney, K.M., et al., (2015) "The Next Immune-Checkpoint Inhibitors: PD-1/PD-L1 Blockade in Melanoma" Clin. Ther. 37:764-782.
Mamalis, A., et al., (2014) "Targeting the PD-1 Pathway: A Promising Future for the Treatment of Melanoma" Arch Dermatol Res. 306(6): 511-519.
Mangsbo, S.M., et al., (2010) "Enhanced Tumor Eradication by Combining CTLA-4 or PD-1 Blockade With CpG Therapy" J. Immunother. 33:225-235.
Marabelle, A. et al., (2013) "Depleting tumor-specific Tregs at a single site eradicates disseminated tumors" The Journal of Clinical Investigation 123(6):2447-2463.
Marrack, P., et al., (1990) "The toxicity of Staphylococcal Enterotoxin B in Mice is Mediated by T Cells" J. Exp. Med. 171:455-464.
Marzec, M., et al., (2008) "Oncogenic kinase NPM/ALK induces through STAT3 expression of immunosuppressive protein CD274 (PD-L1, B7-H1)" Proc. Natl. Acad. Sci. USA 105:20852-20857.
Matsuzaki, K., et al., (2010) "Tumor-infiltrating NY-ESO-1-specific CD8+ T cells are negatively regulated by LAG-3 and PD-1 in human ovarian cancer" Proc. Nat'l. Acad. Sci. USA 107(17):7875-7880.
McCoy, K.D., et al., (1999) "The role of CTLA-4 in the regulation of T cell immune responses" Immunol Cell Biol. 77:1-10.
McDermott, D.F., et al., (2011) "A phase I study to evaluate safety and antitumor activity of biweekly BMS-936558 (Anti-PD-1, MDX-1106/ONO-4538) in patients with RCC and other advanced refractory malignancies" J. Clin. Oncol. 29 (7 suppl. abstr 331).
McDermott, J. et al. (2015) "Pembrolizumab: PD-1 inhibition as a therapeutic strategy in cancer," Drugs of Today, 15(1):7-20.
Meng, X., et al., (2015) "Predictive biomarkers in PD-1/PD-L1 checkpoint blockade immunotherapy" Cancer Treatment Reviews 41(10):868-76.
Merck Sharp & Dohme USA, 2017. Keytruda® (pembrolizumab) Package Insert.
Metzler, W.J., et al., (1997) "Solution structure of human CTLA-4 and delineation of a CD80/CD86 binding site conserved in CD28" Nat. Struct. Biol. 4:527-531.
Mezache, L., et al., (2015) "Enhanced expression of PD L1 in cervical intraepithelial neoplasia and cervical cancers" Modern Pathology 28(12):1594-1602.
Min, L., et al., (2013) "Anti-PD1 Following Ipilimumab for Mucosal Melanoma: Durable Tumor Response Associated with Severe Hypothyroidism and Rhabdomyolysis" Cancer Immunol. Res. 2(1):15-18.
Mittal, D., et al., (2014) "Antimetastatic effects of blocking PD-1 and the adenosine A2A receptor" Cancer Res. 74:3652-3658.
Mkrtichyan, M., et al., (2011) "Anti-PD-1 synergizes with cyclophosphamide to induce potent anti-tumor vaccine effects through novel mechanisms" Eur. J. Immunol. 41:2977-2986.
Moore, K.N., et al., "Phase 1/2 Open-Label, Multiple Ascending Dose Trial of AGEN2034, an anti-PD-1 Monoclonal Antibody, in Advanced Solid Malignancies: Results of Dose Escalation" 18-1200-B ASCO C-700-01, 230933 (2018) J Clin Oncol 36, 2018 (suppl; abstr 3086).
Moreau, T., et al., (1996) "CAMPATH-IH in multiple sclerosis" Mult. Scler. 1:357-365.
Moreau, T., et al., (1996) "Transient increase in symptoms associated with cytokine release in patients with multiple sclerosis" Brain 119 (Pt 1):225-237.

Neilsen, J.Z., et al., (2013) "Anti-PD-1 Blockade and Stereotactic Radiation Produce Long-Term Survival in Mice With Intracranial Gliomas" Int. J. Radiat. Oncol. Biol. Phys. 86(2): 343-349.
Newton, D.W., et al., (1996) "Mutations in the MHC Class II Binding Domains of Staphylococcal Enterotoxin A Differentially Affect T Cell Receptor V? Specificity" The Journal of Immunology 157:3988-3994.
Ngiow, S.F., (2011) "Anti-TIM3 Antibody Promotes T Cell IFN-GAMMA-Mediated Antitumor Immunity and Suppresses Established Tumors" Cancer Research 71(10) 3540:51.
Nielsen, C., et al., (2004) "A putative regulatory polymorphism in PD-1 is associated with nephropathy in a population-based cohort of systemic lupus erythematosus patients" Lupus 13(7):510-6.
Nimmerjahn, F., et al., (2006) "Fcgamma receptors: old friends and new family members" Immunity 24:19-28.
Nimmerjahn, F., et al., (2007) "Antibodies, Fc receptors and cancer" Current Opinion in Immunology 19:239-245.
Nimmerjahn, F., et al., (2007) "Fc-receptors as regulators of immunity" Adv. Immunol. 96:179-204.
Nimmerjahn, F., et al., (2008) "Fc-GAMMA receptors as regulators of immune responses" Nature Reviews 8:34-47.
Nimmerjahn, F., et al., (2012) "Translating basic mechanisms of IgG effector activity into next generation cancer therapies" Cancer Immun. 12:13.
Nishimura et al., (2001) "Autoimmune dilated cardiomyopathy in PD-1 receptor-deficient mice" Science 291:319-22.
Nishimura H, et al., (1996) "Developmentally regulated expression of the PD-1 protein on the surface of double-negative (CD4-CD8-) thymocytes" Int. Immunol. 8(5):773-80.
Nishimura H, et al., (2001) "PD-1: an inhibitory immunoreceptor involved in peripheral tolerance" Trends Immunol. 22(5):265-8.
Nishimura, H., et al., (1999) "Development of lupus-like autoimmune diseases by disruption of the PD-1 gene encoding an ITIM motif-carrying immunoreceptor" Immunity 11:141-51.
Norde, W.J., (2011) "PD-1/PD-L1 Interactions Contribute to Functional T-Cell Impairment in Patients Who Relapse with Cancer After Allogeneic Stem Cell Transplantation" Cancer Res. 71(15):5111-22.
Oddone, N. et al., (2009) "Metastatic cutaneous squamous cell carcinoma of the head and neck: the Immunosuppression, Treatment, Extranodal spread, and Margin status (ITEM) prognostic score to predict outcome and the need to improve survival" Cancer 115(9):1883-1891.
Odorizzi, et al., (2015) "Genetic absence of PD-1 promotes accumulation of terminally differentiated exhausted CD8+ T cells" J. Exp. Med. 212:1125-1137.
Oestreich, K.J., et al., (2008) "NFATc1 regulates PD-1 expression upon T cell activation" J. Immunol. 181:4832-4839.
Ohaegbulam, K.C., et al., (2015) "Human cancer immunotherapy with antibodies to the PD-1 and PD-L1 pathway" Trends in Molecular Medicine 21(1):24-33.
Okada, H., et al., (2015) "Immunotherapy response assessment in neuro-oncology: a report of the RANO working group" Lancet Oncol. 16:e534-42.
Okazaki, T., et al., (2001) "PD-1 immunoreceptor inhibits B cell receptor-mediated signaling by recruiting src homology 2-domain-containing tyrosine phosphatase 2 to phosphotyrosine" Proc. Nat'l. Acad. Sci. USA 98(24):13866-71.
Okazaki, T., et al., (2002) "New regulatory co-receptors: inducible co-stimulator and PD-1" Curr. Opin. Immunol. 14: 779-82.
Okazaki, T., et al., (2007) "PD-1 and PD-1 ligands: from discovery to clinical application" Int. Immunol. 19(7):813-824.
Oken, M.M. et al., (1982) "Toxicity and response criteria of the Eastern Cooperative Oncology Group" American Journal of Clinical Oncology 5(6):649-655.
Ostrom, Q.T., et al., (2013) "CBTRUS Statistical Report: Primary Brain and Central Nervous System Tumors Diagnosed in the United States in 2006-2010" Neuro-Oncology 15:ii1-ii56.
Ott, P.A., et al., (2013) "CTLA-4 and PD-1/PD-L1 Blockade: New Immunotherapeutic Modalities with Durable Clinical Benefit in Melanoma Patients" Clin. Cancer Res. 19(19):5300-9.

(56) References Cited

OTHER PUBLICATIONS

Page, D.B., et al., (2013) "Checkpoint modulation in melanoma: an update on ipilimumab and future directions" Curr. Oncol. Rep. 15:500-8.
Palacios, R. (1982) "Concanavalin A triggers T lymphocytes by directly interacting with their receptors for activation" J. Immunol. 128:337-342.
Pan, Z.K., et al., (2015) "Clinicopathological and prognostic significance of programmed cell death ligand1 (PD-L1) expression in patients with non-small cell lung cancer: a meta-analysis" J. Thorac. Dis. 7(3):462-470.
Pardoll D., et al., (2012) "Immunotherapy earns its spot in the ranks of cancer therapy" J. Exp. Med. 209(2):201-9.
Pardoll DM, (2012) "The blockade of immune checkpoints in cancer immunotherapy" Nat. Rev. Cancer 12(4):252-264.
Parekh, B.S., et al., (2012) "Development and validation of an antibody-dependent cell-mediated cytotoxicity-reporter gene assay" mAbs 4:3, 310-318.
Parish, C.R., et al., (2009) "Use of the intracellular fluorescent dye CFSE to monitor lymphocyte migration and proliferation" Curr. Protoc. Immunol. Chapter 4, Unit4 9.
Parola, et al. (Jan. 2018) "Integrating High-Throughput Screening and Sequencing for Monoclonal Antibody Discovery and Engineering", Immunology, vol. 153, No. 1, pp. 31-41.
Parry, R.et al., (2005) "CTLA-4 and PD-1 receptors inhibit T-cell activation by distinct mechanisms" Mol. Cell Biol. 25(21):9543-9553.
Parsa, A.T., et al., (2007) "Loss of tumor suppressor PTEN function increases B7-H1 expression and immunoresistance in glioma" Nat. Med. 13(1):84-88.
Pascolutti, R., et al., (2016) "Structure and Dynamics of PD-L1 and an Ultra-High-Affinity PD-1 Receptor Mutant" Structure 24:1719-1728.
Patsoukis, N. et al., (2015) "PD-1 alters T-cell metabolic reprogramming by inhibiting glycolysis and promoting lipolysis and fatty acid oxidation" Nat. Commun. 6:6692.
Patsoukis, N., et al., (2012) "Selective effects of PD-1 on Akt and Ras pathways regulate molecular components of the cell cycle and inhibit T cell proliferation" Sci. Signal 5:ra46.
Patsoukis, N., et al., (2013) "PD-1 increases PTEN Phosphatase activity while decreasing PTEN protein stability by inhibiting casein kinase 2" Mol. Cell Biol. 33(16):3091-3098.
Pauken, K.E. et al., (2014) "TIGIT and CD226: Tipping the Balance between Costimulatory and Coinhibitory Molecules to Augment the Cancer Immunotherapy Toolkit" Cancer Cell 26:785-787.
Pauken, K.E., et al., (2015) "Overcoming T cell exhaustion in infection and cancer" Trends Immunol. 36(4):265-276.
Peggs, K.S., et al., (2006) "Principles and use of anti-CTLA4 antibody in human cancer immunotherapy" Current Opinion in Immunology 18:206-213.
Peggs, K.S., et al., (2008) "Cell intrinsic mechanisms of T-cell inhibition and application to cancer therapy" Immunological Reviews 224:141-165.
Peggs, K.S., et al., (2009) "Cancer immunotherapy: co-stimulatory agonists and co-inhibitory antagonists" Clin. Exp. Immunol. 157:9-19.
Peng, W., et al., (2013) "Blockade of the PD-1 pathway enhances the efficacy of adoptive cell therapy against cancer" OncoImmunology 2(2):e22691.
Pentcheba-Hoang, T., et al., (2007) "Programmed death-1 concentration at the immunological synapse is determined by ligand affinity and availability" Proc. Natl. Acad. Sci. USA 104(45):17765-70.
Petersson, K., et al., (2002) "Crystal structure of a SEA variant in complex with MHC class II reveals the ability of SEA to crosslink MHC molecules" Structure 10:1619-1626.
Phan, et al., (2003) "Cancer regression and autoimmunity induced by cytotoxic T lymphocyte-associated antigen 4 blockade in patients with metastatic melanoma" Proc. Nat'l. Acad. Sci. USA 100(14):8372-77.

Philips, G.K., et al., (2014) "Therapeutic uses of anti-PD-1 and anti-PD-L1 antibodies" International Immunology 27(1):39-46.
Pickering, C.R. et al., (2014) "Mutational landscape of aggressive cutaneous squamous cell carcinoma" Clinical Cancer Research 20(24):6582-6592.
Pilon-Thomas, S., et al., (2010) "Blockade of Programmed Death Ligand 1 Enhances the Therapeutic Efficacy of Combination Immunotherapy against Melanoma" The Journal of Immunology 184:3442-3449.
Plieth, J. et al. (2001) "PD-1/PD-L1 Combination Therapies," PD-1 Report. Evaluate Corp. Boston, MA.
Ponce, R., et al., (2009) "Immunogenicity of biologically-derived therapeutics: assessment and interpretation of nonclinical safety studies" Regul. Toxicol. Pharmacol. 54:164-182.
Postow, M.A., et al., (2015) "Immune Checkpoint Blockade in Cancer Therapy" J. Clin. Oncol. 33(17):1974-82.
Postow, M.A., et al., (2015) "Nivolumab and ipilimumab versus ipilimumab in untreated melanoma" N. Engl. J. Med. 372(21):2006-17.
Prasad, D.V.R., (2003) "B7S1, a Novel B7 Family Member that Negatively Regulates T Cell Activation" Immunity 18:863-873.
Presta, L.G., (2008) "Molecular engineering and design of therapeutic antibodies" Curr. Opin. Immunol. 20:460-470.
Preusser, M., et al., (2015) "Prospects of immune checkpoint modulators in the treatment of glioblastoma" Nat. Rev. Neurol. 11(9):504-14.
Prokunina, L., et al., (2004) "Association of the PD-1.3A allele of the PDCD1 gene in patients with rheumatoid arthritis negative for rheumatoid factor and the shared epitope" Arthritis and Rheumatism 50(6):1770-1773.
Prokunina, L., et al., (2004) "The Genetic Basis of Systemic Lupus Erythematosus—Knowledge of Today and Thoughts for Tomorrow" Hum. Mol. Genet. 13(S1):R143-8.
Qureshi, O.S., et al., (2011) "Trans-endocytosis of CD80 and CD86: a molecular basis for the cell-extrinsic function of CTLA-4" Science 332(6029):600-603.
Reagan-Steiner, S., et al., (2016) "National, Regional, State, and Selected Local Area Vaccination Coverage Among Adolescents Aged 13-17 Years—United States" Morbidity and Mortality Weekly Report, 65(33):850-858.
Regnault, M.M., et al., (2016) "Tumour lysis syndrome: an unexpected adverse event associated with ipilimumab" Journal of the European Academy of Dermatology and Venereology 31(2).
Reubern, J.M., et al., (2006) "Biologic and Immunomodulatory Events after CTLA-4 Blockade with Ticilimumab in Patients with Advanced Malignant Melanoma" Cancer 106:2437-44.
Ribas, A., et al., (2012) "Tumor Immunotherapy Directed at PD-1" N. Engl. J. Med. 366(26):2517- 9.
Ribas, A., et al., (2014) "The future of cancer therapy: Selecting patients who respond to PD-1/L1 blockade" Clin. Cancer Res. 20(19):4982-84.
Ribas, A., et al., (2016) "PD-1 Blockade Expands Intratumoral Memory T Cells" Cancer Immunol. Res. 4(3):194-203.
Riley, J.L. (2009) "PD-1 signaling in primary T cells" Immunol. Rev. 229:114-125.
Riley, J.L. et al. (2005) "The CD28 family: a T-cell rheostat for therapeutic control of T-cell activation" Blood 105:13-21.
Rizvi, N.A., et al., (2015) "Cancer immunology. Mutational landscape determines sensitivity to PD-1 blockade in non-small cell lung cancer" Science 348:124-128.
Robert, C., (2014) "Nivolumab in Previously Untreated Melanoma without BRAF Mutation" N. Engl. J. Med. 372:320-330.
Robert, C., et al., (2011) "Ipilimumab plus dacarbazine for previously untreated metastaic melanoma" N. Engl. J. Med. 364:2517-2526.
Robert, C., et al., (2015) "Pembrolizumab versus Ipilimumab in Advanced Melanoma." New England Journal of Medicine 372(26):2521-2532.
Robert, L., et al., (2014) "Distinct immunological mechanisms of CTLA-4 and PD-1 blockade revealed by analyzing TCR usage in blood lymphocytes" Oncoimmunology 3:e29244.
Rodman & Renshaw Annual Global Investment Conference Sep. 2015.

(56) References Cited

OTHER PUBLICATIONS

Rogers, L.M., et al., (2014) "Complement in Monoclonal Antibody Therapy of Cancer" Immunol Res. 59(0):203-210.

Rojko, J.L., et al. (2014) "Formation, clearance, deposition, pathogenicity, and identification of biopharmaceutical-related immune complexes: review and case studies" Toxicol. Pathol. 42:725-764.

Romano, E., et al., (2015) "Ipilimumab-dependent cell-mediated cytotoxicity of regulatory T cells ex vivo by nonclassical monocytes in melanoma patients" Proc. Nat'l. Acad. Sci. USA 112(19):6140-6145.

Rosenblatt, J., et al., (2011) "PD-1 blockade by CT-011, anti PD-1 antibody, enhances ex-vivo T cell responses to autologous dendritic/myeloma fusion vaccine" J. Immunother. 34(5):409-418.

Roth, M.E., et al., (2016) "Left Ventricular Dysfunction After Treatment With Ipilimumab for Metastatic Melanoma" American Journal of Therapeutics 23(6).

Rothstein, D.M., et al., (2003) "T-cell costimulatory pathways in allograft rejection and tolerance" Immunological Reviews 196: 85-108.

Rozali, E.N. et al., (2012) "Programmed death ligand 2 in cancer-induced immune suppression" Clin. Dev. Immunol. 2012:656340.

Sabatier, R., et al., (2015) "Prognostic and predictive value of PDL1 expression in breast cancer" Oncotarget 6:5449-5464.

Sakuishi, K., et al., (2010) "Targeting Tim-3 and PD-1 pathways to reverse T cell exhaustion and restore anti-tumor immunity" J. Exp. Med. 207(10):2187-2194.

Salama, A.D., et al., (2003) "Critical role of the programmed death-1 (PD-1) pathway in regulation of experimental autoimmune encephalomyelitis" J. Exp. Med. 198(1):71-78.

Sampson, J.H., et al., (2010) "Immunologic escape after prolonged progression-free survival with epidermal growth factor receptor variant III peptide vaccination in patients with newly diagnosed glioblastoma" J. Clin. Oncol. 28:4722-4729.

Sarma, J.V., et al., (2011) "The complement system" Cell Tissue Res. 343(1): 227-235.

Sathornsumetee, S., et al., (2010) "Phase II trial of bevacizumab and erlotinib in patients with recurrent malignant glioma" Neuro-Oncology 12(12):1300-1310.

Savitsky, D., et al., "INCAGN02385 Is an Antagonist Antibody Targeting the Co-inhibitory Receptor LAG-3 for the Treatment of Human Malignancies" 3819 Presented at the American Association for Cancer Research 109th Annual Meeting Chicago, IL, USA, Apr. 14-18, 2018.

Schandendorf, D., et al., (2015) "Pooled Analysis of Long-Term Survival Data From Phase II and Phase III Trials of Ipilimumab in Unresectable or Metastatic Melanoma" J. Clin. Oncol. 33:1889-1894.

Scharping, N.E., et al., (2016) "Efficacy of PD-1 Blockade Is Potentiated by Metformin-Induced Reduction of Tumor Hypoxia" Cancer Immunol Res; 5(1):9-16.

Schmidt, L.H., et al., (2015) "PD-1 and PD-L1 Expression in NSCLC Indicate a Favorable Prognosis in Defined Subgroups" PLOS ONE 10(8):e0136023.

Schumacher, T.N., et al., (2015) "Neoantigens in cancer immunotherapy" Science 348(6230):69-74.

Selby et al., (2016) "Preclinical Development of Ipilimumab and Nivolumab Combination Immunotherapy: Mouse Tumor Models, In Vitro Functional Studies, and Cynomolgus Macaque Toxicology," 11(9): e0161779. doi: 10.1371/journal.pone.0161779. eCollection.

Selby, M.J., et al., (2013) "Anti-CTLA-4 antibodies of IgG2a isotype enhance antitumor activity through reduction of intratumoral regulatory T cells" Cancer Immunology Research, 1(1):32-42.

Seung, E., et al., (2013) "PD-1 Blockade in Chronically HIV-1-Infected Humanized Mice Suppresses Viral Loads" PLoS ONE 8(10):e77780.

Sharma, P., et al. (2015) "Immune checkpoint targeting in cancer therapy: toward combination strategies with curative potential" Cell 161:205-214.

Sharma, P., et al. (2015) "The future of immune checkpoint therapy" Science 348(6230):56-61.

Sharma, P., et al., (2016) "Nivolumab monotherapy in recurrent metastatic urothelial carcinoma (CheckMate 032): a multicentre, open-label, two-stage, multi-arm, phase 1/2 trial" The Lancet Oncology 17(11), pp. 1590-1598.

Sharpe, A.H. et al., (2002) "The B7-CD28 superfamily" Nature Reviews. Immunology 2(2):116-126.

Sheehan, J., et al. (2015) "Phage and Yeast Display" Microbiology Spectrum, vol. 3, No. 1, 17 Pages.

Sheppard, K.A. et al., (2004), "PD-1 inhibits T-cell receptor induced phosphorylation of the ZAP70/CD3zeta signalosome and downstream signaling to PKC-Theta" FEBS Lett. 574:37-41.

Sheridan (Apr. 7, 2015): "IDO inhibitors move center stage in immuno-oncology," Nat. Biotechnol. 33(4):321-322.

Shields, R.L., et al., (2001) "High resolution mapping of the binding site on human IgG1 for Fc gamma RI, Fc gamma RII, Fc gamma RIII, and FcRn and design of IgG1 variants with improved binding to the Fc gamma R." The Journal of Biological Chemistry 276:6591-6604.

Shih et al. (2014) "Clinical Impact of Checkpoint Inhibitors as Novel Cancer Therapies," Drugs. 74(17):1993-2013.

Sica, G.L., et al., (2003) "B7-H4, a Molecule of the B7 Family, Negatively Regulates T Cell Immunity" Immunity, 18:849-861.

Siegel (2017) "Cancer Statistics, 2017", CA: A Cancer Journal for Clinicians, vol. 67, No. 1, pp. 7-30.

Simon, S., et al., (2016) "PD-1 expression conditions T cell avidity within an antigen-specific repertoire" Oncoimmunology 5(1):e1104448.

Simpson, T.R. et al., (2013) "Fc-dependent depletion of tumor-infiltrating regulatory T cells co-defines the efficacy of anti-CTLA-4 therapy against melanoma" The Journal of Experimental Medicine 210(9):1695-1710.

Simpson-Abelson, M.R., et al., (2013) "Human ovarian tumor ascites fluids rapidly and reversibly inhibit T cell receptor induced NF-Kappa-B and NFAT signaling in tumor-associated T cells" Cancer Immun. 13:14-24.

Slater, N.A. et al., (2016) "PD-L1 expression in cutaneous squamous cell carcinoma correlates with risk of metastasis" Journal of Cutaneous Pathology 43(8):663-670.

Snyder, A., et al., (2014) "Genetic basis for clinical response to CTLA-4 blockade in melanoma" N. Engl. J. Med. 371:2189-2199.

Soares, K.C., et al., (2015) "PD-1/PD-L1 blockade together with vaccine therapy facilitates effector T cell infiltration into pancreatic tumors" J. Immunother. 38(1): 1-11.

Srivastava, P.K., (2009) et al., "Treating human cancers with heat shock protein-peptide complexes: the road ahead" Expert Opin. Biol. Ther. 9:179-186.

Stamper, C.C., et al., (2001) "Crystal structure of the B7-1/CTLA-4 complex that inhibits human immune responses" Nature 410:608-611.

Stebbings, R., et al., (2007) "Cytokine Storm in the Phase I Trial of Monoclonal Antibody TGN1412: Better Understanding the Causes to Improve PreClinical Testing of Immunotherapeutics" J. Immunol. 179:3325-3331.

Stein, R. "Agonist Checkpoint Modulators: Challenges and Opportunities" PEGS Boston May 8, 2015.

Stein, R. "Immuno-Oncology" RBS Immunotherapy Conference Mar. 27, 2014.

Stein, R., "Next generation immunomodulatory antibodies: optimizing therapeutic impact" Blair Maidstone I-O Conference 2017.

Strome, S.E., et al., (2003) "B7-H1 blockade augments adoptive T-cell immunotherapy for squamous cell carcinoma" Cancer Res. 63:6501-6505.

Stupp, R., et al., (2005) "Radiotherapy plus Concomitant and Adjuvant Temozolomide for Glioblastoma" N. Engl. J. Med. 352(10):987-96.

Sun, Z., et al., (2015) "IL10 and PD-1 Cooperate to Limit the Activity of Tumor-Specific CD8+ T Cells" Cancer Res. 75(8):1635-44.

Sznol et al., (2013) "Antagonist antibodies to PD-1 and B7-H1 (PD-L1) in the treatment of advanced human cancer—response" Clinical Cancer Research 19(19):5542.

(56) References Cited

OTHER PUBLICATIONS

Sznol, M., et al., (2013) "Antagonist antibodies to PD-1 and B7-H1 (PD-L1) in the treatment of advanced human cancer" Clin. Cancer Res. 19:1021-1034.
Tai, X., et al., (2012) "Basis of CTLA-4 function in regulatory and conventional CD4(+) T cells" Blood 119:5155-5163.
Takeda, K., et al., (2010) "Combination therapy of established tumors by antibodies targeting immune activating and suppressing molecules" J. Immunol. 184:5493-5501.
Tamura, Y., et al., (1997) "Immunotherapy of tumors with autologous tumor-derived heat shock protein preparations" Science 278:117-120.
Tan, S., et al., (2016) "An unexpected N-terminal loop in PD-1 dominates binding by nivolumab" Nature Communications 8:14369.
Tang, X., et al., (2015) "The advantages of PD1 activating chimeric receptor (PD1-ACR) engineered lymphocytes for PDL1+ cancer therapy" Am. J. Transl. Res. 7(3):460-473.
Taube, J.M., et al., (2014) "Association of PD-1, PD-1 Ligands, and Other Features of the Tumor Immune Microenvironment with Response to Anti-PD-1 Therapy" Clin Cancer Res; 20(19):5064-74.
Taylor, A., et al., (2016) "Glycogen Synthase Kinase 3 Inactivation Drives T-bet-Mediated Downregulation of Co-receptor PD-1 to Enhance CD8+ Cytolytic T Cell Responses" Immunity 44:274-286.
Tewari, K.S., et al., (2014) "Improved survival with bevacizumab in advanced cervical cancer" N. Engl. J. Med. 370(8):734-743.
Thomas, M. L., (1995) "Of ITAMs and ITIMs: turning on and off the B cell antigen receptor." J. Exp. Med. 181:1953-6.
Thompson, R.H., et al., (2007) "PD-1 is expressed by tumor-infiltrating immune cells and is associated with poor outcome for patients with renal cell carcinoma" Clin. Cancer Res. 13(6):1757-1761.
Three Agenus Abstracts Accepted for Presentation at the American Association for Cancer Research (AACR) 2018 Annual Meeting Apr. 11, 2018 /PRNewswire/.
Tivol, E.A., et al., (1995) "Loss of CTLA-4 leads to massive lymphoproliferation and fatal multiorgan tissue destruction, revealing a critical negative regulatory role of CTLA-4" Immunity 3:541-547.
Topalian, S.L., et al., (2012) "Safety, activity, and immune correlates of anti-PD-1 antibody in cancer" N. Engl. J. Med. 366:2443-2454.
Topalian, S.L., et al., (2012) "Targeting the PD-1/B7-H1 (PD-L1) pathway to activate anti-tumor immunity." Curr. Opin. Immunol. 24(2):207-12.
Topalian, S.L., et al., (2015) "Immune Checkpoint Blockade: A Common Denominator Approach to Cancer Therapy" Cancer Cell 27:450-61.
Torre, L.A., et al., (2015) "Global cancer statistics, 2012" CA: A Cancer Journal for Clinicians 65(2):87-108.
Tseng, S.Y., et al., (2001) "B7-DC, a new dendritic cell molecule with potent costimulatory properties for T cells" J. Exp. Med. 193:839-846.
Turnis, M.E., et al., (2012) "Combinatorial immunotherapy PD-1 may not be LAG-ing behind any more" OncoImmunology 1(7):1172-1174.
Tykodi, S.S., (2014) "PD-1 as an emerging therapeutic target in renal cell carcinoma: current evidence" OncoTargets and Therapy 7:1349-1359.
U.S. Food and Drug Administration (2016). FDA approves new, targeted treatment for bladder cancer.
U.S. Food and Drug Administration (2016). pembrolizumab (KEYTRUDA).
Udono, H., et al., (1993) "Cellular requirements for tumor-specific immunity elicited by heat shock proteins: Tumor rejection antigen gp96 primes CDS+ T cells in vivo" Proc. Natl. Acad. Sci. USA 91:3077-3081.
Udono, H., et al., (1994) "Heat Shock Protein 70-associated Peptides Elicit Specific Cancer Immunity" J. Exp. Med. 178:1391-96.
US Food and Drug Administration (FDA) (1997a). Guidance for Industry: S6 Preclinical Safety Evaluation of Biotechnology-Derived Pharmaceuticals. Center for Drug Evaluation and Research (CDER) and Center for Biologics Evaluation and Research (CBER).
US Food and Drug Administration (FDA) (1997b). Points to Consider in the Manufacture and Testing of Monoclonal Antibody Products for Human Use. Center for Biologics Evaluation and Research (CBER).
US Food and Drug Administration (FDA) (2012). Guidance for Industry: S6 Addendum to Preclinical Safety Evaluation of Biotechnology-Derived Pharmaceuticals. Center for Drug Evaluation and Research (CDER) and Center for Biologics Evaluation and Research (CBER).
Van Den Bent, M.J., et al., (2009) "Randomized Phase II Trial of Erlotinib Versus Temozolomide or Carmustine in Recurrent Glioblastoma: EORTC Brain Tumor Group Study 26034" Journal of Clinical Oncology 27(8):1268-1274.
Van Der Merwe, P.A., et al., (1997) "CD80 (B7-1) Binds Both CD28 and CTLA-4 with a Low Affinity and Very Fast Kinetics" J. Exp. Med. 185(3):393-403.
Van Elsas A, et al., (1999) "Combination Immunotherapy of B16 Melanoma Using Anti-Cytotoxic T Lymphocyte-associated Antigen 4 (CTLA-4) and Granulocyte/ Macrophage Colony-Stimulating Factor (GM-CSF)-producing Vaccines Induces Rejection of Subcutaneous and Metastatic Tumors Accompanied by Autoimmune Depigmentation" J. Exp. Med. 190(3):355-366.
Van Regenmortel, M.H.V., (2018) "Development of a Preventive HIV Vaccine Requires Solving Inverse Problems Which Is Unattainable by Rational Vaccine Design" Frontiers in Immunology, vol. 8, Article 2009, 11 Pages.
Vessillier, S., et al., (2015) "Cytokine release assays for the prediction of therapeutic mAb safety in first-in man trials—Whole blood cytokine release assays are poorly predictive for TGN1412 cytokine storm" J. Immunol. Methods 424:43-52.
Victor, C.T., et al., (2015) "Radiation and dual checkpoint blockade activate non-redundant immune mechanisms in cancer" Nature 520(7547):373-7.
Vidal, J.M., et al., (2010) "In vitro cytokine release assays for predicting cytokine release syndrome: the current state-of-the-science. Report of a European Medicines Agency Workshop" Cytokine 51:213-215.
Vidarsson, G., et al., (2014) "IgG subclasses and allotypes: from structure to effector functions" Frontiers in Immunology 5(520):1-17.
Vigdorovich, V. et al., (2013) "Structure and T cell inhibition properties of B7 family member, B7-H3" Structure 21(5):707-17.
Villasboas, J.C., et al., (2016) "Targeting the PD-1 pathway in patients with relapsed classic Hodgkin lymphoma following allogeneic stem cell transplant is safe and effective" Oncotarget 7(11):13260-4.
Vivier, E., et al., (1997) "Immunoreceptor tyrosine-based inhibition motifs." Immunol. Today 18:286-91.
Vredenburgh, J.J., et al., (2007) "Bevacizumab Plus Irinotecan in Recurrent Glioblastoma Multiforme" Journal of Clinical Oncology 25(30):4722-4729.
Waight, J., et al., "INCAGN02390, a Novel Antagonist Antibody That Targets the Co-Inhibitory Receptor TIM-3" 3825 Presented at the American Association for Cancer Research 109th Annual Meeting Chicago, IL, USA, Apr. 14-18, 2018.
Waight, J.D., et al., (2015) "Cutting edge: epigenetic regulation of Foxp3 defines a stable population of CD4+ regulatory T cells in tumors from mice and humans" J. Immunol. 194:878-882.
Waight, J.D., et al., (2018) "Selective FcgR Co-engagement on APCs Modulates the Activity of Therapeutic Antibodies Targeting T Cell Antigens" Cancer Cell 33:1033-1047.
Waldhauer, I. et al., (2008) "NK cells and cancer immunosurveillance" Oncogene 27:5932-5943.
Walker et al. (2011) "The emerging role of CTLA4 as a cell-extrinsic regulator of T cell responses" Nat. Rev. Immunol. 11(12):852-63.
Walker, L.S.K., et al., (2015) "Confusing signals: recent progress in CTLA-4 biology" Trends in immunology 36(2):63-70.
Wang et al., (2014) "In vitro characterization of the anti-PD-1 antibody nivolumab, BMS-936558, and in vivo toxicology in non-human primates." Cancer Immunol. Res. 2(9):846-56.

(56) References Cited

OTHER PUBLICATIONS

Wang, Li, et al., (2008) "Programmed death 1 ligand signaling regulates the generation of adaptive Foxp3 CD4 regulatory T cells" PNAS 105(27):9331-9336.
Wang, W., et al., (2012) "Biomarkers on melanoma patient T cells associated with ipilimumab treatment" J. Transl. Med. 10:146.
Warncke, M., et al., (2012) "Different adaptations of IgG effector function in human and nonhuman primates and implications for therapeutic antibody treatment" J. Immunol. 188:4405-4411.
Waterhouse, P., et al., (1995) "Lymphoproliferative disorders with early lethality in mice deficient in Ctla-4" Science 270:985-988.
Weber, J.S., et al., (2012) "Management of immune-related adverse events and kinetics of response with ipilimumab" Journal of Clinical Oncology 30(21):2691-2697.
Weng, W., et al., (2004) "Clinical Outcome of Lymphoma Patients After Idiotype Vaccination Is Correlated With Humoral Immune Response and Immunoglobulin G Fc Receptor Genotype" J. Clin. Oncol. 22:4717-4724.
Weng, W.K., et al., (2003) "Two immunoglobulin G fragment C receptor polymorphisms independently predict response to rituximab in patients with follicular lymphoma" J. Clin. Oncol. 21:3940-3947.
Westin, J.R., et al., (2014) "Safety and activity of PD1 blockade by pidilizumab in combination with rituximab in patients with relapsed follicular lymphoma: a single group, open-label, phase 2 trial" Lancet 15:69-77.
Wherry, E.J., et al., (2007) "Molecular signature of CD8+ T cell exhaustion during chronic viral infection" Immunity 27:670-684.
Wherry, E.J., et al., (2015) "Molecular and cellular insights into T cell exhaustion" Nat. Rev. Immunol. 15:486-499.
Wilky, B.A., et al., "Phase 1 Open-Label, Ascending Dose Trial of AGEN1884, an anti-CTLA-4 Monoclonal Antibody, in Advanced Solid Malignancies: Dose Selection for Combination With PD-1 Blockade" 18-1200-A ASCO C-500-01, 225917 (2018).
Willman, J.H., et al., (2001) "Multiplex Analysis of Heterophil Antibodies in Patients With Indeterminate HIV Immunoassay Results" Am. J. Clin. Pathol. 115:764-769.
Wilson, N. "Targeting TNFR Family Members: Therapeutic opportunities in immuno-oncology and immuno-inflammation" PEGS Boston 2016.
Wilson, N.S., et al., (2005) "Regulation of antigen presentation and cross-presentation in the dendritic cell network: facts, hypothesis, and immunological implications" Adv. Immunol. 86:241-305.
Wilson, N.S., et al., (2011) "An Fcgamma receptor-dependent mechanism drives antibody-mediated target-receptor signaling in cancer cells" Cancer Cell 19:101-113.
Wing, K. et al., (2008) "CTLA-4 control over Foxp3+ regulatory T cell function" Science 322(5899):271-275.
Wolchok, J.D. et al., (2016) "Updated results from a phase III trial of nivolumab (NIVO) combined with ipilimumab (IPI) in treatment-naive patients (pts) with advanced melanoma (MEL) (CheckMate 067)" Journal of Clinical Oncology 34(15 suppl.):9505-9505.
Wolchok, J.D., et al., (2009) "Guidelines for the Evaluation of Immune Therapy Activity in Solid Tumors: Immune-Related Response Criteria" Clin. Cancer Res. 15(23):7412-20.
Wolchok, J.D., et al., (2010) "Ipilimumab monotherapy in patients with pretreated advanced melanoma: a randomised, double-blind, multicentre, phase 2, dose-ranging study" The Lancet Oncology 11(2):155-64.
Wolchok, J.D., et al., (2013) "Nivolumab plus ipilimumab in advanced melanoma" N. Engl. J. Med. 369:122-133.
Wolf, B., et al., (2012) "A whole blood in vitro cytokine release assay with aqueous monoclonal antibody presentation for the prediction of therapeutic protein induced cytokine release syndrome in humans" Cytokine 60:828-837.
Wong, E.T., et al., (1999) "Outcomes and Prognostic Factors in Recurrent Glioma Patients Enrolled Onto Phase II Clinical Trials" J. Clin. Oncol. 17:2572-2578.
Wong, R.M., et al., (2007) "Programmed death-1 blockade enhances expansion and functional capacity of human melanoma antigen-specific CTLs" International Immunology, 19(10):1223-1234.

Woo, S., et al., (2011) "Immune Inhibitory Molecules LAG-3 and PD-1 Synergistically Regulate T-cell Function to Promote Tumoral Immune Escape" Cancer Res. 72:917-927.
Wu et al. (May 1, 2013) "Eradication of melanoma by intratumoral injection of attenuated vaccinia virus requires CD8+ T cells and combination of anti-CTLA-4 blockade and virotherapy enhances therapeutic efficacy in advanced melanoma," J. Invest. Dermatol. 133(Suppl 1):S241. Abstract No. 1415.
Wu, J., et al., (1997) "A Novel Polymorphism of Fc-Gamma-RIIIa (CD16) Alters Receptor Function and Predisposes to Autoimmune Disease" J. Clin. Invest. 100(5):1059-1070.
Wu, L.X., et al., (2005) "CD28 Regulates the Translation of BcLXL via the Phosphatidylinositol 3-inase/Mammalian Target Rapamycin Pathway" J. Immunol. 174:180-194.
Xing, K., et al., (2015) "Dexamethasone enhances programmed cell death 1 (PD-1) expression during T cell activation: an insight into the optimum application of glucocorticoids in anti-cancer therapy" BMC Immunol. 16, 39.
Xu, et al., (2012) "Affinity and cross-reactivity engineering of CTLA4-19 to modulate T cell costimulation" J. Immunol. 189(9):4470-7.
Yamaguchi, T., et al., (2013) "Construction of self-recognizing regulatory T cells from conventional T cells by controlling CTLA-4 and IL-2 expression" Proc. Natl. Acad. Sci. USA 110:E2116-2125.
Yang, J.C., et al., (2007) "Ipilimumab (Anti-CTLA4 Antibody) Causes Regression of Metastatic Renal Cell Cancer Associated With Enteritis and Hypophysitis" J. Immunother. 30(8):825-830.
Yang, W., et al., (2013) "Increased expression of programmed death (PD)-1 and its ligand PD-L1 correlates with impaired cell-mediated immunity in high-risk human papillomavirus-related cervical intraepithelial neoplasia" Immunology 139(4):513-522.
Yao, S., et al., (2013) "Advances in targeting cell surface signaling molecules for immune modulation" Nat Rev Drug Discov. 12:130-146.
Yokosuka, T., et al., (2012) "Programmed cell death 1 forms negative costimulatory microclusters that directly inhibit T cell receptor signaling by recruiting phosphatase SHP2" J. Exp. Med. 209:1201-1217.
Young, A., et al., (2014) "Targeting Cancer-Derived Adenosine New Therapeutics Approaches" Cancer Discovery 4:879-888.
Yu, G., et al., (2015) "PD-1 blockade attenuates immunosuppressive myeloid cells due to inhibition of CD47/SIRPa axis in HPV negative head and neck squamous cell carcinoma" Oncotarget 6(39):42067-80.
Yu, S., et al., (2015) "Advancements in Recurrent and Metastatic Cervical Cancer" Am. J. Hematol. Oncol. 11:26-31.
Zaretsky, J.M., et al., (2016) "Mutations Associated with Acquired Resistance to PD-1 Blockade in Melanoma" N. Engl. J. Med. 375(9):819-829.
Zeng J., et al., (2013) "Anti-PD-1 Blockade and Stereotactic Radiation Produce Long-Term Survival in Mice with Intracranial Gliomas" Radiation Oncology Biology 86(2):343-349.
Zha, Y., et al., (2004) "Negative regulation of T-cell function by PD-1" Crit. Rev. Immunol. 24:229-237.
Zhang, X., et al., (2003) "Crystal structure of the receptor-binding domain of human B7-2: insights into organization and signaling" Proc. Natl. Acad. Sci. USA 100:2586-2591.
Zhao, R., et al., (2013) "HHLA2 is a member of the B7 family and inhibits human CD4 and CD8 T-cell function" Proc. Natl. Acad. Sci USA 110:9879-9884.
Zheng, P., et al., (2015) "Human Cancer Immunotherapy with PD-1/PD-L1 Blockade" Biomarkers in Cancer 7(s2):15-18.
Zhou, Q., et al. (2015) "Structural Repertoire Of HIV-1-Neutralizing Antibodies Targeting the CD4 Supersite In 14 Donors" Cell, vol. 161, No. 6, pp. 1280-1292.
Zhou, Q., et al., (2010) "Blockade of programmed death-1 pathway rescues the effector function of tumor-infiltrating T cells and enhances the antitumor efficacy of lentivector immunization" J. Immunol. 185:5082-5092.
Zipfel, P.F., et al., (2009) "Complement regulators and inhibitory proteins" Nat. Rev. Immunol. 9:729-740.

(56) References Cited

OTHER PUBLICATIONS

Zippelius, A., et al., (2015) "Induced PD-L1 expression mediates acquired resistance to agonistic anti-CD40 treatment" Cancer Immunol. Res. 3:236-244.
Zitvogel, L., et al., (2006) "Cancer despite immunosurveillance: immunoselection and immunosubversion" Nature Reviews 6:715-727.
Zitvogel, L., et al., (2012) "Targeting PD-1/PD-L1 interactions for cancer immunotherapy" OncoImmunology 1(8):1223-1225.
Zou, W., (2006) "Regulatory T cells, tumour immunity and immunotherapy" Nat. Rev. Immunol. 6:295-307.
Zou, W., et al., (2008) "Inhibitory B7-family molecules in the tumour microenvironment" Nat. Rev. Immunol. 8:467-477.
Zou, W., et al., (2016) "PD-L1 (B7-H1) and PD-1 pathway blockade for cancer therapy: Mechanisms, response biomarkers, and combinations" Science 8(328):328rv4.
Zwald, F.O., et al., (2011) "Skin cancer in solid organ transplant recipients: advances in therapy and management: part I. Epidemiology of skin cancer in solid organ transplant recipients" Journal of the American Academy of Dermatology 65(2):253-261.

* cited by examiner

Figure 7A

```
P16410 CTLA4_HUMAN    1  MACLGFQRHKAQLNLATRTWPCTLLFFLLFFIPVFCKAMHVAQPAVVLASSRGIASFVCEY   60
G7PL88 CTLA4_MACFA    1  ..............R......R.Y...S...........N..............      60
P09793 CTLA4_MOUSE    1  ....LR.Y...Q.PS...FVA.LT........SE.IQ.T..S......H.V...P...   60
Q62859 CTLA4_RAT      1  ....L..Y.TH.Q.PS...FGV.LS.......I.SE.IQ.T..S......H.V...P...   60
                         ****:*************:* :** .       *: ::*  *:*******:****  *

P16410 CTLA4_HUMAN   61  ASPGKATEVRVTVLRQADSQVTEVCAATYMMGNELTFLDDSICTGTSSGNQVNLTIQGLR  120
G7PL88 CTLA4_MACFA   61  ............................................................  120
P09793 CTLA4_MOUSE   61  SPSHNTD.......................TND.M......T.FTEK.TVG...YPF.S..FNESR.  120
Q62859 CTLA4_RAT     61  ..SHNTD.......................TND........T.FTVK.T.G....PF.S...FNESR.  120
                         ..:****                       *** *        *  **   :  :  ***. ****:

P16410 CTLA4_HUMAN  121  AMDTGLYICKVELMYPPPYYLGIGNGTQIYVIDPEPCPDSDFLLWILAAVSSGLFFYSFL  180
G7PL88 CTLA4_MACFA  121  ............................................................  180
P09793 CTLA4_MOUSE  121  .V.....L......................M..............FV.M.......V...L...  180
Q62859 CTLA4_RAT    121  .A.....F......................................FV.M..........   180
                         .*  :**:* ********************:*************:**. ***:*****

P16410 CTLA4_HUMAN  181  LTAVSLSKMLKKRSPLTTGVYVKMPPTEPECEKQFQPYFIPIN  223
G7PL88 CTLA4_MACFA  181  ............................................  223
P09793 CTLA4_MOUSE  181  VS......................NRT..................  223
Q62859 CTLA4_RAT    181  V.......................NRT..................  223
                        .:***** *******   ***   ***:**:***********
```

Figure 7B

```
SP|P16410|CTLA4_HUMAN    MACLGFQRHKAQLNLATRTWPCTLLFFLLFIP---VFC----------KAMHVAQPAVVLA----  48
TR|G7PL88|G7PL88_MACFA   MACLGFQRHKARLNLATRTRPYTLLFSLLFIP---VFS----------KAMHVAQPAVVLA----  48
SP|P10747|CD28_HUMAN     ---------------MLRLLLALN--LFPS-IQVTGNKILVKQSP-MLV----------------  30
SP|Q9Y6W8|ICOS_HUMAN     -------------MKSGLWY------FF--LFCLRIKVLTGEINGSANYEMFI------------  32
SP|Q7Z6A9|BTLA_HUMAN     ----------MKTLPAMLGTGKLFWV---FFLIPYLDIWNIHGKESCDVQLYIK-----------  41
SP|Q15116|PDCD1_HUMAN    ---------MQIPQAPWPVVWAVLQLGWRPGWFLDSPD-RPWNPPTFSPALLVV-----------  44
                                                  *                    ..

SP|P16410|CTLA4_HUMAN    ----SSRGIASFVCEYASPGKA---TEVRVTVLRQADSQVTEVCAATYMMGNE--LT         96
TR|G7PL88|G7PL88_MACFA   ----NSRGIASFVCEYASPGKA---TEVRVTVLRQADSQVTEVCAATYMMGNE--LT         96
SP|P10747|CD28_HUMAN     ----AYDNAVNLSCKYSYNLFS---REFRASLHKGLDSA-VEVCVVYGNYSQQLQVY         79
SP|Q9Y6W8|ICOS_HUMAN     ----FHNGGVQILCKYPD--IV---QQFKMQLLKGGQ----ILCDLTKTKGSGNTVS         76
SP|Q7Z6A9|BTLA_HUMAN     RQSEHSILAGDPFELECPVKYCANRPHVTWCKLN---GT----TCVKLEDRQ------        86
SP|Q15116|PDCD1_HUMAN    ----TEGDNATFTCSFSNTSESFVLNWYRMSPSNQTDK----LAAFPEDR--------        86
                                       *                            ..      .

SP|P16410|CTLA4_HUMAN    FLDDSICT------GTSSGNQVNLTI---QGLRAMDTGLYICKVELMYPPPYYLGIG-------  144
TR|G7PL88|G7PL88_MACFA   FLDDSICT------GTSSGNQVNLTI---QGLRAMDTGLYICKVELMYPPPYYMGIG-------  144
SP|P10747|CD28_HUMAN     SKTGFNCD------GKLGNESVTFYL---QNLYVNQTDIYFCKIEVMYPPPYLDNEK-------  127
SP|Q9Y6W8|ICOS_HUMAN     IKSLKFCH------SQLSNNSVSFFL---YNLDHSHANYYFCNLSIFDPPPFKVTLT-------  124
SP|Q7Z6A9|BTLA_HUMAN     ----------TSWKEEKNISFFILHFEPVLPNDNGSYRCSANFQSNL---IE------------  125
SP|Q15116|PDCD1_HUMAN    SQPGQDCRFRVTQLPNGRDFHMSV----VRARRNDSGTYLCGAISLAPKAQIKESLRAELR     143
                                                         *       *
```

Figure 7C

```
SP|P16410|CTLA4_HUMAN    -NGTQIYVIDP------EPCPDS------------DFLLWILAAVSSGLFFYSFLLTAVSL--S-KML 190
TR|G7PL88|G7PL88_MACFA   -NGTQIYVIDP------EPCPDS------------DFLLWILAAVSSGLFFYSFLLTAVSL--S-KML 190
SP|P10747|CD28_HUMAN     SNGTIIHVKGK------HLCPSLFPGPSKPFWVLVVVGGVLACYSLLVTVAFI--IFWVR 180
SP|Q9Y6W8|ICOS_HUMAN     --GGYLHIYES------QLCCQL-----KFWLPIGCAA---FVVVCILGCIL--ICWLT 165
SP|Q7Z6A9|BTLA_HUMAN     SHSTTLYVTDVKSASERPSKDEMASR--PWLLYRLLPLGG----LPLLITTCFLFCCLRR 180
SP|Q15116|PDCD1_HUMAN    VTERRAEVPTA------HPSPSPRPAG-QFQTLVVGVVGGLLGSLVLLVWVLAV--ICSRA 195
                                          .:            .                  .:

SP|P16410|CTLA4_HUMAN    KKRSP-----LTTGVYVKMPPTE----PEC-EKQFQPYFIPIN-------------- 223
TR|G7PL88|G7PL88_MACFA   KKRSP-----LTTGVYVKMPPTE----PEC-EKQFQPYFIPIN-------------- 223
SP|P10747|CD28_HUMAN     SKRSR-----LLHSDYMNMTPRR----PGPTRKHYQPYAPPRD--FAAYRS------- 220
SP|Q9Y6W8|ICOS_HUMAN     KKKYSSSVHDPNGEYMFMRAVN----TAKKSRLTDVTL------------------- 199
SP|Q7Z6A9|BTLA_HUMAN     HQGKQNELSDTAGREINLVDAHLKSEQTEASTRQNSQVLLSETGIYDNDPDLCFRMQEGS 240
SP|Q15116|PDCD1_HUMAN    ARG-------TIG--------ARR--------TGQP--LKEDPSAVPVF--SVDYGELDFQWREKT 234
                                      ::

SP|P16410|CTLA4_HUMAN    ----------------------------------------
TR|G7PL88|G7PL88_MACFA   ----------------------------------------
SP|P10747|CD28_HUMAN     ----------------------------------------
SP|Q9Y6W8|ICOS_HUMAN     ----------------------------------------
SP|Q7Z6A9|BTLA_HUMAN     EVYSNPCLEENKP--GIVYASLNHSVIGPNSRLARNVKEAPTEYASI------CVRS- 289
SP|Q15116|PDCD1_HUMAN    PEPPVPCVPEQTEYATIVFP-----SGMGTSSPARRGSADGPRSAQPLRPEDGHCSWPL 288
```

ANTIBODIES AND METHODS OF USE THEREOF

1. RELATED APPLICATIONS

This application is a continuation of International Patent Application No. PCT/US2017/065014, filed Dec. 7, 2017, which claims the benefit of U.S. Provisional Application Nos: 62/431,279, filed Dec. 7, 2016; 62/570,451, filed Oct. 10, 2017; 62/582,814, filed Nov. 7, 2017; and 62/586,605, filed Nov. 15, 2017, each of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Jun. 7, 2019, is named 613531_AGBW094PCCON_Sequence_Listing.txt and is 122,395 bytes in size.

2. FIELD

The instant disclosure relates to antibodies that specifically bind to CTLA-4 (e.g., human CTLA-4) and/or PD-1 (e.g., human PD-1), and methods of using these antibodies.

3. BACKGROUND

CTLA-4 is an inhibitory receptor upregulated on T-cells (Alegre et al., 2001, Nat Rev Immunol 1:220-8). CTLA-4 inhibits the immune response in several ways: it competes with the T cell co-stimulatory receptor CD28 for its ligands, CD80 and CD86, and thus blocks co-stimulation; it negatively signals to inhibit T-cell activation; and it can also capture CD80 and CD86 from opposing cells by trans-endocytosis, resulting in impaired T cell costimulation via CD28 (Krummel and Allison, 1995, J Exp Med 182:459-465; Walunas et al., 1994, Immunity 1:405-413; Qureshi et al., 2011, Science 332:600-603).

PD-1 is another inhibitory receptor that is expressed on activated B cells, T cells, and myeloid cells (Agata et al. (1996) Int Immunol 8:765-72; Okazaki et al. (2002) Curr. Opin. Immunol. 14: 391779-82; Bennett et al. (2003) J Immunol 170:711-8). Two ligands for PD-1 have been identified, PD-L1 and PD-L2, that have been shown to downregulate T cell activation upon binding to PD-1 (Freeman et al. (2000) J Exp Med 192:1027-34; Latchman et al. (2001) Nat Immunol 2:261-8; Carter et al. (2002) Eur J Immunol 32:634-43). The interaction between PD-1 and PD-L1 results in a decrease in tumor infiltrating lymphocytes, a decrease in T cell receptor mediated proliferation, and immune evasion by the cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). This immune suppression can be reversed by inhibiting the local interaction of PD-1 with PD-L1 (Iwai et al. (2002) Proc. Nat'l. Acad. Sci. USA 99:12293-7; Brown et al. (2003) J. Immunol. 170:1257-66).

Given the important role of CTLA-4 and PD-1 in modulating immune responses, therapies designed to antagonize both CTLA-4 and PD-1 signaling hold great promise for the treatment of diseases that involve CTLA-4- and/or PD-1-mediated immune suppression.

4. SUMMARY

The instant disclosure provides antibodies that specifically bind to CTLA-4 (e.g., human CTLA-4) and/or PD-1 (e.g., human PD-1) and antagonize CTLA-4 and/or PD-1 function, e.g., immune suppression mediated by CTLA-4 and/or PD-1. Also provided are pharmaceutical compositions and kits comprising these antibodies, nucleic acids encoding these antibodies, expression vectors and host cells for making these antibodies, and methods of treating a subject using these antibodies. The antibodies described herein are particularly useful for increasing T cell activation in response to an antigen (e.g., a tumor antigen or an infectious disease antigen), and hence for treating cancer in a subject or treating or preventing an infectious disease in a subject.

Accordingly, in one aspect, the instant disclosure provides a method of enhancing or inducing an immune response in a subject, the method comprising administering to the subject an effective amount of a therapeutic combination comprising a first isolated antibody that specifically binds to CTLA-4 (e.g., human CTLA-4) and a second isolated antibody that specifically binds to PD-1 (e.g., human PD-1), wherein the first isolated antibody comprises a heavy chain variable region comprising complementarity determining regions CDRH1, CDRH2, and CDRH3 and a light chain variable region comprising complementarity determining regions CDRL1, CDRL2, and CDRL3, wherein:

(a) CDRH1 comprises the amino acid sequence of SYX-IMX$_2$ (SEQ ID NO: 39), wherein
X$_1$ is S or A; and
X$_2$ is N or S;
(b) CDRH2 comprises the amino acid sequence of SIS-SSSSYIYYADSVKG (SEQ ID NO: 22);
(c) CDRH3 comprises the amino acid sequence of VGLMGPFXI (SEQ ID NO: 115), wherein X is D or N;
(d) CDRL1 comprises the amino acid sequence of RASQSVX$_1$X$_2$YLX$_3$ (SEQ ID NO: 43), wherein:
X$_1$ is S or G;
X$_2$ is R, S, or T; and
X$_3$ is G or A;
(e) CDRL2 comprises the amino acid sequence of X$_1$X$_2$SX$_3$RAT (SEQ ID NO: 44), wherein:
X$_1$ is G or A;
X$_2$ is A or T; and
X$_3$ is T, S, R, or N; and
(f) CDRL3 comprises the amino acid sequence of QQYGX$_1$SPX$_2$T (SEQ ID NO: 45), wherein:
X$_1$ is S or T; and
X$_2$ is W or F,
and wherein the second isolated antibody comprises a heavy chain variable region comprising complementarity determining regions CDRH1, CDRH2 and CDRH3 and a light chain variable region comprising complementarity determining regions CDRL1, CDRL2 and CDRL3, wherein:
(g) CDRH1 comprises the amino acid sequence of SYGMH (SEQ ID NO: 75);
(h) CDRH2 comprises the amino acid sequence of VIWX$_1$DGSNX$_2$YYADSVX$_3$G (SEQ ID NO: 86), wherein
X$_1$ is Y or F;
X$_2$ is K or E; and
X$_3$ is K or M;
(i) CDRH3 comprises the amino acid sequence of NX$_1$DX$_2$ (SEQ ID NO: 87), wherein
X$_1$ is G or V; and
X$_2$ is H or Y;
(j) CDRL1 comprises the amino acid sequence of RASQSVSSNLA (SEQ ID NO: 83);

(k) CDRL2 comprises the amino acid sequence of GAS-TRAT (SEQ ID NO: 84); and
(l) CDRL3 comprises the amino acid sequence of QQYNNWPRT (SEQ ID NO: 85).

In another aspect, the instant disclosure provides a method of treating cancer in a subject, the method comprising administering to the subject an effective amount of a therapeutic combination comprising a first isolated antibody that specifically binds to CTLA-4 (e.g., human CTLA-4) and a second isolated antibody that specifically binds to PD-1 (e.g., human PD-1), wherein the first isolated antibody comprises a heavy chain variable region comprising complementarity determining regions CDRH1, CDRH2, and CDRH3 and a light chain variable region comprising complementarity determining regions CDRL1, CDRL2, and CDRL3, wherein:

(a) CDRH1 comprises the amino acid sequence of SYX$_1$MX$_2$ (SEQ ID NO: 39), wherein
X$_1$ is S or A; and
X$_2$ is N or S;
(b) CDRH2 comprises the amino acid sequence of SISSSSSYIYYADSVKG (SEQ ID NO: 22);
(c) CDRH3 comprises the amino acid sequence of VGLMGPFXI (SEQ ID NO: 115), wherein X is D or N;
(d) CDRL1 comprises the amino acid sequence of RASQSVX$_1$X$_2$YLX$_3$ (SEQ ID NO: 43), wherein:
X$_1$ is S or G;
X$_2$ is R, S, or T; and
X$_3$ is G or A;
(e) CDRL2 comprises the amino acid sequence of X$_1$X$_2$SX$_3$RAT (SEQ ID NO: 44), wherein:
X$_1$ is G or A;
X$_2$ is A or T; and
X$_3$ is T, S, R, or N; and
(f) CDRL3 comprises the amino acid sequence of QQYGX$_1$SPX$_2$T (SEQ ID NO: 45), wherein:
X$_1$ is S or T; and
X$_2$ is W or F,
and wherein the second isolated antibody comprises a heavy chain variable region comprising complementarity determining regions CDRH1, CDRH2 and CDRH3 and a light chain variable region comprising complementarity determining regions CDRL1, CDRL2 and CDRL3, wherein:
(g) CDRH1 comprises the amino acid sequence of SYGMH (SEQ ID NO: 75);
(h) CDRH2 comprises the amino acid sequence of VIWX$_1$DGSNX$_2$YYADSVX$_3$G (SEQ ID NO: 86), wherein
X$_1$ is Y or F;
X$_2$ is K or E; and
X$_3$ is K or M;
(i) CDRH3 comprises the amino acid sequence of NX$_1$DX$_2$ (SEQ ID NO: 87), wherein
X$_1$ is G or V; and
X$_2$ is H or Y;
(j) CDRL1 comprises the amino acid sequence of RASQSVSSNLA (SEQ ID NO: 83);
(k) CDRL2 comprises the amino acid sequence of GASTRAT (SEQ ID NO: 84); and
(l) CDRL3 comprises the amino acid sequence of QQYNNWPRT (SEQ ID NO: 85).

In another aspect, the instant disclosure provides a method of treating an infectious disease in a subject, the method comprising administering to the subject an effective amount of a therapeutic combination comprising a first isolated antibody that specifically binds to CTLA-4 (e.g., human CTLA-4) and a second isolated antibody that specifically binds to PD-1 (e.g., human PD-1), wherein the first isolated antibody comprises a heavy chain variable region comprising complementarity determining regions CDRH1, CDRH2, and CDRH3 and a light chain variable region comprising complementarity determining regions CDRL1, CDRL2, and CDRL3, wherein:

(a) CDRH1 comprises the amino acid sequence of SYX$_1$MX$_2$ (SEQ ID NO: 39), wherein
X$_1$ is S or A; and
X$_2$ is N or S;
(b) CDRH2 comprises the amino acid sequence of SISSSSSYIYYADSVKG (SEQ ID NO: 22);
(c) CDRH3 comprises the amino acid sequence of VGLMGPFXI (SEQ ID NO: 115), wherein X is D or N;
(d) CDRL1 comprises the amino acid sequence of RASQSVX$_1$X$_2$YLX$_3$ (SEQ ID NO: 43), wherein:
X$_1$ is S or G;
X$_2$ is R, S, or T; and
X$_3$ is G or A;
(e) CDRL2 comprises the amino acid sequence of X$_1$X$_2$SX$_3$RAT (SEQ ID NO: 44), wherein:
X$_1$ is G or A;
X$_2$ is A or T; and
X$_3$ is T, S, R, or N; and
(f) CDRL3 comprises the amino acid sequence of QQYGX$_1$SPX$_2$T (SEQ ID NO: 45), wherein:
X$_1$ is S or T; and
X$_2$ is W or F,
and wherein the second isolated antibody comprises a heavy chain variable region comprising complementarity determining regions CDRH1, CDRH2 and CDRH3 and a light chain variable region comprising complementarity determining regions CDRL1, CDRL2 and CDRL3, wherein:
(g) CDRH1 comprises the amino acid sequence of SYGMH (SEQ ID NO: 75);
(h) CDRH2 comprises the amino acid sequence of VIWX$_1$DGSNX$_2$YYADSVX$_3$G (SEQ ID NO: 86), wherein
X$_1$ is Y or F;
X$_2$ is K or E; and
X$_3$ is K or M;
(i) CDRH3 comprises the amino acid sequence of NX$_1$DX$_2$ (SEQ ID NO: 87), wherein
X$_1$ is G or V; and
X$_2$ is H or Y;
(j) CDRL1 comprises the amino acid sequence of RASQSVSSNLA (SEQ ID NO: 83);
(k) CDRL2 comprises the amino acid sequence of GASTRAT (SEQ ID NO: 84); and
(l) CDRL3 comprises the amino acid sequence of QQYNNWPRT (SEQ ID NO: 85).

In another aspect, the instant disclosure provides a method of enhancing or inducing an immune response in a subject, the method comprising administering to the subject an effective amount of a therapeutic combination comprising a first isolated antibody that specifically binds to human CTLA-4 and a second isolated antibody that specifically binds to human PD-1, wherein the first isolated antibody comprises a heavy chain variable region comprising complementarity determining regions CDRH1, CDRH2, and CDRH3 and a light chain variable region comprising complementarity determining regions CDRL1, CDRL2, and CDRL3, wherein:

(a) CDRH1 comprises the amino acid sequence of SYX$_1$MX$_2$ (SEQ ID NO: 39), wherein
   X$_1$ is S or A; and
   X$_2$ is N or S;
(b) CDRH2 comprises the amino acid sequence of SISSSSSYIYYADSVKG (SEQ ID NO: 22);
(c) CDRH3 comprises the amino acid sequence of VGLMGPFXI (SEQ ID NO: 115), wherein X is D or N;
(d) CDRL1 comprises the amino acid sequence of RASQSVX$_1$X$_2$YLX$_3$ (SEQ ID NO: 43), wherein:
   X$_1$ is S or G;
   X$_2$ is R, S, or T; and
   X$_3$ is G or A;
(e) CDRL2 comprises the amino acid sequence of X$_1$X$_2$SX$_3$RAT (SEQ ID NO: 44), wherein:
   X$_1$ is G or A;
   X$_2$ is A or T; and
   X$_3$ is T, S, R, or N; and
(f) CDRL3 comprises the amino acid sequence of QQYGX$_1$SPX$_2$T (SEQ ID NO: 45), wherein:
   X$_1$ is S or T; and
   X$_2$ is W or F.

In another aspect, the instant disclosure provides a method of treating cancer in a subject, the method comprising administering to the subject an effective amount of a therapeutic combination comprising a first isolated antibody that specifically binds to human CTLA-4 and a second isolated antibody that specifically binds to human PD-1, wherein the first isolated antibody comprises a heavy chain variable region comprising complementarity determining regions CDRH1, CDRH2, and CDRH3 and a light chain variable region comprising complementarity determining regions CDRL1, CDRL2, and CDRL3, wherein:

(a) CDRH1 comprises the amino acid sequence of SYX$_1$MX$_2$ (SEQ ID NO: 39), wherein
   X$_1$ is S or A; and
   X$_2$ is N or S;
(b) CDRH2 comprises the amino acid sequence of SISSSSSYIYYADSVKG (SEQ ID NO: 22);
(c) CDRH3 comprises the amino acid sequence of VGLMGPFXI (SEQ ID NO: 115), wherein X is D or N;
(d) CDRL1 comprises the amino acid sequence of RASQSVX$_1$X$_2$YLX$_3$ (SEQ ID NO: 43), wherein:
   X$_1$ is S or G;
   X$_2$ is R, S, or T; and
   X$_3$ is G or A;
(e) CDRL2 comprises the amino acid sequence of X$_1$X$_2$SX$_3$RAT (SEQ ID NO: 44), wherein:
   X$_1$ is G or A;
   X$_2$ is A or T; and
   X$_3$ is T, S, R, or N; and
(f) CDRL3 comprises the amino acid sequence of QQYGX$_1$SPX$_2$T (SEQ ID NO: 45), wherein:
   X$_1$ is S or T; and
   X$_2$ is W or F.

In another aspect, the instant disclosure provides a method of treating an infectious disease in a subject, the method comprising administering to the subject an effective amount of a therapeutic combination comprising a first isolated antibody that specifically binds to human CTLA-4 and a second isolated antibody that specifically binds to human PD-1, wherein the first isolated antibody comprises a heavy chain variable region comprising complementarity determining regions CDRH1, CDRH2, and CDRH3 and a light chain variable region comprising complementarity determining regions CDRL1, CDRL2, and CDRL3, wherein:

(a) CDRH1 comprises the amino acid sequence of SYX$_1$MX$_2$ (SEQ ID NO: 39), wherein
   X$_1$ is S or A; and
   X$_2$ is N or S;
(b) CDRH2 comprises the amino acid sequence of SISSSSSYIYYADSVKG (SEQ ID NO: 22);
(c) CDRH3 comprises the amino acid sequence of VGLMGPFXI (SEQ ID NO: 115), wherein X is D or N;
(d) CDRL1 comprises the amino acid sequence of RASQSVX$_1$X$_2$YLX$_3$ (SEQ ID NO: 43), wherein:
   X$_1$ is S or G;
   X$_2$ is R, S, or T; and
   X$_3$ is G or A;
(e) CDRL2 comprises the amino acid sequence of X$_1$X$_2$SX$_3$RAT (SEQ ID NO: 44), wherein:
   X$_1$ is G or A;
   X$_2$ is A or T; and
   X$_3$ is T, S, R, or N; and
(f) CDRL3 comprises the amino acid sequence of QQYGX$_1$SPX$_2$T (SEQ ID NO: 45), wherein:
   X$_1$ is S or T; and
   X$_2$ is W or F.

In another aspect, the instant disclosure provides a method of enhancing or inducing an immune response in a subject, the method comprising administering to the subject an effective amount of a therapeutic combination comprising a first isolated antibody that specifically binds to human CTLA-4 and a second isolated antibody that specifically binds to human PD-1, wherein the second isolated antibody comprises a heavy chain variable region comprising complementarity determining regions CDRH1, CDRH2 and CDRH3 and a light chain variable region comprising complementarity determining regions CDRL1, CDRL2 and CDRL3, wherein:

(a) CDRH1 comprises the amino acid sequence of SYGMH (SEQ ID NO: 75);
(b) CDRH2 comprises the amino acid sequence of VIWX$_1$DGSNX$_2$YYADSVX$_3$G (SEQ ID NO: 86), wherein
   X$_1$ is Y or F;
   X$_2$ is K or E; and
   X$_3$ is K or M;
(c) CDRH3 comprises the amino acid sequence of NX$_1$DX$_2$ (SEQ ID NO: 87), wherein
   X$_1$ is G or V; and
   X$_2$ is H or Y;
(d) CDRL1 comprises the amino acid sequence of RASQSVSSNLA (SEQ ID NO: 83);
(e) CDRL2 comprises the amino acid sequence of GASTRAT (SEQ ID NO: 84); and
(f) CDRL3 comprises the amino acid sequence of QQYNNWPRT (SEQ ID NO: 85).

In another aspect, the instant disclosure provides a method of treating cancer in a subject, the method comprising administering to the subject an effective amount of a therapeutic combination comprising a first isolated antibody that specifically binds to human CTLA-4 and a second isolated antibody that specifically binds to human PD-1, wherein the second isolated antibody comprises a heavy chain variable region comprising complementarity determining regions CDRH1, CDRH2 and CDRH3 and a light chain variable region comprising complementarity determining regions CDRL1, CDRL2 and CDRL3, wherein:

(a) CDRH1 comprises the amino acid sequence of SYGMH (SEQ ID NO: 75);
(b) CDRH2 comprises the amino acid sequence of VIWX$_1$DGSNX$_2$YYADSVX$_3$G (SEQ ID NO: 86), wherein
    X$_1$ is Y or F;
    X$_2$ is K or E; and
    X$_3$ is K or M;
(c) CDRH3 comprises the amino acid sequence of NX$_1$DX$_2$ (SEQ ID NO: 87), wherein
    X$_1$ is G or V; and
    X$_2$ is H or Y;
(d) CDRL1 comprises the amino acid sequence of RASQSVSSNLA (SEQ ID NO: 83);
(e) CDRL2 comprises the amino acid sequence of GASTRAT (SEQ ID NO: 84); and
(f) CDRL3 comprises the amino acid sequence of QQYNNWPRT (SEQ ID NO: 85).

In another aspect, the instant disclosure provides a method of treating an infectious disease in a subject, the method comprising administering to the subject an effective amount of a therapeutic combination comprising a first isolated antibody that specifically binds to human CTLA-4 and a second isolated antibody that specifically binds to human PD-1, wherein the second isolated antibody comprises a heavy chain variable region comprising complementarity determining regions CDRH1, CDRH2 and CDRH3 and a light chain variable region comprising complementarity determining regions CDRL1, CDRL2 and CDRL3, wherein:
(a) CDRH1 comprises the amino acid sequence of SYGMH (SEQ ID NO: 75);
(b) CDRH2 comprises the amino acid sequence of VIWX$_1$DGSNX$_2$YYADSVX$_3$G (SEQ ID NO: 86), wherein
    X$_1$ is Y or F;
    X$_2$ is K or E; and
    X$_3$ is K or M;
(c) CDRH3 comprises the amino acid sequence of NX$_1$DX$_2$ (SEQ ID NO: 87), wherein
    X$_1$ is G or V; and
    X$_2$ is H or Y;
(d) CDRL1 comprises the amino acid sequence of RASQSVSSNLA (SEQ ID NO: 83);
(e) CDRL2 comprises the amino acid sequence of GASTRAT (SEQ ID NO: 84); and
(f) CDRL3 comprises the amino acid sequence of QQYNNWPRT (SEQ ID NO: 85).

In another aspect, the instant disclosure provides a method of enhancing or inducing an immune response in a subject, the method comprising administering to the subject an effective amount of a first isolated antibody that specifically binds to human CTLA-4, optionally as a monotherapy, wherein the first isolated antibody comprises a heavy chain variable region comprising complementarity determining regions CDRH1, CDRH2, and CDRH3 and a light chain variable region comprising complementarity determining regions CDRL1, CDRL2, and CDRL3, wherein:
(a) CDRH1 comprises the amino acid sequence of SYX$_1$MX$_2$ (SEQ ID NO: 39), wherein
    X$_1$ is S or A; and
    X$_2$ is N or S;
(b) CDRH2 comprises the amino acid sequence of SISSSSSYIYYADSVKG (SEQ ID NO: 22);
(c) CDRH3 comprises the amino acid sequence of VGLMGPFXI (SEQ ID NO: 115), wherein X is D or N;
(d) CDRL1 comprises the amino acid sequence of RASQSVX$_1$X$_2$YLX$_3$ (SEQ ID NO: 43), wherein:
    X$_1$ is S or G;
    X$_2$ is R, S, or T; and
    X$_3$ is G or A;
(e) CDRL2 comprises the amino acid sequence of X$_1$X$_2$SX$_3$RAT (SEQ ID NO: 44), wherein:
    X$_1$ is G or A;
    X$_2$ is A or T; and
    X$_3$ is T, S, R, or N; and
(f) CDRL3 comprises the amino acid sequence of QQYGX$_1$SPX$_2$T (SEQ ID NO: 45), wherein:
    X$_1$ is S or T; and
    X$_2$ is W or F.

In another aspect, the instant disclosure provides a method of treating cancer in a subject, the method comprising administering to the subject an effective amount of a first isolated antibody that specifically binds to human CTLA-4, optionally as a monotherapy, wherein the first isolated antibody comprises a heavy chain variable region comprising complementarity determining regions CDRH1, CDRH2, and CDRH3 and a light chain variable region comprising complementarity determining regions CDRL1, CDRL2, and CDRL3, wherein:
(a) CDRH1 comprises the amino acid sequence of SYX$_1$MX$_2$ (SEQ ID NO: 39), wherein
    X$_1$ is S or A; and
    X$_2$ is N or S;
(b) CDRH2 comprises the amino acid sequence of SISSSSSYIYYADSVKG (SEQ ID NO: 22);
(c) CDRH3 comprises the amino acid sequence of VGLMGPFXI (SEQ ID NO: 115), wherein X is D or N;
(d) CDRL1 comprises the amino acid sequence of RASQSVX$_1$X$_2$YLX$_3$ (SEQ ID NO: 43), wherein:
    X$_1$ is S or G;
    X$_2$ is R, S, or T; and
    X$_3$ is G or A;
(e) CDRL2 comprises the amino acid sequence of X$_1$X$_2$SX$_3$RAT (SEQ ID NO: 44), wherein:
    X$_1$ is G or A;
    X$_2$ is A or T; and
    X$_3$ is T, S, R, or N; and
(f) CDRL3 comprises the amino acid sequence of QQYGX$_1$SPX$_2$T (SEQ ID NO: 45), wherein:
    X$_1$ is S or T; and
    X$_2$ is W or F.

In another aspect, the instant disclosure provides a method of treating an infectious disease in a subject, the method comprising administering to the subject an effective amount of a first isolated antibody that specifically binds to human CTLA-4, optionally as a monotherapy, wherein the first isolated antibody comprises a heavy chain variable region comprising complementarity determining regions CDRH1, CDRH2, and CDRH3 and a light chain variable region comprising complementarity determining regions CDRL1, CDRL2, and CDRL3, wherein:
(a) CDRH1 comprises the amino acid sequence of SYX$_1$MX$_2$ (SEQ ID NO: 39), wherein
    X$_1$ is S or A; and
    X$_2$ is N or S;
(b) CDRH2 comprises the amino acid sequence of SISSSSSYIYYADSVKG (SEQ ID NO: 22);
(c) CDRH3 comprises the amino acid sequence of VGLMGPFXI (SEQ ID NO: 115), wherein X is D or N;

(d) CDRL1 comprises the amino acid sequence of RASQSVX$_1$X$_2$YLX$_3$ (SEQ ID NO: 43), wherein:
   X$_1$ is S or G;
   X$_2$ is R, S, or T; and
   X$_3$ is G or A;
(e) CDRL2 comprises the amino acid sequence of X$_1$X$_2$SX$_3$RAT (SEQ ID NO: 44), wherein:
   X$_1$ is G or A;
   X$_2$ is A or T; and
   X$_3$ is T, S, R, or N; and
(f) CDRL3 comprises the amino acid sequence of QQYGX$_1$SPX$_2$T (SEQ ID NO: 45), wherein:
   X$_1$ is S or T; and
   X$_2$ is W or F.

In another aspect, the instant disclosure provides a method of enhancing or inducing an immune response in a subject, the method comprising administering to the subject an effective amount of a second isolated antibody that specifically binds to human PD-1, optionally as a monotherapy, wherein the second isolated antibody comprises a heavy chain variable region comprising complementarity determining regions CDRH1, CDRH2 and CDRH3 and a light chain variable region comprising complementarity determining regions CDRL1, CDRL2 and CDRL3, wherein:
   (a) CDRH1 comprises the amino acid sequence of SYGMH (SEQ ID NO: 75);
   (b) CDRH2 comprises the amino acid sequence of VIWX$_1$DGSNX$_2$YYADSVX$_3$G (SEQ ID NO: 86), wherein
   X$_1$ is Y or F;
   X$_2$ is K or E; and
   X$_3$ is K or M;
   (c) CDRH3 comprises the amino acid sequence of NX$_1$DX$_2$ (SEQ ID NO: 87), wherein
   X$_1$ is G or V; and
   X$_2$ is H or Y;
   (d) CDRL1 comprises the amino acid sequence of RASQSVSSNLA (SEQ ID NO: 83);
   (e) CDRL2 comprises the amino acid sequence of GASTRAT (SEQ ID NO: 84); and
   (f) CDRL3 comprises the amino acid sequence of QQYNNWPRT (SEQ ID NO: 85).

In another aspect, the instant disclosure provides a method of treating cancer in a subject, the method comprising administering to the subject an effective amount of a second isolated antibody that specifically binds to human PD-1, optionally as a monotherapy, wherein the second isolated antibody comprises a heavy chain variable region comprising complementarity determining regions CDRH1, CDRH2 and CDRH3 and a light chain variable region comprising complementarity determining regions CDRL1, CDRL2 and CDRL3, wherein:
   (a) CDRH1 comprises the amino acid sequence of SYGMH (SEQ ID NO: 75);
   (b) CDRH2 comprises the amino acid sequence of VIWX$_1$DGSNX$_2$YYADSVX$_3$G (SEQ ID NO: 86), wherein
   X$_1$ is Y or F;
   X$_2$ is K or E; and
   X$_3$ is K or M;
   (c) CDRH3 comprises the amino acid sequence of NX$_1$DX$_2$ (SEQ ID NO: 87), wherein
   X$_1$ is G or V; and
   X$_2$ is H or Y;
   (d) CDRL1 comprises the amino acid sequence of RASQSVSSNLA (SEQ ID NO: 83);
   (e) CDRL2 comprises the amino acid sequence of GASTRAT (SEQ ID NO: 84); and
   (f) CDRL3 comprises the amino acid sequence of QQYNNWPRT (SEQ ID NO: 85).

In another aspect, the instant disclosure provides a method of treating an infectious disease in a subject, the method comprising administering to the subject an effective amount of a second isolated antibody that specifically binds to human PD-1, optionally as a monotherapy, wherein the second isolated antibody comprises a heavy chain variable region comprising complementarity determining regions CDRH1, CDRH2 and CDRH3 and a light chain variable region comprising complementarity determining regions CDRL1, CDRL2 and CDRL3, wherein:
   (a) CDRH1 comprises the amino acid sequence of SYGMH (SEQ ID NO: 75);
   (b) CDRH2 comprises the amino acid sequence of VIWX$_1$DGSNX$_2$YYADSVX$_3$G (SEQ ID NO: 86), wherein
   X$_1$ is Y or F;
   X$_2$ is K or E; and
   X$_3$ is K or M;
   (c) CDRH3 comprises the amino acid sequence of NX$_1$DX$_2$ (SEQ ID NO: 87), wherein
   X$_1$ is G or V; and
   X$_2$ is H or Y;
   (d) CDRL1 comprises the amino acid sequence of RASQSVSSNLA (SEQ ID NO: 83);
   (e) CDRL2 comprises the amino acid sequence of GASTRAT (SEQ ID NO: 84); and
   (f) CDRL3 comprises the amino acid sequence of QQYNNWPRT (SEQ ID NO: 85).

In certain embodiments, CDRH1 of the first isolated antibody comprises the amino acid sequence of SEQ ID NO: 20 or 21. In certain embodiments, CDRH3 of the first isolated antibody comprises the amino acid sequence of SEQ ID NO: 24 or 26. In certain embodiments, CDRL1 of the first isolated antibody comprises the amino acid sequence of SEQ ID NO: 27, 28, or 29. In certain embodiments, CDRL2 of the first isolated antibody comprises an amino acid sequence selected from the group consisting of SEQ ID NOs: 30-35. In certain embodiments, CDRL3 of the first isolated antibody comprises the amino acid sequence of SEQ ID NO: 36, 37, or 38. In certain embodiments, CDRH1, CDRH2, and CDRH3 of the first isolated antibody comprise the CDRH1, CDRH2, and CDRH3 amino acid sequences set forth in SEQ ID NOs: 20, 22, and 24; 21, 22, and 24; or 21, 22, and 26, respectively. In certain embodiments, CDRL1, CDRL2, and CDRL3 of the first isolated antibody comprise the CDRL1, CDRL2, and CDRL3 amino acid sequences set forth in SEQ ID NOs: 27, 30, and 36; 28, 31, and 36; 29, 32, and 37; 29, 33, and 38; 29, 34, and 36; or 29, 35, and 38, respectively.

In certain embodiments, CDRH1, CDRH2, CDRH3, CDRL1, CDRL2, and CDRL3 of the first isolated antibody comprise the amino acid sequences set forth in SEQ ID NOs: 20, 22, 24, 27, 30, and 36; 20, 22, 24, 29, 32, and 37; 20, 22, 24, 29, 33, and 38; 21, 22, 24, 27, 30, and 36; 21, 22, 24, 29, 33, and 38; 20, 22, 24, 28, 31, and 36; 20, 22, 24, 29, 34, and 36; 20, 22, 24, 29, 35, and 38; 21, 22, 26, 27, 30, and 36; 21, 22, 26, 29, 32, and 37; 21, 22, 26, 29, 33, and 38; or 21, 22, 26, 29, 35, and 38, respectively. In certain embodiments, CDRH1, CDRH2, CDRH3, CDRL1, CDRL2, and CDRL3 of the first isolated antibody comprise the amino acid sequences set forth in SEQ ID NOs: 20, 22, 24, 27, 30, and 36, respectively.

In certain embodiments, the first isolated antibody comprises a heavy chain variable region comprising the amino acid sequence of SEQ ID NO: 116. In certain embodiments, the first isolated antibody comprises a heavy chain variable region comprising an amino acid sequence which is at least 75%, 80%, 85%, 90%, 95%, or 100% identical to an amino acid sequence selected from the group consisting of SEQ ID NOs: 1 and 9-13. In certain embodiments, the heavy chain variable region of the first isolated antibody comprises an amino acid sequence selected from the group consisting of SEQ ID NOs: 1 and 9-13.

In certain embodiments, the first isolated antibody comprises a light chain variable region comprising the amino acid sequence of SEQ ID NO: 47. In certain embodiments, the first isolated antibody comprises a light chain variable region comprising an amino acid sequence which is at least 75%, 80%, 85%, 90%, 95%, or 100% identical to an amino acid sequence selected from the group consisting of SEQ ID NOs: 14-19. In certain embodiments, the light chain variable region of the first isolated antibody comprises an amino acid sequence selected from the group consisting of SEQ ID NOs: 14-19.

In certain embodiments, the heavy chain variable region and the light chain variable region of the first isolated antibody comprise the amino acid sequences set forth in SEQ ID NOs: 1 and 14; 1 and 16, 1 and 17; 9 and 14; 9 and 17; 10 and 15; 10 and 17; 10 and 18; 10 and 19; 11 and 15; 11 and 14; 11 and 16; 11 and 17; 12 and 14; 12 and 16; 12 and 17; 12 and 19; 13 and 15; or 13 and 17, respectively. In certain embodiments, the heavy chain variable region and the light chain variable region of the first isolated antibody comprise the amino acid sequences set forth in SEQ ID NOs: 1 and 14, respectively.

In certain embodiments, the first isolated antibody comprises a heavy chain variable region having an amino acid sequence derived from a human IGHV3-21 germline sequence. In certain embodiments, the first isolated antibody comprises a light chain variable region having an amino acid sequence derived from a human IGKV3-20 or IGKV3-11 germline sequence.

In certain embodiments, the first isolated antibody comprises a heavy chain comprising an amino acid sequence selected from the group consisting of SEQ ID NOs: 51-54 and 117, and a light chain comprising the amino acid sequence of SEQ ID NO: 59. In certain embodiments, the first isolated antibody comprises a heavy chain comprising the amino acid sequence of SEQ ID NOs: 51, and a light chain comprising the amino acid sequence of SEQ ID NO: 59. In certain embodiments, the first isolated antibody comprises a heavy chain comprising the amino acid sequence of SEQ ID NOs: 117, and a light chain comprising the amino acid sequence of SEQ ID NO: 59.

In certain embodiments, the first isolated antibody comprises a heavy chain constant region selected from the group consisting of human IgG$_1$, IgG$_2$, IgG$_3$, IgG$_4$, IgA$_1$, IgA$_2$. In certain embodiments, the first isolated antibody comprises an IgG$_1$ heavy chain constant region. In certain embodiments, the first isolated antibody comprises a heavy chain constant region comprising the amino acid sequence of SEQ ID NO: 60. In certain embodiments, the amino acid sequence of the IgG$_1$ heavy chain constant region comprises S239D/I332E mutations, numbered according to the EU numbering system. In certain embodiments, the first isolated antibody comprises a heavy chain constant region comprising the amino acid sequence of SEQ ID NO: 61. In certain embodiments, the amino acid sequence of the IgG$_1$ heavy chain constant region comprises S239D/A330L/I332E mutations, numbered according to the EU numbering system. In certain embodiments, the first isolated antibody comprises a heavy chain constant region comprising the amino acid sequence of SEQ ID NO: 62. In certain embodiments, the amino acid sequence of the IgG$_1$ heavy chain constant region comprises L235V/F243L/R292P/Y300L/P396L mutations, numbered according to the EU numbering system. In certain embodiments, the first isolated antibody comprises a heavy chain constant region comprising the amino acid sequence of SEQ ID NO: 63. In certain embodiments, the IgG$_1$ heavy chain constant region is non-fucosylated IgG$_1$. In certain embodiments, the first isolated antibody comprises an IgG$_2$ heavy chain constant region. In certain embodiments, the first isolated antibody comprises a heavy chain constant region comprising the amino acid sequence of SEQ ID NO: 118.

In certain embodiments, the first isolated antibody comprises a light chain constant region selected from the group consisting of human Igκ and Igλ. In certain embodiments, the first isolated antibody comprises an Igκ light chain constant region. In certain embodiments, the first isolated antibody comprises a light chain constant region comprising the amino acid sequence of SEQ ID NO: 64.

In certain embodiments, the first isolated antibody binds to the same epitope of human CTLA-4 as an antibody comprising a heavy chain variable region comprising the amino acid sequence of SEQ ID NO: 1 and a light chain variable region comprising the amino acid sequence of SEQ ID NO: 14. In certain embodiments, the first isolated antibody binds to an epitope located within a region of human CTLA-4 consisting of an amino acid sequence selected from the group consisting of SEQ ID NO: 97-102.

In certain embodiments, the first isolated antibody is antagonistic to human CTLA-4.

In certain embodiments, CDRH2 of the second isolated antibody comprises an amino acid sequence selected from the group consisting of SEQ ID NOs: 76-79. In certain embodiments, CDRH3 of the second isolated antibody comprises the amino acid sequence of SEQ ID NO: 80, 81, or 82. In certain embodiments, CDRH1, CDRH2, and CDRH3 of the second isolated antibody comprise the CDRH1, CDRH2, and CDRH3 amino acid sequences set forth in SEQ ID NOs: 75, 76, and 80; 75, 76, and 81; 75, 76, and 82; 75, 77, and 81; 75, 78, and 81; or 75, 79, and 81, respectively.

In certain embodiments, CDRH1, CDRH2, CDRH3, CDRL1, CDRL2, and CDRL3 of the second isolated antibody comprise the amino acid sequences set forth in SEQ ID NOs: 75, 76, 80, 83, 84, and 85; 75, 76, 81, 83, 84, and 85; 75, 76, 82, 83, 84, and 85; 75, 77, 81, 83, 84, and 85; 75, 78, 81, 83, 84, and 85; or 75, 79, 81, 83, 84, and 85, respectively. In certain embodiments, CDRH1, CDRH2, CDRH3, CDRL1, CDRL2, and CDRL3 of the second isolated antibody comprise the amino acid sequences set forth in SEQ ID NOs: 75, 76, 81, 83, 84, and 85, respectively.

In certain embodiments, the second isolated antibody comprises a heavy chain variable region comprising the amino acid sequence of SEQ ID NO: 88. In certain embodiments, the second isolated antibody comprises a heavy chain variable region comprising an amino acid sequence which is at least 75%, 80%, 85%, 90%, 95%, or 100% identical to an amino acid sequence selected from the group consisting of SEQ ID NOs: 66-73. In certain embodiments, the heavy chain variable region of the second isolated antibody comprises an amino acid sequence selected from the group consisting of SEQ ID NOs: 66-73. In certain embodiments, the second isolated antibody comprises a light chain variable region comprising an amino acid sequence which is at least 75%, 80%, 85%, 90%, 95%, or 100% identical to the amino acid sequence of SEQ ID NO: 74. In certain embodiments, the light chain variable region of the second isolated antibody comprises the amino acid sequence of SEQ ID NO: 74.

In certain embodiments, the heavy chain variable region and the light chain variable region of the second isolated antibody comprise the amino acid sequences set forth in SEQ ID NOs: 66 and 74; 67 and 74; 68 and 74; 69 and 74; 70 and 74; 71 and 74; 72 and 74; or 73 and 74, respectively. In certain embodiments, the heavy chain variable region and the light chain variable region of the second isolated antibody comprise the amino acid sequences set forth in SEQ ID NOs: 66 and 74, respectively.

In certain embodiments, the second isolated antibody comprises a heavy chain variable region having an amino acid sequence derived from a human IGHV3-33 germline sequence. In certain embodiments, the second isolated antibody comprises a light chain variable region having an amino acid sequence derived from a human IGKV3-15 germline sequence.

In certain embodiments, the second isolated antibody comprises a heavy chain comprising the amino acid sequence of SEQ ID NO: 91 and a light chain comprising the amino acid sequence of SEQ ID NO: 93. In certain embodiments, the second isolated antibody comprises a heavy chain comprising the amino acid sequence of SEQ ID NO: 92 and a light chain comprising the amino acid sequence of SEQ ID NO: 93. In certain embodiments, the second isolated antibody comprises a heavy chain comprising the amino acid sequence of SEQ ID NO: 120 and a light chain comprising the amino acid sequence of SEQ ID NO: 93.

In certain embodiments, the second isolated antibody comprises a heavy chain constant region selected from the group consisting of human $IgG_1$, $IgG_2$, $IgG_3$, $IgG_4$, $IgA_1$, and $IgA_2$. In certain embodiments, the second isolated antibody comprises an $IgG_1$ heavy chain constant region. In certain embodiments, the amino acid sequence of the $IgG_1$ heavy chain constant region comprises an N297A mutation, numbered according to the EU numbering system. In certain embodiments, the second isolated antibody comprises a heavy chain constant region comprising the amino acid sequence of SEQ ID NO: 94. In certain embodiments, the second isolated antibody comprises an $IgG_4$ heavy chain constant region. In certain embodiments, the amino acid sequence of the $IgG_4$ heavy chain constant region comprises an S228P mutation, numbered according to the EU numbering system. In certain embodiments, the second isolated antibody comprises a heavy chain constant region comprising the amino acid sequence of SEQ ID NO: 95.

In certain embodiments, the second isolated antibody comprises a light chain constant region selected from the group consisting of human Igκ and Igλ. In certain embodiments, the second isolated antibody comprises an Igκ light chain constant region. In certain embodiments, the second isolated antibody comprises a light chain constant region comprising the amino acid sequence of SEQ ID NO: 64.

In certain embodiments, the second isolated antibody binds to the same epitope of human PD-1 as an antibody comprising a heavy chain variable region comprising the amino acid sequence of SEQ ID NO: 66 and a light chain variable region comprising the amino acid sequence of SEQ ID NO: 74. In certain embodiments, the second isolated antibody binds to an epitope located within a region of human PD-1 consisting of an amino acid sequence selected from the group consisting of SEQ ID NO: 103-107.

In certain embodiments, the second isolated antibody is antagonistic to human PD-1.

In certain embodiments, the second isolated antibody is selected from the group consisting of pembrolizumab, nivolumab, and pidilizumab. In certain embodiments, the second isolated antibody is pembrolizumab.

In certain embodiments, the first isolated antibody is selected from the group consisting of ipilimumab and tremelimumab. In certain embodiments, the first isolated antibody is ipilimumab.

In certain embodiments, the first isolated antibody is administered at 0.3 mg/kg or 1 mg/kg. In certain embodiments, the second isolated antibody is administered at 1 mg/kg, 3 mg/kg, or 6 mg/kg. In certain embodiments, the second isolated antibody is administered at the dose of 200 mg, optionally wherein the second isolated antibody is pembrolizumab. In certain embodiments, the first isolated antibody is administered at 0.3 mg/kg or 1 mg/kg, and the second isolated antibody is administered at 1 mg/kg, 3 mg/kg, or 6 mg/kg. In certain embodiments, the first isolated antibody is administered at 0.3 mg/kg, and the second isolated antibody is administered at 1 mg/kg. In certain embodiments, the first isolated antibody is administered at 1 mg/kg, and the second isolated antibody is administered at 1 mg/kg. In certain embodiments, the first isolated antibody is administered at 1 mg/kg, and the second isolated antibody is administered at 3 mg/kg. In certain embodiments, the first isolated antibody is administered at 1 mg/kg, and the second isolated antibody is administered at 6 mg/kg. In certain embodiments, the first isolated antibody is administered at about 0.3 mg/kg or 1 mg/kg, and the second isolated antibody is administered at about 1 mg/kg or 3 mg/kg. In certain embodiments, the first isolated antibody is administered at about 0.3 mg/kg, and the second isolated antibody is administered at about 1 mg/kg. In certain embodiments, the first isolated antibody is administered at about 1 mg/kg, and the second isolated antibody is administered at about 1 mg/kg. In certain embodiments, the first isolated antibody is administered at about 1 mg/kg, and the second isolated antibody is administered at about 3 mg/kg. In certain embodiments, the first isolated antibody is administered at about 1 mg/kg, and the second isolated antibody is administered at about 6 mg/kg. In certain embodiments, the first isolated antibody is administered every six weeks. In certain embodiments, the second isolated antibody is administered every two weeks or every three weeks. In certain embodiments, the first isolated antibody is administered every six weeks, and the second isolated antibody is administered every two weeks or every three weeks. In certain embodiments, the first isolated antibody is administered about every six weeks, and the second isolated antibody is administered about every two weeks or about every three weeks. In certain embodiments, the first isolated antibody is administered at 0.3 mg/kg every six weeks, and the second isolated antibody is administered at 1 mg/kg every two weeks. In certain embodiments, the first isolated antibody is administered at 1 mg/kg every six weeks, and the second isolated antibody is administered at 1 mg/kg every two weeks. In certain embodiments, the first isolated antibody is administered at 1 mg/kg every six weeks, and the second isolated antibody is administered at 3 mg/kg every two weeks. In certain embodiments, the first isolated antibody is administered at 1 mg/kg every six weeks, and the second isolated antibody is administered at 6 mg/kg every three weeks. In certain embodiments, the first isolated antibody is administered at about 0.3 mg/kg about every six weeks, and the second isolated antibody is administered at about 1 mg/kg about every two weeks. In certain embodiments, the first isolated antibody is administered at about 1 mg/kg about every six weeks, and the second isolated antibody is administered at about 1 mg/kg about every two weeks. In certain embodiments, the first isolated antibody is administered at about 1 mg/kg about every six weeks, and the second isolated antibody is administered at about 3 mg/kg about every two weeks. In certain embodiments, the first isolated antibody is administered at about 1 mg/kg about every six weeks, and the second isolated antibody is administered at about 6 mg/kg about every three weeks. In certain embodiments, the first isolated antibody is administered intravenously. In certain embodiments, the second isolated antibody is administered intravenously. In certain embodiments, the first isolated antibody and the second isolated antibody are both administered intravenously.

In certain embodiments, the subject has cancer. In certain embodiments, the subject has a metastatic or locally advanced solid tumor.

In certain embodiments, the cancer is a cervical cancer. In certain embodiments, the cancer is a metastatic or locally advanced, unresectable squamous cell carcinoma, adenosquamous carcinoma, or adenocarcinoma of the cervix. In certain embodiments, the metastatic or locally advanced solid tumor is a metastatic or locally advanced, unresectable squamous cell carcinoma, adenosquamous carcinoma, or adenocarcinoma of the cervix. In certain embodiments, no standard therapy is available for the cancer (e.g., cervical cancer) or metastatic or locally advanced solid tumor. In certain embodiments, the cancer (e.g., cervical cancer) or metastatic or locally advanced solid tumor is refractory to a standard therapy. In certain embodiments, the cancer (e.g., cervical cancer) or metastatic or locally advanced solid tumor has relapsed after a standard therapy. In certain embodiments, the standard therapy comprises a platinum-containing chemotherapy. In certain embodiments, the standard therapy is a platinum-containing doublet. In certain embodiments, the cancer (e.g., cervical cancer) is a metastatic or locally advanced, unresectable squamous cell carcinoma, adenosquamous carcinoma, or adenocarcinoma of the cervix that has relapsed after a platinum-containing doublet administered for treatment of advanced (recurrent, unresectable, or metastatic) disease. In certain embodiments, the cancer (e.g., cervical cancer) or metastatic or locally advanced solid tumor is HPV positive. In certain embodiments, the cancer or metastatic or locally advanced solid tumor is head and neck cancer, melanoma, renal cell carcinoma, urothelial carcinoma, or endometrial carcinoma. In certain embodiments, the cancer (e.g., cervical cancer) or metastatic or locally advanced solid tumor is associated with microsatellite instability.

In certain embodiments, the subject has cervical cancer (e.g., a metastatic or locally advanced, unresectable squamous cell carcinoma, adenosquamous carcinoma, or adenocarcinoma of the cervix), and the method comprises administering to the subject an effective amount of an anti-PD-1 antibody described herein, e.g., AGEN2034 (IgG$_4$ S228P), or pharmaceutical composition comprising such anti-PD-1 antibody as a first cancer therapy after diagnosis of the cervical cancer (e.g., within 1, 2, 3, 4, 5, or 6 days; 1, 2, 3, 4, 6, 8, or 12 weeks; or, 1, 2, 3, 4, 6, 8, or 12 months after diagnosis), optionally wherein the anti-PD-1 antibody described herein, e.g., AGEN2034 (IgG$_4$ S228P) or pharmaceutical composition comprising such anti-PD-1 antibody is administered at the dosage and at the frequency shown in a single row of Table 13 herein. In certain embodiments, the subject has cervical cancer (e.g., a metastatic or locally advanced, unresectable squamous cell carcinoma, adenosquamous carcinoma, or adenocarcinoma of the cervix), and the method comprises administering to the subject an effective amount of a therapeutic combination comprising (a) an anti-CTLA-4 antibody described herein, e.g., AGEN1884 (IgG$_1$), or pharmaceutical composition comprising such anti-CTLA-4 antibody; and (b) an anti-PD-1 antibody described herein, e.g., AGEN2034 (IgG$_4$ S228P), or pharmaceutical composition comprising such anti-PD-1 antibody as a first cancer therapy after diagnosis of the cervical cancer (e.g., within 1, 2, 3, 4, 5, or 6 days; 1, 2, 3, 4, 6, 8, or 12 weeks; or, 1, 2, 3, 4, 6, 8, or 12 months after diagnosis), optionally wherein the anti-CTLA-4 antibody described herein, e.g., AGEN1884 (IgG$_1$), or pharmaceutical composition comprising such anti-CTLA-4 antibody, and the anti-PD-1 antibody described herein, e.g., AGEN2034 (IgG$_4$ S228P), or pharmaceutical composition comprising such anti-PD-1 antibody, are administered at the dosage and at the frequency shown in a single row of Table 13 herein. In certain embodiments, the subject has cervical cancer (e.g., a metastatic or locally advanced, unresectable squamous cell carcinoma, adenosquamous carcinoma, or adenocarcinoma of the cervix), and the method comprises administering to the subject an effective amount of a therapeutic combination comprising (a) an anti-CTLA-4 antibody described herein, e.g., AGEN1884 (IgG$_1$), or pharmaceutical composition comprising such anti-CTLA-4 antibody and (b) pembrolizumab or pharmaceutical composition comprising pembrolizumab as a first cancer therapy after diagnosis of the cervical cancer (e.g., within 1, 2, 3, 4, 5, or 6 days; 1, 2, 3, 4, 6, 8, or 12 weeks; or, 1, 2, 3, 4, 6, 8, or 12 months after diagnosis), optionally wherein the anti-CTLA-4 antibody described herein, e.g., AGEN1884 (IgG$_1$), or pharmaceutical composition comprising such anti-CTLA-4 antibody is administered at the dosage and at the frequency shown in a single row of Table 13 herein, and pembrolizumab or composition comprising pembrolizumab is administered at 200 mg every three weeks.

In certain embodiments, the cancer expresses PD-L1. In certain embodiments, the percentage of tumor cells in a sample of the cancer that exhibit detectable membrane expression (e.g., partial or complete membrane expression) of PD-L1 is at least 1% (e.g., at least 2%, 3%, 4%, 5%, 10%, 15%, 20%, 25%, 30%, 35%, 40%, 45%, 50%, 60%, 70%, 80%, or 90%). In certain embodiments, the percentage of tumor cells in a sample of the cancer that exhibit detectable membrane expression (e.g., partial or complete membrane expression) of PD-L1 is at least 1%. In certain embodiments, the percentage of tumor cells in a sample of the cancer that exhibit detectable membrane expression (e.g., partial or complete membrane expression) of PD-L1 is at least 5%. In certain embodiments, the percentage of tumor cells in a sample of the cancer that exhibit detectable membrane expression (e.g., partial or complete membrane expression) of PD-L1 is at least 25%. In certain embodiments, the percentage of tumor cells in a sample of the cancer that exhibit detectable membrane expression (e.g., partial or complete membrane expression) of PD-L1 is at least 50%. Membrane expression of PD-L1 may be detected by any method known in the art, e.g., immunohistochemistry. Exemplary immunohistochemistry assays for detecting PD-L1 membrane expression in tumor cells are provided in Hirsch et al. (2017, J. Thoracic Oncol. 12(2): 208-222), Rimm et al. (2017, JAMA Oncol. 3(8): 1051-1058), and Diggs and Hsueh (2017, Biomarker Res. 5:12), which are incorporated by reference herein in their entirety.

In certain embodiments, the metastatic or locally advanced tumor expresses PD-L1. In certain embodiments, the percentage of tumor cells in a sample of the metastatic or locally advanced tumor that exhibit detectable membrane expression (e.g., partial or complete membrane expression) of PD-L1 is at least 1% (e.g., at least 2%, 3%, 4%, 5%, 10%, 15%, 20%, 25%, 30%, 35%, 40%, 45%, 50%, 60%, 70%, 80%, or 90%). In certain embodiments, the percentage of tumor cells in a sample of the metastatic or locally advanced tumor that exhibit detectable membrane expression (e.g., partial or complete membrane expression) of PD-L1 is at least 1%. In certain embodiments, the percentage of tumor cells in a sample of the metastatic or locally advanced tumor that exhibit detectable membrane expression (e.g., partial or complete membrane expression) of PD-L1 is at least 5%. In certain embodiments, the percentage of tumor cells in a sample of the metastatic or locally advanced tumor that exhibit detectable membrane expression (e.g., partial or complete membrane expression) of PD-L1 is at least 25%. In certain embodiments, the percentage of tumor cells in a sample of the metastatic or locally advanced tumor that exhibit detectable membrane expression (e.g., partial or complete membrane expression) of PD-L1 is at least 50%. Membrane expression of PD-L1 may be detected by any method known in the art, e.g., immunohistochemistry. Exemplary immunohistochemistry assays for detecting PD-L1 membrane expression in tumor cells are provided in Hirsch et al. (2017, J. Thoracic Oncol. 12(2): 208-222), Rimm et al. (2017, JAMA Oncol. 3(8): 1051-1058), and Diggs and Hsueh (2017, Biomarker Res. 5:12), which are incorporated by reference herein in their entirety.

In certain embodiments, the cancer is a non-small cell lung cancer (NSCLC). In certain embodiments, the NSCLC is a Stage IV NSCLC. In certain embodiments, the NSCLC is diagnosed histologically or cytologically according to the eighth edition of the American Joint Committee on Cancer staging manual. In certain embodiments, the percentage of tumor cells in a sample of the NSCLC that exhibit detectable membrane expression (e.g., partial or complete membrane expression) of PD-L1 is at least 1% (e.g., at least 2%, 3%, 4%, 5%, 10%, 15%, 20%, 25%, 30%, 35%, 40%, 45%, 50%, 60%, 70%, 80%, or 90%). In certain embodiments, the percentage of tumor cells in a sample of the NSCLC that exhibit detectable membrane expression (e.g., partial or complete membrane expression) of PD-L1 is at least 1%. In certain embodiments, the percentage of tumor cells in a sample of the NSCLC that exhibit detectable membrane expression (e.g., partial or complete membrane expression) of PD-L1 is at least 5%. In certain embodiments, the percentage of tumor cells in a sample of the NSCLC that exhibit detectable membrane expression (e.g., partial or complete membrane expression) of PD-L1 is at least 25%. In certain embodiments, the percentage of tumor cells in a sample of the NSCLC that exhibit detectable membrane expression (e.g., partial or complete membrane expression) of PD-L1 is at least 50%. In certain embodiments, the NSCLC has no EGFR or ALK genomic tumor aberrations. In certain embodiments, the NSCLC has no EGFR sensitizing mutation (e.g., mutation that is amenable to treatment with a tyrosine kinase inhibitor including erlotinib, gefitinib, or afatanib) or ALK translocation. In certain embodiments, the subject has received no prior systemic chemotherapy treatment for NSCLC.

In certain embodiments, the metastatic or locally advanced solid tumor is a metastatic or locally advanced NSCLC. In certain embodiments, the metastatic or locally advanced solid tumor is a metastatic NSCLC. In certain embodiments, the metastatic or locally advanced solid tumor is a Stage IV, metastatic, or locally advanced NSCLC. In certain embodiments, the metastatic or locally advanced solid tumor is a Stage IV NSCLC. In certain embodiments, the percentage of tumor cells in a sample of the metastatic or locally advanced NSCLC that exhibit detectable membrane expression (e.g., partial or complete membrane expression) of PD-L1 is at least 1% (e.g., at least 2%, 3%, 4%, 5%, 10%, 15%, 20%, 25%, 30%, 35%, 40%, 45%, 50%, 60%, 70%, 80%, or 90%). In certain embodiments, the percentage of tumor cells in a sample of the metastatic or locally advanced NSCLC that exhibit detectable membrane expression (e.g., partial or complete membrane expression) of PD-L1 is at least 1%. In certain embodiments, the percentage of tumor cells in a sample of the metastatic or locally advanced NSCLC that exhibit detectable membrane expression (e.g., partial or complete membrane expression) of PD-L1 is at least 5%. In certain embodiments, the percentage of tumor cells in a sample of the metastatic or locally advanced NSCLC that exhibit detectable membrane expression (e.g., partial or complete membrane expression) of PD-L1 is at least 25%. In certain embodiments, the percentage of tumor cells in a sample of the metastatic or locally advanced NSCLC that exhibit detectable membrane expression (e.g., partial or complete membrane expression) of PD-L1 is at least 50%. In certain embodiments, the metastatic or locally advanced NSCLC has no EGFR or ALK genomic tumor aberrations. In certain embodiments, the metastatic or locally advanced NSCLC has no EGFR sensitizing mutation (e.g., mutation that is amenable to treatment with a tyrosine kinase inhibitor including erlotinib, gefitinib, or afatanib) or ALK translocation. In certain embodiments, the subject has received no prior systemic chemotherapy treatment for metastatic or locally advanced NSCLC.

In certain embodiments, the subject has NSCLC (e.g., Stage IV, metastatic, or locally advanced NSCLC), optionally wherein the percentage of tumor cells in a sample of the NSCLC that exhibit detectable expression (e.g., membrane expression, partial or complete membrane expression) of PD-L1 is at least 1%, 2%, 3%, 4%, 5%, 10%, 15%, 20%, 25%, 30%, 35%, 40%, 45%, 50%, 60%, 70%, 80%, or 90%, and the method comprises administering to the subject an effective amount of an anti-PD-1 antibody described herein, e.g., AGEN2034 (IgG$_4$ S228P), or pharmaceutical composition comprising such anti-PD-1 antibody as a first cancer therapy after diagnosis of the cervical cancer (e.g., within 1, 2, 3, 4, 5, or 6 days; 1, 2, 3, 4, 6, 8, or 12 weeks; or, 1, 2, 3, 4, 6, 8, or 12 months after diagnosis), optionally wherein the anti-PD-1 antibody described herein, e.g., AGEN2034 (IgG$_4$ S228P), or pharmaceutical composition comprising such anti-PD-1 antibody is administered at the dosage and at the frequency shown in a single row of Table 13 herein. In certain embodiments, the subject has NSCLC (e.g., Stage IV, metastatic, or locally advanced NSCLC), optionally wherein the percentage of tumor cells in a sample of the NSCLC that exhibit detectable expression (e.g., membrane expression, partial or complete membrane expression) of PD-L1 is at least 1%, 2%, 3%, 4%, 5%, 10%, 15%, 20%, 25%, 30%, 35%, 40%, 45%, 50%, 60%, 70%, 80%, or 90%, and the method comprises administering to the subject an effective amount of a therapeutic combination comprising (a) an anti-CTLA-4 antibody described herein, e.g., AGEN1884 (IgG$_1$), or pharmaceutical composition comprising such anti-CTLA-4 antibody; and (b) an anti-PD-1 antibody described herein, e.g., AGEN2034 (IgG$_4$ S228P), or pharmaceutical composition comprising such anti-PD-1 antibody as a first cancer therapy after diagnosis of the cervical cancer (e.g., within 1, 2, 3, 4, 5, or 6 days; 1, 2, 3, 4, 6, 8, or 12 weeks; or, 1, 2, 3, 4, 6, 8, or 12 months after diagnosis), optionally wherein the anti-CTLA-4 antibody described herein, e.g., AGEN1884 (IgG$_1$), or pharmaceutical composition comprising such anti-CTLA-4 antibody, and the anti-PD-1 antibody described herein, e.g., AGEN2034 (IgG$_4$ S228P), or pharmaceutical composition comprising such anti-PD-1 antibody, are administered at the dosage and at the frequency shown in a single row of Table 13 herein. In certain embodiments, the subject has NSCLC (e.g., Stage IV, metastatic, or locally advanced NSCLC), optionally wherein the percentage of tumor cells in a sample of the NSCLC that exhibit detectable expression (e.g., membrane expression, partial or complete membrane expression) of PD-L1 is at least 1%, 2%, 3%, 4%, 5%, 10%, 15%, 20%, 25%, 30%, 35%, 40%, 45%, 50%, 60%, 70%, 80%, or 90%, and the method comprises administering to the subject a therapeutic combination comprising (a) an anti-CTLA-4 antibody described herein, e.g., AGEN1884 (IgG$_1$), or pharmaceutical composition comprising such anti-CTLA-4 antibody, and (b) pembrolizumab or pharmaceutical composition comprising pembrolizumab as a first cancer therapy after diagnosis of the cervical cancer (e.g., within 1, 2, 3, 4, 5, or 6 days; 1, 2, 3, 4, 6, 8, or 12 weeks; or, 1, 2, 3, 4, 6, 8, or 12 months after diagnosis), optionally wherein the anti-CTLA-4 antibody described herein, e.g., AGEN1884 (IgG$_1$), or pharmaceutical composition comprising such anti-CTLA-4 antibody is administered at the dosage and at the frequency shown in a single row of Table 13 herein, and pembrolizumab or pharmaceutical composition comprising pembrolizumab is administered at 200 mg every three weeks.

In certain embodiments, the cancer is a cutaneous squamous-cell carcinoma (cSCC) (e.g., a Stage IV cSCC). In certain embodiments, the metastatic or locally advanced solid tumor is a Stage IV cSCC. In certain embodiments, the cSCC is diagnosed histologically or cytologically according to the eighth edition of the American Joint Committee on Cancer staging manual. In certain embodiments, the cSCC is not curable with radiation therapy. In certain embodiments, the subject has cSCC (e.g., Stage IV cSCC), and the method comprises administering to the subject an effective amount of an anti-PD-1 antibody described herein, e.g., AGEN2034 (IgG$_4$ S228P), or pharmaceutical composition comprising such anti-PD-1 antibody as a first cancer therapy after diagnosis of the cSCC (e.g., within 1, 2, 3, 4, 5, or 6 days; 1, 2, 3, 4, 6, 8, or 12 weeks; or, 1, 2, 3, 4, 6, 8, or 12 months after diagnosis), optionally wherein the anti-PD-1 antibody described herein, e.g., AGEN2034 (IgG$_4$ S228P), or pharmaceutical composition comprising such anti-PD-1 antibody is administered at the dosage and at the frequency shown in a single row of Table 13 herein. In certain embodiments, the subject has cSCC (e.g., Stage IV cSCC), and the method comprises administering to the subject an effective amount of a therapeutic combination comprising (a) an anti-CTLA-4 antibody described herein, e.g., AGEN1884 (IgG$_1$), or pharmaceutical composition comprising such anti-CTLA-4 antibody; and (b) an anti-PD-1 antibody described herein, e.g., AGEN2034 (IgG$_4$ S228P), or pharmaceutical composition comprising such anti-PD-1 antibody as a first cancer therapy after diagnosis of the cSCC (e.g., within 1, 2, 3, 4, 5, or 6 days; 1, 2, 3, 4, 6, 8, or 12 weeks; or, 1, 2, 3, 4, 6, 8, or 12 months after diagnosis), optionally wherein the anti-CTLA-4 antibody described herein, e.g., AGEN1884 (IgG$_1$), or pharmaceutical composition comprising such anti-CTLA-4 antibody and the anti-PD-1 antibody described herein, e.g., AGEN2034 (IgG$_4$ S228P), or pharmaceutical composition comprising such anti-PD-1 antibody are administered at the dosage and at the frequency shown in a single row of Table 13 herein. In certain embodiments, the subject has cSCC (e.g., Stage IV cSCC), and the method comprises administering to the subject an effective amount of a therapeutic combination comprising (a) an anti-CTLA-4 antibody described herein, e.g., AGEN1884 (IgG$_1$), or pharmaceutical composition comprising such anti-CTLA-4 antibody; and (b) pembrolizumab or pharmaceutical composition comprising pembrolizumab as a first cancer therapy after diagnosis of the cSCC (e.g., within 1, 2, 3, 4, 5, or 6 days; 1, 2, 3, 4, 6, 8, or 12 weeks; or, 1, 2, 3, 4, 6, 8, or 12 months after diagnosis), optionally wherein the anti-CTLA-4 antibody described herein, e.g., AGEN1884 (IgG$_1$), or pharmaceutical composition comprising such anti-CTLA-4 antibody is administered at the dosage and at the frequency shown in a single row of Table 13 herein, and pembrolizumab or pharmaceutical composition comprising pembrolizumab is administered at 200 mg every three weeks.

In certain embodiments, any of the antibodies and therapeutic combinations described herein (e.g., the first and/or second isolated antibodies, or a combination of the first antibody and pembrolizumab) can be administered as a first cancer therapy after diagnosis of the metastatic or locally advanced solid tumor (e.g., within 1, 2, 3, 4, 5, or 6 days; 1, 2, 3, 4, 6, 8, or 12 weeks; or, 1, 2, 3, 4, 6, 8, or 12 months after diagnosis). In certain embodiments, any of the antibodies and therapeutic combinations described herein (e.g., the first and/or second isolated antibodies, or a combination of the first antibody and pembrolizumab) can be administered as the first cancer therapy after diagnosis of tumor progression (e.g., within 1, 2, 3, 4, 5, or 6 days; 1, 2, 3, 4, 6, 8, or 12 weeks; or, 1, 2, 3, 4, 6, 8, or 12 months after diagnosis of tumor progression) that has occurred despite previous treatment of the tumor with a different cancer therapy, optionally wherein the isolated antibody or therapeutic combination is the second cancer therapy administered. In certain embodiments, any of the antibodies and therapeutic combinations described herein (e.g., the first and/or second isolated antibodies, or a combination of the first antibody and pembrolizumab) can be administered as the first cancer therapy after diagnosis of toxicity of a different cancer therapy (e.g., within 1, 2, 3, 4, 5, or 6 days; 1, 2, 3, 4, 6, 8, or 12 weeks; or, 1, 2, 3, 4, 6, 8, or 12 months after diagnosis of toxicity of the different cancer therapy), optionally wherein the isolated antibody or therapeutic combination is the second cancer therapy administered. In certain embodiments, the first and second isolated antibodies are administered as the first cancer therapy about 1, 2, 3, 4, 5, or 6 days after diagnosis of the metastatic or locally advanced solid tumor. In certain embodiments, the first and second isolated antibodies are administered as the first cancer therapy about 1 or 2 weeks after diagnosis of the metastatic or locally advanced solid tumor.

In another aspect, the instant disclosure provides a method of treating cancer in a subject, the method comprising administering to the subject an effective amount of a therapeutic combination comprising a first isolated antibody that specifically binds to CTLA-4 (e.g., human CTLA-4) and a second isolated antibody that specifically binds to PD-1 (e.g., human PD-1), wherein the first isolated antibody binds to the same epitope of human CTLA-4 as an antibody comprising a heavy chain variable region comprising the amino acid sequence of SEQ ID NO: 1 and a light chain variable region comprising the amino acid sequence of SEQ ID NO: 14.

In another aspect, the instant disclosure provides a method of treating cancer in a subject, the method comprising administering to the subject an effective amount of a therapeutic combination comprising a first isolated antibody that specifically binds to CTLA-4 (e.g., human CTLA-4) and a second isolated antibody that specifically binds to PD-1 (e.g., human PD-1), wherein the second isolated antibody binds to the same epitope of human PD-1 as an antibody comprising a heavy chain variable region comprising the amino acid sequence of SEQ ID NO: 66 and a light chain variable region comprising the amino acid sequence of SEQ ID NO: 74.

In another aspect, the instant disclosure provides a method of treating cancer in a subject, the method comprising administering to the subject an effective amount of a therapeutic combination comprising a first isolated antibody that specifically binds to CTLA-4 (e.g., human CTLA-4) and a second isolated antibody that specifically binds to PD-1 (e.g., human PD-1), wherein the first isolated antibody binds to the same epitope of human CTLA-4 as an antibody comprising a heavy chain variable region comprising the amino acid sequence of SEQ ID NO: 1 and a light chain variable region comprising the amino acid sequence of SEQ ID NO: 14, and wherein the second isolated antibody binds to the same epitope of human PD-1 as an antibody comprising a heavy chain variable region comprising the amino acid sequence of SEQ ID NO: 66 and a light chain variable region comprising the amino acid sequence of SEQ ID NO: 74.

In certain embodiments, the second isolated antibody is antagonistic to human PD-1.

In another aspect, the instant disclosure provides a method of enhancing or inducing an immune response in a subject, the method comprising administering to the subject an effective amount of a therapeutic combination comprising a first isolated antibody that specifically binds to human CTLA-4 and a second isolated antibody that specifically binds to human PD-1, wherein:
  a) the first isolated antibody comprises a heavy chain variable region having an amino acid sequence derived from a human IGHV3-21 germline sequence, and optionally a light chain variable region having an amino acid sequence derived from a human IGKV3-20 or IGKV3-11 germline sequence; and/or
  b) the second isolated antibody comprises a heavy chain variable region having an amino acid sequence derived from a human IGHV3-33 germline sequence, and optionally a light chain variable region having an amino acid sequence derived from a human IGKV3-15 germline sequence.

In another aspect, the instant disclosure provides a method of treating cancer in a subject, the method comprising administering to the subject an effective amount of a therapeutic combination comprising a first isolated antibody that specifically binds to human CTLA-4 and a second isolated antibody that specifically binds to human PD-1, wherein:
  a) the first isolated antibody comprises a heavy chain variable region having an amino acid sequence derived from a human IGHV3-21 germline sequence, and optionally a light chain variable region having an amino acid sequence derived from a human IGKV3-20 or IGKV3-11 germline sequence; and/or
  b) the second isolated antibody comprises a heavy chain variable region having an amino acid sequence derived from a human IGHV3-33 germline sequence, and optionally a light chain variable region having an amino acid sequence derived from a human IGKV3-15 germline sequence.

In another aspect, the instant disclosure provides a method of treating infectious disease in a subject, the method comprising administering to the subject an effective amount of a therapeutic combination comprising a first isolated antibody that specifically binds to human CTLA-4 and a second isolated antibody that specifically binds to human PD-1, wherein:
  a) the first isolated antibody comprises a heavy chain variable region having an amino acid sequence derived from a human IGHV3-21 germline sequence, and optionally a light chain variable region having an amino acid sequence derived from a human IGKV3-20 or IGKV3-11 germline sequence; and/or
  b) the second isolated antibody comprises a heavy chain variable region having an amino acid sequence derived from a human IGHV3-33 germline sequence, and optionally a light chain variable region having an amino acid sequence derived from a human IGKV3-15 germline sequence.

In another aspect, the instant disclosure provides a pharmaceutical composition comprising a first isolated antibody that specifically binds to CTLA-4 (e.g., human CTLA-4) and a second isolated antibody that specifically binds to PD-1 (e.g., human PD-1), wherein the first isolated antibody comprises a heavy chain variable region comprising complementarity determining regions CDRH1, CDRH2, and CDRH3 and a light chain variable region comprising complementarity determining regions CDRL1, CDRL2, and CDRL3, wherein:
  (a) CDRH1 comprises the amino acid sequence of SYX$_1$MX$_2$ (SEQ ID NO: 39), wherein
    X$_1$ is S or A; and
    X$_2$ is N or S;
  (b) CDRH2 comprises the amino acid sequence of SISSSSSYIYYADSVKG (SEQ ID NO: 22);
  (c) CDRH3 comprises the amino acid sequence of VGLMGPFXI (SEQ ID NO: 115), wherein X is D or N;
  (d) CDRL1 comprises the amino acid sequence of RASQSVX$_1$X$_2$YLX$_3$ (SEQ ID NO: 43), wherein:
    X$_1$ is S or G;
    X$_2$ is R, S, or T; and
    X$_3$ is G or A;
  (e) CDRL2 comprises the amino acid sequence of X$_1$X$_2$SX$_3$RAT (SEQ ID NO: 44), wherein:
    X$_1$ is G or A;
    X$_2$ is A or T; and
    X$_3$ is T, S, R, or N; and
  (f) CDRL3 comprises the amino acid sequence of QQYGX$_1$SPX$_2$T (SEQ ID NO: 45), wherein:
    X$_1$ is S or T; and
    X$_2$ is W or F,
  and wherein the second isolated antibody comprises a heavy chain variable region comprising complementarity determining regions CDRH1, CDRH2 and CDRH3 and a light chain variable region comprising complementarity determining regions CDRL1, CDRL2 and CDRL3, wherein:
  (g) CDRH1 comprises the amino acid sequence of SYGMH (SEQ ID NO: 75);
  (h) CDRH2 comprises the amino acid sequence of VIWX$_1$DGSNX$_2$YYADSVX$_3$G (SEQ ID NO: 86), wherein
    X$_1$ is Y or F;
    X$_2$ is K or E; and
    X$_3$ is K or M;

(i) CDRH3 comprises the amino acid sequence of NX$_1$DX$_2$ (SEQ ID NO: 87), wherein
X$_1$ is G or V; and
X$_2$ is H or Y;
(j) CDRL1 comprises the amino acid sequence of RASQSVSSNLA (SEQ ID NO: 83);
(k) CDRL2 comprises the amino acid sequence of GASTRAT (SEQ ID NO: 84); and
(l) CDRL3 comprises the amino acid sequence of QQYNNWPRT (SEQ ID NO: 85).

In certain embodiments of the pharmaceutical composition, CDRH1, CDRH2, CDRH3, CDRL1, CDRL2, and CDRL3 of the first isolated antibody comprise the amino acid sequences set forth in SEQ ID NOs: 20, 22, 24, 27, 30, and 36; 20, 22, 24, 29, 32, and 37; 20, 22, 24, 29, 33, and 38; 21, 22, 24, 27, 30, and 36; 21, 22, 24, 29, 33, and 38; 20, 22, 24, 28, 31, and 36; 20, 22, 24, 29, 34, and 36; 20, 22, 24, 29, 35, and 38; 21, 22, 26, 27, 30, and 36; 21, 22, 26, 29, 32, and 37; 21, 22, 26, 29, 33, and 38; or 21, 22, 26, 29, 35, and 38, respectively, and wherein CDRH1, CDRH2, CDRH3, CDRL1, CDRL2, and CDRL3 of the second isolated antibody comprise the amino acid sequences set forth in SEQ ID NOs: 75, 76, 80, 83, 84, and 85; 75, 76, 81, 83, 84, and 85; 75, 76, 82, 83, 84, and 85; 75, 77, 81, 83, 84, and 85; 75, 78, 81, 83, 84, and 85; or 75, 79, 81, 83, 84, and 85, respectively.

In certain embodiments of the pharmaceutical composition, the heavy chain variable region and the light chain variable region of the first isolated antibody comprise the amino acid sequences set forth in SEQ ID NOs: 1 and 14; 1 and 16, 1 and 17; 9 and 14; 9 and 17; 10 and 15; 10 and 17; 10 and 18; 10 and 19; 11 and 15; 11 and 14; 11 and 16; 11 and 17; 12 and 14; 12 and 16; 12 and 17; 12 and 19; 13 and 15; or 13 and 17, respectively, and wherein the heavy chain variable region and the light chain variable region of the second isolated antibody comprise the amino acid sequences set forth in SEQ ID NOs: 66 and 74; 67 and 74; 68 and 74; 69 and 74; 70 and 74; 71 and 74; 72 and 74; or 73 and 74, respectively.

In another aspect, the instant disclosure provides a kit comprising a first isolated antibody that specifically binds to CTLA-4 (e.g., human CTLA-4) and a second isolated antibody that specifically binds to PD-1 (e.g., human PD-1), wherein the first isolated antibody comprises a heavy chain variable region comprising complementarity determining regions CDRH1, CDRH2, and CDRH3 and a light chain variable region comprising complementarity determining regions CDRL1, CDRL2, and CDRL3, wherein:
(a) CDRH1 comprises the amino acid sequence of SYX$_1$MX$_2$ (SEQ ID NO: 39), wherein
X$_1$ is S or A; and
X$_2$ is N or S;
(b) CDRH2 comprises the amino acid sequence of SISSSSSYIYYADSVKG (SEQ ID NO: 22);
(c) CDRH3 comprises the amino acid sequence of VGLMGPFXI (SEQ ID NO: 115), wherein X is D or N;
(d) CDRL1 comprises the amino acid sequence of RASQSVX$_1$X$_2$YLX$_3$ (SEQ ID NO: 43), wherein:
X$_1$ is S or G;
X$_2$ is R, S, or T; and
X$_3$ is G or A;
(e) CDRL2 comprises the amino acid sequence of X$_1$X$_2$SX$_3$RAT (SEQ ID NO: 44), wherein:
X$_1$ is G or A;
X$_2$ is A or T; and
X$_3$ is T, S, R, or N; and
(f) CDRL3 comprises the amino acid sequence of QQYGX$_1$SPX$_2$T (SEQ ID NO: 45), wherein:
X$_1$ is S or T; and
X$_2$ is W or F,
and wherein the second isolated antibody comprises a heavy chain variable region comprising complementarity determining regions CDRH1, CDRH2 and CDRH3 and a light chain variable region comprising complementarity determining regions CDRL1, CDRL2 and CDRL3, wherein:
(g) CDRH1 comprises the amino acid sequence of SYGMH (SEQ ID NO: 75);
(h) CDRH2 comprises the amino acid sequence of VIWX$_1$DGSNX$_2$YYADSVX$_3$G (SEQ ID NO: 86), wherein
X$_1$ is Y or F;
X$_2$ is K or E; and
X$_3$ is K or M;
(i) CDRH3 comprises the amino acid sequence of NX$_1$DX$_2$ (SEQ ID NO: 87), wherein
X$_1$ is G or V; and
X$_2$ is H or Y;
(j) CDRL1 comprises the amino acid sequence of RASQSVSSNLA (SEQ ID NO: 83);
(k) CDRL2 comprises the amino acid sequence of GASTRAT (SEQ ID NO: 84); and
(l) CDRL3 comprises the amino acid sequence of QQYNNWPRT (SEQ ID NO: 85).

In certain embodiments of the kit, the CDRH1, CDRH2, CDRH3, CDRL1, CDRL2, and CDRL3 of the first isolated antibody comprise the amino acid sequences set forth in SEQ ID NOs: 20, 22, 24, 27, 30, and 36; 20, 22, 24, 29, 32, and 37; 20, 22, 24, 29, 33, and 38; 21, 22, 24, 27, 30, and 36; 21, 22, 24, 29, 33, and 38; 20, 22, 24, 28, 31, and 36; 20, 22, 24, 29, 34, and 36; 20, 22, 24, 29, 35, and 38; 21, 22, 26, 27, 30, and 36; 21, 22, 26, 29, 32, and 37; 21, 22, 26, 29, 33, and 38; or 21, 22, 26, 29, 35, and 38, respectively, and wherein CDRH1, CDRH2, CDRH3, CDRL1, CDRL2, and CDRL3 of the second isolated antibody comprise the amino acid sequences set forth in SEQ ID NOs: 75, 76, 80, 83, 84, and 85; 75, 76, 81, 83, 84, and 85; 75, 76, 82, 83, 84, and 85; 75, 77, 81, 83, 84, and 85; 75, 78, 81, 83, 84, and 85; or 75, 79, 81, 83, 84, and 85, respectively.

In certain embodiments of the kit, the heavy chain variable region and the light chain variable region of the first isolated antibody comprise the amino acid sequences set forth in SEQ ID NOs: 1 and 14; 1 and 16, 1 and 17; 9 and 14; 9 and 17; 10 and 15; 10 and 17; 10 and 18; 10 and 19; 11 and 15; 11 and 14; 11 and 16; 11 and 17; 12 and 14; 12 and 16; 12 and 17; 12 and 19; 13 and 15; or 13 and 17, respectively, and wherein the heavy chain variable region and the light chain variable region of the second isolated antibody comprise the amino acid sequences set forth in SEQ ID NOs: 66 and 74; 67 and 74; 68 and 74; 69 and 74; 70 and 74; 71 and 74; 72 and 74; or 73 and 74, respectively.

In another aspect, the instant disclosure provides a kit comprising a first isolated antibody that specifically binds to CTLA-4 (e.g., human CTLA-4) and a second isolated antibody that specifically binds to PD-1 (e.g., human PD-1), wherein the heavy chain variable region and the light chain variable region of the first isolated antibody comprise the amino acid sequences set forth in SEQ ID NOs: 1 and 14, respectively, and wherein the heavy chain variable region and the light chain variable region of the second isolated antibody comprise the amino acid sequences set forth in SEQ ID NOs: 66 and 74, respectively.

In another aspect, the instant disclosure provides a kit comprising a first isolated antibody that specifically binds to CTLA-4 (e.g., human CTLA-4) and a second isolated antibody that specifically binds to PD-1 (e.g., human PD-1), wherein the heavy chain variable region and the light chain variable region of the first isolated antibody comprise the amino acid sequences set forth in SEQ ID NOs: 1 and 14, respectively, and wherein the heavy chain variable region and the light chain variable region of the second isolated antibody comprise the amino acid sequences set forth in SEQ ID NOs: 67 and 74, respectively.

In another aspect, the instant disclosure provides a kit comprising a first isolated antibody that specifically binds to CTLA-4 (e.g., human CTLA-4) and a second isolated antibody that specifically binds to PD-1 (e.g., human PD-1), wherein the heavy chain and the light chain of the first isolated antibody comprise the amino acid sequences set forth in SEQ ID NOs: 51 and 59; or 117 and 59, respectively, and wherein the heavy chain variable region and the light chain variable region of the second isolated antibody comprise the amino acid sequences set forth in SEQ ID NOs: 91 and 93; 92 and 93; or 120 and 93, respectively.

In another aspect, the instant disclosure provides a kit comprising a first isolated antibody that specifically binds to CTLA-4 (e.g., human CTLA-4) and a second isolated antibody that specifically binds to PD-1 (e.g., human PD-1), wherein the heavy chain and the light chain of the first isolated antibody comprise the amino acid sequences set forth in SEQ ID NOs: 51 and 59, respectively, and wherein the heavy chain variable region and the light chain variable region of the second isolated antibody comprise the amino acid sequences set forth in SEQ ID NOs: 91 and 93, respectively.

In another aspect, the instant disclosure provides a kit comprising a first isolated antibody that specifically binds to CTLA-4 (e.g., human CTLA-4) and a second isolated antibody that specifically binds to PD-1 (e.g., human PD-1), wherein the heavy chain and the light chain of the first isolated antibody comprise the amino acid sequences set forth in SEQ ID NOs: 51 and 59, respectively, and wherein the heavy chain variable region and the light chain variable region of the second isolated antibody comprise the amino acid sequences set forth in SEQ ID NOs: 92 and 93, respectively.

In another aspect, the instant disclosure provides a kit comprising a first isolated antibody that specifically binds to CTLA-4 (e.g., human CTLA-4) and a second isolated antibody that specifically binds to PD-1 (e.g., human PD-1), wherein the heavy chain and the light chain of the first isolated antibody comprise the amino acid sequences set forth in SEQ ID NOs: 51 and 59, respectively, and wherein the heavy chain variable region and the light chain variable region of the second isolated antibody comprise the amino acid sequences set forth in SEQ ID NOs: 120 and 93, respectively.

In another aspect, the instant disclosure provides a multispecific antibody comprising a first antigen-binding region that specifically binds to CTLA-4 (e.g., human CTLA-4) and a second antigen-binding region that specifically binds to PD-1 (e.g., human PD-1), wherein the first antigen-binding region comprises a heavy chain variable region comprising complementarity determining regions CDRH1, CDRH2, and CDRH3 and a light chain variable region comprising complementarity determining regions CDRL1, CDRL2, and CDRL3, wherein:
(a) CDRH1 comprises the amino acid sequence of SYX$_1$MX$_2$ (SEQ ID NO: 39), wherein
X$_1$ is S or A; and
X$_2$ is N or S;

(b) CDRH2 comprises the amino acid sequence of SISSSSSYIYYADSVKG (SEQ ID NO: 22);
(c) CDRH3 comprises the amino acid sequence of VGLMGPFXI (SEQ ID NO: 115), wherein X is D or N;
(d) CDRL1 comprises the amino acid sequence of RASQSVX$_1$X$_2$YLX$_3$ (SEQ ID NO: 43), wherein:
X$_1$ is S or G;
X$_2$ is R, S, or T; and
X$_3$ is G or A;
(e) CDRL2 comprises the amino acid sequence of X$_1$X$_2$SX$_3$RAT (SEQ ID NO: 44), wherein:
X$_1$ is G or A;
X$_2$ is A or T; and
X$_3$ is T, S, R, or N; and
(f) CDRL3 comprises the amino acid sequence of QQYGX$_1$SPX$_2$T (SEQ ID NO: 45), wherein:
X$_1$ is S or T; and
X$_2$ is W or F, and wherein the second antigen-binding region comprises a heavy chain variable region comprising complementarity determining regions CDRH1, CDRH2 and CDRH3 and a light chain variable region comprising complementarity determining regions CDRL1, CDRL2 and CDRL3, wherein:
(g) CDRH1 comprises the amino acid sequence of SYGMH (SEQ ID NO: 75);
(h) CDRH2 comprises the amino acid sequence of VIWX$_1$DGSNX$_2$YYADSVX$_3$G (SEQ ID NO: 86), wherein
X$_1$ is Y or F;
X$_2$ is K or E; and
X$_3$ is K or M;
(i) CDRH3 comprises the amino acid sequence of NX$_1$DX$_2$ (SEQ ID NO: 87), wherein
X$_1$ is G or V; and
X$_2$ is H or Y;
(j) CDRL1 comprises the amino acid sequence of RASQSVSSNLA (SEQ ID NO: 83);
(k) CDRL2 comprises the amino acid sequence of GASTRAT (SEQ ID NO: 84); and
(l) CDRL3 comprises the amino acid sequence of QQYNNWPRT (SEQ ID NO: 85).

In certain embodiments of the multispecific antibody, CDRH1, CDRH2, CDRH3, CDRL1, CDRL2, and CDRL3 of the first antigen-binding region comprise the amino acid sequences set forth in SEQ ID NOs: 20, 22, 24, 27, 30, and 36; 20, 22, 24, 29, 32, and 37; 20, 22, 24, 29, 33, and 38; 21, 22, 24, 27, 30, and 36; 21, 22, 24, 29, 33, and 38; 20, 22, 24, 28, 31, and 36; 20, 22, 24, 29, 34, and 36; 20, 22, 24, 29, 35, and 38; 21, 22, 26, 27, 30, and 36; 21, 22, 26, 29, 32, and 37; 21, 22, 26, 29, 33, and 38; or 21, 22, 26, 29, 35, and 38, respectively, and wherein CDRH1, CDRH2, CDRH3, CDRL1, CDRL2, and CDRL3 of the second antigen-binding region comprise the amino acid sequences set forth in SEQ ID NOs: 75, 76, 80, 83, 84, and 85; 75, 76, 81, 83, 84, and 85; 75, 76, 82, 83, 84, and 85; 75, 77, 81, 83, 84, and 85; 75, 78, 81, 83, 84, and 85; or 75, 79, 81, 83, 84, and 85, respectively.

In certain embodiments of the multispecific antibody, the heavy chain variable region and the light chain variable region of the first antigen-binding region comprise the amino acid sequences set forth in SEQ ID NOs: 1 and 14; 1 and 16, 1 and 17; 9 and 14; 9 and 17; 10 and 15; 10 and 17; 10 and 18; 10 and 19; 11 and 15; 11 and 14; 11 and 16; 11 and 17; 12 and 14; 12 and 16; 12 and 17; 12 and 19; 13 and 15; or 13 and 17, respectively, and wherein the heavy chain variable region and the light chain variable region of the second antigen-binding region comprise the amino acid sequences set forth in SEQ ID NOs: 66 and 74; 67 and 74; 68 and 74; 69 and 74; 70 and 74; 71 and 74; 72 and 74; or 73 and 74, respectively.

In another aspect, the instant disclosure provides a multispecific antibody comprising a first antigen-binding region that specifically binds to CTLA-4 (e.g., human CTLA-4) and a second antigen-binding region that specifically binds to PD-1 (e.g., human PD-1), wherein the first antigen-binding region comprises a heavy chain variable region and a light chain variable region comprising the amino acid sequences set forth in SEQ ID NOs: 1 and 14, respectively, and wherein the second antigen-binding region comprises a heavy chain variable region and a light chain variable region comprising the amino acid sequences set forth in SEQ ID NOs: 66 and 74, respectively.

In another aspect, the instant disclosure provides a multispecific antibody comprising a first antigen-binding region that specifically binds to CTLA-4 (e.g., human CTLA-4) and a second antigen-binding region that specifically binds to PD-1 (e.g., human PD-1), wherein the first antigen-binding region comprises a heavy chain variable region and a light chain variable region comprising the amino acid sequences set forth in SEQ ID NOs: 1 and 14, respectively, and wherein the second antigen-binding region comprises a heavy chain variable region and a light chain variable region comprising the amino acid sequences set forth in SEQ ID NOs: 67 and 74, respectively.

In another aspect, the instant disclosure provides a multispecific antibody comprising a first antigen-binding region that specifically binds to CTLA-4 (e.g., human CTLA-4) and a second antigen-binding region that specifically binds to PD-1 (e.g., human PD-1), wherein the first antigen-binding region comprises a heavy chain and a light chain comprising the amino acid sequences set forth in SEQ ID NOs: 51 and 59; or 117 and 59, respectively, and wherein the second antigen-binding region comprises a heavy chain and a light chain comprising the amino acid sequences set forth in SEQ ID NOs: 91 and 93; 92 and 93; or 120 and 93, respectively.

In another aspect, the instant disclosure provides a multispecific antibody comprising a first antigen-binding region that specifically binds to CTLA-4 (e.g., human CTLA-4) and a second antigen-binding region that specifically binds to PD-1 (e.g., human PD-1), wherein the first antigen-binding region comprises a heavy chain and a light chain comprising the amino acid sequences set forth in SEQ ID NOs: 51 and 59, respectively, and wherein the second antigen-binding region comprises a heavy chain and a light chain comprising the amino acid sequences set forth in SEQ ID NOs: 91 and 93, respectively.

In another aspect, the instant disclosure provides a multispecific antibody comprising a first antigen-binding region that specifically binds to CTLA-4 (e.g., human CTLA-4) and a second antigen-binding region that specifically binds to PD-1 (e.g., human PD-1), wherein the first antigen-binding region comprises a heavy chain and a light chain comprising the amino acid sequences set forth in SEQ ID NOs: 51 and 59, respectively, and wherein the second antigen-binding region comprises a heavy chain and a light chain comprising the amino acid sequences set forth in SEQ ID NOs: 92 and 93, respectively.

In another aspect, the instant disclosure provides a multispecific antibody comprising a first antigen-binding region that specifically binds to CTLA-4 (e.g., human CTLA-4) and a second antigen-binding region that specifically binds to PD-1 (e.g., human PD-1), wherein the first antigen-binding region comprises a heavy chain and a light chain comprising the amino acid sequences set forth in SEQ ID NOs: 51 and 59, respectively, and wherein the second antigen-binding region comprises a heavy chain and a light chain comprising the amino acid sequences set forth in SEQ ID NOs: 120 and 93, respectively.

A multispecific antibody comprising a first antigen-binding region that specifically binds to human CTLA-4 and a second antigen-binding region that specifically binds to human PD-1, wherein:
  a) the first antigen-binding region comprises a heavy chain variable region having an amino acid sequence derived from a human IGHV3-21 germline sequence, and optionally a light chain variable region having an amino acid sequence derived from a human IGKV3-20 or IGKV3-11 germline sequence; and/or
  b) the second antigen-binding region comprises a heavy chain variable region having an amino acid sequence derived from a human IGHV3-33 germline sequence, and optionally a light chain variable region having an amino acid sequence derived from a human IGKV3-15 germline sequence.

In another aspect, the instant disclosure provides a method of enhancing or inducing an immune response in a subject, the method comprising administering to the subject a multispecific antibody described herein.

In another aspect, the instant disclosure provides a method of treating cancer in a subject, the method comprising administering to the subject a multispecific antibody described herein.

In another aspect, the instant disclosure provides a method of treating infectious disease in a subject, the method comprising administering to the subject a multispecific antibody described herein.

In another aspect, the instant disclosure provides a therapeutic combination, a multispecific antibody, a kit, and/or a pharmaceutical composition described herein for use in treating cancer, treating infectious disease, or enhancing or inducing an immune response in a subject.

In another aspect, the instant disclosure provides a therapeutic combination, a multispecific antibody, a kit, and/or a pharmaceutical composition described herein for use in the preparation of a medicament for treating cancer, treating infectious disease, or enhancing or inducing an immune response in a subject.

In another aspect, the instant disclosure provides the use of a therapeutic combination, a multispecific antibody, a kit, and/or a pharmaceutical composition described herein in the preparation of a medicament for treating cancer, treating infectious disease, or enhancing or inducing an immune response in a subject. The instant disclosure also provides the use of the therapeutic combination or multispecific antibody for preparing a kit, and/or a pharmaceutical composition for treating cancer, treating infectious disease, or enhancing or inducing an immune response in a subject.

In certain embodiments of any one of the methods, pharmaceutical compositions, therapeutic combinations, or kits described herein, the N-terminal amino acid residue of the heavy chain variable region and/or the light chain variable region of the first antibody has been converted to pyroglutamate. In certain embodiments of any one of the methods, pharmaceutical compositions, therapeutic combinations, or kits described herein, the N-terminal amino acid residue of the heavy chain variable region and/or the light chain variable region of the second antibody has been converted to pyroglutamate. In certain embodiments of any one of the methods, pharmaceutical compositions, therapeutic combinations, or kits described herein, the N-terminal amino acid residue of the heavy chain variable region and/or the light chain variable region of the first antibody has been converted to pyroglutamate, and the N-terminal amino acid residue of the heavy chain variable region and/or the light chain variable region of the second antibody has been converted to pyroglutamate.

In certain embodiments of any one of the multispecific antibodies described herein, the N-terminal amino acid residue of the heavy chain variable region and/or the light chain variable region of the first antigen-binding region has been converted to pyroglutamate. In certain embodiments of any one of the multispecific antibodies described herein, the N-terminal amino acid residue of the heavy chain variable region and/or the light chain variable region of the second antigen-binding region has been converted to pyroglutamate. In certain embodiments of any one of the multispecific antibodies described herein, the N-terminal amino acid residue of the heavy chain variable region and/or the light chain variable region of the first antigen-binding region has been converted to pyroglutamate, and the N-terminal amino acid residue of the heavy chain variable region and/or the light chain variable region of the second antigen-binding region has been converted to pyroglutamate.

5. BRIEF DESCRIPTION OF THE DRAWINGS

Figure 1B:
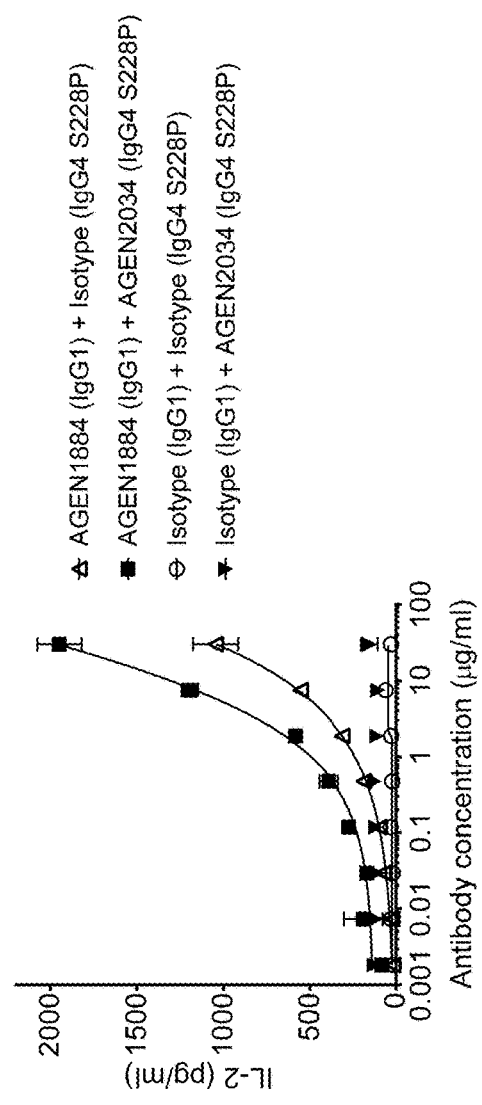

FIGS. 1A and 1B are graphs showing IL-2 production of primary human PBMCs following incubation with the Staphylococcal Enterotoxin A (SEA) superantigen in the presence of a dose titration of an anti-CTLA-4 antibody AGEN1884 ($IgG_1$) or an isotype control antibody ($IgG_1$) in combination with 10 μg/ml of an anti-PD-1 antibody AGEN2034 ($IgG_4$ S228P) or an isotype control antibody ($IgG_4$ S228P). Shown in FIGS. 1A and 1B are data generated using PBMCs from two different donors.

Figure 2A:
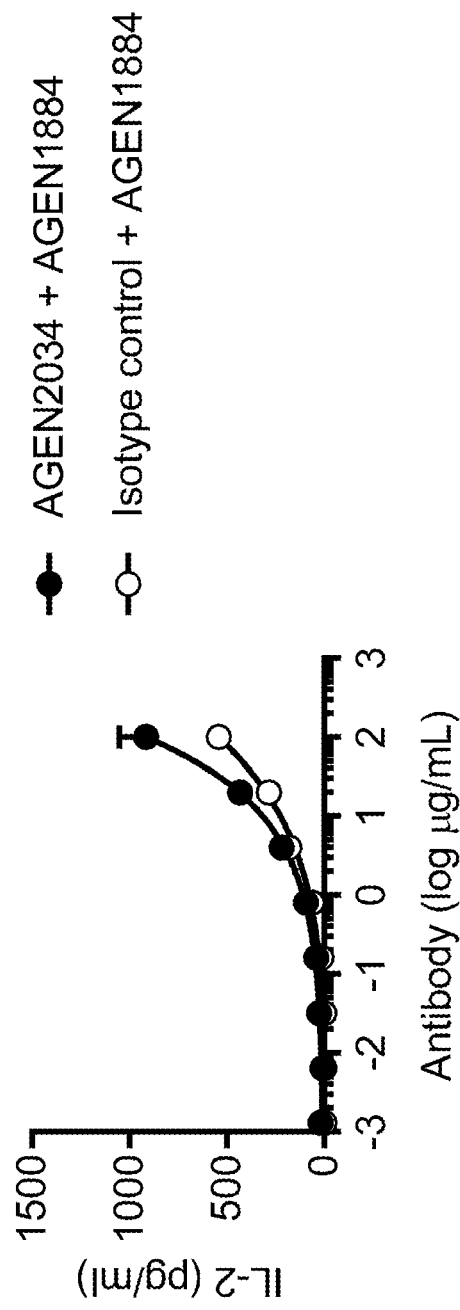
Figure 2B:
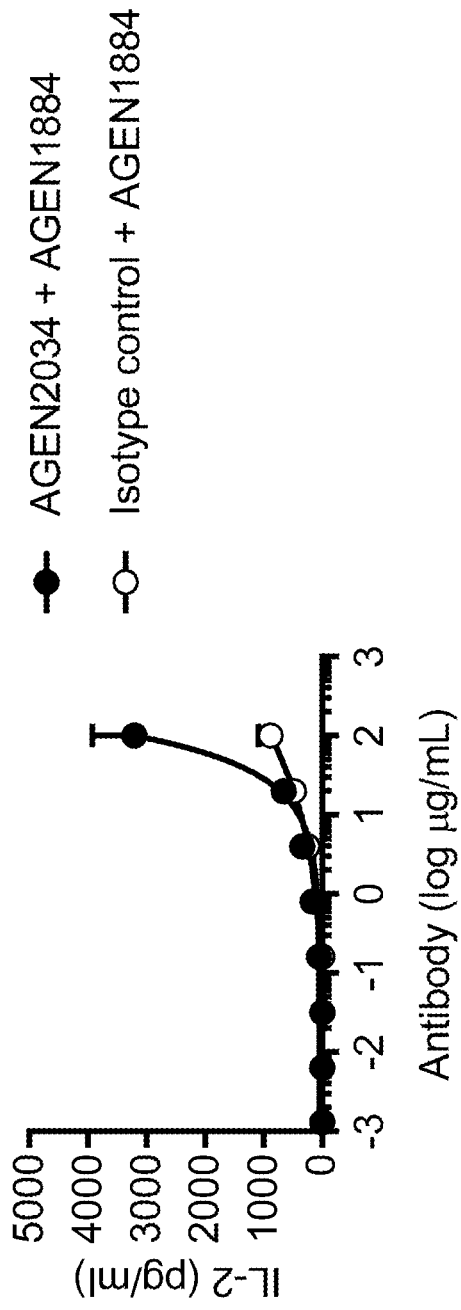

FIGS. 2A and 2B are graphs showing IL-2 production by primary human PBMCs following incubation with SEA superantigen in the presence of a dose titration of anti-CTLA-4 antibody AGEN1884 ($IgG_1$) in combination with 20 μg/ml of anti-PD-1 antibody AGEN2034 ($IgG_4$ S228P) or an isotype control antibody ($IgG_4$ S228P). Shown in FIGS. 2A and 2B are data generated using PBMCs from two different donors.

Figure 3:
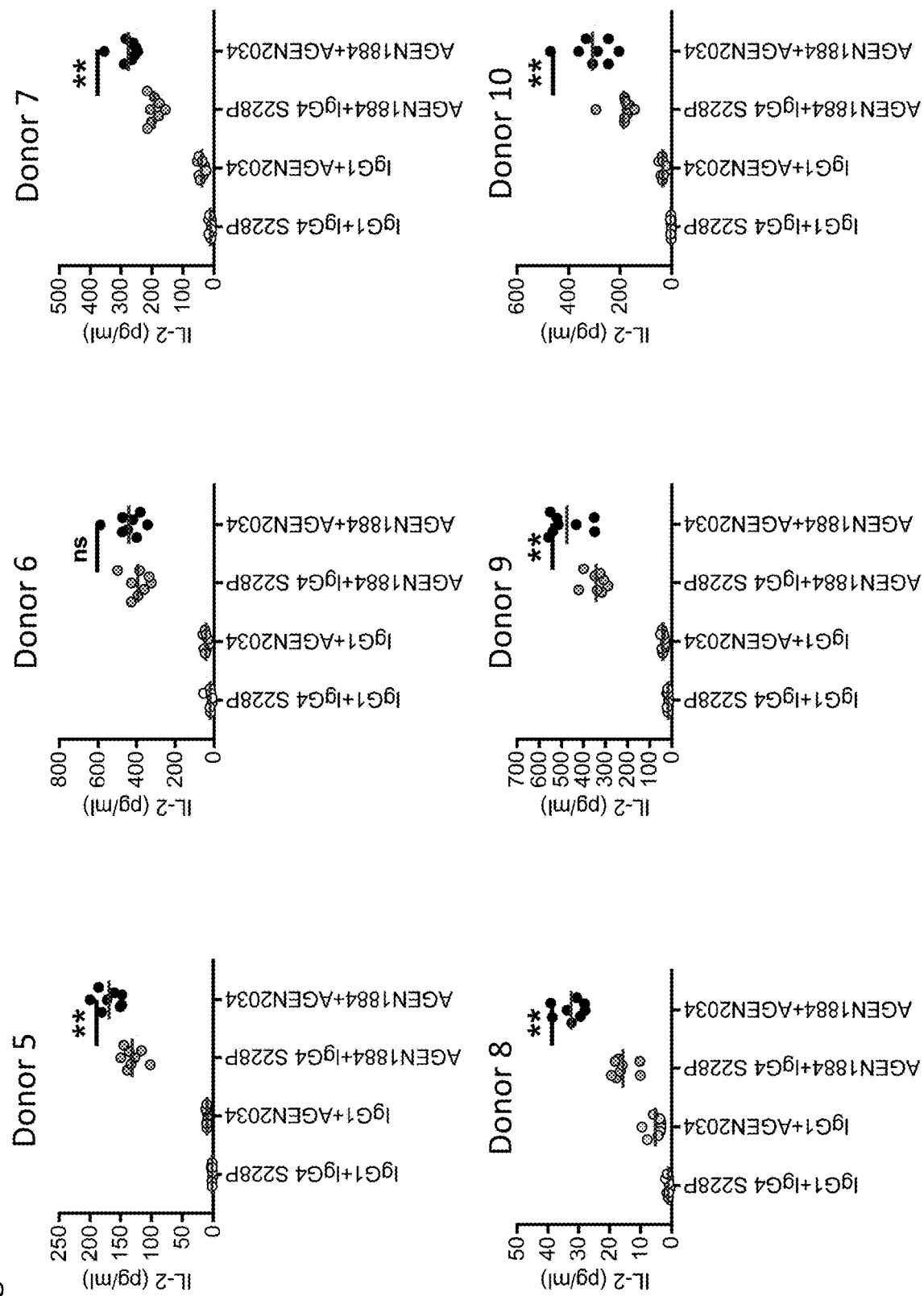

FIG. 3 is a series of graphs showing IL-2 production by primary human PBMCs following incubation with SEA superantigen in the presence of 10 μg/ml of an anti-CTLA-4 antibody AGEN1884 ($IgG_1$) or an isotype control antibody ($IgG_1$) in combination with 10 μg/ml of an anti-PD-1 antibody AGEN2034 ($IgG_4$ S228P) or an isotype control antibody ($IgG_4$ S228P). Each graph in FIG. 3 shows data generated using PBMCs from a different donor, as indicated. Calculated p-values are shown as: ns=not significant, *=p<0.05, **=p<0.005.

Figure 4:
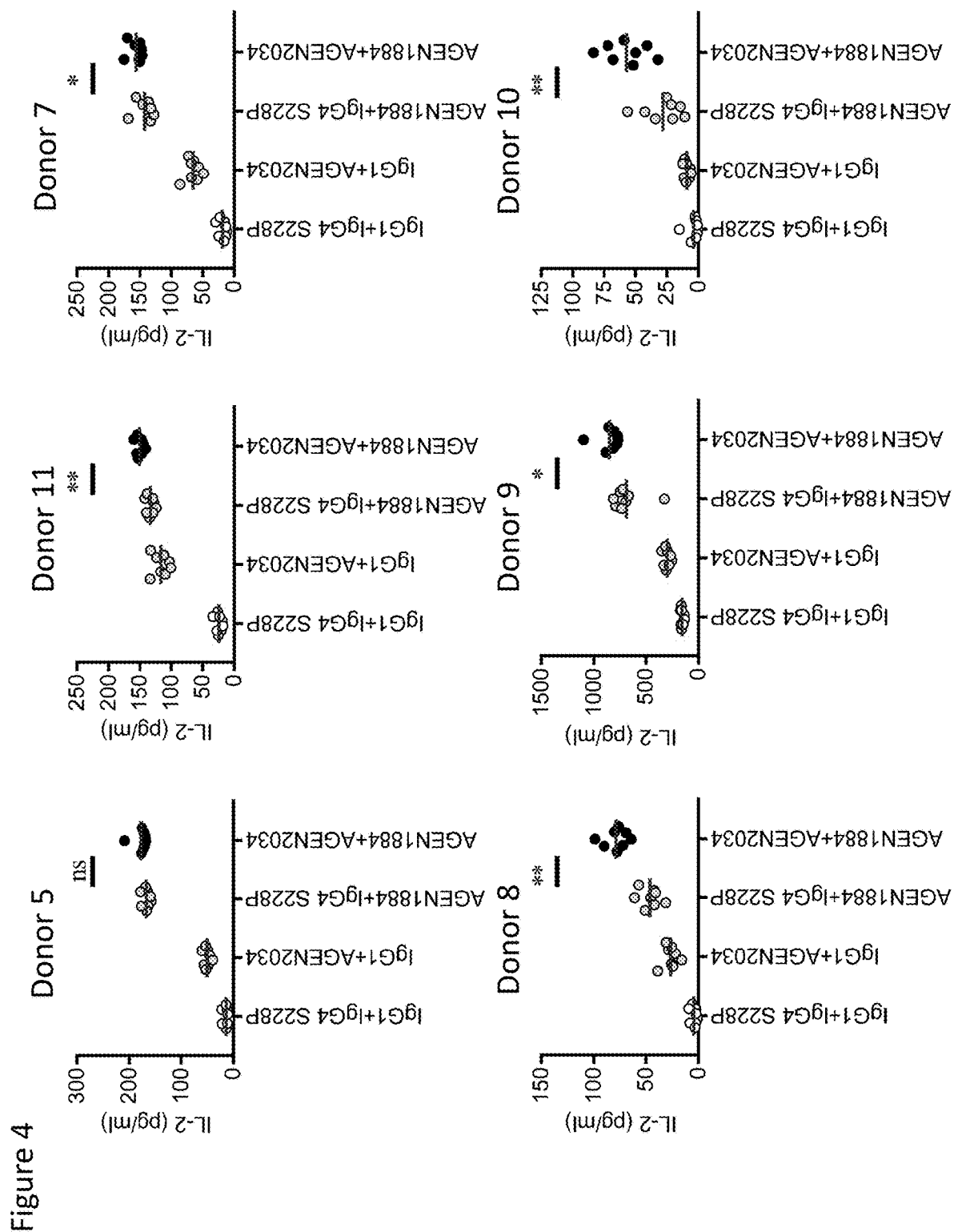

FIG. 4 is a series of graphs showing IL-2 production by primary human PBMCs following incubation with SEA superantigen in the presence of 10 μg/ml of an anti-CTLA-4 antibody AGEN1884 ($IgG_1$) or an isotype control antibody ($IgG_1$) in combination with 10 μg/ml of an anti-PD-1 antibody AGEN2034 ($IgG_4$ S228P) or an isotype control antibody ($IgG_4$ S228P). Each graph in FIG. 4 shows data generated using PBMCs from a different donor, as indicated. Calculated p-values are shown as ns=not significant, *=p<0.05, **=p<0.005.

Figures 5A, 5B, 5C:
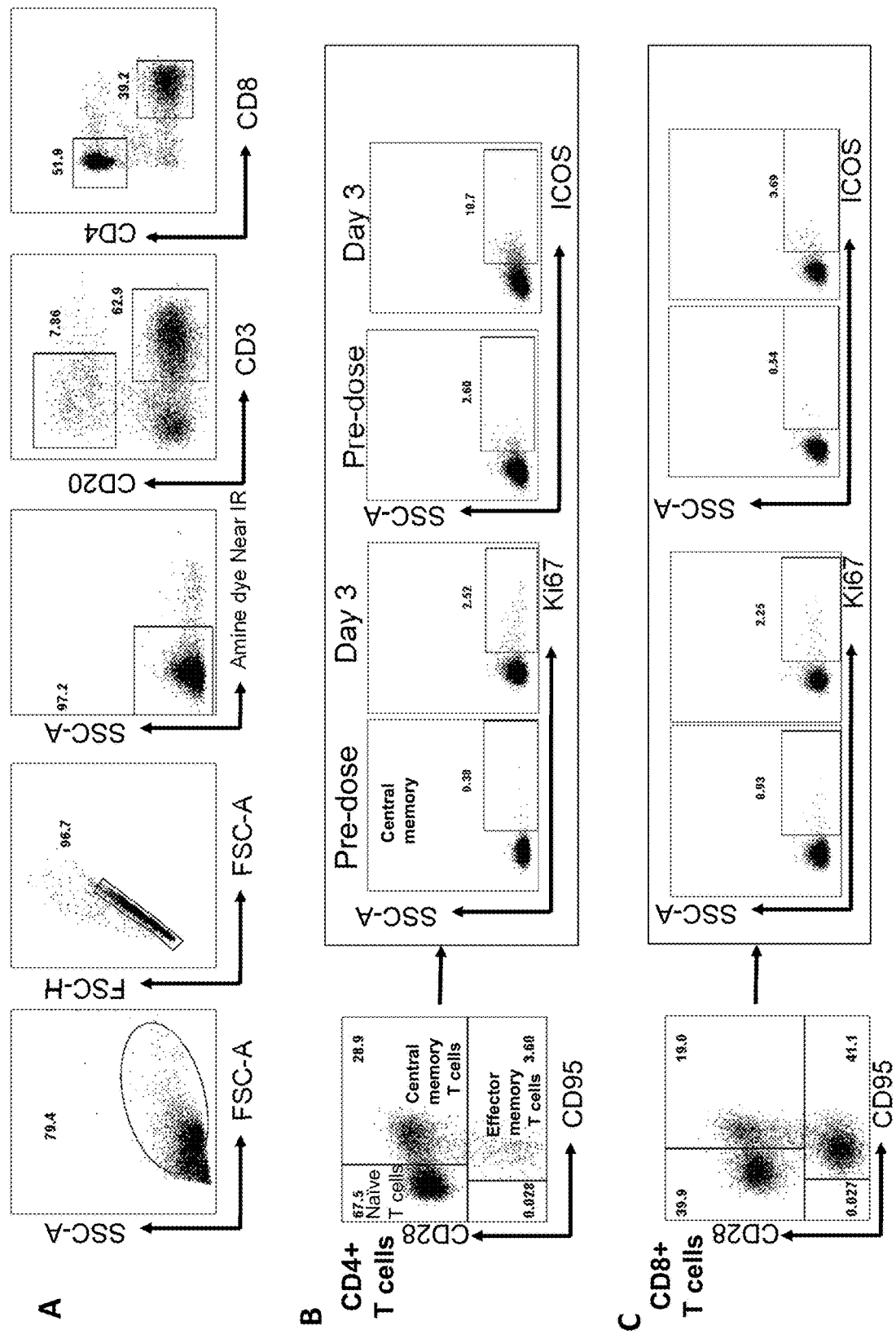

FIGS. 5A-5C are a series of graphs showing the effect of the combination of anti-CTLA-4 antibody AGEN1884 ($IgG_1$) and anti-PD-1 antibody AGEN2034 ($IgG_4$ S228P) on central memory T cell activation and proliferation in a non-human primate. FIG. 5A shows a gating strategy and representative flow cytometry plots for T cell populations from primary PBMCs isolated from a cynomolgus monkey. In this gating strategy, lymphocytes were gated based on side scatter (SSC-A) vs. forward scatter (FSC-A), followed by singlets (FSC-A vs FSC-H). Live cells were selected (SSC-A vs. amine dye NearIR) and then CD20+ B cells and CD3+ T cells were selected. T cell populations were then defined as follows: CD4 naïve T cells (CD3+, CD4+, CD28+, CD95−), CD8 naïve T cells (CD3+, CD8+, CD28+, CD95−), CD4 central memory T cells (CD3+, CD4+, CD28+, CD95+), CD8 central memory T cells (CD3+, CD8+, CD28+, CD95+), CD4 effector memory T cells (CD3+, CD4+, CD28−, CD95+), and CD8 effector memory T cells (CD3+, CD8+, CD28−, CD95+). FIGS. 5B and 5C show representative flow cytometry plots for the frequencies of Ki67+(proliferating) or ICOS+(activated) CD4+ central memory T cells, or Ki67+(proliferating) or ICOS+(activated) CD8+ central memory T cells, respectively.

Figures 6A, 6B, 6C, 6D:
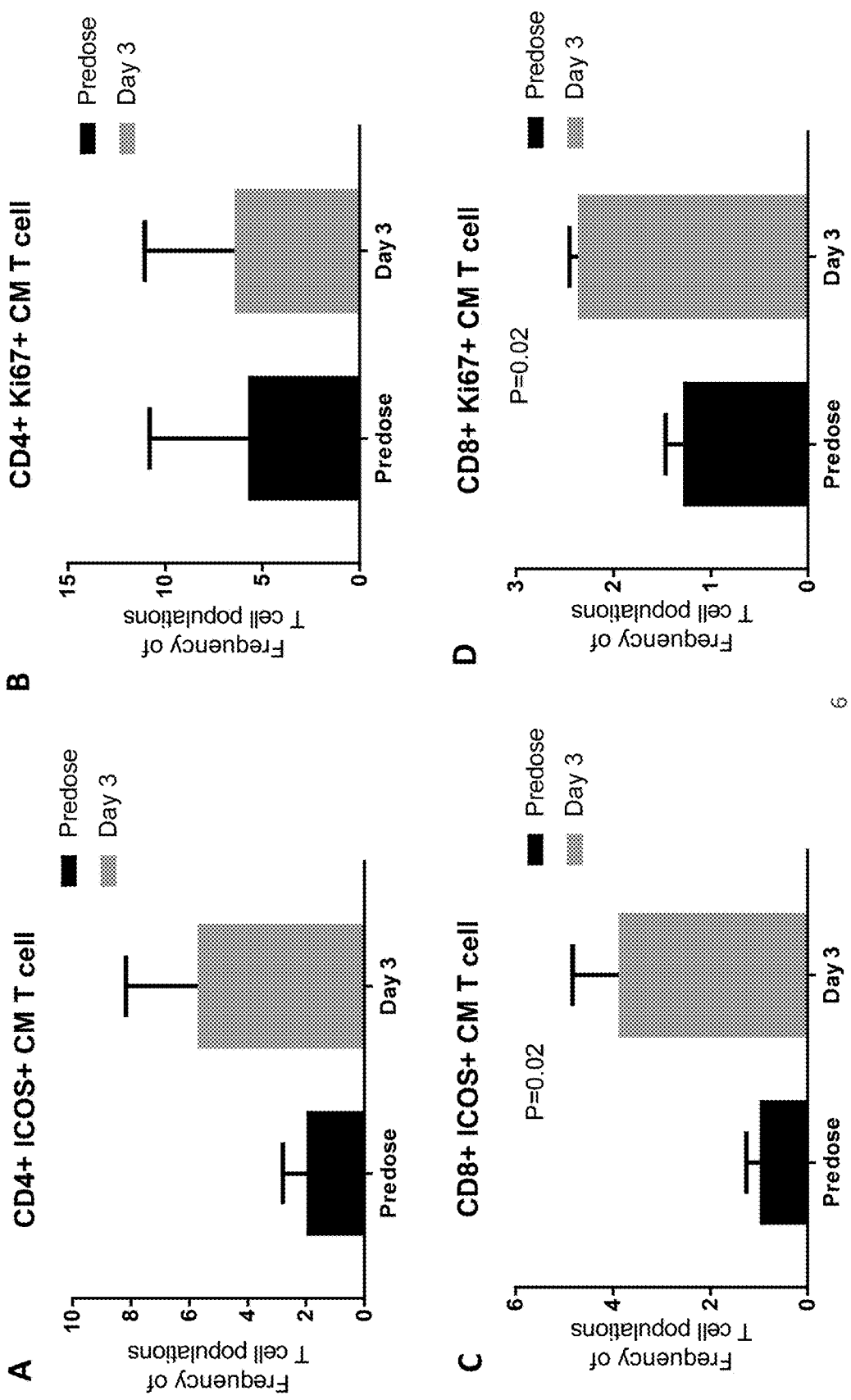

FIGS. 6A-6D are a series of graphs showing elevated central memory T cell activation and proliferation in cynomolgus monkey PBMCs three days after treatment with AGEN1884 ($IgG_1$) and AGEN2034 ($IgG_4$ S228P), relative to pre-dose levels (n=4 animals, including the animal for which flow cytometry plots are shown in FIG. 5). The frequency of each of the following T cell populations was determined by flow cytometry: $CD4^+ICOS^+$ central memory T cells (FIG. 6A); $CD4^+Ki67^+$ central memory T cells (FIG. 6B); $CD8^+ICOS^+$central memory T cells (FIG. 6C); and $CD8^+Ki67^+$central memory T cells (FIG. 6D).

FIGS. 7A, 7B, and 7C are a series of sequence alignments. FIG. 7A is a sequence alignment for human CTLA-4 (SEQ ID NO: 65), cynomolgus monkey CTLA-4 (SEQ ID NO: 108), mouse CTLA-4 (SEQ ID NO: 109), and rat CTLA-4 (SEQ ID NO: 110). Dots represent residues identical to corresponding human residues. An "*" (asterisk) indicates positions which have a single, fully conserved residue. A ":" (colon) indicates conservation between groups of strongly similar properties. A "." (period) indicates conservation between groups of weakly similar properties. FIGS. 7B and 7C are sequence alignments for human CTLA-4 (residues 1-144 and 145-223 of SEQ ID NO: 65, respectively), cynomolgus monkey CTLA-4 (residues 1-144 and 145-223 of SEQ ID NO: 108, respectively), human CD28 (residues 1-127 and 128-220 of SEQ ID NO: 111, respectively), human ICOS (residues 1-124 and 125-199 of SEQ ID NO: 112, respectively), human BTLA (residues 1-125 and 126-289 of SEQ ID NO: 113, respectively), and human PD-1 (residues 1-143 and 144-288 of SEQ ID NO: 96, respectively). The two regions showing strong decrease in deuterium uptake when human CTLA-4 was bound to AGEN1884-Fab are underlined in FIGS. 7A-C: residues 80-82 (QVT, SEQ ID NO: 102) and residues 135-149 (YPPPYYLGIGNGTQI, SEQ ID NO: 100), numbered according to SEQ ID NO: 65.

6. DETAILED DESCRIPTION

The instant disclosure provides antibodies that specifically bind to CTLA-4 (e.g., human CTLA-4) and/or PD-1 (e.g., human PD-1) and antagonize CTLA-4 and/or PD-1 function, e.g., immune suppression mediated by CTLA-4 and/or PD-1. Also provided are pharmaceutical compositions and kits comprising these antibodies, nucleic acids encoding these antibodies, expression vectors and host cells for making these antibodies, and methods of treating a subject using these antibodies. The antibodies described herein are particularly useful for increasing T cell activation in response to an antigen (e.g., a tumor antigen or an infectious disease antigen), and hence for treating cancer in a subject or treating or preventing an infectious disease in a subject.

The skilled worker will appreciate that a glutamate (E) or glutamine (Q) amino acid residue at the N-terminus of a heavy chain variable region and/or a light chain variable region of any one of the antibodies described herein (e.g., an anti-PD-1 antibody, an anti-CTLA4 antibody, or an anti-CTLA-4/PD-1 antibody) can, under certain conditions, spontaneously convert to pyroglutamate by post-translational cyclization of the free amino group to form a lactam. Accordingly, in certain embodiments of each and every one of the methods, uses, pharmaceutical compositions, multispecific antibodies, or kits described herein, the N-terminal amino acid residue of one or more heavy chain variable regions and/or light chain variable regions of an anti-PD-1 antibody, an anti-CTLA4 antibody, and/or an anti-CTLA-4/PD-1 antibody has been converted to pyroglutamate (e.g., as a result of post-translational cyclization of the free amino group of the N-terminal E or Q residue).

6.1 Definitions

As used herein, the terms "about" and "approximately," when used to modify a numeric value or numeric range, indicate that deviations of 5% to 10% above and 5% to 10% below the value or range remain within the intended meaning of the recited value or range.

As used herein, the term "CTLA-4" refers to cytotoxic T-lymphocyte-associated protein 4. As used herein, the term "human CTLA-4" refers to a human CTLA-4 protein encoded by a wild type human CTLA-4 gene, e.g., GenBank™ accession number NM_005214.4 or NM_001037631.2. An exemplary immature amino acid sequence of human CTLA-4 is provided as SEQ ID NO: 65.

As used herein, the term "PD-1" refers to programmed cell death protein 1. As used herein, the term "human PD-1" refers to a human PD-1 protein encoded by a wild type human PD-1 gene, e.g., GenBank™ accession number NM_005018.2, XM_006712573.2 or XM_017004293.1. An exemplary immature amino acid sequence of human PD-1 is provided as SEQ ID NO: 96.

As used herein, the terms "antibody" and "antibodies" include full length antibodies, antigen-binding fragments of full length antibodies, and molecules comprising antibody CDRs, VH regions or VL regions. Examples of antibodies include monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA or IgY), any class (e.g., IgG$_1$, IgG$_2$, IgG$_3$, IgG$_4$, IgA$_1$ or IgA$_2$), or any subclass (e.g., IgG$_{2a}$ or IgG$_{2b}$) of immunoglobulin molecule. In certain embodiments, antibodies described herein are IgG antibodies, or a class (e.g., human IgG$_1$ or IgG$_4$) or subclass thereof. In a specific embodiment, the antibody is a humanized monoclonal antibody. In another specific embodiment, the antibody is a human monoclonal antibody.

"Multispecific" antibodies are antibodies with at least two different antigen-binding sites. Multispecific antibodies include bispecific antibodies that contain two different antigen-binding sites (exclusive of the Fc region). Examples of multispecific antibodies include recombinantly produced antibodies, human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-Id) antibodies (including, e.g., anti-anti-Id antibodies), and antigen-binding fragments of any of the above. Multispecific antibodies can be of any type (e.g., IgG, IgE, IgM, IgD, IgA or IgY), any class (e.g., IgG$_1$, IgG$_2$, IgG$_3$, IgG$_4$, IgA$_1$ or IgA$_2$), or any subclass (e.g., IgG$_{2a}$ or IgG$_{2b}$) of immunoglobulin molecule. In certain embodiments, multispecific antibodies described herein are IgG antibodies, or a class (e.g., human IgG$_1$ or IgG$_4$) or subclass thereof.

As used herein, the term "anti-CTLA-4/PD-1" antibody refers to a multispecific antibody (e.g., a bispecific antibody) that contains an antigen-binding region that specifically binds to CTLA-4 (e.g., human CTLA-4) and an antigen-binding region that specifically binds to PD-1 (e.g., human PD-1).

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), by Chothia et al., J. Mol. Biol. 196:901-917 (1987), and by MacCallum et al., J. Mol. Biol. 262:732-745 (1996), all of which are incorporated by reference in their entireties, where the definitions include overlapping or subsets of amino acid residues when compared against each other. CDRH1, CDRH2 and CDRH3 denote the heavy chain CDRs, and CDRL1, CDRL2 and CDRL3 denote the light chain CDRs.

As used herein, the term "framework (FR) amino acid residues" refers to those amino acids in the framework region of an immunoglobulin chain. The term "framework region" or "FR region" as used herein, includes the amino acid residues that are part of the variable region, but are not part of the CDRs (e.g., using the Kabat or MacCallum definition of CDRs).

As used herein, the terms "variable region" and "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable region are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

As used herein, the terms "constant region" and "constant domain" are interchangeable and are common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable region.

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

The term "Kabat numbering" and like terms are recognized in the art and refer to a system of numbering amino acid residues in the heavy and light chain variable regions of an antibody, or an antigen-binding portion thereof. In certain aspects, the CDRs of an antibody can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242, each of which is herein incorporated by reference in its entirety). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

As used herein, the terms "constant region" and "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable region.

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., IgG1, IgG2, IgG3, and IgG4.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

As used herein, the term "EU numbering system" refers to the EU numbering convention for the constant regions of an antibody, as described in Edelman, G. M. et al., Proc. Natl. Acad. USA, 63, 78-85 (1969) and Kabat et al, Sequences of Proteins of Immunological Interest, U.S. Dept. Health and Human Services, 5th edition, 1991.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIAcore® or KinExA.

As used herein, the terms "specifically binds," "specifically recognizes," "immunospecifically binds," and "immunospecifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, ID), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind non-specifically to another antigen.

In another embodiment, molecules that specifically bind to an antigen do not cross react with other proteins under similar binding conditions. In one specific embodiment, an anti-CTLA-4 antibody, an anti-PD-1 antibody, and an anti-CTLA-4/anti-PD-1 antibody do not cross react with other non-CTLA-4 proteins, non PD-1-proteins, and non-CTLA-4 and non PD-1-proteins, respectively. In a specific embodiment, provided herein is an antibody that specifically binds to CTLA-4 (e.g., human CTLA-4) and/or PD-1 (e.g., human PD-1) with higher affinity than to another unrelated antigen. In certain embodiments, provided herein is an antibody that specifically binds to CTLA-4 (e.g., human CTLA-4) and/or PD-1 (e.g., human PD-1) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an anti-CTLA-4 antibody described herein to an unrelated, non-CTLA-4 protein is less than 10%, 15%, or 20% of the binding of the antibody to CTLA-4 protein as measured by, e.g., a radioimmunoassay. In another specific embodiment, the extent of binding of an anti-PD-1 antibody described herein to an unrelated, non-PD-1 protein is less than 10%, 15%, or 20% of the binding of the antibody to PD-1 protein as measured by, e.g., a radioimmunoassay. In another specific embodiment, the extent of binding of an anti-CTLA-4/PD-1 antibody described herein to an unrelated, non-CTLA-4 and non-PD-1 protein is less than 10%, 15%, or 20% of the binding of the antibody to CTLA-4 and/or PD-1 protein as measured by, e.g., a radioimmunoassay.

As used herein, the term "afucosylation" or "afucosylated" in the context of an Fc refers to a substantial lack of a fucose covalently attached, directly or indirectly, to residue 297 of the human $IgG_1$ Fc region, numbered according to the EU index (Kabat et al., Sequences of Proteins of Immunological Interest, 5th Ed. Public Health Service, National Institutes of Health, Bethesda, Md. (1991)), or the corresponding residue in non-$IgG_1$ or non-human $IgG_1$ immunoglobulins. Thus, in a composition comprising a plurality of afucosylated antibodies, at least 70% of the antibodies will not be fucosylated, directly or indirectly (e.g., via intervening sugars) at residue 297 of the Fc region of the antibodies, and in some embodiments at least 80%, 85%, 90%, 95%, or 99% will not be fucosylated, directly or indirectly, at residue 297 of the Fc region.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization may be accomplished using any of the known methods in the art (e.g., Giege R et al., (1994) Acta Crystallogr D Biol Crystallogr 50 (Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. 2004/0014194), and BUSTER (Bricogne G (1993) Acta Crystallogr D Biol Crystallogr 49 (Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques. In a specific embodiment, the epitope of an antibody is determined using alanine scanning mutagenesis studies.

As used herein, the term "treat," "treating," and "treatment" refer to therapeutic or preventative measures described herein. The methods of "treatment" employ administration of an antibody to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "therapeutic combination" refers to the combination of a first therapy and the second therapy administered to a subject. The first therapy and the second therapy can be administered simultaneously (in the same pharmaceutical composition or in separate pharmaceutical compositions) or sequentially in any order.

As used herein, the term "effective amount" in the context of the administration of a therapy to a subject refers to the amount of a therapy that achieves a desired prophylactic or therapeutic effect. The effective amount of a therapeutic combination of a first therapy and a second therapy includes a first amount of the first therapy and a second amount of the second therapy, wherein the administration of the therapeutic combination achieves a desired prophylactic or therapeutic effect.

As used herein with respect to the response of a cancer to a therapy, the terms "refractory" and "resistant" have their art-recognized meaning and are used interchangeably.

As used herein, the term "subject" includes any human or non-human animal.

As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell are not necessarily identical to the parent cell transfected with the nucleic acid molecule, e.g., due to mutations or environmental influences that may occur in succeeding generations or integration of the nucleic acid molecule into the host cell genome.

The determination of "percent identity" between two sequences (e.g., amino acid sequences or nucleic acid sequences) can also be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993)

PNAS 90: 5873-5877. Such an algorithm is incorporated into the NBLAST and XBLAST programs of Altschul S F et al., (1990) J Mol Biol 215: 403. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

As used herein, the term "internalization" or "internalized" refers to the uptake of an antibody into an intracellular compartment of a cell upon binding of the antibody to an antigen expressed at the surface of the cell.

6.2 Antibodies

6.2.1 Anti-CTLA-4 Antibodies

In one aspect, the instant disclosure provides antibodies that specifically bind to CTLA-4 (e.g., human CTLA-4) and antagonize CTLA-4 function. Also provided herein are multispecific antibodies that comprise a first antigen-binding region that specifically binds to human CTLA-4 (e.g., human CTLA-4) and, optionally, a second antigen-binding region that does not specifically bind to CTLA-4 (e.g., human CTLA-4). The amino acid sequences of exemplary antibodies are set forth in Tables 1-5, herein.

TABLE 1

Amino acid sequences of exemplary anti-CTLA-4 antibodies.*

| SEQ ID NO: | Description | Amino acid sequence |
|---|---|---|
| 1 | AGEN1884 VH | EVQLVESGGGLVKPGGSLRLSCAASGFTFSSYSMNWVRQAP GKGLEWVSSISSSSSYIYYADSVKGRFTISRDNAKNSLYLQ MNSLRAEDTAVYYCARVGLMGPFDIWGQGTMVTVSS |
| 9 | BADD412-2356 VH | EVQLLESGGGLVQPGGSLRLSCAASGFTFSSYAMSWVRQAP GKGLVWVSSISSSSSYIYYADSVKGRFTISRDNAKNSLYLQ MNSLRAEDTAVYYCARVGLMGPFDIWGQGTMVTVSS |
| 10 | BADD412-2357 VH | EVQLVESGGGLVKPGGSLRLSCAASGFTFSSYSMNWVRQAP GKGLEWVSSISSSSSYIYYADSVKGRFTISRDNAKNTLYLQ MNSLRAEDTAVYYCARVGLMGPFDIWGQGTMVTVSS |
| 11 | BADD412-2358 VH | EVQLLESGGGLVKPGGSLRLSCAASGFTFSSYSMNWVRQAP GKGLEWVSSISSSSSYIYYADSVKGRFTISRDNAKNSLYLQ MNSLRAEDTAVYYCARVGLMGPFDIWGQGTMVTVSS |
| 12 | BADD412-2359 VH | EVQLLESGGGLVQPGGSLRLSCAASGFTFSSYAMSWVRQAP GKGLVWVSSISSSSSYIYYADSVKGRFTISRDNAKNSLYLQ MNSLRAEDTAVYYCARVGLMGPFNIWGQGTMVTVSS |
| 13 | BADD412-2360 VH | EVQLVESGGGLVQPGGSLTLSCAASGFTFSSYSMNWVRQAP GKGLEWVSSISSSSSYIYYADSVKGRFTISRDNAKNSLYLQ MNSLRAEDTAVYYCARVGLMGPFDIWGQGTMVTVSS |
| 14 | AGEN1884 VL | EIVLTQSPGTLSLSPGERATLSCRASQSVSRYLGWYQQKPG QAPRLLIYGASTRATGIPDRFSGSGSGTDFTLTITRLEPED FAVYYCQQYGSSPWTFGQGTKVEIK |
| 15 | BADD412-2367 VL | EIVLTQSPATLSLSPGERATLSCRASQSVGTYLAWYQHKVG QAPRLLIYGASRRATGIPDRFSGSGSGTDFTLTISRLEPED FAVYYCQQYGSSPWTFGQGTKVEIK |
| 16 | BADD412-2382 VL | EIVLTQSPATLSLSPGERATLSCRASQSVSSYLAWYQQKPG QAPSLLIYATSSRATGIPDRFSGSGSVSGTDFTLTISRLEPED FAVYYCQQYGTSPWTFGQGTKVEIK |
| 17 | BADD412-2384 VL | EIVLTQSPATLSFSPGERATLSCRASQSVSSYLAWYQQKPG QAPRLLIYGASSRATGIPDRFSGSGSGTDFTFTISRLEPED FAVYYCQQYGSSPFTFGPGTKVDIK |
| 18 | BADD412-2390 VL | EIVLTQSPATLSVSPGERATLSCRASQSVSSYLAWYQQKPG QAPRLLIYAASTRATGIPDRFSGSASGTDFTLTISRLEPED FAVYYCQQYGSSPWTFGQGTKVEIK |

TABLE 1-continued

Amino acid sequences of exemplary anti-CTLA-4 antibodies.*

| SEQ ID NO: | Description | Amino acid sequence |
|---|---|---|
| 19 | BADD412-2393 VL | EIVLTQSPATLSLSPGERATLSCRASQSVSSYLAWYQQKPG<br>QAPRLLIYGASNRATGIPARFSGSGSGTDFTLTISSLEPED<br>FAVYYCQQYGSSPFTFGPGTKVDIK |
| 20 | CDRH1 | SYSMN |
| 21 | CDRH1 | SYAMS |
| 22 | CDRH2 | SISSSSSYIYYADSVKG |
| 24 | CDRH3 | VGLMGPFDI |
| 26 | CDRH3 | VGLMGPFNI |
| 27 | CDRL1 | RASQSVSRYLG |
| 28 | CDRL1 | RASQSVGTYLA |
| 29 | CDRL1 | RASQSVSSYLA |
| 30 | CDRL2 | GASTRAT |
| 31 | CDRL2 | GASRRAT |
| 32 | CDRL2 | ATSSRAT |
| 33 | CDRL2 | GASSRAT |
| 34 | CDRL2 | AASTRAT |
| 35 | CDRL2 | GASNRAT |
| 36 | CDRL3 | QQYGSSPWT |
| 37 | CDRL3 | QQYGTSPWT |
| 38 | CDRL3 | QQYGSSPFT |
| 39 | CDRH1 consensus sequence | SYX$_1$MX$_2$, wherein<br>X$_1$ is S or A; and<br>X$_2$ is N or S |
| 115 | CDRH3 consensus sequence 1 | VGLMGPFXI, wherein<br>X is D or N |
| 43 | CDRL1 consensus sequence | RASQSVX$_1$X$_2$YLX$_3$, wherein<br>X$_1$ is S or G;<br>X$_2$ is R, S, or T; and<br>X$_3$ is G or A |
| 44 | CDRL2 consensus sequence | X$_1$X$_2$SX$_3$RAT, wherein<br>X$_1$ is G or A;<br>X$_2$ is A or T; and<br>X$_3$ is T, S, R, or N |
| 45 | CDRL3 consensus sequence | QQYGX$_1$SPX$_2$T, wherein<br>X$_1$ is S or T; and<br>X$_2$ is W or F |
| 116 | VH consensus sequence | EVQLX$_1$ESGGGLVX$_2$PGGSLX$_3$LSCAASGFTFSSYX$_4$MX$_5$WVR<br>QAPGKGLX$_6$WVSSISSSSSYIYYADSVKGRFTISRDNAKNX$_7$<br>LYLQMNSLRAEDTAVYYCARVGLMGPFX$_8$IWGQGTMVTVSS,<br>wherein<br>X$_1$ is V or L;<br>X$_2$ is K or Q;<br>X$_3$ is R or T;<br>X$_4$ is S or A;<br>X$_5$ is N or S;<br>X$_6$ is E or V;<br>X$_7$ is S or T; and<br>X$_8$ is D or N |

TABLE 1-continued

Amino acid sequences of exemplary anti-CTLA-4 antibodies.*

| SEQ ID NO: | Description | Amino acid sequence |
|---|---|---|
| 47 | VL consensus sequence | EIVLTQSPX$_1$TLSX$_2$SPGERATLSCRASQSVX$_3$X$_4$YLX$_5$WYQX$_6$KX$_7$GQAPX$_8$LLIYX$_9$X$_{10}$SX$_{11}$RATGIPX$_{12}$RFSGSX$_{13}$SGTDF TX$_{14}$TIX$_{15}$X$_{16}$LEPEDFAVYYCQQYGX$_{17}$SPX$_{18}$TFGX$_{19}$GTKV X$_{20}$IK, wherein<br>X$_1$ is G or A;<br>X$_2$ is L, V, or F;<br>X$_3$ is S or G;<br>X$_4$ is R, T, or S;<br>X$_5$ is G or A;<br>X$_6$ is Q or H;<br>X$_7$ is P or V;<br>X$_8$ is R or S;<br>X$_9$ is G or A;<br>X$_{10}$ is A or T;<br>X$_{11}$ is T, R, S, or N;<br>X$_{12}$ is D or A;<br>X$_{13}$ is G, V, or A;<br>X$_{14}$ is L or F;<br>X$_{15}$ is T or S;<br>X$_{16}$ is R or S;<br>X$_{17}$ is S or T;<br>X$_{18}$ is W or F;<br>X$_{19}$ is Q or P; and<br>X$_{20}$ is E or D |
| 48 | Germline sequence: IGHV3-21*01 | EVQLVESGGGLVKPGGSLRLSCAASGFTFSSYSMNWVRQAP GKGLEWVSSISSSSSYIYYADSVKGRFTISRDNAKNSLYLQ MNSLRAEDTAVYYCAR |
| 49 | Germline sequence: IGKV3-20*01 | EIVLTQSPGTLSLSPGERATLSCRASQSVSSSYLAWYQQKP GQAPRLLIYGASSRATGIPDRFSGSGSGTDFTLTISRLEPE DFAVYYCQQYGSSP |
| 50 | Germline sequence: IGKV3-11*01 | EIVLTQSPATLSLSPGERATLSCRASQSVSSYLAWYQQKPG QAPRLLIYDASNRATGIPARFSGSGSGTDFTLTISSLEPED FAVYYCQQRSNWPP |
| 51 | AGEN1884 (IgG1) heavy chain | EVQLVESGGGLVKPGGSLRLSCAASGFTFSSYSMNWVRQAP GKGLEWVSSISSSSSYIYYADSVKGRFTISRDNAKNSLYLQ MNSLRAEDTAVYYCARVGLMGPFDIWGQGTMVTVSSASTKG PSVFPLAPSSKSTSGGTAALGCLVKDYFPEPVTVSWNSGAL TSGVHTFPAVLQSSGLYSLSSVVTVPSSSLGTQTYICNVNH KPSNTKVDKRVEPKSCDKTHTCPPCPAPELLGGPSVFLFPP KPKDTLMISRTPEVTCVVVDVSHEDPEVKFNWYVDGVEVHN AKTKPREEQYNSTYRVVSVLTVLHQDWLNGKEYKCKVSNKA LPAPIEKTISKAKGQPREPQVYTLPPSREEMTKNQVSLTCL VKGFYPSDIAVEWESNGQPENNYKTTPPVLDSDGSFFLYSK LTVDKSRWQQGNVFSCSVMHEALHNHYTQKSLSLSPG |
| 52 | AGEN1884 (IgG1 S239D/I332E) heavy chain | EVQLVESGGGLVKPGGSLRLSCAASGFTFSSYSMNWVRQAP GKGLEWVSSISSSSSYIYYADSVKGRFTISRDNAKNSLYLQ MNSLRAEDTAVYYCARVGLMGPFDIWGQGTMVTVSSASTKG PSVFPLAPSSKSTSGGTAALGCLVKDYFPEPVTVSWNSGAL TSGVHTFPAVLQSSGLYSLSSVVTVPSSSLGTQTYICNVNH KPSNTKVDKRVEPKSCDKTHTCPPCPAPELLGGPDVFLFPP KPKDTLMISRTPEVTCVVVDVSHEDPEVKFNWYVDGVEVHN AKTKPREEQYNSTYRVVSVLTVLHQDWLNGKEYKCKVSNKA LPAPEEKTISKAKGQPREPQVYTLPPSREEMTKNQVSLTCL VKGFYPSDIAVEWESNGQPENNYKTTPPVLDSDGSFFLYSK LTVDKSRWQQGNVFSCSVMHEALHNHYTQKSLSLSPG |
| 53 | AGEN1884 (IgG1 S239D/A330L/I332E) heavy chain | EVQLVESGGGLVKPGGSLRLSCAASGFTFSSYSMNWVRQAP GKGLEWVSSISSSSSYIYYADSVKGRFTISRDNAKNSLYLQ MNSLRAEDTAVYYCARVGLMGPFDIWGQGTMVTVSSASTKG PSVFPLAPSSKSTSGGTAALGCLVKDYFPEPVTVSWNSGAL TSGVHTFPAVLQSSGLYSLSSVVTVPSSSLGTQTYICNVNH KPSNTKVDKRVEPKSCDKTHTCPPCPAPELLGGPDVFLFPP KPKDTLMISRTPEVTCVVVDVSHEDPEVKFNWYVDGVEVHN AKTKPREEQYNSTYRVVSVLTVLHQDWLNGKEYKCKVSNKA LPLPEEKTISKAKGQPREPQVYTLPPSREEMTKNQVSLTCL VKGFYPSDIAVEWESNGQPENNYKTTPPVLDSDGSFFLYSK LTVDKSRWQQGNVFSCSVMHEALHNHYTQKSLSLSPG |

TABLE 1-continued

Amino acid sequences of exemplary anti-CTLA-4 antibodies.*

| SEQ ID NO: | Description | Amino acid sequence |
|---|---|---|
| 54 | AGEN1884 (IgG1 L235V/F243L/R292P/Y300L/ P396L) heavy chain | EVQLVESGGGLVKPGGSLRLSCAASGFTFSSYSMNWVRQAP GKGLEWVSSISSSSSYIYYADSVKGRFTISRDNAKNSLYLQ MNSLRAEDTAVYYCARVGLMGPFDIWGQGTMVTVSSASTKG PSVFPLAPSSKSTSGGTAALGCLVKDYFPEPVTVSWNSGAL TSGVHTFPAVLQSSGLYSLSSVVTVPSSSLGTQTYICNVNH KPSNTKVDKRVEPKSCDKTHTCPPCPAPELVGGPSVFLLPP KPKDTLMISRTPEVTCVVVDVSHEDPEVKFNWYVDGVEVHN AKTKPPEEQYNSTLRVVSVLTVLHQDWLNGKEYKCKVSNKA LPAPIEKTISKAKGQPREPQVYTLPPSREEMTKNQVSLTCL VKGFYPSDIAVEWESNGQPENNYKTTPLVLDSDGSFFLYSK LTVDKSRWQQGNVFSCSVMHEALHNHYTQKSLSLSPG |
| 117 | AGEN2041 (IgG2) heavy chain | EVQLVESGGGLVKPGGSLRLSCAASGFTFSSYSMNWVRQAP GKGLEWVSSISSSSSYIYYADSVKGRFTISRDNAKNSLYLQ MNSLRAEDTAVYYCARVGLMGPFDIWGQGTMVTVSSASTKG PSVFPLAPCSRSTSESTAALGCLVKDYFPEPVTVSWNSGAL TSGVHTFPAVLQSSGLYSLSSVVTVPSSNFGTQTYTCNVDH KPSNTKVDKTVERKCCVECPPCPAPPVAGPSVFLFPPKPKD TLMISRTPEVTCVVVDVSHEDPEVQFNWYVDGVEVHNAKTK PREEQFNSTFRVVSVLTVVHQDWLNGKEYKCKVSNKGLPAP IEKTISKTKGQPREPQVYTLPPSREEMTKNQVSLTCLVKGF YPSDIAVEWESNGQPENNYKTTPPMLDSDGSFFLYSKLTVD KSRWQQGNVFSCSVMHEALHNHYTQKSLSLSPG |
| 59 | AGEN1884 light chain | EIVLTQSPGTLSLSPGERATLSCRASQSVSRYLGWYQQKPG QAPRLLIYGASTRATGIPDRFSGSGSGTDFTLTITRLEPED FAVYYCQQYGSSPWTFGQGTKVEIKRTVAAPSVFIFPPSDE QLKSGTASVVCLLNNFYPREAKVQWKVDNALQSGNSQESVT EQDSKDSTYSLSSTLTLSKADYEKHKVYACEVTHQGLSSPV TKSFNRGEC |
| 60 | IgG1 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKRVEPKSCDKTHTCPPCPAPELLGGPSV FLFPPKPKDTLMISRTPEVTCVVVDVSHEDPEVKFNWYVDG VEVHNAKTKPREEQYNSTYRVVSVLTVLHQDWLNGKEYKCK VSNKALPAPIEKTISKAKGQPREPQVYTLPPSREEMTKNQV SLTCLVKGFYPSDIAVEWESNGQPENNYKTTPPVLDSDGSF FLYSKLTVDKSRWQQGNVFSCSVMHEALHNHYTQKSLSLSP G |
| 61 | IgG1 S239D/I332E | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKRVEPKSCDKTHTCPPCPAPELLGGPDV FLFPPKPKDTLMISRTPEVTCVVVDVSHEDPEVKFNWYVDG VEVHNAKTKPREEQYNSTYRVVSVLTVLHQDWLNGKEYKCK VSNKALPAPEEKTISKAKGQPREPQVYTLPPSREEMTKNQV SLTCLVKGFYPSDIAVEWESNGQPENNYKTTPPVLDSDGSF FLYSKLTVDKSRWQQGNVFSCSVMHEALHNHYTQKSLSLSP G |
| 62 | IgG1 S239D/A330L/I332E | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKRVEPKSCDKTHTCPPCPAPELLGGPDV FLFPPKPKDTLMISRTPEVTCVVVDVSHEDPEVKFNWYVDG VEVHNAKTKPREEQYNSTYRVVSVLTVLHQDWLNGKEYKCK VSNKALPLPEEKTISKAKGQPREPQVYTLPPSREEMTKNQV SLTCLVKGFYPSDIAVEWESNGQPENNYKTTPPVLDSDGSF FLYSKLTVDKSRWQQGNVFSCSVMHEALHNHYTQKSLSLSP G |
| 63 | IgG1 L235V/F243L/R292P/Y300L/ P396L | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKRVEPKSCDKTHTCPPCPAPELVGGPSV FLLPPKPKDTLMISRTPEVTCVVVDVSHEDPEVKFNWYVDG VEVHNAKTKPPEEQYNSTLRVVSVLTVLHQDWLNGKEYKCK VSNKALPAPIEKTISKAKGQPREPQVYTLPPSREEMTKNQV SLTCLVKGFYPSDIAVEWESNGQPENNYKTTPLVLDSDGSF FLYSKLTVDKSRWQQGNVFSCSVMHEALHNHYTQKSLSLSP G |
| 118 | IgG2 | ASTKGPSVFPLAPCSRSTSESTAALGCLVKDYFPEPVTVSW NSGALTSGVHTFPAVLQSSGLYSLSSVVTVPSSNFGTQTYT CNVDHKPSNTKVDKTVERKCCVECPPCPAPPVAGPSVFLFP |

TABLE 1-continued

Amino acid sequences of exemplary anti-CTLA-4 antibodies.*

| SEQ ID NO: | Description | Amino acid sequence |
|---|---|---|
| | | PKPKDTLMISRTPEVTCVVVDVSHEDPEVQFNWYVDGVEVH NAKTKPREEQFNSTFRVVSVLTVVHQDWLNGKEYKCKVSNK GLPAPIEKTISKTKGQPREPQVYTLPPSREEMTKNQVSLTC LVKGFYPSDIAVEWESNGQPENNYKTTPPMLDSDGSFFLYS KLTVDKSRWQQGNVFSCSVMHEALHNHYTQKSLSLSPG |
| 64 | Light chain constant region | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |

*CDRs are defined according to the Kabat numbering system.

TABLE 2

Heavy chain CDR amino acid sequences of exemplary anti-CTLA-4 antibodies.*

| VH (SEQ ID NO:) | CDRH1 (SEQ ID NO:) | CDRH2 (SEQ ID NO:) | CDRH3 (SEQ ID NO:) |
|---|---|---|---|
| AGEN1884 VH (1) | SYSMN (20) | SISSSSSYIYYADSVKG (22) | VGLMGPFDI (24) |
| BADD412-2356 VH (9) | SYAMS (21) | SISSSSSYIYYADSVKG (22) | VGLMGPFDI (24) |
| BADD412-2357 VH (10) | SYSMN (20) | SISSSSSYIYYADSVKG (22) | VGLMGPFDI (24) |
| BADD412-2358 VH (11) | SYSMN (20) | SISSSSSYIYYADSVKG (22) | VGLMGPFDI (24) |
| BADD412-2359 VH (12) | SYAMS (21) | SISSSSSYIYYADSVKG (22) | VGLMGPFNI (26) |
| BADD412-2360 VH (13) | SYSMN (20) | SISSSSSYIYYADSVKG (22) | VGLMGPFDI (24) |

*Defined according to the Kabat numbering system.

TABLE 3

Light chain CDR amino acid sequences of exemplary anti-CTLA-4 antibodies.*

| VL (SEQ ID NO:) | CDRL1 (SEQ ID NO:) | CDRL2 (SEQ ID NO:) | CDRL3 (SEQ ID NO:) |
|---|---|---|---|
| AGEN1884 VL (14) | RASQSVSRYLG (27) | GASTRAT (30) | QQYGSSPWT (36) |
| BADD412-2367 VL (15) | RASQSVGTYLA (28) | GASRRAT (31) | QQYGSSPWT (36) |
| BADD412-2382 VL (16) | RASQSVSSYLA (29) | ATSSRAT (32) | QQYGTSPWT (37) |
| BADD412-2384 VL (17) | RASQSVSSYLA (29) | GASSRAT (33) | QQYGSSPFT (38) |
| BADD412-2390 VL (18) | RASQSVSSYLA (29) | AASTRAT (34) | QQYGSSPWT (36) |
| BADD412-2393 VL (19) | RASQSVSSYLA (29) | GASNRAT (35) | QQYGSSPFT (38) |

*Defined according to the Kabat numbering system.

TABLE 4

Exemplary anti-CTLA-4 antibodies.

| Antibody | Heavy chain variable region | SEQ ID NO: | Light chain variable region | SEQ ID NO: |
|---|---|---|---|---|
| AGEN1884 | AGEN1884 VH | 1 | AGEN1884 VL | 14 |
| AGEN1885 | AGEN1884 VH | 1 | BADD412-2382 VL | 16 |
| AGEN1886 | AGEN1884 VH | 1 | BADD412-2384 VL | 17 |
| AGEN1887 | BADD412-2356 VH | 9 | AGEN1884 VL | 14 |
| AGEN1888 | BADD412-2356 VH | 9 | BADD412-2384 VL | 17 |
| AGEN1889 | BADD412-2357 VH | 10 | BADD412-2367 VL | 15 |
| AGEN1890 | BADD412-2357 VH | 10 | BADD412-2384 VL | 17 |
| AGEN1891 | BADD412-2357 VH | 10 | BADD412-2390 VL | 18 |
| AGEN1892 | BADD412-2357 VH | 10 | BADD412-2393 VL | 19 |
| AGEN1893 | BADD412-2358 VH | 11 | BADD412-2367 VL | 15 |
| AGEN1894 | BADD412-2358 VH | 11 | AGEN1884 VL | 14 |
| AGEN1895 | BADD412-2358 VH | 11 | BADD412-2382 VL | 16 |
| AGEN1896 | BADD412-2358 VH | 11 | BADD412-2384 VL | 17 |
| AGEN1897 | BADD412-2359 VH | 12 | AGEN1884 VL | 14 |
| AGEN1898 | BADD412-2359 VH | 12 | BADD412-2382 VL | 16 |
| AGEN1899 | BADD412-2359 VH | 12 | BADD412-2384 VL | 17 |
| AGEN1900 | BADD412-2359 VH | 12 | BADD412-2393 VL | 19 |
| AGEN1901 | BADD412-2360 VH | 13 | BADD412-2367 VL | 15 |
| AGEN1902 | BADD412-2360 VH | 13 | BADD412-2384 VL | 17 |

TABLE 5

Exemplary sequences of CTLA-4.

| SEQ ID NO: | Description* | Amino acid Sequence |
|---|---|---|
| 65 | Human CTLA-4 immature protein (P16410) | MACLGFQRHKAQLNLATRTWPCTLLFFLLFIPVFCKA MHVAQPAVVLASSRGIASFVCEYASPGKATEVRVTVL RQADSQVTEVCAATYMMGNELTFLDDSICTGTSSGNQ VNLTIQGLRAMDTGLYICKVELMYPPPYYLGIGNGTQ IYVIDPEPCPDSDFLLWILAAVSSGLFFYSFLLTAVS LSKMLKKRSPLTTGVYVKMPPTEPECEKQFQPYFIPI N |
| 97 | CTLA-4 epitope | YLGI |
| 98 | CTLA-4 epitope | YPPPYYLGI |
| 99 | CTLA-4 epitope | YLGIGNGTQI |
| 100 | CTLA-4 epitope | YPPPYYLGIGNGTQI |
| 101 | CTLA-4 epitope | MYPPPYY |
| 102 | CTLA-4 epitope | QVT |
| 108 | MACFA CTLA-4 (G7PL88) | MACLGFQRHKARLNLATRTRPYTLLFSLLFIPVFSKA MHVAQPAVVLANSRGIASFVCEYASPGKATEVRVTVL RQADSQVTEVCAATYMMGNELTFLDDSICTGTSSGNQ VNLTIQGLRAMDTGLYICKVELMYPPPYYMGIGNGTQ IYVIDPEPCPDSDFLLWILAAVSSGLFFYSFLLTAVS LSKMLKKRSPLTTGVYVKMPPTEPECEKQFQPYFIPI N |
| 109 | Mouse CTLA-4 (P09793) | MACLGLRRYKAQLQLPSRTWPFVALLTLLFIPVFSEA IQVTQPSVVLASSHGVASFPCEYSPSHNTDEVRVTVL RQTNDQMTEVCATTFTEKNTVGFLDYPPFCSGTFNESR VNLTIQGLRAVDTGLYLCKVELMYPPPYFVGMGNGTQ IYVIDPEPCPDSDFLLWILVAVSLGLFFYSFLVSAVS LSKMLKKRSPLTTGVYVKMPPTEPECEKQFQPYFIPI N |
| 110 | Rat CTLA-4 (Q62859) | MACLGLQRYKTHLQLPSRTWPFGVLLSLLFIPIFSEA IQVTQPSVVLASSHGVASFPCEYASSHNTDEVRVTVL RQTNDQVTEVCATTFTVKNTLGFLDDPFCSGTFNESR VNLTIQGLRAADTGLYFCKVELMYPPPYFVGMGNGTQ IYVIDPEPCPDSDFLLWILAAVSSGLFFYSFLVTAVS LNRTLKKRSPLTTGVYVKMPPTEPECEKQFQPYFIPI N |
| 111 | Human CD28 (P10747) | MLRLLLALNLFPSIQVTGNKILVKQSPMLVAYDNAVN LSCKYSYNLFSREFRASLHKGLDSAVEVCVVYGNYSQ QLQVYSKTGFNCDGKLGNESVTFYLQNLYVNQTDIYF CKIEVMYPPPYLDNEKSNGTIIHVKGKHLCPSPLFPG PSKPFWVLVVVGGVLACYSLLVTVAFIIFWVRSKRSR LLHSDYMNMTPRRPGPTRKHYQPYAPPRDFAAYRS |

TABLE 5-continued

Exemplary sequences of CTLA-4.

| SEQ ID NO: | Description* | Amino acid Sequence |
|---|---|---|
| 112 | Human ICOS (Q9Y6W8) | MKSGLWYFFLFCLRIKVLTGEINGSANYEMFIFHNGG VQILCKYPDIVQQFKMQLLKGGQILCDLTKTKGSGNT VSIKSLKFCHSQLSNNSVSFFLYNLDHSHANYYFCNL SIFDPPPFKVTLTGGYLHIYESQLCCQLKFWLPIGCA AFVVVCILGCILICWLTKKKYSSSVHDPNGEYMFMRA VNTAKKSRLTDVTL |
| 113 | Human BTLA (Q7Z6A9) | MKTLPAMLGTGKLFWVFFLIPYLDIWNIHGKESCDVQ LYIKRQSEHSILAGDPFELECPVKYCANRPHVTWCKL NGTTCVKLEDRQTSWKEEKNISFFILHFEPVLPNDNG SYRCSANFQSNLIESHSTTLYVTDVKSASERPSKDEM ASRPWLLYRLLPLGGLPLLITTCFCLFCCLRRHQGKQ NELSDTAGREINLVDAHLKSEQTEASTRQNSQVLLSE TGIYDNDPDLCFRMQEGSEVYSNPCLEENKPGIVYAS LNHSVIGPNSRLARNVKEAPTEYASICVRS |

In certain embodiments, the instant disclosure provides an isolated antibody that specifically binds to CTLA-4 (e.g., human CTLA-4), the antibody comprising a VH domain comprising one, two, or all three of the CDRs of a VH domain set forth in in Table 1 herein. In certain embodiments, the antibody comprises the CDRH1 of one of the VH domains set forth in in Table 1 herein. In certain embodiments, the antibody comprises the CDRH2 of one of the VH domains set forth in in Table 1 herein. In certain embodiments, the antibody comprises the CDRH3 of one of the VH domains set forth in in Table 1 herein.

In certain embodiments, the instant disclosure provides an isolated antibody that specifically binds to CTLA-4 (e.g., human CTLA-4), the antibody comprising a VL domain comprising one, two, or all three of the CDRs of a VL domain set forth in in Table 1 herein. In certain embodiments, the antibody comprises the CDRL1 of a VL domain set forth in in Table 1 herein. In certain embodiments, the antibody comprises the CDRL2 of a VL domain set forth in in Table 1 herein. In certain embodiments, the antibody comprises the CDRL3 of a VL domain set forth in in Table 1 herein.

In certain embodiments, the CDRs of an antibody can be determined according to Kabat et al., J. Biol. Chem. 252, 6609-6616 (1977) and Kabat et al., Sequences of protein of immunological interest (1991), each of which is herein incorporated by reference in its entirety.

In certain embodiments, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226, all of which are herein incorporated by reference in their entireties). Typically, when using the Kabat numbering convention, the Chothia CDRH1 loop is present at heavy chain amino acids 26 to 32, 33, or 34, the Chothia CDRH2 loop is present at heavy chain amino acids 52 to 56, and the Chothia CDRH3 loop is present at heavy chain amino acids 95 to 102, while the Chothia CDRL1 loop is present at light chain amino acids 24 to 34, the Chothia CDRL2 loop is present at light chain amino acids 50 to 56, and the Chothia CDRL3 loop is present at light chain amino acids 89 to 97. The end of the Chothia CDRH1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain embodiments, the instant disclosure provides an isolated antibody that specifically binds to CTLA-4 (e.g., human CTLA-4), the antibody comprising the Chothia VH CDRs of a VH disclosed in Table 1 herein. In certain embodiments, the instant disclosure provides an isolated antibody that specifically binds to CTLA-4 (e.g., human CTLA-4), the antibody comprising the Chothia VL CDRs of a VL disclosed in Table 1 herein. In certain embodiments, the instant disclosure provides an isolated antibody that specifically binds to CTLA-4 (e.g., human CTLA-4), the antibody comprising the Chothia VH CDRs and Chothia VL CDRs of an antibody disclosed in Table 1 herein. In certain embodiments, antibodies that specifically bind to CTLA-4 (e.g., human CTLA-4) comprise one or more CDRs, in which the Chothia and Kabat CDRs have the same amino acid sequence. In certain embodiments, the instant disclosure provides an isolated antibody that specifically binds to CTLA-4 (e.g., human CTLA-4) and comprises a combination of Kabat CDRs and Chothia CDRs.

In certain embodiments, the CDRs of an antibody can be determined according to the IMGT numbering system as described in Lefranc M-P, (1999) The Immunologist 7: 132-136 and Lefranc M-P et al., (1999) Nucleic Acids Res 27: 209-212, each of which is herein incorporated by reference in its entirety. In certain embodiments, the instant disclosure provides antibodies that specifically bind to CTLA-4 (e.g., human CTLA-4) and comprise CDRs of an antibody disclosed in Table 1 herein, as determined by the IMGT numbering system, for example, as described in Lefranc M-P (1999) supra and Lefranc M-P et al., (1999) supra.

In certain embodiments, the instant disclosure provides an isolated antibody that specifically binds to CTLA-4 (e.g., human CTLA-4), the antibody comprising the IMGT VH CDRs of a VH disclosed in Table 1 herein. In certain embodiments, the instant disclosure provides an isolated antibody that specifically binds to CTLA-4 (e.g., human CTLA-4), the antibody comprising the IMGT VL CDRs of a VL disclosed in Table 1 herein. In certain embodiments, the instant disclosure provides an isolated antibody that specifically binds to CTLA-4 (e.g., human CTLA-4), the antibody comprising the IMGT VH CDRs and IMGT VL CDRs of an antibody disclosed in Table 1 herein. In certain embodiments, the instant disclosure provides an isolated antibody that specifically binds to CTLA-4 (e.g., human CTLA-4) and comprises a combination of Kabat CDRs and IMGT CDRs.

In certain embodiments, the CDRs of an antibody can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety. In a particular embodiment, the instant disclosure provides antibodies that specifically bind to CTLA-4 (e.g., human CTLA-4) and comprise CDRs of an antibody disclosed in Table 1 herein as determined by the AbM numbering scheme.

In certain embodiments, the CDRs of an antibody can be determined according to MacCallum R M et al., (1996) J Mol Biol 262: 732-745, herein incorporated by reference in its entirety. See also, e.g., Martin A. "Protein Sequence and Structure Analysis of Antibody Variable Domains," in Antibody Engineering, Kontermann and Dubel, eds., Chapter 31, pp. 422-439, Springer-Verlag, Berlin (2001), herein incorporated by reference in its entirety. In a particular embodiment, the instant disclosure provides antibodies that specifically bind to CTLA-4 (e.g., human CTLA-4) and comprise CDRs of an antibody disclosed in Table 1 herein as determined by the MacCallum numbering scheme.

Accordingly, in certain embodiments, the instant disclosure provides an isolated antibody that specifically binds to CTLA-4 (e.g., human CTLA-4), wherein the antibody comprises a heavy chain variable region comprising the CDRH1, CDRH2, and CDRH3 region amino acid sequences of a heavy chain variable region set forth in SEQ ID NO: 1, 9, 10, 11, 12, or 13, and a light chain variable region comprising the CDRL1, CDRL2, and CDRL3 region amino acid sequences of a light chain variable region set forth in SEQ ID NO: 14, 15, 16, 17, 18, or 19, wherein each CDR is defined in accordance with the Kabat definition, the Chothia definition, the combination of the Kabat definition and the Chothia definition, the IMGT numbering system, the AbM definition, or the contact definition of CDR.

In certain embodiments, the instant disclosure provides an isolated antibody that specifically binds to CTLA-4 (e.g., human CTLA-4), the antibody comprising:
(a) CDRH1 comprises the amino acid sequence of SYX$_1$MX$_2$ (SEQ ID NO: 39), wherein X$_1$ is S or A; and X$_2$ is N or S; and/or
(b) CDRH2 comprises the amino acid sequence of SISSSSSYIYYADSVKG (SEQ ID NO: 22); wherein X is D or E; and/or
(c) CDRH3 comprises the amino acid sequence of VGLMGPFXI (SEQ ID NO: 115), wherein X is D or N; and/or
(d) CDRL1 comprises the amino acid sequence of RASQSVX$_1$X$_2$YLX$_3$ (SEQ ID NO: 43), wherein X$_1$ is S or G; X$_2$ is R, S, or T; and X$_3$ is G or A; and/or
(e) CDRL2 comprises the amino acid sequence of X$_1$X$_2$SX$_3$RAT (SEQ ID NO: 44), wherein X$_1$ is G or A; X$_2$ is A or T; and X$_3$ is T, S, R, or N; and/or
(f) CDRL3 comprises the amino acid sequence of QQYGX$_1$SPX$_2$T (SEQ ID NO: 45), wherein X$_1$ is S or T; and X$_2$ is W or F.

In certain embodiments, the instant disclosure provides an isolated antibody that specifically binds to CTLA-4 (e.g., human CTLA-4), the antibody comprising:
(a) CDRH1 comprises the amino acid sequence of SYX$_1$MX$_2$ (SEQ ID NO: 39), wherein X$_1$ is S or A; and X$_2$ is N or S;
(b) CDRH2 comprises the amino acid sequence of SISSSSSYIYYADSVKG (SEQ ID NO: 22);
(c) CDRH3 comprises the amino acid sequence of VGLMGPFXI (SEQ ID NO: 115), wherein X is D or N;
(d) CDRL1 comprises the amino acid sequence of RASQSVX$_1$X$_2$YLX$_3$ (SEQ ID NO: 43), wherein X$_1$ is S or G; X$_2$ is R, S, or T; and X$_3$ is G or A;
(e) CDRL2 comprises the amino acid sequence of X$_1$X$_2$SX$_3$RAT (SEQ ID NO: 44), wherein X$_1$ is G or A; X$_2$ is A or T; and X$_3$ is T, S, R, or N; and
(f) CDRL3 comprises the amino acid sequence of QQYGX$_1$SPX$_2$T (SEQ ID NO: 45), wherein X$_1$ is S or T; and X$_2$ is W or F.

In certain embodiments, the CDRH1 comprises an amino acid sequence selected from the group consisting of SEQ ID NOs: 20 and 21. In certain embodiments, the CDRH3 comprises an amino acid sequence selected from the group consisting of SEQ ID NOs: 24 and 26. In certain embodiments, CDRL1 comprises an amino acid sequence selected from the group consisting of SEQ ID NOs: 27, 28, and 29. In certain embodiments, CDRL2 comprises an amino acid sequence selected from the group consisting of SEQ ID NOs: 30-35. In certain embodiments, CDRL3 comprises an amino acid sequence selected from the group consisting of SEQ ID NOs: 36, 37, and 38. In certain embodiments, CDRH1, CDRH2, and CDRH3 comprise the CDRH1, CDRH2, and CDRH3 amino acid sequences, respectively, of an antibody in Table 2. In certain embodiments, CDRL1, CDRL2, and CDRL3 comprise the CDRL1, CDRL2, and CDRL3 amino acid sequences, respectively, of an antibody in Table 3.

In certain embodiments, the instant disclosure provides an isolated antibody that specifically binds to CTLA-4 (e.g., human CTLA-4), comprising a heavy chain variable region comprising complementarity determining regions CDRH1, CDRH2 and CDRH3, wherein the CDRH1, CDRH2 and CDRH3 comprise the CDRH1, CDRH2 and CDRH3 amino acid sequences, respectively, set forth in SEQ ID NOs: 20, 22, and 24; 20, 22, and; 21, 22, and 24; or 21, 22, and 26.

In certain embodiments, the instant disclosure provides an isolated antibody that specifically binds to CTLA-4 (e.g., human CTLA-4), comprising a light chain variable region comprising complementarity determining regions CDRL1, CDRL2 and CDRL3, wherein the CDRL1, CDRL2 and CDRL3 comprise the CDRL1, CDRL2 and CDRL3 amino acid sequences, respectively, set forth in SEQ ID NOs: 27, 30, and 36; 28, 31, and 36; 29, 32, and 37; 29, 33, and 38; 29, 34, and 36; or 29, 35, and 38.

In certain embodiments, the instant disclosure provides an isolated antibody that specifically binds to CTLA-4 (e.g., human CTLA-4), comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2 and CDRL3 comprise the CDRH1, CDRH2, CDRH3, CDRL1, CDRL2 and CDRL3 amino acid sequences, respectively, set forth in SEQ ID NOs: 20, 22, 24, 27, 30, and 36; 20, 22, 24, 29, 32, and 37; 20, 22, 24, 29, 33, and 38; 21, 22, 24, 27, 30, and 36; 21, 22, 24, 29, 33, and 38; 20, 22, 24, 28, 31, and 36; 20, 22, 24, 29, 34, and 36; 20, 22, 24, 29, 35, and 38; 21, 22, 26, 27, 30, and 36; 21, 22, 26, 29, 32, and 37; 21, 22, 26, 29, 33, and 38; or 21, 22, 26, 29, 35, and 38, respectively.

In certain embodiments, the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences, respectively, set forth in SEQ ID NOs: 20, 22, 24, 27, 30, and 36.

In certain embodiments, the instant disclosure provides an isolated antibody that specifically binds to CTLA-4 (e.g., human CTLA-4), comprising a heavy chain variable region comprising the amino acid sequence of SEQ ID NO: 116.

In certain embodiments, the instant disclosure provides an isolated antibody that specifically binds to CTLA-4 (e.g., human CTLA-4), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to an amino acid sequence selected from the group consisting of SEQ ID NOs: 1, 9, 10, 11, 12, or 13. In certain embodiments, the antibody comprises a heavy chain variable region having an amino acid sequence selected from the group consisting of SEQ ID NOs: 1, 9, 10, 11, 12, or 13. In certain embodiments, the antibody comprises a heavy chain variable region having the amino acid sequence set forth in SEQ ID NO: 1. In certain embodiments, the antibody comprises a heavy chain variable region having the amino acid sequence set forth in SEQ ID NO: 9. In certain embodiments, the antibody comprises a heavy chain variable region having the amino acid sequence set forth in SEQ ID NO: 10. In certain embodiments, the antibody comprises a heavy chain variable region having the amino acid sequence set forth in SEQ ID NO: 11. In certain embodiments, the antibody comprises a heavy chain variable region having the amino acid sequence set forth in SEQ ID NO: 12. In certain embodiments, the antibody comprises a heavy chain variable region having the amino acid sequence set forth in SEQ ID NO: 13.

In certain embodiments, the instant disclosure provides an isolated antibody that specifically binds to CTLA-4 (e.g., human CTLA-4), comprising a light chain variable region comprising the amino acid sequence of SEQ ID NO: 47.

In certain embodiments, the instant disclosure provides an isolated antibody that specifically binds to CTLA-4 (e.g., human CTLA-4), comprising a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to an amino acid sequence selected from the group consisting of SEQ ID NOs: 14-19. In certain embodiments, the antibody comprises a light chain variable region having an amino acid sequence selected from the group consisting of SEQ ID NOs: 14-19. In certain embodiments, the antibody comprises a light chain variable region having the amino acid sequence set forth in SEQ ID NO: 14. In certain embodiments, the antibody comprises a light chain variable region having the amino acid sequence set forth in SEQ ID NO: 15. In certain embodiments, the antibody comprises a light chain variable region having the amino acid sequence set forth in SEQ ID NO: 16. In certain embodiments, the antibody comprises a light chain variable region having the amino acid sequence set forth in SEQ ID NO: 17. In certain embodiments, the antibody comprises a light chain variable region having the amino acid sequence set forth in SEQ ID NO: 18. In certain embodiments, the antibody comprises a light chain variable region having the amino acid sequence set forth in SEQ ID NO: 19.

In certain embodiments, the instant disclosure provides an isolated antibody that specifically binds to CTLA-4 (e.g., human CTLA-4), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 1, 9, 10, 11, 12, or 13, and a light chain variable region that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 14, 15, 16, 17, 18, or 19. In certain embodiments, the instant disclosure provides an isolated antibody that specifically binds to CTLA-4 (e.g., human CTLA-4), comprising a heavy chain variable region comprising an amino acid sequence set forth in SEQ ID NO: 1, 9, 10, 11, 12, or 13, and a light chain variable region set forth in SEQ ID NO: 14, 15, 16, 17, 18, or 19. In certain embodiments, the antibody comprises a heavy chain variable region and light chain variable region having the amino acid sequences set forth in SEQ ID NOs: 1 and 14; 1 and 16, 1 and 17; 9 and 14; 9 and 17; 10 and 15; 10 and 17; 10 and 18; 10 and 19; 11 and 15; 11 and 14; 11 and 16; 11 and 17; 12 and 14; 12 and 16; 12 and 17; 12 and 19; 13 and 15; or 13 and 17, respectively. In certain embodiments, the antibody comprises a heavy chain variable region and light chain variable region having the amino acid sequences set forth in SEQ ID NOs: 1 and 14, respectively. In certain embodiments, the antibody comprises a heavy chain variable region and light chain variable region having the amino acid sequences set forth in SEQ ID NOs: 1 and 16, respectively. In certain embodiments, the antibody comprises a heavy chain variable region and light chain variable region having the amino acid sequences set forth in SEQ ID NOs: 1 and 17, respectively. In certain embodiments, the antibody comprises a heavy chain variable region and light chain variable region having the amino acid sequences set forth in SEQ ID NOs: 9 and 14, respectively. In certain embodiments, the antibody comprises a heavy chain variable region and light chain variable region having the amino acid sequences set forth in SEQ ID NOs: 9 and 17, respectively. In certain embodiments, the antibody comprises a heavy chain variable region and light chain variable region having the amino acid sequences set forth in SEQ ID NOs: 10 and 15, respectively. In certain embodiments, the antibody comprises a heavy chain variable region and light chain variable region having the amino acid sequences set forth in SEQ ID NOs: 10 and 17, respectively. In certain embodiments, the antibody comprises a heavy chain variable region and light chain variable region having the amino acid sequences set forth in SEQ ID NOs: 10 and 18, respectively. In certain embodiments, the antibody comprises a heavy chain variable region and light chain variable region having the amino acid sequences set forth in SEQ ID NOs: 10 and 19, respectively. In certain embodiments, the antibody comprises a heavy chain variable region and light chain variable region having the amino acid sequences set forth in SEQ ID NOs: 11 and 15, respectively. In certain embodiments, the antibody comprises a heavy chain variable region and light chain variable region having the amino acid sequences set forth in SEQ ID NOs: 11 and 14, respectively. In certain embodiments, the antibody comprises a heavy chain variable region and light chain variable region having the amino acid sequences set forth in SEQ ID NOs: 11 and 16, respectively. In certain embodiments, the antibody comprises a heavy chain variable region and light chain variable region having the amino acid sequences set forth in SEQ ID NOs: 11 and 17, respectively. In certain embodiments, the antibody comprises a heavy chain variable region and light chain variable region having the amino acid sequences set forth in SEQ ID NOs: 12 and 14, respectively. In certain embodiments, the antibody comprises a heavy chain variable region and light chain variable region having the amino acid sequences set forth in SEQ ID NOs: 12 and 16, respectively. In certain embodiments, the antibody comprises a heavy chain variable region and light chain variable region having the amino acid sequences set forth in SEQ ID NOs: 12 and 17, respectively. In certain embodiments, the antibody comprises a heavy chain variable region and light chain variable region having the amino acid sequences set forth in SEQ ID NOs: 12 and 19, respectively. In certain embodiments, the antibody comprises a heavy chain variable region and light chain variable region having the amino acid sequences set forth in SEQ ID NOs: 13 and 15, respectively. In certain embodiments, the antibody comprises a heavy chain variable region and light chain variable region having the amino acid sequences set forth in SEQ ID NOs: 13 and 17, respectively.

In certain embodiments, the instant disclosure provides an isolated antibody that specifically binds to CTLA-4 (e.g., human CTLA-4), comprising a heavy chain variable region having an amino acid sequence derived from a human IGHV3-21 germline sequence (e.g., IGHV3-21*01, e.g., having the amino acid sequence of SEQ ID NO: 48). One or more regions selected from framework 1, framework 2, framework 3, CDRH1, and CDRH2 (e.g., two, three, four or five of these regions) can be derived from a human IGHV3-21 germline sequence. In one embodiment, framework 1, framework 2, framework 3, CDRH1, and CDRH2 are all derived from a human IGHV3-21 germline sequence.

In certain embodiments, the instant disclosure provides an isolated antibody that specifically binds to CTLA-4 (e.g., human CTLA-4), comprising a light chain variable region having an amino acid sequence derived from a human IGKV3-20 germline sequence (e.g., IGKV3-20*01, e.g., having the amino acid sequence of SEQ ID NO: 49) or a human IGKV3-11 germline sequence (e.g., IGKV3-11*01, e.g., having the amino acid sequence of SEQ ID NO: 50). One or more regions selected from framework 1, framework 2, framework 3, CDRL1, and CDRL2 (e.g., two, three, four or five of these regions) can be derived from a human IGKV3-20 or IGKV3-11 germline sequence. In one embodiment, framework 1, framework 2, framework 3, CDRL1, and CDRL2 are all derived from a human IGKV3-20 or IGKV3-11 germline sequence.

In certain embodiments, the instant disclosure provides an isolated antibody that specifically binds to CTLA-4 (e.g., human CTLA-4), comprising a heavy chain variable region having an amino acid sequence derived from a human IGHV3-21 germline sequence (e.g., IGHV3-21*01, e.g., having the amino acid sequence of SEQ ID NO: 48), and a light chain variable region having an amino acid sequence derived from a human IGKV3-20 germline sequence (e.g., IGKV3-20*01, e.g., having the amino acid sequence of SEQ ID NO: 49) or a human IGKV3-11 germline sequence (e.g., IGKV3-11*01, e.g., having the amino acid sequence of SEQ ID NO: 50). One or more regions selected from framework 1, framework 2, framework 3, CDRH1, and CDRH2 of the heavy chain variable region (e.g., two, three, four or five of these regions) can be derived from a human IGHV3-21 germline sequence. In one embodiment, framework 1, framework 2, framework 3, CDRH1, and CDRH2 are all derived from a human IGHV3-21 germline sequence. One or more regions selected from framework 1, framework 2, framework 3, CDRL1, and CDRL2 of the light chain variable region (e.g., two, three, four or five of these regions) can be derived from a human IGKV3-20 or IGKV3-11 germline sequence. In one embodiment, framework 1, framework 2, framework 3, CDRL1, and CDRL2 are all derived from a human IGKV3-20 or IGKV3-11 germline sequence.

In certain embodiments, the antibody comprises a heavy chain having an amino acid sequence selected from the group consisting of SEQ ID NOs: 51-54, and 117. In certain embodiments, the antibody comprises a heavy chain having the amino acid sequence set forth in SEQ ID NO: 51. In certain embodiments, the antibody comprises a heavy chain having the amino acid sequence set forth in SEQ ID NO: 52. In certain embodiments, the antibody comprises a heavy chain having the amino acid sequence set forth in SEQ ID NO: 53. In certain embodiments, the antibody comprises a heavy chain having the amino acid sequence set forth in SEQ ID NO: 54. In certain embodiments, the antibody comprises a heavy chain having the amino acid sequence set forth in SEQ ID NO: 117.

In certain embodiments, the antibody comprises a light chain having the amino acid sequence of SEQ ID NO: 59.

In certain embodiments, the instant disclosure provides an isolated antibody that specifically binds to CTLA-4 (e.g., human CTLA-4), comprising a heavy chain comprising an amino acid sequence selected from the group consisting of SEQ ID NOs: 51-54, and 117, and a light chain comprising the amino acid sequence of SEQ ID NO: 59. In certain embodiments, the antibody comprises a heavy chain and light chain having the amino acid sequences set forth in SEQ ID NOs: 51 and 59, respectively. In certain embodiments, the antibody comprises a heavy chain and light chain having the amino acid sequences set forth in SEQ ID NOs: 52 and 59, respectively. In certain embodiments, the antibody comprises a heavy chain and light chain having the amino acid sequences set forth in SEQ ID NOs: 53 and 59, respectively. In certain embodiments, the antibody comprises a heavy chain and light chain having the amino acid sequences set forth in SEQ ID NOs: 54 and 59, respectively. In certain embodiments, the antibody comprises a heavy chain and light chain having the amino acid sequences set forth in SEQ ID NOs: 117 and 59, respectively.

In certain embodiments, the instant disclosure provides an isolated antibody that cross-competes for binding to CTLA-4 (e.g., human CTLA-4) with an antibody comprising the heavy and light chain variable region amino acid sequences set forth in SEQ ID NOs: 1 and 14; 1 and 16, 1 and 17; 9 and 14; 9 and 17; 10 and 15; 10 and 17; 10 and 18; 10 and 19; 11 and 15; 11 and 14; 11 and 16; 11 and 17; 12 and 14; 12 and 16; 12 and 17; 12 and 19; 13 and 15; or 13 and 17, respectively. In certain embodiments, the instant disclosure provides an isolated antibody that cross-competes for binding to CTLA-4 (e.g., human CTLA-4) with an antibody comprising the heavy and light chain variable region amino acid sequences set forth in SEQ ID NOs: 1 and 14, respectively.

In certain embodiments, the instant disclosure provides an isolated antibody that binds to the same epitope on CTLA-4 (e.g., human CTLA-4) as an antibody comprising the heavy and light chain variable region amino acid sequences set forth in SEQ ID NOs: 1 and 14; 1 and 16, 1 and 17; 9 and 14; 9 and 17; 10 and 15; 10 and 17; 10 and 18; 10 and 19; 11 and 15; 11 and 14; 11 and 16; 11 and 17; 12 and 14; 12 and 16; 12 and 17; 12 and 19; 13 and 15; or 13 and 17, respectively. In certain embodiments, the instant disclosure provides an isolated antibody that binds to the same epitope on CTLA-4 (e.g., human CTLA-4) as an antibody comprising the heavy and light chain variable region amino acid sequences set forth in SEQ ID NOs: 1 and 14, respectively. In certain embodiments, the isolated antibody binds to an epitope located within a region of human CTLA-4 consisting of the amino acid sequence of SEQ ID NO: 100. In certain embodiments, the isolated antibody binds to an epitope located within a region of human CTLA-4 consisting of the amino acid sequence of SEQ ID NO: 99. In certain embodiments, the isolated antibody binds to an epitope located within a region of human CTLA-4 consisting of the amino acid sequence of SEQ ID NO: 98. In certain embodiments, the isolated antibody binds to an epitope located within a region of human CTLA-4 consisting of the amino acid sequence of SEQ ID NO: 97. In certain embodiments, the isolated antibody binds to an epitope located within a region of human CTLA-4 consisting of the amino acid sequence of SEQ ID NO: 101. In certain embodiments, the isolated antibody binds to an epitope located within a region of human CTLA-4 consisting of the amino acid sequence of SEQ ID NO: 102.

In certain embodiments, the instant disclosure provides an isolated antibody that specifically binds to human CTLA-4 and functions as an antagonist.

In certain embodiments, the instant disclosure provides an isolated antibody that specifically binds to human CTLA-4 and decreases CTLA-4 activity by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to CTLA-4 activity without any antibody or with an unrelated antibody (e.g., an antibody that does not specifically bind to CTLA-4). In certain embodiments, the instant disclosure provides an isolated antibody that specifically binds to human CTLA-4 and decreases CTLA-4 activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to CTLA-4 activity without any antibody or with an unrelated antibody (e.g., an antibody that does not specifically bind to CTLA-4). Non-limiting examples of CTLA-4 activity can include CTLA-4 signaling, CTLA-4 binding to CTLA-4 ligand (e.g., CD80 or CD86), inhibition of cytokine production (e.g., IL-2 or IFNγ), and inhibition of T cell proliferation. In certain embodiments, the instant disclosure provides an isolated antibody that specifically binds to human CTLA-4 and deactivates, reduces, or inhibits a CTLA-4 activity. In specific embodiments, a decrease in a CTLA-4 activity is assessed as described in the Examples, infra.

In specific embodiments, the instant disclosure provides an isolated antibody that specifically binds to human CTLA-4 and decreases CTLA-4 binding to its ligand (e.g., CD80 or CD86) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to CTLA-4 binding to its ligand (e.g., CD80 or CD86) without any antibody or with an unrelated antibody (e.g., an antibody that does not specifically bind to CTLA-4). In specific embodiments, the instant disclosure provides an isolated antibody that specifically binds to human CTLA-4 and decreases CTLA-4 binding to its ligand (e.g., CD80 or CD86) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to CTLA-4 binding to its ligand (e.g., CD80 or CD86) without any antibody or with an unrelated antibody (e.g., an antibody that does not specifically bind to CTLA-4).

In specific embodiments, the instant disclosure provides an isolated antibody that specifically binds to human CTLA-4 and increases cytokine production (e.g., IL-2 or IFNγ) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to cytokine production without any antibody or with an unrelated antibody (e.g., an antibody that does not specifically bind to CTLA-4). In specific embodiments, the instant disclosure provides an isolated antibody that specifically binds to human CTLA-4 and increases cytokine production (e.g., IL-2 or IFNγ) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to cytokine production without any antibody or with an unrelated antibody (e.g., an antibody that does not specifically bind to CTLA-4).

In specific embodiments, the instant disclosure provides an isolated antibody that specifically binds to CTLA-4 (e.g., human CTLA-4) and either alone or in combination with an anti-CTLA-4 antibody (e.g., ipilimumab or tremelimumab), an anti-TIGIT antibody, an anti-CD137 antibody (e.g., urelumab or utomilumab), or an anti-OX40 antibody (e.g., pogalizumab or tavolixizumab) increases IL-2 production in human peripheral blood mononuclear cells (PBMCs) in response to *Staphylococcus* Enterotoxin A (SEA) stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to IL-2 production without any antibody or with an unrelated antibody (e.g., an antibody that does not specifically bind to CTLA-4).

In certain embodiments, human peripheral blood mononuclear cells (PBMCs) stimulated with *Staphylococcus* Enterotoxin A (SEA) in the presence of an antibody described herein, which specifically binds to human CTLA-4, either alone or in combination with an anti-PD-1 antibody (e.g., nivolumab or pembrolizumab), an anti-TIGIT antibody, an anti-CD137 antibody (e.g., urelumab or utomilumab), or an anti-OX40 antibody (e.g., pogalizumab or tavolixizumab), have increased IL-2 production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to PBMCs only stimulated with SEA without any antibody or with an unrelated antibody (e.g., an antibody that does not specifically bind to CTLA-4), as assessed by methods described herein (see the Examples, infra) or known to one of skill in the art.

In specific embodiments, the instant disclosure provides an isolated antibody that specifically binds to human CTLA-4 and increases IFNγ production of a co-culture of human T cells and allogenic dendritic cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to IFNγ production of a co-culture of human T cells and allogenic dendritic cells without any antibody or with an unrelated antibody (e.g., an antibody that does not specifically bind to CTLA-4).

In certain embodiments, a co-culture of human T cells and allogenic dendritic cells in the presence of an antibody described herein, which specifically binds to human CTLA-4, has increased IFNγ production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to a co-culture of human T cells and allogenic dendritic cells without any antibody or with an unrelated antibody (e.g., an antibody that does not specifically bind to CTLA-4), as assessed by methods described herein (see the Examples, infra) or known to one of skill in the art.

In specific embodiments, the instant disclosure provides an isolated antibody that specifically binds to human CTLA-4 and increases T cell proliferation by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to T cell proliferation without any antibody or with an unrelated antibody (e.g., an antibody that does not specifically bind to CTLA-4). In specific embodiments, the instant disclosure provides an isolated antibody that specifically binds to human CTLA-4 and increases T cell proliferation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to T cell proliferation without any antibody or with an unrelated antibody (e.g., an antibody that does not specifically bind to CTLA-4).

In specific embodiments, the instant disclosure provides an isolated antibody that specifically binds to human CTLA-4 and increases proliferation of anti-CD3-antibody-stimulated CD4+ or CD8+ T cells co-cultured with ovarian cancer ascites fluid by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to proliferation of anti-CD3-antibody-stimulated CD4+ or CD8+ T cells co-cultured with ovarian cancer ascites fluid without any antibody or with an unrelated antibody (e.g., an antibody that does not specifically bind to CTLA-4).

In certain embodiments, an antibody described herein is an activatable antibody that in an activated state binds human CTLA-4 protein. In certain embodiments, the activatable antibody comprises a masking moiety that inhibits the binding of the antibody in an uncleaved state to human CTLA-4 protein, and at least one cleavable moiety coupled to the antibody, e.g., wherein the cleavable moiety is a polypeptide that functions as a substrate for a protease that is enriched in the tumor microenvironment. Exemplary activatable antibodies are described, e.g., in U.S. Pat. Nos. 8,513,390 and 8,518,404, and U.S. Patent Application Publication Nos. US 2014/0255313, US 2014/0010810, US 2014/0023664, which are incorporated herein by reference.

In certain embodiments, the activatable antibody comprises a human IgG heavy chain constant region that is a variant of a wild type human IgG heavy chain constant region, wherein the variant human IgG heavy chain constant region binds to human FcγRIIIA with higher affinity than the wild type human IgG heavy chain constant region binds to human FcγRIIIA.

6.2.2 Anti-PD-1 Antibodies

In one aspect, the instant disclosure provides antibodies that specifically bind to PD-1 (e.g., human PD-1) and antagonize PD-1 function. Also provided herein are multispecific antibodies that comprise a first antigen-binding region that specifically binds to human PD-1 (e.g., human PD-1) and, optionally, a second antigen-binding region that does not specifically bind to PD-1 (e.g., human PD-1). The amino acid sequences of exemplary antibodies are set forth in Tables 6-10, herein.

TABLE 6

Amino acid sequences of exemplary anti-PD-1 antibodies.*

| SEQ ID NO: | Description | Amino acid sequence |
|---|---|---|
| 66 | AGEN2034 VH (BADD438-2744) | QVQLVESGGGVVQPGRSLRLSCAASGFTFSSYGMHWVRQAP GKGLEWVAVIWYDGSNKYYADSVKGRFTISRDNSKNTLYLQ MNSLRAEDTAVYYCASNGDHWGQGTLVTVSS |
| 67 | BADD438-2742 VH | QVQLVESGGGVVQPGRSLRLSCAASGFTFSSYGMHWVRQAP GKGLEWVAVIWYDGSNKYYADSVKGRFTISRDNSKNTLYLQ MNSLRAEDTAVYYCASNVDYWGQGTLVTVSS |
| 68 | BADD426-2614 VH | QVQLVESGGGVVQPGRSLRLSCAASGFTFSSYGMHWVRQAP GKGLEWVAVIWYDGSNKYYADSVKGRFTISRDNSKNTLYLQ MNSLRAEDTAVYYCATNGDYWGQGTLVTVSS |

TABLE 6-continued

Amino acid sequences of exemplary anti-PD-1 antibodies.*

| SEQ ID NO: | Description | Amino acid sequence |
|---|---|---|
| 69 | BADD426-2615 VH | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCASNGDYWGQGTLVTVSS |
| 70 | BADD438-2743 VH | QVQLVESGGGVVQPGRSLRLSCAASGFTFSSYGMHWVRQAPGKGLEWVAVIWYDGSNEYYADSVKGRFTISRDNSKNTLYLQMNSLRAEDTAVYYCASNGDHWGQGTLVTVSS |
| 71 | BADD438-2745 VH | QVQLVESGGGMVQPGRSLRLSCAASGFTFSSYGMHWVRQAPGKGLEWVAVIWFDGSNKYYADSVKGRFTISRDNSKNTLYLQMNSLRAEDTAVYYCASNGDHWGQGTLVTVSS |
| 72 | BADD438-2746 VH | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCASNGDHWGHGTLVTVSS |
| 73 | BADD438-2747 VH | QVQLVESGGGVVQPGRSLRLSCAASGFTFSSYGMHWVRQAPGKGLEWVAVIWYDGSNKYYADSVMGRFTISRDNSKNTLYLQMNSLRAEDTAVYYCASNGDHWGQGTLVTVSS |
| 74 | AGEN2034 VL/3738 VL | EIVMTQSPATLSVSPGERATLSCRASQSVSSNLAWYQQKPGQAPRLLIYGASTRATGIPARFSGSGSGTEFTLTISSLQSEDFAVYYCQQYNNWPRTFGQGTKVEIK |
| 75 | CDRH1 | SYGMH |
| 76 | CDRH2 | VIWYDGSNKYYADSVKG |
| 77 | CDRH2 | VIWYDGSNEYYADSVKG |
| 78 | CDRH2 | VIWFDGSNKYYADSVKG |
| 79 | CDRH2 | VIWYDGSNKYYADSVMG |
| 80 | CDRH3 | NVDY |
| 81 | CDRH3 | NGDH |
| 82 | CDRH3 | NGDY |
| 83 | CDRL1 | RASQSVSSNLA |
| 84 | CDRL2 | GASTRAT |
| 85 | CDRL3 | QQYNNWPRT |
| 86 | CDRH2 consensus | VIWX$_1$DGSNX$_2$YYADSVX$_3$G, wherein<br>X$_1$ is Y or F;<br>X$_2$ is K or E; and<br>X$_3$ is K or M |
| 87 | CDRH3 consensus | NX$_1$DX$_2$, wherein<br>X$_1$ is G or V; and<br>X$_2$ is H or Y |
| 88 | VH consensus sequence | QVQLVESGGGX$_1$VQPGRSLRLSCAASGFTFSSYGMHWVRQAPGKGLEWVAVIWX$_2$DGSNX$_3$YYADSVX$_4$GRFTISRDNSKNTLYLQMNSLRAEDTAVYYCAX$_5$NX$_6$DX$_7$WGX$_8$GTLVTVSS, wherein<br>X$_1$ is V or M;<br>X$_2$ is Y or F;<br>X$_3$ is K or E;<br>X$_4$ is K or M;<br>X$_5$ is S or T;<br>X$_6$ is G or V;<br>X$_7$ is H or Y; and<br>X$_8$ is Q or H |
| 89 | Germline sequence: IGHV3-33*01 | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCAR |

TABLE 6-continued

Amino acid sequences of exemplary anti-PD-1 antibodies.*

| SEQ ID NO: | Description | Amino acid sequence |
|---|---|---|
| 90 | Germline sequence: IGKV3-15*01 | EIVMTQSPATLSVSPGERATLSCRASQSVSSNLAWYQQKPGQAPRLLIYGASTRATGIPARFSGSGSGTEFTLTISSLQSEDFAVYYCQQYNNWP |
| 91 | AGEN2034 (IgG4 S228P) heavy chain | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCASNGDHWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG |
| 92 | AGEN2034 (IgG1 N297A) heavy chain | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCASNGDHWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 120 | AGEN2033 (IgG4 S228P) heavy chain | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCASNVDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG |
| 93 | AGEN2034 light chain | EIVMTQSPATLSVSPGERATLSCRASQSVSSNLAWYQQKPGQAPRLLIYGASTRATGIPARFSGSGSGTEFTLTISSLQSEDFAVYYCQQYNNWPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 60 | IgG1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 94 | IgG1 N297A | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 95 | IgG4 S228P | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSN |

TABLE 6-continued

Amino acid sequences of exemplary anti-PD-1 antibodies.*

| SEQ ID NO: | Description | Amino acid sequence |
|---|---|---|
| | | KGLPSSIEKTISKAKGQPREPQVYTLPPSQEEMTKNQVSLT CLVKGFYPSDIAVEWESNGQPENNYKTTPPVLDSDGSFFLY SRLTVDKSRWQEGNVFSCSVMHEALHNHYTQKSLSLSLG |
| 64 | Light chain constant region | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |

*CDRs are defined according to the Kabat numbering system.

TABLE 7

Heavy chain CDR amino acid sequences of exemplary anti-PD-1 antibodies.*

| VH (SEQ ID NO:) | CDRH1 (SEQ ID NO:) | CDRH2 (SEQ ID NO:) | CDRH3 (SEQ ID NO:) |
|---|---|---|---|
| BADD438-2742 VH (67) | SYGMH (75) | VIWYDGSNKYYADSVKG (76) | NVDY (80) |
| AGEN2034 VH (66) | SYGMH (75) | VIWYDGSNKYYADSVKG (76) | NGDH (81) |
| BADD426-2614 VH (68) | SYGMH (75) | VIWYDGSNKYYADSVKG (76) | NGDY (82) |
| BADD426-2615 VH (69) | SYGMH (75) | VIWYDGSNKYYADSVKG (76) | NGDY (82) |
| BADD438-2743 VH (70) | SYGMH (75) | VIWYDGSNEYYADSVKG (77) | NGDH (81) |
| BADD438-2745 VH (71) | SYGMH (75) | VIWFDGSNKYYADSVKG (78) | NGDH (81) |
| BADD438-2746 VH (72) | SYGMH (75) | VIWYDGSNKYYADSVKG (76) | NGDH (81) |
| BADD438-2747 VH (73) | SYGMH (75) | VIWYDGSNKYYADSVMG (79) | NGDH (81) |

*Defined according to the Kabat numbering system.

TABLE 8

Light chain CDR amino acid sequences of exemplary anti-PD-1 antibodies.

| VL (SEQ ID NO:) | CDRL1 (SEQ ID NO:) | CDRL2 (SEQ ID NO:) | CDRL3 (SEQ ID NO:) |
|---|---|---|---|
| AGEN2034 VL/3738 VL (74) | RASQSVSSNLA (83) | GASTRAT (84) | QQYNNWPRT (85) |

*Defined according to the Kabat numbering system.

TABLE 9

Exemplary anti-PD-1 antibodies.

| Antibody | Heavy chain variable region | SEQ ID NO: | Light chain variable region | SEQ ID NO: |
|---|---|---|---|---|
| AGEN2033 | BADD438-2742 VH | 67 | 3738 VL | 74 |
| AGEN2034 | AGEN2034 VH | 66 | 3738 VL | 74 |
| AGEN2001 | BADD426-2614 VH | 68 | 3738 VL | 74 |
| AGEN2002 | BADD426-2615 VH | 69 | 3738 VL | 74 |
| EP11_pl1_B03 | BADD438-2743 VH | 70 | 3738 VL | 74 |
| EP11_pl1_B05 | BADD438-2745 VH | 71 | 3738 VL | 74 |
| EP11_pl1_C02 | BADD438-2746 VH | 72 | 3738 VL | 74 |
| EP11_pl1_C03 | BADD438-2747 VH | 73 | 3738 VL | 74 |

TABLE 10

Exemplary sequences of PD-1.

| SEQ ID NO: | Description* | Amino acid Sequence |
|---|---|---|
| 96 | Human PD-1 immature protein (Q15116) | MQIPQAPWPVVWAVLQLGWRPGWFLDSPDRPWNPPTFSPAL LVVTEGDNATFTCSFSNTSESFVLNWYRMSPSNQTDKLAAF PEDRSQPGQDCRFRVTQLPNGRDFHMSVVRARRNDSGTYLC GAISLAPKAQIKESLRAELRVTERRAEVPTAHPSPSPRPAG QFQTLVVGVVGGLLGSLVLLVWVLAVICSRAARGTIGARRT GQPLKEDPSAVPVFSVDYGELDFQWREKTPEPPVPCVPEQT EYATIVFPSGMGTSSPARRGSADGPRSAQPLRPEDGHCSWP L |
| 103 | PD-1 epitope | SLAPKAQIKESLRAEL |
| 104 | PD-1 epitope | LDSPDRPWNPPTFSPALL |
| 105 | PD-1 epitope | DSPDRPWNPP |
| 106 | PD-1 epitope | EVPTAHPSP |
| 107 | PD-1 epitope | ISLAPKAQ |

In certain embodiments, the instant disclosure provides an isolated antibody that specifically binds to PD-1 (e.g., human PD-1), the antibody comprising a heavy chain variable region comprising one, two, or all three of the CDRs of a heavy chain variable region set forth in Table 6 herein. In certain embodiments, the antibody comprises the CDRH1 of one of heavy chain variable regions set forth in Table 6. In certain embodiments, the antibody comprises the CDRH2 of one of the heavy chain variable regions set forth in Table 6. In certain embodiments, the antibody comprises the CDRH3 of one of the heavy chain variable regions set forth in Table 6.

In certain embodiments, the instant disclosure provides an isolated antibody that specifically binds to PD-1 (e.g., human PD-1), the antibody comprising a light chain variable region comprising one, two, or all three of the CDRs of a light chain variable region disclosed in Table 6 herein. In certain embodiments, the antibody comprises the CDRL1 of one of light chain variable regions set forth in Table 6. In certain embodiments, the antibody comprises the CDRL2 of one of the light chain variable regions set forth in Table 6. In certain embodiments, the antibody comprises the CDRL3 of one of the light chain variable regions set forth in Table 6.

In certain embodiments, the CDRs of an antibody can be determined according to Kabat et al., J. Biol. Chem. 252, 6609-6616 (1977) and Kabat et al., Sequences of protein of immunological interest (1991), each of which is herein incorporated by reference in its entirety.

In certain embodiments, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226, all of which are herein incorporated by reference in their entireties). Typically, when using the Kabat numbering convention, the Chothia CDRH1 loop is present at heavy chain amino acids 26 to 32, 33, or 34, the Chothia CDRH2 loop is present at heavy chain amino acids 52 to 56, and the Chothia CDRH3 loop is present at heavy chain amino acids 95 to 102, while the Chothia CDRL1 loop is present at light chain amino acids 24 to 34, the Chothia CDRL2 loop is present at light chain amino acids 50 to 56, and the Chothia CDRL3 loop is present at light chain amino acids 89 to 97. The end of the Chothia CDRH1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain embodiments, the instant disclosure provides an isolated antibody that specifically binds to PD-1 (e.g., human PD-1), the antibody comprising the Chothia VH CDRs of a VH disclosed in Table 6 herein. In certain embodiments, the instant disclosure provides an isolated antibody that specifically binds to PD-1 (e.g., human PD-1), the antibody comprising the Chothia VL CDRs of a VL disclosed in Table 6 herein. In certain embodiments, the instant disclosure provides an isolated antibody that specifically binds to PD-1 (e.g., human PD-1), the antibody comprising the Chothia VH CDRs and Chothia VL CDRs of an antibody disclosed in Table 6 herein. In certain embodiments, antibodies that specifically bind to PD-1 (e.g., human PD-1) comprise one or more CDRs, in which the Chothia and Kabat CDRs have the same amino acid sequence. In certain embodiments, the instant disclosure provides an isolated antibody that specifically binds to PD-1 (e.g., human PD-1) and comprises a combination of Kabat CDRs and Chothia CDRs.

In certain embodiments, the CDRs of an antibody can be determined according to the IMGT numbering system as described in Lefranc M-P, (1999) supra and Lefranc M-P et al., (1999) supra, each of which is herein incorporated by reference in its entirety. In certain embodiments, the instant disclosure provides antibodies that specifically bind to PD-1 (e.g., human PD-1) and comprise CDRs of an antibody disclosed in Table 6 herein, as determined by the IMGT numbering system, for example, as described in Lefranc M-P (1999) supra and Lefranc M-P et al., (1999) supra.

In certain embodiments, the instant disclosure provides an isolated antibody that specifically binds to PD-1 (e.g., human PD-1), the antibody comprising the IMGT VH CDRs of a VH disclosed in Table 6 herein. In certain embodiments, the instant disclosure provides an isolated antibody that specifically binds to PD-1 (e.g., human PD-1), the antibody comprising the IMGT VL CDRs of a VL disclosed in Table 6 herein. In certain embodiments, the instant disclosure provides an isolated antibody that specifically binds to PD-1 (e.g., human PD-1), the antibody comprising the IMGT VH CDRs and IMGT VL CDRs of an antibody disclosed in Table 6 herein. In certain embodiments, the instant disclosure provides an isolated antibody that specifically binds to PD-1 (e.g., human PD-1) and comprises a combination of Kabat CDRs and IMGT CDRs.

In certain embodiments, the CDRs of an antibody can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety. In a particular embodiment, the instant disclosure provides antibodies that specifically bind to PD-1 (e.g., human PD-1) and comprise CDRs of an antibody disclosed in Table 6 herein as determined by the AbM numbering scheme.

In certain embodiments, the CDRs of an antibody can be determined according to MacCallum R M et al., (1996) J Mol Biol 262: 732-745, herein incorporated by reference in its entirety. See also, e.g., Martin A. "Protein Sequence and Structure Analysis of Antibody Variable Domains," in Antibody Engineering, Kontermann and Dubel, eds., Chapter 31, pp. 422-439, Springer-Verlag, Berlin (2001), herein incorporated by reference in its entirety. In a particular embodiment, the instant disclosure provides antibodies that specifically bind to PD-1 (e.g., human PD-1) and comprise CDRs of an antibody disclosed in Table 6 herein as determined by the MacCallum numbering scheme.

Accordingly, in certain embodiments, the instant disclosure provides an isolated antibody that specifically binds to PD-1 (e.g., human PD-1), wherein the antibody comprises a heavy chain variable region comprising the CDRH1, CDRH2, and CDRH3 region amino acid sequences of a heavy chain variable region set forth in SEQ ID NO: 66, 67, 68, 69, 70, 71, 72, or 73, and a light chain variable region comprising the CDRL1, CDRL2, and CDRL3 region amino acid sequences of a light chain variable region set forth in SEQ ID NO: 74, wherein each CDR is defined in accordance with the Kabat definition, the Chothia definition, the combination of the Kabat definition and the Chothia definition, the IMGT numbering system, the AbM definition, or the contact definition of CDR.

In certain embodiments, the instant disclosure provides an isolated antibody that specifically binds to PD-1 (e.g., human PD-1), the antibody comprising:
(a) CDRH1 comprises the amino acid sequence of SYGMH (SEQ ID NO: 75); and/or
(b) CDRH2 comprises the amino acid sequence of VIWX$_1$DGSNX$_2$YYADSVX$_3$G (SEQ ID NO: 86), wherein X$_1$ is Y or F; X$_2$ is K or E; and X$_3$ is K or M; and/or
(c) CDRH3 comprises the amino acid sequence of NX$_1$DX$_2$ (SEQ ID NO: 87), wherein X$_1$ is G or V; and X$_2$ is H or Y; and/or
(d) CDRL1 comprises the amino acid sequence of RASQSVSSNLA (SEQ ID NO: 83); and/or
(e) CDRL2 comprises the amino acid sequence of GASTRAT (SEQ ID NO: 84); and/or
(f) CDRL3 comprises the amino acid sequence of QQYNNWPRT (SEQ ID NO: 85).

In certain embodiments, the instant disclosure provides an isolated antibody that specifically binds to PD-1 (e.g., human PD-1), the antibody comprising:
(a) CDRH1 comprises the amino acid sequence of SYGMH (SEQ ID NO: 75);
(b) CDRH2 comprises the amino acid sequence of VIWX$_1$DGSNX$_2$YYADSVX$_3$G (SEQ ID NO: 86), wherein X$_1$ is Y or F; X$_2$ is K or E; and X$_3$ is K or M;
(c) CDRH3 comprises the amino acid sequence of NX$_1$DX$_2$ (SEQ ID NO: 87), wherein X$_1$ is G or V; and X$_2$ is H or Y;
(d) CDRL1 comprises the amino acid sequence of RASQSVSSNLA (SEQ ID NO: 83);
(e) CDRL2 comprises the amino acid sequence of GASTRAT (SEQ ID NO: 84); and
(f) CDRL3 comprises the amino acid sequence of QQYNNWPRT (SEQ ID NO: 85).

In certain embodiments, the CDRH2 comprises an amino acid sequence selected from the group consisting of SEQ ID NOs: 76-79. In certain embodiments, the CDRH3 comprises an amino acid sequence selected from the group consisting of SEQ ID NOs: 80-82. In certain embodiments, CDRH1, CDRH2, and CDRH3 comprise the CDRH1, CDRH2, and CDRH3 amino acid sequences, respectively, of an antibody in Table 7. In certain embodiments, CDRL1, CDRL2, and CDRL3 comprise the CDRL1, CDRL2, and CDRL3 amino acid sequences, respectively, of an antibody in Table 8.

In certain embodiments, the instant disclosure provides an isolated antibody that specifically binds to PD-1 (e.g., human PD-1), comprising a heavy chain variable region comprising complementarity determining regions CDRH1, CDRH2 and CDRH3, wherein the CDRH1, CDRH2 and CDRH3 comprise the CDRH1, CDRH2 and CDRH3 amino acid sequences, respectively, set forth in SEQ ID NOs: 75, 76, and 80; 75, 76, and 81; 75, 76, and 82; 75, 77, and 81; 75, 78, and 81; or 75, 79, and 81.

In certain embodiments, the instant disclosure provides an isolated antibody that specifically binds to PD-1 (e.g., human PD-1), comprising a light chain variable region comprising complementarity determining regions CDRL1, CDRL2 and CDRL3, wherein the CDRL1, CDRL2 and CDRL3 comprise the CDRL1, CDRL2 and CDRL3 amino acid sequences, respectively, set forth in SEQ ID NOs: 83, 84, and 85.

In certain embodiments, the instant disclosure provides an isolated antibody that specifically binds to PD-1 (e.g., human PD-1), comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2 and CDRL3 comprise the CDRH1, CDRH2, CDRH3, CDRL1, CDRL2 and CDRL3 amino acid sequences, respectively, set forth in SEQ ID NOs: 75, 76, 80, 83, 84, and 85; 75, 76, 81, 83, 84, and 85; 75, 76, 82, 83, 84, and 85; 75, 77, 81, 83, 84, and 85; 75, 78, 81, 83, 84, and 85; or 75, 79, 81, 83, 84, and 85, respectively.

In certain embodiments, the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 75, 76, 81, 83, 84, and 85, respectively.

In certain embodiments, the instant disclosure provides an isolated antibody that specifically binds to PD-1 (e.g., human PD-1), comprising a heavy chain variable region comprising the amino acid sequence of SEQ ID NO: 88.

In certain embodiments, the instant disclosure provides an isolated antibody that specifically binds to PD-1 (e.g., human PD-1), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to an amino acid sequence selected from the group consisting of SEQ ID NOs: 66-73. In certain embodiments, the antibody comprises a heavy chain variable region having an amino acid sequence selected from the group consisting of SEQ ID NOs: 66-73. In certain embodiments, the antibody comprises a heavy chain variable region having the amino acid sequence set forth in SEQ ID NO: 66. In certain embodiments, the antibody comprises a heavy chain variable region having the amino acid sequence set forth in SEQ ID NO: 67. In certain embodiments, the antibody comprises a heavy chain variable region having the amino acid sequence set forth in SEQ ID NO: 68. In certain embodiments, the antibody comprises a heavy chain variable region having the amino acid sequence set forth in SEQ ID NO: 69. In certain embodiments, the antibody comprises a heavy chain variable region having the amino acid sequence set forth in SEQ ID NO: 70. In certain embodiments, the antibody comprises a heavy chain variable region having the amino acid sequence set forth in SEQ ID NO: 71. In certain embodiments, the antibody comprises a heavy chain variable region having the amino acid sequence set forth in SEQ ID NO: 72. In certain embodiments, the antibody comprises a heavy chain variable region having the amino acid sequence set forth in SEQ ID NO: 73.

In certain embodiments, the instant disclosure provides an isolated antibody that specifically binds to PD-1 (e.g., human PD-1), comprising a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence of SEQ ID NO: 74. In certain embodiments, the antibody comprises a light chain variable region having the amino acid sequence of SEQ ID NO: 74.

In certain embodiments, the instant disclosure provides an isolated antibody that specifically binds to PD-1 (e.g., human PD-1), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 66, 67, 68, 69, 70, 71, 72, or 73, and a light chain variable region that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 74. In certain embodiments, the instant disclosure provides an isolated antibody that specifically binds to PD-1 (e.g., human PD-1), comprising a heavy chain variable region comprising an amino acid sequence set forth in SEQ ID NO: 66, 67, 68, 69, 70, 71, 72, or 73, and a light chain variable region set forth in SEQ ID NO: 74. In certain embodiments, the antibody comprises a heavy chain variable region and light chain variable region having the amino acid sequences set forth in SEQ ID NOs: 66 and 74; 67 and 74; 68 and 74; 69 and 74; 70 and 74; 71 and 74; 72 and 74; or 73 and 74, respectively. In certain embodiments, the antibody comprises a heavy chain variable region and light chain variable region having the amino acid sequences set forth in SEQ ID NOs: 66 and 74, respectively. In certain embodiments, the antibody comprises a heavy chain variable region and light chain variable region having the amino acid sequences set forth in SEQ ID NOs: 67 and 74, respectively. In certain embodiments, the antibody comprises a heavy chain variable region and light chain variable region having the amino acid sequences set forth in SEQ ID NOs: 68 and 74, respectively. In certain embodiments, the antibody comprises a heavy chain variable region and light chain variable region having the amino acid sequences set forth in SEQ ID NOs: 69 and 74, respectively. In certain embodiments, the antibody comprises a heavy chain variable region and light chain variable region having the amino acid sequences set forth in SEQ ID NOs: 70 and 74, respectively. In certain embodiments, the antibody comprises a heavy chain variable region and light chain variable region having the amino acid sequences set forth in SEQ ID NOs: 71 and 74, respectively. In certain embodiments, the antibody comprises a heavy chain variable region and light chain variable region having the amino acid sequences set forth in SEQ ID NOs: 72 and 74, respectively. In certain embodiments, the antibody comprises a heavy chain variable region and light chain variable region having the amino acid sequences set forth in SEQ ID NOs: 73 and 74, respectively.

In certain embodiments, the instant disclosure provides an isolated antibody that specifically binds to PD-1 (e.g., human PD-1), comprising a heavy chain variable region having an amino acid sequence derived from a human IGHV3-33 germline sequence (e.g., IGHV3-33*01, e.g., having the amino acid sequence of SEQ ID NO: 89). One or more regions selected from framework 1, framework 2, framework 3, CDRH1, and CDRH2 (e.g., two, three, four or five of these regions) can be derived from a human IGHV3-33 germline sequence. In one embodiment, framework 1, framework 2, framework 3, CDRH1, and CDRH2 are all derived from a human IGHV3-33 germline sequence.

In certain embodiments, the instant disclosure provides an isolated antibody that specifically binds to PD-1 (e.g., human PD-1), comprising a light chain variable region having an amino acid sequence derived from a human IGKV3-15 germline sequence (e.g., IGKV3-15*01, e.g., having the amino acid sequence of SEQ ID NO: 90). One or more regions selected from framework 1, framework 2, framework 3, CDRL1, and CDRL2 (e.g., two, three, four or five of these regions) can be derived from a human IGKV3-15 germline sequence. In one embodiment, framework 1, framework 2, framework 3, CDRL1, and CDRL2 are all derived from a human IGKV3-15 germline sequence.

In certain embodiments, the instant disclosure provides an isolated antibody that specifically binds to PD-1 (e.g., human PD-1), comprising a heavy chain variable region having an amino acid sequence derived from a human IGHV3-33 germline sequence (e.g., IGHV3-33*01, e.g., having the amino acid sequence of SEQ ID NO: 89), and a light chain variable region having an amino acid sequence derived from a human IGKV3-15 germline sequence (e.g., IGKV3-15*01, e.g., having the amino acid sequence of SEQ ID NO: 90). One or more regions selected from framework 1, framework 2, framework 3, CDRH1, and CDRH2 of the heavy chain variable region (e.g., two, three, four or five of these regions) can be derived from a human IGHV3-33 germline sequence. In one embodiment, framework 1, framework 2, framework 3, CDRH1, and CDRH2 are all derived from a human IGHV3-33 germline sequence. One or more regions selected from framework 1, framework 2, framework 3, CDRL1, and CDRL2 of the light chain variable region (e.g., two, three, four or five of these regions) can be derived from a human IGKV3-15 germline sequence. In one embodiment, framework 1, framework 2, framework 3, CDRL1, and CDRL2 are all derived from a human IGKV3-15 germline sequence.

In certain embodiments, the antibody comprises a heavy chain having an amino acid sequence selected from the group consisting of SEQ ID NOs: 91 and 92. In certain embodiments, the antibody comprises a heavy chain having the amino acid sequence set forth in SEQ ID NO: 91. In certain embodiments, the antibody comprises a heavy chain having the amino acid sequence set forth in SEQ ID NO: 92.

In certain embodiments, the antibody comprises a light chain having the amino acid sequence of SEQ ID NO: 93.

In certain embodiments, the instant disclosure provides an isolated antibody that specifically binds to PD-1 (e.g., human PD-1), comprising a heavy chain comprising the amino acid sequence of SEQ ID NO: 91 or 92, and a light chain comprising the amino acid sequence of SEQ ID NO: 93. In certain embodiments, the antibody comprises a heavy chain and light chain having the amino acid sequences set forth in SEQ ID NOs: 91 and 93, respectively. In certain embodiments, the antibody comprises a heavy chain and light chain having the amino acid sequences set forth in SEQ ID NOs: 92 and 93, respectively.

In certain embodiments, the instant disclosure provides an isolated antibody that cross-competes for binding to PD-1 (e.g., human PD-1), with an antibody comprising the heavy and light chain variable region amino acid sequences set forth in SEQ ID NOs: 66 and 74; 67 and 74; 68 and 74; 69 and 74; 70 and 74; 71 and 74; 72 and 74; or 73 and 74, respectively. In certain embodiments, the instant disclosure provides an isolated antibody that cross-competes for binding to PD-1 (e.g., human PD-1), with an antibody comprising the heavy and light chain variable region amino acid sequences set forth in SEQ ID NOs: 66 and 74, respectively.

In certain embodiments, the instant disclosure provides an isolated antibody that binds to the same epitope on CTLA-4 (e.g., human CTLA-4) as an antibody comprising the heavy and light chain variable region amino acid sequences set forth in SEQ ID NOs: 66 and 74; 67 and 74; 68 and 74; 69 and 74; 70 and 74; 71 and 74; 72 and 74; or 73 and 74, respectively. In certain embodiments, the instant disclosure provides an isolated antibody that binds to the same epitope on CTLA-4 (e.g., human CTLA-4) as an antibody comprising the heavy and light chain variable region amino acid sequences set forth in SEQ ID NOs: 66 and 74, respectively. In certain embodiments, the isolated antibody binds to an epitope located within a region of human CTLA-4 consisting of the amino acid sequence of SEQ ID NO: 103. In certain embodiments, the isolated antibody binds to an epitope located within a region of human CTLA-4 consisting of the amino acid sequence of SEQ ID NO: 104. In certain embodiments, the isolated antibody binds to an epitope located within a region of human CTLA-4 consisting of the amino acid sequence of SEQ ID NO: 105. In certain embodiments, the isolated antibody binds to an epitope located within a region of human CTLA-4 consisting of the amino acid sequence of SEQ ID NO: 106. In certain embodiments, the isolated antibody binds to an epitope located within a region of human CTLA-4 consisting of the amino acid sequence of SEQ ID NO: 107.

In certain embodiments, the instant disclosure provides an isolated antibody that specifically binds to human PD-1 and functions as an antagonist.

In certain embodiments, the instant disclosure provides an isolated antibody that specifically binds to human PD-1 and decreases PD-1 activity by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to PD-1 activity without any antibody or with an unrelated antibody (e.g., an antibody that does not specifically bind to PD-1). In certain embodiments, the instant disclosure provides an isolated antibody that specifically binds to human PD-1 and decreases PD-1 activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to PD-1 activity without any antibody or with an unrelated antibody (e.g., an antibody that does not specifically bind to PD-1). Non-limiting examples of PD-1 activity can include PD-1 signaling, PD-1 binding to PD-1 ligand (e.g., PD-L1 or PD-L2), inhibition of cytokine production (e.g., IL-2 or IFNγ), and inhibition of T cell proliferation. In certain embodiments, the instant disclosure provides an isolated antibody that specifically binds to human PD-1 and deactivates, reduces, or inhibits a PD-1 activity. In specific embodiments, a decrease in a PD-1 activity is assessed as described in the Examples, infra.

In specific embodiments, the instant disclosure provides an isolated antibody that specifically binds to human PD-1 and decreases PD-1 binding to its ligand (e.g., PD-L1 or PD-L2) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to PD-1 binding to its ligand (e.g., PD-L1 or PD-L2) without any antibody or with an unrelated antibody (e.g., an antibody that does not specifically bind to PD-1). In specific embodiments, the instant disclosure provides an isolated antibody that specifically binds to human PD-1 and decreases PD-1 binding to its ligand (e.g., PD-L1 or PD-L2) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to PD-1 binding to its ligand (e.g., PD-L1 or PD-L2) without any antibody or with an unrelated antibody (e.g., an antibody that does not specifically bind to PD-1).

In specific embodiments, the instant disclosure provides an isolated antibody that specifically binds to human PD-1 and increases cytokine production (e.g., IL-2 or IFNγ) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to cytokine production without any antibody or with an unrelated antibody (e.g., an antibody that does not specifically bind to PD-1). In specific embodiments, the instant disclosure provides an isolated antibody that specifically binds to human PD-1 and increases cytokine production (e.g., IL-2 or IFNγ) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to cytokine production without any antibody or with an unrelated antibody (e.g., an antibody that does not specifically bind to PD-1).

In specific embodiments, the instant disclosure provides an isolated antibody that specifically binds to PD-1 (e.g., human PD-1) and either alone or in combination with an anti-CTLA-4 antibody (e.g., ipilimumab or tremelimumab), an anti-TIGIT antibody, an anti-CD137 antibody (e.g., urelumab or utomilumab), or an anti-OX40 antibody (e.g., pogalizumab or tavolixizumab) increases IL-2 production in human peripheral blood mononuclear cells (PBMCs) in response to *Staphylococcus* Enterotoxin A (SEA) stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to IL-2 production without any antibody or with an unrelated antibody (e.g., an antibody that does not specifically bind to PD-1).

In certain embodiments, human peripheral blood mononuclear cells (PBMCs) stimulated with *Staphylococcus* Enterotoxin A (SEA) in the presence of an antibody described herein, which specifically binds to human PD-1, either alone or in combination with an anti-CTLA-4 antibody (e.g., ipilimumab or tremelimumab), an anti-TIGIT antibody, an anti-CD137 antibody (e.g., urelumab or utomilumab), or an anti-OX40 antibody (e.g., pogalizumab or tavolixizumab), have increased IL-2 production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to PBMCs only stimulated with SEA without any antibody or with an unrelated antibody (e.g., an antibody that does not specifically bind to PD-1), as assessed by methods described herein (see the Examples, infra) or known to one of skill in the art.

In specific embodiments, the instant disclosure provides an isolated antibody that specifically binds to human PD-1 and increases IFNγ production of a co-culture of human T cells and allogenic dendritic cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to IFNγ production of a co-culture of human T cells and allogenic dendritic cells without any antibody or with an unrelated antibody (e.g., an antibody that does not specifically bind to PD-1).

In certain embodiments, a co-culture of human T cells and allogenic dendritic cells in the presence of an antibody described herein, which specifically binds to human PD-1, has increased IFNγ production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to a co-culture of human T cells and allogenic dendritic cells without any antibody or with an unrelated antibody (e.g., an antibody that does not specifically bind to PD-1), as assessed by methods described herein (see the Examples, infra) or known to one of skill in the art.

In specific embodiments, the instant disclosure provides an isolated antibody that specifically binds to human PD-1 and increases T cell proliferation by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to T cell proliferation without any antibody or with an unrelated antibody (e.g., an antibody that does not specifically bind to PD-1). In specific embodiments, the instant disclosure provides an isolated antibody that specifically binds to human PD-1 and increases T cell proliferation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to T cell proliferation without any antibody or with an unrelated antibody (e.g., an antibody that does not specifically bind to PD-1).

In specific embodiments, the instant disclosure provides an isolated antibody that specifically binds to human PD-1 and increases proliferation of anti-CD3-antibody-stimulated CD4+ or CD8+ T cells co-cultured with ovarian cancer ascites fluid by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to proliferation of anti-CD3-antibody-stimulated CD4+ or CD8+ T cells co-cultured with ovarian cancer ascites fluid without any antibody or with an unrelated antibody (e.g., an antibody that does not specifically bind to PD-1).

In specific embodiments, the instant disclosure provides an isolated antibody that specifically binds to human PD-1 and increases NFAT signaling in PD-1-expressing NFAT-luciferase reporter cells co-cultured with PD-L1-expressing target cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to NFAT signaling in PD-1-expressing NFAT-luciferase reporter cells co-cultured with PD-L1-expressing target cells without any antibody or with an unrelated antibody (e.g., an antibody that does not specifically bind to PD-1).

6.2.3 Multispecific Antibodies that Specifically Bind to CTLA-4 and/or PD-1

In one aspect, provided herein are multispecific antibodies (e.g., bispecific antibodies) that specifically bind to CTLA-4 and PD-1 (e.g., human CTLA-4 and human PD-1). For instance, a multispecific (e.g., bispecific) antibody provided herein can comprise a first antigen-binding region that specifically binds to CTLA-4 (e.g., human CTLA-4) and a second antigen-binding region that specifically binds to PD-1 (e.g., human PD-1). Such multispecific antibodies advantageously show greater specificity for certain subsets of immune cells containing the combination of target proteins than monospecific bivalent antibodies that only bind to CTLA-4 or PD-1.

In one embodiment, an antibody provided herein that specifically binds to CTLA-4 and PD-1 contains a combination of CDRs shown in a single row of Table 11 below.

TABLE 11

CDR sequences of exemplary anti-CTLA-4/PD-1 antibodies.*

| SEQ ID NOs of CDRs of the first antigen-binding domain that specifically binds to human CTLA-4 | | | | | | SEQ ID NOs of CDRs of the second antigen-binding domain that specifically binds to human PD-1 | | | | | |
|---|---|---|---|---|---|---|---|---|---|---|---|
| VH CDR 1 | VH CDR 2 | VH CDR 3 | VL CDR 1 | VL CDR 2 | VL CDR 3 | VH CDR 1 | VH CDR 2 | VH CDR 3 | VL CDR 1 | VL CDR 2 | VL CDR 3 |
| 20 | 22 | 24 | 27 | 30 | 36 | 75 | 76 | 80 | 83 | 84 | 85 |
| 20 | 22 | 24 | 29 | 32 | 37 | 75 | 76 | 80 | 83 | 84 | 85 |
| 20 | 22 | 24 | 29 | 33 | 38 | 75 | 76 | 80 | 83 | 84 | 85 |
| 21 | 22 | 24 | 27 | 30 | 36 | 75 | 76 | 80 | 83 | 84 | 85 |
| 21 | 22 | 24 | 29 | 33 | 38 | 75 | 76 | 80 | 83 | 84 | 85 |
| 20 | 22 | 24 | 28 | 31 | 36 | 75 | 76 | 80 | 83 | 84 | 85 |
| 20 | 22 | 24 | 29 | 34 | 36 | 75 | 76 | 80 | 83 | 84 | 85 |
| 20 | 22 | 24 | 29 | 35 | 38 | 75 | 76 | 80 | 83 | 84 | 85 |
| 21 | 22 | 26 | 27 | 30 | 36 | 75 | 76 | 80 | 83 | 84 | 85 |
| 21 | 22 | 26 | 29 | 32 | 37 | 75 | 76 | 80 | 83 | 84 | 85 |
| 21 | 22 | 26 | 29 | 33 | 38 | 75 | 76 | 80 | 83 | 84 | 85 |
| 21 | 22 | 26 | 29 | 35 | 38 | 75 | 76 | 80 | 83 | 84 | 85 |
| 20 | 22 | 24 | 27 | 30 | 36 | 75 | 76 | 81 | 83 | 84 | 85 |
| 20 | 22 | 24 | 29 | 32 | 37 | 75 | 76 | 81 | 83 | 84 | 85 |
| 20 | 22 | 24 | 29 | 33 | 38 | 75 | 76 | 81 | 83 | 84 | 85 |
| 21 | 22 | 24 | 27 | 30 | 36 | 75 | 76 | 81 | 83 | 84 | 85 |
| 21 | 22 | 24 | 29 | 33 | 38 | 75 | 76 | 81 | 83 | 84 | 85 |
| 20 | 22 | 24 | 28 | 31 | 36 | 75 | 76 | 81 | 83 | 84 | 85 |
| 20 | 22 | 24 | 29 | 34 | 36 | 75 | 76 | 81 | 83 | 84 | 85 |
| 20 | 22 | 24 | 29 | 35 | 38 | 75 | 76 | 81 | 83 | 84 | 85 |
| 21 | 22 | 26 | 27 | 30 | 36 | 75 | 76 | 81 | 83 | 84 | 85 |
| 21 | 22 | 26 | 29 | 32 | 37 | 75 | 76 | 81 | 83 | 84 | 85 |
| 21 | 22 | 26 | 29 | 33 | 38 | 75 | 76 | 81 | 83 | 84 | 85 |
| 21 | 22 | 26 | 29 | 35 | 38 | 75 | 76 | 81 | 83 | 84 | 85 |
| 20 | 22 | 24 | 27 | 30 | 36 | 75 | 76 | 82 | 83 | 84 | 85 |
| 20 | 22 | 24 | 29 | 32 | 37 | 75 | 76 | 82 | 83 | 84 | 85 |
| 20 | 22 | 24 | 29 | 33 | 38 | 75 | 76 | 82 | 83 | 84 | 85 |
| 21 | 22 | 24 | 27 | 30 | 36 | 75 | 76 | 82 | 83 | 84 | 85 |
| 21 | 22 | 24 | 29 | 33 | 38 | 75 | 76 | 82 | 83 | 84 | 85 |
| 20 | 22 | 24 | 28 | 31 | 36 | 75 | 76 | 82 | 83 | 84 | 85 |
| 20 | 22 | 24 | 29 | 34 | 36 | 75 | 76 | 82 | 83 | 84 | 85 |
| 20 | 22 | 24 | 29 | 35 | 38 | 75 | 76 | 82 | 83 | 84 | 85 |
| 21 | 22 | 26 | 27 | 30 | 36 | 75 | 76 | 82 | 83 | 84 | 85 |
| 21 | 22 | 26 | 29 | 32 | 37 | 75 | 76 | 82 | 83 | 84 | 85 |
| 21 | 22 | 26 | 29 | 33 | 38 | 75 | 76 | 82 | 83 | 84 | 85 |
| 21 | 22 | 26 | 29 | 35 | 38 | 75 | 76 | 82 | 83 | 84 | 85 |
| 20 | 22 | 24 | 27 | 30 | 36 | 75 | 77 | 81 | 83 | 84 | 85 |
| 20 | 22 | 24 | 29 | 32 | 37 | 75 | 77 | 81 | 83 | 84 | 85 |
| 20 | 22 | 24 | 29 | 33 | 38 | 75 | 77 | 81 | 83 | 84 | 85 |
| 21 | 22 | 24 | 27 | 30 | 36 | 75 | 77 | 81 | 83 | 84 | 85 |
| 21 | 22 | 24 | 29 | 33 | 38 | 75 | 77 | 81 | 83 | 84 | 85 |
| 20 | 22 | 24 | 28 | 31 | 36 | 75 | 77 | 81 | 83 | 84 | 85 |
| 20 | 22 | 24 | 29 | 34 | 36 | 75 | 77 | 81 | 83 | 84 | 85 |
| 20 | 22 | 24 | 29 | 35 | 38 | 75 | 77 | 81 | 83 | 84 | 85 |
| 21 | 22 | 26 | 27 | 30 | 36 | 75 | 77 | 81 | 83 | 84 | 85 |
| 21 | 22 | 26 | 29 | 32 | 37 | 75 | 77 | 81 | 83 | 84 | 85 |
| 21 | 22 | 26 | 29 | 33 | 38 | 75 | 77 | 81 | 83 | 84 | 85 |
| 21 | 22 | 26 | 29 | 35 | 38 | 75 | 77 | 81 | 83 | 84 | 85 |
| 20 | 22 | 24 | 27 | 30 | 36 | 75 | 78 | 81 | 83 | 84 | 85 |
| 20 | 22 | 24 | 29 | 32 | 37 | 75 | 78 | 81 | 83 | 84 | 85 |
| 20 | 22 | 24 | 29 | 33 | 38 | 75 | 78 | 81 | 83 | 84 | 85 |
| 21 | 22 | 24 | 27 | 30 | 36 | 75 | 78 | 81 | 83 | 84 | 85 |
| 21 | 22 | 24 | 29 | 33 | 38 | 75 | 78 | 81 | 83 | 84 | 85 |
| 20 | 22 | 24 | 28 | 31 | 36 | 75 | 78 | 81 | 83 | 84 | 85 |
| 20 | 22 | 24 | 29 | 34 | 36 | 75 | 78 | 81 | 83 | 84 | 85 |
| 20 | 22 | 24 | 29 | 35 | 38 | 75 | 78 | 81 | 83 | 84 | 85 |
| 21 | 22 | 26 | 27 | 30 | 36 | 75 | 78 | 81 | 83 | 84 | 85 |
| 21 | 22 | 26 | 29 | 32 | 37 | 75 | 78 | 81 | 83 | 84 | 85 |
| 21 | 22 | 26 | 29 | 33 | 38 | 75 | 78 | 81 | 83 | 84 | 85 |
| 21 | 22 | 26 | 29 | 35 | 38 | 75 | 78 | 81 | 83 | 84 | 85 |
| 20 | 22 | 24 | 27 | 30 | 36 | 75 | 79 | 81 | 83 | 84 | 85 |
| 20 | 22 | 24 | 29 | 32 | 37 | 75 | 79 | 81 | 83 | 84 | 85 |
| 20 | 22 | 24 | 29 | 33 | 38 | 75 | 79 | 81 | 83 | 84 | 85 |
| 21 | 22 | 24 | 27 | 30 | 36 | 75 | 79 | 81 | 83 | 84 | 85 |
| 21 | 22 | 24 | 29 | 33 | 38 | 75 | 79 | 81 | 83 | 84 | 85 |
| 20 | 22 | 24 | 28 | 31 | 36 | 75 | 79 | 81 | 83 | 84 | 85 |
| 20 | 22 | 24 | 29 | 34 | 36 | 75 | 79 | 81 | 83 | 84 | 85 |
| 20 | 22 | 24 | 29 | 35 | 38 | 75 | 79 | 81 | 83 | 84 | 85 |
| 21 | 22 | 26 | 27 | 30 | 36 | 75 | 79 | 81 | 83 | 84 | 85 |
| 21 | 22 | 26 | 29 | 32 | 37 | 75 | 79 | 81 | 83 | 84 | 85 |

TABLE 11-continued

CDR sequences of exemplary anti-CTLA-4/PD-1 antibodies.*

| SEQ ID NOs of CDRs of the first antigen-binding domain that specifically binds to human CTLA-4 | | | | | | SEQ ID NOs of CDRs of the second antigen-binding domain that specifically binds to human PD-1 | | | | | |
|---|---|---|---|---|---|---|---|---|---|---|---|
| VH CDR 1 | VH CDR 2 | VH CDR 3 | VL CDR 1 | VL CDR 2 | VL CDR 3 | VH CDR 1 | VH CDR 2 | VH CDR 3 | VL CDR 1 | VL CDR 2 | VL CDR 3 |
| 21 | 22 | 26 | 29 | 33 | 38 | 75 | 79 | 81 | 83 | 84 | 85 |
| 21 | 22 | 26 | 29 | 35 | 38 | 75 | 79 | 81 | 83 | 84 | 85 |

*Defined according to the Kabat numbering system.

In one embodiment, an antibody provided herein that specifically binds to CTLA-4 and PD-1 contains a combination of two heavy chain variable regions and two light chain variable regions shown in a single row of Table 12 below.

TABLE 12

Heavy chain variable region (VH) and light chain variable region (VL) sequences of exemplary anti-CTLA-4/PD-1 antibodies.

| SEQ ID NOs of variable regions of the first antigen-binding domain that specifically binds to human CTLA-4 | | SEQ ID NOs of variable regions of the second antigen-binding domain that specifically binds to human PD-1 | |
|---|---|---|---|
| VH SEQ ID NO: | VL SEQ ID NO: | VH SEQ ID NO: | VL SEQ ID NO: |
| 1 | 14 | 67 | 74 |
| 1 | 16 | 67 | 74 |
| 1 | 17 | 67 | 74 |
| 9 | 14 | 67 | 74 |
| 9 | 17 | 67 | 74 |
| 10 | 15 | 67 | 74 |
| 10 | 17 | 67 | 74 |
| 10 | 18 | 67 | 74 |
| 10 | 19 | 67 | 74 |
| 11 | 15 | 67 | 74 |
| 11 | 14 | 67 | 74 |
| 11 | 16 | 67 | 74 |
| 11 | 17 | 67 | 74 |
| 12 | 14 | 67 | 74 |
| 12 | 16 | 67 | 74 |
| 12 | 17 | 67 | 74 |
| 12 | 19 | 67 | 74 |
| 13 | 15 | 67 | 74 |
| 13 | 17 | 67 | 74 |
| 1 | 14 | 66 | 74 |
| 1 | 16 | 66 | 74 |
| 1 | 17 | 66 | 74 |
| 9 | 14 | 66 | 74 |
| 9 | 17 | 66 | 74 |
| 10 | 15 | 66 | 74 |
| 10 | 17 | 66 | 74 |
| 10 | 18 | 66 | 74 |
| 10 | 19 | 66 | 74 |
| 11 | 15 | 66 | 74 |
| 11 | 14 | 66 | 74 |
| 11 | 16 | 66 | 74 |
| 11 | 17 | 66 | 74 |
| 12 | 14 | 66 | 74 |
| 12 | 16 | 66 | 74 |
| 12 | 17 | 66 | 74 |
| 12 | 19 | 66 | 74 |
| 13 | 15 | 66 | 74 |
| 13 | 17 | 66 | 74 |
| 1 | 14 | 68 | 74 |
| 1 | 16 | 68 | 74 |
| 1 | 17 | 68 | 74 |
| 9 | 14 | 68 | 74 |
| 9 | 17 | 68 | 74 |
| 10 | 15 | 68 | 74 |
| 10 | 17 | 68 | 74 |
| 10 | 18 | 68 | 74 |
| 10 | 19 | 68 | 74 |
| 11 | 15 | 68 | 74 |
| 11 | 14 | 68 | 74 |
| 11 | 16 | 68 | 74 |
| 11 | 17 | 68 | 74 |
| 12 | 14 | 68 | 74 |
| 12 | 16 | 68 | 74 |
| 12 | 17 | 68 | 74 |
| 12 | 19 | 68 | 74 |
| 13 | 15 | 68 | 74 |
| 13 | 17 | 68 | 74 |
| 1 | 14 | 69 | 74 |
| 1 | 16 | 69 | 74 |
| 1 | 17 | 69 | 74 |
| 9 | 14 | 69 | 74 |
| 9 | 17 | 69 | 74 |
| 10 | 15 | 69 | 74 |
| 10 | 17 | 69 | 74 |
| 10 | 18 | 69 | 74 |
| 10 | 19 | 69 | 74 |
| 11 | 15 | 69 | 74 |
| 11 | 14 | 69 | 74 |
| 11 | 16 | 69 | 74 |
| 11 | 17 | 69 | 74 |
| 12 | 14 | 69 | 74 |
| 12 | 16 | 69 | 74 |
| 12 | 17 | 69 | 74 |
| 12 | 19 | 69 | 74 |
| 13 | 15 | 69 | 74 |
| 13 | 17 | 69 | 74 |
| 1 | 14 | 70 | 74 |
| 1 | 16 | 70 | 74 |
| 1 | 17 | 70 | 74 |
| 9 | 14 | 70 | 74 |
| 9 | 17 | 70 | 74 |
| 10 | 15 | 70 | 74 |
| 10 | 17 | 70 | 74 |
| 10 | 18 | 70 | 74 |
| 10 | 19 | 70 | 74 |
| 11 | 15 | 70 | 74 |
| 11 | 14 | 70 | 74 |
| 11 | 16 | 70 | 74 |
| 11 | 17 | 70 | 74 |
| 12 | 14 | 70 | 74 |
| 12 | 16 | 70 | 74 |
| 12 | 17 | 70 | 74 |
| 12 | 19 | 70 | 74 |

TABLE 12-continued

Heavy chain variable region (VH) and light chain variable region (VL) sequences of exemplary anti-CTLA-4/PD-1 antibodies.

| SEQ ID NOs of variable regions of the first antigen-binding domain that specifically binds to human CTLA-4 | | SEQ ID NOs of variable regions of the second antigen-binding domain that specifically binds to human PD-1 | |
|---|---|---|---|
| VH SEQ ID NO: | VL SEQ ID NO: | VH SEQ ID NO: | VL SEQ ID NO: |
| 13 | 15 | 70 | 74 |
| 13 | 17 | 70 | 74 |
| 1  | 14 | 71 | 74 |
| 1  | 16 | 71 | 74 |
| 1  | 17 | 71 | 74 |
| 9  | 14 | 71 | 74 |
| 9  | 17 | 71 | 74 |
| 10 | 15 | 71 | 74 |
| 10 | 17 | 71 | 74 |
| 10 | 18 | 71 | 74 |
| 10 | 19 | 71 | 74 |
| 11 | 15 | 71 | 74 |
| 11 | 14 | 71 | 74 |
| 11 | 16 | 71 | 74 |
| 11 | 17 | 71 | 74 |
| 12 | 14 | 71 | 74 |
| 12 | 16 | 71 | 74 |
| 12 | 17 | 71 | 74 |
| 12 | 19 | 71 | 74 |
| 13 | 15 | 71 | 74 |
| 13 | 17 | 71 | 74 |
| 1  | 14 | 72 | 74 |
| 1  | 16 | 72 | 74 |
| 1  | 17 | 72 | 74 |
| 9  | 14 | 72 | 74 |
| 9  | 17 | 72 | 74 |
| 10 | 15 | 72 | 74 |
| 10 | 17 | 72 | 74 |
| 10 | 18 | 72 | 74 |
| 10 | 19 | 72 | 74 |
| 11 | 15 | 72 | 74 |
| 11 | 14 | 72 | 74 |
| 11 | 16 | 72 | 74 |
| 11 | 17 | 72 | 74 |
| 12 | 14 | 72 | 74 |
| 12 | 16 | 72 | 74 |
| 12 | 17 | 72 | 74 |
| 12 | 19 | 72 | 74 |
| 13 | 15 | 72 | 74 |
| 13 | 17 | 72 | 74 |
| 1  | 14 | 73 | 74 |
| 1  | 16 | 73 | 74 |
| 1  | 17 | 73 | 74 |
| 9  | 14 | 73 | 74 |
| 9  | 17 | 73 | 74 |
| 10 | 15 | 73 | 74 |
| 10 | 17 | 73 | 74 |
| 10 | 18 | 73 | 74 |
| 10 | 19 | 73 | 74 |
| 11 | 15 | 73 | 74 |
| 11 | 14 | 73 | 74 |
| 11 | 16 | 73 | 74 |
| 11 | 17 | 73 | 74 |
| 12 | 14 | 73 | 74 |
| 12 | 16 | 73 | 74 |
| 12 | 17 | 73 | 74 |
| 12 | 19 | 73 | 74 |
| 13 | 15 | 73 | 74 |
| 13 | 17 | 73 | 74 |

In certain embodiments, the first antigen-binding region that specifically binds to CTLA-4 (e.g., human CTLA-4) comprises a heavy chain variable region comprising one, two, or all three of the CDRs of a heavy chain variable region set forth in Table 1 herein. In certain embodiments, the first antigen-binding region comprises the CDRH1 of one of heavy chain variable regions set forth in Table 1. In certain embodiments, the first antigen-binding region comprises the CDRH2 of one of the heavy chain variable regions set forth in Table 1. In certain embodiments, the first antigen-binding region comprises the CDRH3 of one of the heavy chain variable regions set forth in Table 1.

In certain embodiments, the first antigen-binding region that specifically binds to CTLA-4 (e.g., human CTLA-4) comprises a light chain variable region comprising one, two, or all three of the CDRs of a light chain variable region disclosed in Table 1 herein. In certain embodiments, the first antigen-binding region comprises the CDRL1 of one of light chain variable regions set forth in Table 1. In certain embodiments, the first antigen-binding region comprises the CDRL2 of one of the light chain variable regions set forth in Table 1. In certain embodiments, the first antigen-binding region comprises the CDRL3 of one of the light chain variable regions set forth in Table 1.

In certain embodiments, the CDRs of the first antigen-binding region can be determined according to Kabat et al., J. Biol. Chem. 252, 6609-6616 (1977) and Kabat et al., Sequences of protein of immunological interest (1991), each of which is herein incorporated by reference in its entirety.

In certain embodiments, the CDRs of the first antigen-binding region can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226, all of which are herein incorporated by reference in their entireties). In certain embodiments, the first antigen-binding region that specifically binds to CTLA-4 (e.g., human CTLA-4) comprises the Chothia VH CDRs of a VH disclosed in Table 1 herein. In certain embodiments, the first antigen-binding region that specifically binds to CTLA-4 (e.g., human CTLA-4) comprises the Chothia VL CDRs of a VL disclosed in Table 1. In certain embodiments, the first antigen-binding region that specifically binds to CTLA-4 (e.g., human CTLA-4) comprises the Chothia VH CDRs and Chothia VL CDRs of an antibody disclosed in Table 1 herein. In certain embodiments, the first antigen-binding region that specifically binds to CTLA-4 (e.g., human CTLA-4) comprises one or more CDRs, in which the Chothia and Kabat CDRs have the same amino acid sequence. In certain embodiments, the first antigen-binding region that specifically binds to CTLA-4 (e.g., human CTLA-4) comprises a combination of Kabat CDRs and Chothia CDRs.

In certain embodiments, the first antigen-binding region that specifically binds to CTLA-4 (e.g., human CTLA-4) comprises CDRs of an antibody disclosed in Table 1 herein, as determined by the IMGT numbering system, for example, as described in Lefranc M-P (1999) supra and Lefranc M-P et al., (1999) supra.

In certain embodiments, the first antigen-binding region that specifically binds to CTLA-4 (e.g., human CTLA-4) comprises CDRs of an antibody disclosed in Table 1 herein as determined by the AbM numbering scheme.

In certain embodiments, the first antigen-binding region that specifically binds to CTLA-4 (e.g., human CTLA-4) comprises CDRs of an antibody disclosed in Table 1 herein as determined by the MacCallum numbering scheme.

Accordingly, in certain embodiments, the first antigen-binding region that specifically binds to CTLA-4 (e.g., human CTLA-4) comprises a heavy chain variable region comprising the CDRH1, CDRH2, and CDRH3 region amino acid sequences of a heavy chain variable region set forth in SEQ ID NO: 1, 9, 10, 11, 12, or 13, and a light chain variable region comprising the CDRL1, CDRL2, and CDRL3 region amino acid sequences of a light chain variable region set forth in SEQ ID NO: 14, 15, 16, 17, 18, or 19, wherein each CDR is defined in accordance with the Kabat definition, the Chothia definition, the combination of the Kabat definition and the Chothia definition, the IMGT numbering system, the AbM definition, or the contact definition of CDR.

In certain embodiments, the first antigen-binding region that specifically binds to CTLA-4 (e.g., human CTLA-4) comprises:
  (a) CDRH1 comprises the amino acid sequence of SYX$_1$MX$_2$ (SEQ ID NO: 39), wherein X$_1$ is S or A; and X$_2$ is N or S; and/or
  (b) CDRH2 comprises the amino acid sequence of SIS-SSSSYIYYADSVKG (SEQ ID NO: 22); and/or
  (c) CDRH3 comprises the amino acid sequence of VGLMGPFXI (SEQ ID NO:115), wherein X is D or N; and/or
  (d) CDRL1 comprises the amino acid sequence of RASQSVX$_1$X$_2$YLX$_3$ (SEQ ID NO: 43), wherein X$_1$ is S or G; X$_2$ is R, S, or T; and X$_3$ is G or A; and/or
  (e) CDRL2 comprises the amino acid sequence of X$_1$X$_2$SX$_3$RAT (SEQ ID NO: 44), wherein X$_1$ is G or A; X$_2$ is A or T; and X$_3$ is T, S, R, or N; and/or
  (f) CDRL3 comprises the amino acid sequence of QQYGX$_1$SPX$_2$T (SEQ ID NO: 45), wherein X$_1$ is S or T; and X$_2$ is W or F.

In certain embodiments, the first antigen-binding region that specifically binds to CTLA-4 (e.g., human CTLA-4) comprises:
  (a) CDRH1 comprises the amino acid sequence of SYX$_1$MX$_2$ (SEQ ID NO: 39), wherein X$_1$ is S or A; and X$_2$ is N or S;
  (b) CDRH2 comprises the amino acid sequence of SIS-SSSSYIYYADSVKG (SEQ ID NO: 22);
  (c) CDRH3 comprises the amino acid sequence of VGLMGPFXI (SEQ ID NO: 115), wherein X is D or N;
  (d) CDRL1 comprises the amino acid sequence of RASQSVX$_1$X$_2$YLX$_3$ (SEQ ID NO: 43), wherein X$_1$ is S or G; X$_2$ is R, S, or T; and X$_3$ is G or A;
  (e) CDRL2 comprises the amino acid sequence of X$_1$X$_2$SX$_3$RAT (SEQ ID NO: 44), wherein X$_1$ is G or A; X$_2$ is A or T; and X$_3$ is T, S, R, or N; and
  (f) CDRL3 comprises the amino acid sequence of QQYGX$_1$SPX$_2$T (SEQ ID NO: 45), wherein X$_1$ is S or T; and X$_2$ is W or F.

In certain embodiments, the CDRH1 comprises an amino acid sequence selected from the group consisting of SEQ ID NOs: 20 and 21. In certain embodiments, the CDRH3 comprises an amino acid sequence selected from the group consisting of SEQ ID NOs: 24 and 26. In certain embodiments, CDRL1 comprises an amino acid sequence selected from the group consisting of SEQ ID NOs: 27, 28, and 29. In certain embodiments, CDRL2 comprises an amino acid sequence selected from the group consisting of SEQ ID NOs: 30-35. In certain embodiments, CDRL3 comprises an amino acid sequence selected from the group consisting of SEQ ID NOs: 36, 37, and 38. In certain embodiments, CDRH1, CDRH2, and CDRH3 comprise the CDRH1, CDRH2, and CDRH3 amino acid sequences, respectively, of an antibody in Table 2. In certain embodiments, CDRL1, CDRL2, and CDRL3 comprise the CDRL1, CDRL2, and CDRL3 amino acid sequences, respectively, of an antibody in Table 3.

In certain embodiments, the first antigen-binding region that specifically binds to CTLA-4 (e.g., human CTLA-4) comprises a heavy chain variable region comprising complementarity determining regions CDRH1, CDRH2 and CDRH3, wherein the CDRH1, CDRH2 and CDRH3 comprise the CDRH1, CDRH2 and CDRH3 amino acid sequences, respectively, set forth in SEQ ID NOs: 20, 22, and 24; 21, 22, and 24; or 21, 22, and 26.

In certain embodiments, the first antigen-binding region that specifically binds to CTLA-4 (e.g., human CTLA-4) comprises a light chain variable region comprising complementarity determining regions CDRL1, CDRL2 and CDRL3, wherein the CDRL1, CDRL2 and CDRL3 comprise the CDRL1, CDRL2 and CDRL3 amino acid sequences, respectively, set forth in SEQ ID NOs: 27, 30, and 36; 28, 31, and 36; 29, 32, and 37; 29, 33, and 38; 29, 34, and 36; or 29, 35, and 38.

In certain embodiments, the first antigen-binding region that specifically binds to CTLA-4 (e.g., human CTLA-4) comprises a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2 and CDRL3 comprise the CDRH1, CDRH2, CDRH3, CDRL1, CDRL2 and CDRL3 amino acid sequences, respectively, set forth in SEQ ID NOs: 20, 22, 24, 27, 30, and 36; 20, 22, 24, 29, 32, and 37; 20, 22, 24, 29, 33, and 38; 21, 22, 24, 27, 30, and 36; 21, 22, 24, 29, 33, and 38; 20, 22, 24, 28, 31, and 36; 20, 22, 24, 29, 34, and 36; 20, 22, 24, 29, 35, and 38; 21, 22, 26, 27, 30, and 36; 21, 22, 26, 29, 32, and 37; 21, 22, 26, 29, 33, and 38; or 21, 22, 26, 29, 35, and 38, respectively.

In certain embodiments, the first antigen-binding region that specifically binds to CTLA-4 (e.g., human CTLA-4) comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 20, 22, 24, 27, 30, and 36, respectively.

In certain embodiments, the first antigen-binding region that specifically binds to CTLA-4 (e.g., human CTLA-4) comprises a heavy chain variable region comprising the amino acid sequence of SEQ ID NO: 46.

In certain embodiments, the first antigen-binding region that specifically binds to CTLA-4 (e.g., human CTLA-4) comprises a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 1, 9, 10, 11, 12, or 13. In certain embodiments, the first antigen-binding region comprises a heavy chain variable region having the amino acid sequence set forth in SEQ ID NO: 1, 9, 10, 11, 12, or 13. In certain embodiments, the first antigen-binding region comprises a heavy chain variable region having the amino acid sequence set forth in SEQ ID NO: 1. In certain embodiments, the first antigen-binding region comprises a heavy chain variable region having the amino acid sequence set forth in SEQ ID NO: 9. In certain embodiments, the first antigen-binding region comprises a heavy chain variable region having the amino acid sequence set forth in SEQ ID NO: 10. In certain embodiments, the first antigen-binding region comprises a heavy chain variable region having the amino acid sequence set forth in SEQ ID NO: 11. In certain embodiments, the first antigen-binding region comprises a heavy chain variable region having the amino acid sequence set forth in SEQ ID NO: 12. In certain embodiments, the first antigen-binding region comprises a heavy chain variable region having the amino acid sequence set forth in SEQ ID NO: 13.

In certain embodiments, the first antigen-binding region that specifically binds to CTLA-4 (e.g., human CTLA-4) comprises a light chain variable region comprising the amino acid sequence of SEQ ID NO: 47.

In certain embodiments, the first antigen-binding region that specifically binds to CTLA-4 (e.g., human CTLA-4) comprises a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 14, 15, 16, 17, 18, or 19. In certain embodiments, the first antigen-binding region comprises a light chain variable region having the amino acid sequence set forth in SEQ ID NO: 14, 15, 16, 17, 18, or 19. In certain embodiments, the first antigen-binding region comprises a light chain variable region having the amino acid sequence set forth in SEQ ID NO: 14. In certain embodiments, the first antigen-binding region comprises a light chain variable region having the amino acid sequence set forth in SEQ ID NO: 15. In certain embodiments, the first antigen-binding region comprises a light chain variable region having the amino acid sequence set forth in SEQ ID NO: 16. In certain embodiments, the first antigen-binding region comprises a light chain variable region having the amino acid sequence set forth in SEQ ID NO: 17. In certain embodiments, the first antigen-binding region comprises a light chain variable region having the amino acid sequence set forth in SEQ ID NO: 18. In certain embodiments, the first antigen-binding region comprises a light chain variable region having the amino acid sequence set forth in SEQ ID NO: 19.

In certain embodiments, the first antigen-binding region that specifically binds to CTLA-4 (e.g., human CTLA-4) comprises a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 1, 9, 10, 11, 12, or 13, and a light chain variable region that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 14, 15, 16, 17, 18, or 19. In certain embodiments, the first antigen-binding region that specifically binds to CTLA-4 (e.g., human CTLA-4) comprises a heavy chain variable region comprising the amino acid sequence set forth in SEQ ID NO: 1, 9, 10, 11, 12, or 13, and a light chain variable region comprising the amino acid sequence set forth in SEQ ID NO: 14, 15, 16, 17, 18, or 19. In certain embodiments, the first antigen-binding region comprises a heavy chain variable region and light chain variable region having the amino acid sequences set forth in SEQ ID NOs: 1 and 14; 1 and 16, 1 and 17; 9 and 14; 9 and 17; 10 and 15; 10 and 17; 10 and 18; 10 and 19; 11 and 15; 11 and 14; 11 and 16; 11 and 17; 12 and 14; 12 and 16; 12 and 17; 12 and 19; 13 and 15; or 13 and 17, respectively. In certain embodiments, the first antigen-binding region comprises a heavy chain variable region and light chain variable region having the amino acid sequences set forth in SEQ ID NOs: 1 and 14, respectively. In certain embodiments, the first antigen-binding region comprises a heavy chain variable region and light chain variable region having the amino acid sequences set forth in SEQ ID NOs: 1 and 16, respectively. In certain embodiments, the first antigen-binding region comprises a heavy chain variable region and light chain variable region having the amino acid sequences set forth in SEQ ID NOs: 1 and 17, respectively. In certain embodiments, the first antigen-binding region comprises a heavy chain variable region and light chain variable region having the amino acid sequences set forth in SEQ ID NOs: 9 and 14, respectively. In certain embodiments, the first antigen-binding region comprises a heavy chain variable region and light chain variable region having the amino acid sequences set forth in SEQ ID NOs: 9 and 17, respectively. In certain embodiments, the first antigen-binding region comprises a heavy chain variable region and light chain variable region having the amino acid sequences set forth in SEQ ID NOs: 10 and 15, respectively. In certain embodiments, the first antigen-binding region comprises a heavy chain variable region and light chain variable region having the amino acid sequences set forth in SEQ ID NOs: 10 and 17, respectively. In certain embodiments, the first antigen-binding region comprises a heavy chain variable region and light chain variable region having the amino acid sequences set forth in SEQ ID NOs: 10 and 18, respectively. In certain embodiments, the first antigen-binding region comprises a heavy chain variable region and light chain variable region having the amino acid sequences set forth in SEQ ID NOs: 10 and 19, respectively. In certain embodiments, the first antigen-binding region comprises a heavy chain variable region and light chain variable region having the amino acid sequences set forth in SEQ ID NOs: 11 and 15, respectively. In certain embodiments, the first antigen-binding region comprises a heavy chain variable region and light chain variable region having the amino acid sequences set forth in SEQ ID NOs: 11 and 14, respectively. In certain embodiments, the first antigen-binding region comprises a heavy chain variable region and light chain variable region having the amino acid sequences set forth in SEQ ID NOs: 11 and 16, respectively. In certain embodiments, the first antigen-binding region comprises a heavy chain variable region and light chain variable region having the amino acid sequences set forth in SEQ ID NOs: 11 and 17, respectively. In certain embodiments, the first antigen-binding region comprises a heavy chain variable region and light chain variable region having the amino acid sequences set forth in SEQ ID NOs: 12 and 14, respectively. In certain embodiments, the first antigen-binding region comprises a heavy chain variable region and light chain variable region having the amino acid sequences set forth in SEQ ID NOs: 12 and 16, respectively. In certain embodiments, the first antigen-binding region comprises a heavy chain variable region and light chain variable region having the amino acid sequences set forth in SEQ ID NOs: 12 and 17, respectively. In certain embodiments, the first antigen-binding region comprises a heavy chain variable region and light chain variable region having the amino acid sequences set forth in SEQ ID NOs: 12 and 19, respectively. In certain embodiments, the first antigen-binding region comprises a heavy chain variable region and light chain variable region having the amino acid sequences set forth in SEQ ID NOs: 13 and 15, respectively. In certain embodiments, the first antigen-binding region comprises a heavy chain variable region and light chain variable region having the amino acid sequences set forth in SEQ ID NOs: 13 and 17, respectively.

In certain embodiments, the first antigen-binding region that specifically binds to CTLA-4 (e.g., human CTLA-4) comprises a heavy chain variable region having an amino acid sequence derived from a human IGHV3-21 germline sequence (e.g., IGHV3-21*01, e.g., having the amino acid sequence of SEQ ID NO: 48). One or more regions selected from framework 1, framework 2, framework 3, CDRH1, and CDRH2 (e.g., two, three, four or five of these regions) can be derived from a human IGHV3-21 germline sequence. In one embodiment, framework 1, framework 2, framework 3, CDRH1, and CDRH2 are all derived from a human IGHV3-21 germline sequence.

In certain embodiments, the first antigen-binding region that specifically binds to CTLA-4 (e.g., human CTLA-4) comprises a light chain variable region having an amino acid sequence derived from a human IGKV3-20 germline sequence (e.g., IGKV3-20*01, e.g., having the amino acid sequence of SEQ ID NO: 49) or a human IGKV3-11 germline sequence (e.g., IGKV3-11*01, e.g., having the amino acid sequence of SEQ ID NO: 50). One or more regions selected from framework 1, framework 2, framework 3, CDRL1, and CDRL2 (e.g., two, three, four or five of these regions) can be derived from a human IGKV3- or IGKV3-11 germline sequence. In one embodiment, framework 1, framework 2, framework 3, CDRL1, and CDRL2 are all derived from a human IGKV3-20 or IGKV3-11 germline sequence.

In certain embodiments, the first antigen-binding region that specifically binds to CTLA-4 (e.g., human CTLA-4) comprises a heavy chain variable region having an amino acid sequence derived from a human IGHV3-21 germline sequence (e.g., IGHV3-21*01, e.g., having the amino acid sequence of SEQ ID NO: 48), and a light chain variable region having an amino acid sequence derived from a human IGKV3-20 germline sequence (e.g., IGKV3-20*01, e.g., having the amino acid sequence of SEQ ID NO: 49) or a human IGKV3-11 germline sequence (e.g., IGKV3-11*01, e.g., having the amino acid sequence of SEQ ID NO: 50). One or more regions selected from framework 1, framework 2, framework 3, CDRH1, and CDRH2 of the heavy chain variable region (e.g., two, three, four or five of these regions) can be derived from a human IGHV3-21 germline sequence. In one embodiment, framework 1, framework 2, framework 3, CDRH1, and CDRH2 are all derived from a human IGHV3-21 germline sequence. One or more regions selected from framework 1, framework 2, framework 3, CDRL1, and CDRL2 of the light chain (e.g., two, three, four or five of these regions) can be derived from a human IGKV3-20 or IGKV3-11 germline sequence. In one embodiment, framework 1, framework 2, framework 3, CDRL1, and CDRL2 are all derived from a human IGKV3-20 or IGKV3-11 germline sequence.

In certain embodiments, the first antigen-binding region that specifically binds to CTLA-4 (e.g., human CTLA-4) comprises a heavy chain having an amino acid sequence selected from the group consisting of SEQ ID NOs: 51-54 and 117. In certain embodiments, the first antigen-binding region comprises a heavy chain having the amino acid sequence set forth in SEQ ID NO: 51. In certain embodiments, the first antigen-binding region comprises a heavy chain having the amino acid sequence set forth in SEQ ID NO: 52. In certain embodiments, the first antigen-binding region comprises a heavy chain having the amino acid sequence set forth in SEQ ID NO: 53. In certain embodiments, the first antigen-binding region comprises a heavy chain having the amino acid sequence set forth in SEQ ID NO: 54. In certain embodiments, the first antigen-binding region comprises a heavy chain having the amino acid sequence set forth in SEQ ID NO: 117.

In certain embodiments, the first antigen-binding region that specifically binds to CTLA-4 (e.g., human CTLA-4) comprises a light chain having the amino acid sequence of SEQ ID NO: 59.

In certain embodiments, the first antigen-binding region that specifically binds to CTLA-4 (e.g., human CTLA-4) comprises a heavy chain comprising an amino acid sequence selected from the group consisting of SEQ ID NOs: 51-54 and 117, and a light chain comprising the amino acid sequence of SEQ ID NO: 59. In certain embodiments, the first antigen-binding region comprises a heavy chain and light chain having the amino acid sequences set forth in SEQ ID NOs: 51 and 59, respectively. In certain embodiments, the first antigen-binding region comprises a heavy chain and light chain having the amino acid sequences set forth in SEQ ID NOs: 52 and 59, respectively. In certain embodiments, the first antigen-binding region comprises a heavy chain and light chain having the amino acid sequences set forth in SEQ ID NOs: 53 and 59, respectively. In certain embodiments, the first antigen-binding region comprises a heavy chain and light chain having the amino acid sequences set forth in SEQ ID NOs: 54 and 59, respectively. In certain embodiments, the first antigen-binding region comprises a heavy chain and light chain having the amino acid sequences set forth in SEQ ID NOs: 117 and 59, respectively.

In certain embodiments, the first antigen-binding region cross-competes for binding to CTLA-4 (e.g., human CTLA-4) with an antibody comprising the heavy and light chain variable region amino acid sequences set forth in SEQ ID NOs: 1 and 14; 1 and 16, 1 and 17; 9 and 14; 9 and 17; 10 and 15; 10 and 17; 10 and 18; 10 and 19; 11 and 15; 11 and 14; 11 and 16; 11 and 17; 12 and 14; 12 and 16; 12 and 17; 12 and 19; 13 and 15; or 13 and 17, respectively. In certain embodiments, the first antigen-binding region cross-competes for binding to CTLA-4 (e.g., human CTLA-4) with an antibody comprising the heavy and light chain variable region amino acid sequences set forth in SEQ ID NOs: 1 and 14, respectively.

In certain embodiments, the first antigen-binding region binds to the same epitope on CTLA-4 (e.g., human CTLA-4) as an antibody comprising the heavy and light chain variable region amino acid sequences set forth in SEQ ID NOs: 1 and 14; 1 and 16, 1 and 17; 9 and 14; 9 and 17; 10 and 15; 10 and 17; 10 and 18; 10 and 19; 11 and 15; 11 and 14; 11 and 16; 11 and 17; 12 and 14; 12 and 16; 12 and 17; 12 and 19; 13 and 15; or 13 and 17, respectively. In certain embodiments, the first antigen-binding region binds to the same epitope on CTLA-4 (e.g., human CTLA-4) as an antibody comprising the heavy and light chain variable region amino acid sequences set forth in SEQ ID NOs: 1 and 14, respectively. In certain embodiments, the first antigen-binding region binds to an epitope located within a region of human CTLA-4 consisting of the amino acid sequence of SEQ ID NO: 100. In certain embodiments, the first antigen-binding region binds to an epitope located within a region of human CTLA-4 consisting of the amino acid sequence of SEQ ID NO: 99. In certain embodiments, the first antigen-binding region binds to an epitope located within a region of human CTLA-4 consisting of the amino acid sequence of SEQ ID NO: 98. In certain embodiments, the first antigen-binding region binds to an epitope located within a region of human CTLA-4 consisting of the amino acid sequence of SEQ ID NO: 97. In certain embodiments, the first antigen-binding region binds to an epitope located within a region of human CTLA-4 consisting of the amino acid sequence of SEQ ID NO: 101. In certain embodiments, the first antigen-binding region binds to an epitope located within a region of human CTLA-4 consisting of the amino acid sequence of SEQ ID NO: 102.

In certain embodiments, the second antigen-binding region that specifically binds to PD-1 (e.g., human PD-1) comprises a heavy chain variable region comprising one, two, or all three of the CDRs of a heavy chain variable region set forth in Table 6 herein. In certain embodiments, the second antigen-binding region that specifically binds to PD-1 (e.g., human PD-1) comprises the CDRH1 of one of heavy chain variable regions set forth in Table 6. In certain embodiments, the second antigen-binding region that specifically binds to PD-1 (e.g., human PD-1) comprises the CDRH2 of one of the heavy chain variable regions set forth in Table 6. In certain embodiments, the second antigen-binding region that specifically binds to PD-1 (e.g., human PD-1) comprises the CDRH3 of one of the heavy chain variable regions set forth in Table 6.

In certain embodiments, the second antigen-binding region that specifically binds to PD-1 (e.g., human PD-1) comprises a light chain variable region comprising one, two, or all three of the CDRs of a light chain variable region disclosed in Table 6 herein. In certain embodiments, the second antigen-binding region that specifically binds to PD-1 (e.g., human PD-1) comprises the CDRL1 of one of light chain variable regions set forth in Table 6. In certain embodiments, the second antigen-binding region that specifically binds to PD-1 (e.g., human PD-1) comprises the CDRL2 of one of the light chain variable regions set forth in Table 6. In certain embodiments, the second antigen-binding region that specifically binds to PD-1 (e.g., human PD-1) comprises the CDRL3 of one of the light chain variable regions set forth in Table 6.

In certain embodiments, the CDRs of the second antigen-binding region can be determined according to Kabat et al., J. Biol. Chem. 252, 6609-6616 (1977) and Kabat et al., Sequences of protein of immunological interest (1991), each of which is herein incorporated by reference in its entirety.

In certain embodiments, the CDRs of the second antigen-binding region can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226, all of which are herein incorporated by reference in their entireties). In certain embodiments, the second antigen-binding region that specifically binds to PD-1 (e.g., human PD-1) comprises the Chothia VH CDRs of a VH disclosed in Table 6 herein. In certain embodiments, the second antigen-binding region that specifically binds to PD-1 (e.g., human PD-1) comprises the Chothia VL CDRs of a VL disclosed in Table 6 herein. In certain embodiments, the second antigen-binding region that specifically binds to PD-1 (e.g., human PD-1) comprises the Chothia VH CDRs and Chothia VL CDRs of an antibody disclosed in Table 6 herein. In certain embodiments, the second antigen-binding region that specifically binds to PD-1 (e.g., human PD-1) comprises one or more CDRs, in which the Chothia and Kabat CDRs have the same amino acid sequence. In certain embodiments, the second antigen-binding region that specifically binds to PD-1 (e.g., human PD-1) comprises a combination of Kabat CDRs and Chothia CDRs.

In certain embodiments, the CDRs of the second antigen-binding region that specifically binds to PD-1 (e.g., human PD-1) comprise CDRs of an antibody disclosed in Table 6 herein, as determined by the IMGT numbering system, for example, as described in Lefranc M-P (1999) supra and Lefranc M-P et al., (1999) supra.

In certain embodiments, the CDRs of the second antigen-binding region that specifically binds to PD-1 (e.g., human PD-1) comprise CDRs of an antibody disclosed in Table 6 herein as determined by the AbM numbering scheme.

In certain embodiments, the CDRs of the second antigen-binding region that specifically binds to PD-1 (e.g., human PD-1) comprise CDRs of an antibody disclosed in Table 6 herein as determined by the MacCallum numbering scheme.

Accordingly, in certain embodiments, the second antigen-binding region that specifically binds to PD-1 (e.g., human PD-1) comprises a heavy chain variable region comprising the CDRH1, CDRH2, and CDRH3 region amino acid sequences of a heavy chain variable region set forth in SEQ ID NO: 66, 67, 68, 69, 70, 71, 72, or 73, and a light chain variable region comprising the CDRL1, CDRL2, and CDRL3 region amino acid sequences of a light chain variable region set forth in SEQ ID NO: 74, wherein each CDR is defined in accordance with the Kabat definition, the Chothia definition, the combination of the Kabat definition and the Chothia definition, the IMGT numbering system, the AbM definition, or the contact definition of CDR.

In certain embodiments, the second antigen-binding region that specifically binds to PD-1 (e.g., human PD-1) comprises:
   (a) CDRH1 comprises the amino acid sequence of SYGMH (SEQ ID NO: 75); and/or
   (b) CDRH2 comprises the amino acid sequence of VIWX$_1$DGSNX$_2$YYADSVX$_3$G (SEQ ID NO: 86), wherein X$_1$ is Y or F; X$_2$ is K or E; and X$_3$ is K or M; and/or
   (c) CDRH3 comprises the amino acid sequence of NX$_1$DX$_2$ (SEQ ID NO: 87), wherein X$_1$ is G or V; and X$_2$ is H or Y; and/or
   (d) CDRL1 comprises the amino acid sequence of RASQSVSSNLA (SEQ ID NO: 83); and/or
   (e) CDRL2 comprises the amino acid sequence of GASTRAT (SEQ ID NO: 84); and/or
   (f) CDRL3 comprises the amino acid sequence of QQYNNWPRT (SEQ ID NO: 85).

In certain embodiments, the second antigen-binding region that specifically binds to PD-1 (e.g., human PD-1) comprises:
   (a) CDRH1 comprises the amino acid sequence of SYGMH (SEQ ID NO: 75);
   (b) CDRH2 comprises the amino acid sequence of VIWX$_1$DGSNX$_2$YYADSVX$_3$G (SEQ ID NO: 86), wherein X$_1$ is Y or F; X$_2$ is K or E; and X$_3$ is K or M;
   (c) CDRH3 comprises the amino acid sequence of NX$_1$DX$_2$ (SEQ ID NO: 87), wherein X$_1$ is G or V; and X$_2$ is H or Y;
   (d) CDRL1 comprises the amino acid sequence of RASQSVSSNLA (SEQ ID NO: 83);
   (e) CDRL2 comprises the amino acid sequence of GASTRAT (SEQ ID NO: 84); and
   (f) CDRL3 comprises the amino acid sequence of QQYNNWPRT (SEQ ID NO: 85).

In certain embodiments, the CDRH2 comprises an amino acid sequence selected from the group consisting of SEQ ID NOs: 76-79. In certain embodiments, the CDRH3 comprises an amino acid sequence selected from the group consisting of SEQ ID NOs: 80-82. In certain embodiments, CDRH1, CDRH2, and CDRH3 comprise the CDRH1, CDRH2, and CDRH3 amino acid sequences, respectively, of an antibody in Table 7. In certain embodiments, CDRL1, CDRL2, and CDRL3 comprise the CDRL1, CDRL2, and CDRL3 amino acid sequences, respectively, of an antibody in Table 8.

In certain embodiments, the second antigen-binding region that specifically binds to PD-1 (e.g., human PD-1) comprises a heavy chain variable region comprising complementarity determining regions CDRH1, CDRH2 and CDRH3, wherein the CDRH1, CDRH2 and CDRH3 comprise the CDRH1, CDRH2 and CDRH3 amino acid sequences, respectively, set forth in SEQ ID NOs: 75, 76, and 80; 75, 76, and 81; 75, 76, and 82; 75, 77, and 81; 75, 78, and 81; or 75, 79, and 81.

In certain embodiments, the second antigen-binding region that specifically binds to PD-1 (e.g., human PD-1) comprises a light chain variable region comprising complementarity determining regions CDRL1, CDRL2 and CDRL3, wherein the CDRL1, CDRL2 and CDRL3 comprise the CDRL1, CDRL2 and CDRL3 amino acid sequences, respectively, set forth in SEQ ID NOs: 83, 84, and 85.

In certain embodiments, the second antigen-binding region that specifically binds to PD-1 (e.g., human PD-1) comprises a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2 and CDRL3 comprise the CDRH1, CDRH2, CDRH3, CDRL1, CDRL2 and CDRL3 amino acid sequences, respectively, set forth in SEQ ID NOs: 75, 76, 80, 83, 84, and 85; 75, 76, 81, 83, 84, and 85; 75, 76, 82, 83, 84, and 85; 75, 77, 81, 83, 84, and 85; 75, 78, 81, 83, 84, and 85; or 75, 79, 81, 83, 84, and 85, respectively.

In certain embodiments, the second antigen-binding region that specifically binds to PD-1 (e.g., human PD-1) comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 75, 76, 81, 83, 84, and 85, respectively.

In certain embodiments, the second antigen-binding region that specifically binds to PD-1 (e.g., human PD-1) comprises a heavy chain variable region comprising the amino acid sequence of SEQ ID NO: 88.

In certain embodiments, the second antigen-binding region that specifically binds to PD-1 (e.g., human PD-1) comprises a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to an amino acid sequence selected from the group consisting of SEQ ID NOs: 66-73. In certain embodiments, the second antigen-binding region that specifically binds to PD-1 (e.g., human PD-1) comprises a heavy chain variable region having an amino acid sequence selected from the group consisting of SEQ ID NOs: 66-73. In certain embodiments, the second antigen-binding region that specifically binds to PD-1 (e.g., human PD-1) comprises a heavy chain variable region having the amino acid sequence set forth in SEQ ID NO: 66. In certain embodiments, the second antigen-binding region comprises a heavy chain variable region having the amino acid sequence set forth in SEQ ID NO: 67. In certain embodiments, the second antigen-binding region comprises a heavy chain variable region having the amino acid sequence set forth in SEQ ID NO: 68. In certain embodiments, the second antigen-binding region comprises a heavy chain variable region having the amino acid sequence set forth in SEQ ID NO: 69. In certain embodiments, the second antigen-binding region comprises a heavy chain variable region having the amino acid sequence set forth in SEQ ID NO: 70. In certain embodiments, the second antigen-binding region comprises a heavy chain variable region having the amino acid sequence set forth in SEQ ID NO: 71. In certain embodiments, the second antigen-binding region comprises a heavy chain variable region having the amino acid sequence set forth in SEQ ID NO: 72. In certain embodiments, the second antigen-binding region comprises a heavy chain variable region having the amino acid sequence set forth in SEQ ID NO: 73.

In certain embodiments, the second antigen-binding region that specifically binds to PD-1 (e.g., human PD-1) comprises a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence of SEQ ID NO: 74. In certain embodiments, the second antigen-binding region that specifically binds to PD-1 (e.g., human PD-1) comprises a light chain variable region having the amino acid sequence of SEQ ID NO: 74.

In certain embodiments, the second antigen-binding region that specifically binds to PD-1 (e.g., human PD-1) comprises a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 66, 67, 68, 69, 70, 71, 72, or 73, and a light chain variable region that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 74. In certain embodiments, the second antigen-binding region that specifically binds to PD-1 (e.g., human PD-1) comprises a heavy chain variable region comprising an amino acid sequence set forth in SEQ ID NO: 66, 67, 68, 69, 70, 71, 72, or 73, and a light chain variable region set forth in SEQ ID NO: 74. In certain embodiments, the second antigen-binding region that specifically binds to PD-1 (e.g., human PD-1) comprises a heavy chain variable region and light chain variable region having the amino acid sequences set forth in SEQ ID NOs: 66 and 74; 67 and 74; 68 and 74; 69 and 74; 70 and 74; 71 and 74; 72 and 74; or 73 and 74, respectively. In certain embodiments, the second antigen-binding region that specifically binds to PD-1 (e.g., human PD-1) comprises a heavy chain variable region and light chain variable region having the amino acid sequences set forth in SEQ ID NOs: 66 and 74, respectively. In certain embodiments, the second antigen-binding region comprises a heavy chain variable region and light chain variable region having the amino acid sequences set forth in SEQ ID NOs: 67 and 74, respectively. In certain embodiments, the second antigen-binding region comprises a heavy chain variable region and light chain variable region having the amino acid sequences set forth in SEQ ID NOs: 68 and 74, respectively. In certain embodiments, the second antigen-binding region comprises a heavy chain variable region and light chain variable region having the amino acid sequences set forth in SEQ ID NOs: 69 and 74, respectively. In certain embodiments, the second antigen-binding region comprises a heavy chain variable region and light chain variable region having the amino acid sequences set forth in SEQ ID NOs: 70 and 74, respectively. In certain embodiments, the second antigen-binding region comprises a heavy chain variable region and light chain variable region having the amino acid sequences set forth in SEQ ID NOs: 71 and 74, respectively. In certain embodiments, the second antigen-binding region comprises a heavy chain variable region and light chain variable region having the amino acid sequences set forth in SEQ ID NOs: 72 and 74, respectively. In certain embodiments, the second antigen-binding region comprises a heavy chain variable region and light chain variable region having the amino acid sequences set forth in SEQ ID NOs: 73 and 74, respectively.

In certain embodiments, the second antigen-binding region that specifically binds to PD-1 (e.g., human PD-1) comprises a heavy chain variable region having an amino acid sequence derived from a human IGHV3-33 germline sequence (e.g., IGHV3-33*01, e.g., having the amino acid sequence of SEQ ID NO: 89). One or more regions selected from framework 1, framework 2, framework 3, CDRH1, and CDRH2 (e.g., two, three, four or five of these regions) can be derived from a human IGHV3-33 germline sequence. In one embodiment, framework 1, framework 2, framework 3, CDRH1, and CDRH2 are all derived from a human IGHV3-33 germline sequence.

In certain embodiments, the second antigen-binding region that specifically binds to PD-1 (e.g., human PD-1) comprises a light chain variable region having an amino acid sequence derived from a human IGKV3-15 germline sequence (e.g., IGKV3-15*01, e.g., having the amino acid sequence of SEQ ID NO: 90). One or more regions selected from framework 1, framework 2, framework 3, CDRL1, and CDRL2 (e.g., two, three, four or five of these regions) can be derived from a human IGKV3-15 germline sequence. In one embodiment, framework 1, framework 2, framework 3, CDRL1, and CDRL2 are all derived from a human IGKV3-15 germline sequence.

In certain embodiments, the second antigen-binding region that specifically binds to PD-1 (e.g., human PD-1) comprises a heavy chain variable region having an amino acid sequence derived from a human IGHV3-33 germline sequence (e.g., IGHV3-33*01, e.g., having the amino acid sequence of SEQ ID NO: 89), and a light chain variable region having an amino acid sequence derived from a human IGKV3-15 germline sequence (e.g., IGKV3-15*01, e.g., having the amino acid sequence of SEQ ID NO: 90). One or more regions selected from framework 1, framework 2, framework 3, CDRH1, and CDRH2 of the heavy chain variable region (e.g., two, three, four or five of these regions) can be derived from a human IGHV3-33 germline sequence. In one embodiment, framework 1, framework 2, framework 3, CDRH1, and CDRH2 are all derived from a human IGHV3-33 germline sequence. One or more regions selected from framework 1, framework 2, framework 3, CDRL1, and CDRL2 of the light chain (e.g., two, three, four or five of these regions) can be derived from a human IGKV3-15 germline sequence. In one embodiment, framework 1, framework 2, framework 3, CDRL1, and CDRL2 are all derived from a human IGKV3-15 germline sequence.

In certain embodiments, the second antigen-binding region that specifically binds to PD-1 (e.g., human PD-1) comprises a heavy chain having an amino acid sequence selected from the group consisting of SEQ ID NOs: 91 and 92. In certain embodiments, the second antigen-binding region that specifically binds to PD-1 (e.g., human PD-1) comprises a heavy chain having the amino acid sequence set forth in SEQ ID NO: 91. In certain embodiments, the second antigen-binding region that specifically binds to PD-1 (e.g., human PD-1) comprises a heavy chain having the amino acid sequence set forth in SEQ ID NO: 92.

In certain embodiments, the second antigen-binding region that specifically binds to PD-1 (e.g., human PD-1) comprises a light chain having the amino acid sequence of SEQ ID NO: 93.

In certain embodiments, the second antigen-binding region that specifically binds to PD-1 (e.g., human PD-1) comprises a heavy chain comprising the amino acid sequence of SEQ ID NO: 91 or 92, and a light chain comprising the amino acid sequence of SEQ ID NO: 93. In certain embodiments, the second antigen-binding region that specifically binds to PD-1 (e.g., human PD-1) comprises a heavy chain and light chain having the amino acid sequences set forth in SEQ ID NOs: 91 and 93, respectively. In certain embodiments, the second antigen-binding region that specifically binds to PD-1 (e.g., human PD-1) comprises a heavy chain and light chain having the amino acid sequences set forth in SEQ ID NOs: 92 and 93, respectively.

In certain embodiments, the second antigen-binding region cross-competes for binding to PD-1 (e.g., human PD-1) with an antibody comprising the heavy and light chain variable region amino acid sequences set forth in SEQ ID NOs: 66 and 74; 67 and 74; 68 and 74; 69 and 74; 70 and 74; 71 and 74; 72 and 74; or 73 and 74, respectively. In certain embodiments, the second antigen-binding region cross-competes for binding to PD-1 (e.g., human PD-1), with an antibody comprising the heavy and light chain variable region amino acid sequences set forth in SEQ ID NOs: 66 and 74, respectively.

In certain embodiments, the second antigen-binding region binds to the same epitope on PD-1 (e.g., human PD-1) as an antibody comprising the heavy and light chain variable region amino acid sequences set forth in SEQ ID NOs: 66 and 74; 67 and 74; 68 and 74; 69 and 74; 70 and 74; 71 and 74; 72 and 74; or 73 and 74, respectively. In certain embodiments, the second antigen-binding region binds to the same epitope on PD-1 (e.g., human PD-1) as an antibody comprising the heavy and light chain variable region amino acid sequences set forth in SEQ ID NOs: 66 and 74, respectively. In certain embodiments, the second antigen-binding region binds to an epitope located within a region of human PD-1 consisting of the amino acid sequence of SEQ ID NO: 103. In certain embodiments, the second antigen-binding region binds to an epitope located within a region of human PD-1 consisting of the amino acid sequence of SEQ ID NO: 104. In certain embodiments, the second antigen-binding region binds to an epitope located within a region of human PD-1 consisting of the amino acid sequence of SEQ ID NO: 105. In certain embodiments, the second antigen-binding region binds to an epitope located within a region of human PD-1 consisting of the amino acid sequence of SEQ ID NO: 106. In certain embodiments, the second antigen-binding region binds to an epitope located within a region of human PD-1 consisting of the amino acid sequence of SEQ ID NO: 107.

In certain embodiments, the instant disclosure provides an isolated multispecific antibody comprising a first antigen-binding region that specifically binds to CTLA-4 (e.g., human CTLA-4) and a second antigen-binding region that specifically binds to PD-1 (e.g., human PD-1), wherein CDRH1, CDRH2, CDRH3, CDRL1, CDRL2, and CDRL3 of the first antigen-binding region and CDRH1, CDRH2, CDRH3, CDRL1, CDRL2, and CDRL3 of the second antigen-binding region comprise the amino acid sequences listed in a single row of Table 11. In certain embodiments, the instant disclosure provides an isolated multispecific antibody comprising a first antigen-binding region that specifically binds to CTLA-4 (e.g., human CTLA-4) and a second antigen-binding region that specifically binds to PD-1 (e.g., human PD-1), wherein CDRH1, CDRH2, CDRH3, CDRL1, CDRL2, and CDRL3 of the first antigen-binding region and CDRH1, CDRH2, CDRH3, CDRL1, CDRL2, and CDRL3 of the second antigen-binding region respectively comprise the amino acid sequences set forth in SEQ ID NOs: 20, 22, 24, 27, 30, 36, 75, 76, 80, 83, 84, and 85; 20, 22, 24, 29, 32, 37, 75, 76, 80, 83, 84, and 85; 20, 22, 24, 29, 33, 38, 75, 76, 80, 83, 84, and 85; 21, 22, 24, 27, 30, 36, 75, 76, 80, 83, 84, and 85; 21, 22, 24, 29, 33, 38, 75, 76, 80, 83, 84, and 85; 20, 22, 24, 28, 31, 36, 75, 76, 80, 83, 84, and 85; 20, 22, 24, 29, 34, 36, 75, 76, 80, 83, 84, and 85; 20, 22, 24, 29, 35, 38, 75, 76, 80, 83, 84, and 85; 21, 22, 26, 27, 30, 36, 75, 76, 80, 83, 84, and 85; 21, 22, 26, 29, 32, 37, 75, 76, 80, 83, 84, and 85; 21, 22, 26, 29, 33, 38, 75, 76, 80, 83, 84, and 85; 21, 22, 26, 29, 35, 38, 75, 76, 80, 83, 84, and 85; 20, 22, 24, 27, 30, 36, 75, 76, 81, 83, 84, and 85; 20, 22, 24, 29, 32, 37, 75, 76, 81, 83, 84, and 85; 20, 22, 24, 29, 33, 38, 75, 76, 81, 83, 84, and 85; 21, 22, 24, 27, 30, 36, 75, 76, 81, 83, 84, and 85; 21, 22, 24, 29, 33, 38, 75, 76, 81, 83, 84, and 85; 20, 22, 24, 28, 31, 36, 75, 76, 81, 83, 84, and 85; 20, 22, 24, 29, 34, 36, 75, 76, 81, 83, 84, and 85; 20, 22, 24, 29, 35, 38, 75, 76, 81, 83, 84, and 85; 21, 22, 26, 27, 30, 36, 75, 76, 81, 83, 84, and 85; 21, 22, 26, 29, 32, 37, 75, 76, 81, 83, 84, and 85; 21, 22, 26, 29, 33, 38, 75, 76, 81, 83, 84, and 85; 21, 22, 26, 29, 35, 38, 75, 76, 81, 83, 84, and 85; 20, 22, 24, 27, 30, 36, 75, 76, 82, 83, 84, and 85; 20, 22, 24, 29, 32, 37, 75, 76, 82, 83, 84, and 85; 20, 22, 24, 29, 33, 38, 75, 76, 82, 83, 84, and 85; 21, 22, 24, 27, 30, 36, 75, 76, 82, 83, 84, and 85; 21, 22, 24, 29, 33, 38, 75, 76, 82, 83, 84, and 85; 20, 22, 24, 28, 31, III 36, 75, 76, 82, 83, 84, and 85; 20, 22, 24, 29, 34, 36, 75, 76, 82, 83, 84, and 85; 20, 22, 24, 29, 35, 38, 75, 76, 82, 83, 84, and 85; 21, 22, 26, 27, 30, 36, 75, 76, 82, 83, 84, and 85; 21, 22, 26, 29, 32, 37, 75, 76, 82, 83, 84, and 85; 21, 22, 26, 29, 33, 38, 75, 76, 82, 83, 84, and 85; 21, 22, 26, 29, 35, 38, 75, 76, 82, 83, 84, and 85; 20, 22, 24, 27, 30, 36, 75, 77, 81, 83, 84, and 85; 20, 22, 24, 29, 32, 37, 75, 77, 81, 83, 84, and 85; 20, 22, 24, 29, 33, 38, 75, 77, 81, 83, 84, and 85; 21, 22, 24, 27, 30, 36, 75, 77, 81, 83, 84, and 85; 21, 22, 24, 29, 33, 38, 75, 77, 81, 83, 84, and 85; 20, 22, 24, 28, 31, 36, 75, 77, 81, 83, 84, and 85; 20, 22, 24, 29, 34, 36, 75, 77, 81, 83, 84, and 85; 20, 22, 24, 29, 35, 38, 75, 77, 81, 83, 84, and 85; 21, 22, 26, 27, 30, 36, 75, 77, 81, 83, 84, and 85; 21, 22, 26, 29, 32, 37, 75, 77, 81, 83, 84, and 85; 21, 22, 26, 29, 33, 38, 75, 77, 81, 83, 84, and 85; 21, 22, 26, 29, 35, 38, 75, 77, 81, 83, 84, and 85; 20, 22, 24, 27, 30, 36, 75, 78, 81, 83, 84, and 85; 20, 22, 24, 29, 32, 37, 75, 78, 81, 83, 84, and 85; 20, 22, 24, 29, 33, 38, 75, 78, 81, 83, 84, and 85; 21, 22, 24, 27, 30, 36, 75, 78, 81, 83, 84, and 85; 21, 22, 24, 29, 33, 38, 75, 78, 81, 83, 84, and 85; 20, 22, 24, 28, 31, 36, 75, 78, 81, 83, 84, and 85; 20, 22, 24, 29, 34, 36, 75, 78, 81, 83, 84, and 85; 20, 22, 24, 29, 35, 38, 75, 78, 81, 83, 84, and 85; 21, 22, 26, 27, 30, 36, 75, 78, 81, 83, 84, and 85; 21, 22, 26, 29, 32, 37, 75, 78, 81, 83, 84, and 85; 21, 22, 26, 29, 33, 38, 75, 78, 81, 83, 84, and 85; 21, 22, 26, 29, 35, 38, 75, 78, 81, 83, 84, and 85; 20, 22, 24, 27, 30, 36, 75, 79, 81, 83, 84, and 85; 20, 22, 24, 29, 32, 37, 75, 79, 81, 83, 84, and 85; 20, 22, 24, 29, 33, 38, 75, 79, 81, 83, 84, and 85; 21, 22, 24, 27, 30, 36, 75, 79, 81, 83, 84, and 85; 21, 22, 24, 29, 33, 38, 75, 79, 81, 83, 84, and 85; 20, 22, 24, 28, 31, 36, 75, 79, 81, 83, 84, and 85; 20, 22, 24, 29, 34, 36, 75, 79, 81, 83, 84, and 85; 20, 22, 24, 29, 35, 38, 75, 79, 81, 83, 84, and 85; 21, 22, 26, 27, 30, 36, 75, 79, 81, 83, 84, and 85; 21, 22, 26, 29, 32, 37, 75, 79, 81, 83, 84, and 85; 21, 22, 26, 29, 33, 38, 75, 79, 81, 83, 84, and 85; or 21, 22, 26, 29, 35, 38, 75, 79, 81, 83, 84, and 85.

In certain embodiments, the instant disclosure provides an isolated multispecific antibody comprising a first antigen-binding region that specifically binds to CTLA-4 (e.g., human CTLA-4) and a second antigen-binding region that specifically binds to PD-1 (e.g., human PD-1), wherein the heavy chain variable region and the light chain variable region of the first antigen-binding region and the heavy chain variable region and the light chain variable region of the second antigen-binding region comprise the amino acid sequences listed in a single row of Table 12. In certain embodiments, the instant disclosure provides an isolated multispecific antibody comprising a first antigen-binding region that specifically binds to CTLA-4 (e.g., human CTLA-4) and a second antigen-binding region that specifically binds to PD-1 (e.g., human PD-1), wherein the heavy chain variable region and the light chain variable region of the first antigen-binding region and the heavy chain variable region and the light chain variable region of the second antigen-binding region respectively comprise the amino acid sequences set forth in SEQ ID NOs: 1, 14, 67, and 74; 1, 16, 67, and 74; 1, 17, 67, and 74; 9, 14, 67, and 74; 9, 17, 67, and 74; 10, 15, 67, and 74; 10, 17, 67, and 74; 10, 18, 67, and 74; 10, 19, 67, and 74; 11, 15, 67, and 74; 11, 14, 67, and 74; 11, 16, 67, and 74; 11, 17, 67, and 74; 12, 14, 67, and 74; 12, 16, 67, and 74; 12, 17, 67, and 74; 12, 19, 67, and 74; 13, 15, 67, and 74; 13, 17, 67, and 74; 1, 14, 66, and 74; 1, 16, 66, and 74; 1, 17, 66, and 74; 9, 14, 66, and 74; 9, 17, 66, and 74; 10, 15, 66, and 74; 10, 17, 66, and 74; 10, 18, 66, and 74; 10, 19, 66, and 74; 11, 15, 66, and 74; 11, 14, 66, and 74; 11, 16, 66, and 74; 11, 17, 66, and 74; 12, 14, 66, and 74; 12, 16, 66, and 74; 12, 17, 66, and 74; 12, 19, 66, and 74; 13, 15, 66, and 74; 13, 17, 66, and 74; 1, 14, 68, and 74; 1, 16, 68, and 74; 1, 17, 68, and 74; 9, 14, 68, and 74; 9, 17, 68, and 74; 10, 15, 68, and 74; 10, 17, 68, and 74; 10, 18, 68, and 74; 10, 19, 68, and 74; 11, 15, 68, and 74; 11, 14, 68, and 74; 11, 16, 68, and 74; 11, 17, 68, and 74; 12, 14, 68, and 74; 12, 16, 68, and 74; 12, 17, 68, and 74; 12, 19, 68, and 74; 13, 15, 68, and 74; 13, 17, 68, and 74; 1, 14, 69, and 74; 1, 16, 69, and 74; 1, 17, 69, and 74; 9, 14, 69, and 74; 9, 17, 69, and 74; 10, 15, 69, and 74; 10, 17, 69, and 74; 10, 18, 69, and 74; 10, 19, 69, and 74; 11, 15, 69, and 74; 11, 14, 69, and 74; 11, 16, 69, and 74; 11, 17, 69, and 74; 12, 14, 69, and 74; 12, 16, 69, and 74; 12, 17, 69, and 74; 12, 19, 69, and 74; 13, 15, 69, and 74; 13, 17, 69, and 74; 1, 14, 70, and 74; 1, 16, 70, and 74; 1, 17, 70, and 74; 9, 14, 70, and 74; 9, 17, 70, and 74; 10, 15, 70, and 74; 10, 17, 70, and 74; 10, 18, 70, and 74; 10, 19, 70, and 74; 11, 15, 70, and 74; 11, 14, 70, and 74; 11, 16, 70, and 74; 11, 17, 70, and 74; 12, 14, 70, and 74; 12, 16, 70, and 74; 12, 17, 70, and 74; 12, 19, 70, and 74; 13, 15, 70, and 74; 13, 17, 70, and 74; 1, 14, 71, and 74; 1, 16, 71, and 74; 1, 17, 71, and 74; 9, 14, 71, and 74; 9, 17, 71, and 74; 10, 15, 71, and 74; 10, 17, 71, and 74; 10, 18, 71, and 74; 10, 19, 71, and 74; 11, 15, 71, and 74; 11, 14, 71, and 74; 11, 16, 71, and 74; 11, 17, 71, and 74; 12, 14, 71, and 74; 12, 16, 71, and 74; 12, 17, 71, and 74; 12, 19, 71, and 74; 13, 15, 71, and 74; 13, 17, 71, and 74; 1, 14, 72, and 74; 1, 16, 72, and 74; 1, 17, 72, and 74; 9, 14, 72, and 74; 9, 17, 72, and 74; 10, 15, 72, and 74; 10, 17, 72, and 74; 10, 18, 72, and 74; 10, 19, 72, and 74; 11, 15, 72, and 74; 11, 14, 72, and 74; 11, 16, 72, and 74; 11, 17, 72, and 74; 12, 14, 72, and 74; 12, 16, 72, and 74; 12, 17, 72, and 74; 12, 19, 72, and 74; 13, 15, 72, and 74; 13, 17, 72, and 74; 1, 14, 73, and 74; 1, 16, 73, and 74; 1, 17, 73, and 74; 9, 14, 73, and 74; 9, 17, 73, and 74; 10, 15, 73, and 74; 10, 17, 73, and 74; 10, 18, 73, and 74; 10, 19, 73, and 74; 11, 15, 73, and 74; 11, 14, 73, and 74; 11, 16, 73, and 74; 11, 17, 73, and 74; 12, 14, 73, and 74; 12, 16, 73, and 74; 12, 17, 73, and 74; 12, 19, 73, and 74; 13, 15, 73, and 74; or 13, 17, 73, and 74.

In certain embodiments, an isolated anti-CTLA-4/PD-1 antibody as provided herein can decreases CTLA-4 and/or PD-1 activity by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to CTLA-4 and/or PD-1 activity without any antibody or with an unrelated antibody (e.g., an antibody that does not specifically bind to CTLA-4 or PD-1). In certain embodiments, a multispecific antibody that specifically binds to CTLA-4 (e.g., human CTLA-4) and PD-1 (e.g., human PD-1) as provided herein decreases CTLA-4 and/or PD-1 activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to CTLA-4 and/or PD-1 activity without any antibody or with an unrelated antibody (e.g., an antibody that does not specifically bind to CTLA-4 or PD-1). Non-limiting examples of CTLA-4 activity can include CTLA-4 signaling, CTLA-4 binding to CTLA-4 ligand (e.g., CD80 or CD86), inhibition of cytokine production (e.g., IL-2 or IFNγ), and inhibition of T cell proliferation. Non-limiting examples of PD-1 activity can include PD-1 signaling, PD-1 binding to PD-1 ligand (e.g., PD-L1 or PD-L2), inhibition of cytokine production (e.g., IL-2 or IFNγ), and inhibition of T cell proliferation. In certain embodiments, the instant disclosure provides an isolated antibody that specifically binds to CTLA-4 (e.g., human CTLA-4) and PD-1 (e.g., human PD-1), and deactivates, reduces, or inhibits a CTLA-4 and/or PD-1 activity. In specific embodiments, a decrease in a CTLA-4 and/or PD-1 activity is assessed as described in the Examples, infra.

In certain embodiments, an isolated anti-CTLA-4/PD-1 antibody as provided herein can decreases CTLA-4 binding to its ligand (e.g., CD80 or CD86) and/or PD-1 binding to its ligand (e.g., PD-L1 or PD-L2) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to CTLA-4 binding to its ligand (e.g., CD80 or CD86) without any antibody or with an unrelated antibody (e.g., an antibody that does not specifically bind to CTLA-4), and/or relative to PD-1 binding to its ligand (e.g., PD-L1 or PD-L2) without any antibody or with an unrelated antibody (e.g., an antibody that does not specifically bind to PD-1). In certain embodiments, an isolated anti-CTLA-4/PD-1 antibody as provided herein can decrease CTLA-4 binding to its ligand (e.g., CD80 or CD86) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to CTLA-4 binding to its ligand (e.g., CD80 or CD86) without any antibody or with an unrelated antibody (e.g., an antibody that does not specifically bind to CTLA-4), and/or can decrease PD-1 binding to its ligand (e.g., PD-L1 or PD-L2) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, relative to PD-1 binding to its ligand (e.g., PD-L1 or PD-L2) without any antibody or with an unrelated antibody (e.g., an antibody that does not specifically bind to PD-1).

In certain embodiments, an isolated anti-CTLA-4/PD-1 antibody as provided herein can antagonize CTLA-4 and/or PD-1 functions, for example, by stimulating T cell activation. For instance, an isolated anti-CTLA-4/PD-1 antibody comprising a combination of CDR sequences specified herein, a combination of VH and/or VL sequences having at least 70%, at least 75%, at least 80%, at least 85%, at least 90%, at least 95%, at least 98%, at least 99%, or 100% sequence identity with a combination of VH and/or VL sequences specified herein, or a combination of heavy and/or light chains specified herein, can stimulate T cell activation, optionally wherein T cell activation is a substantially increasing function of antibody concentrations.

In specific embodiments, an isolated anti-CTLA-4/PD-1 antibody as provided herein can increase cytokine production (e.g., IL-2 or IFNγ) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to cytokine production without any antibody or with an unrelated antibody (e.g., an antibody that does not specifically bind to CTLA-4 or PD-1). In specific embodiments, an isolated anti-CTLA-4/PD-1 antibody as provided herein can increase cytokine production (e.g., IL-2 or IFNγ) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to cytokine production without any antibody or with an unrelated antibody (e.g., an antibody that does not specifically bind to CTLA-4 or PD-1).

In specific embodiments, the instant disclosure provides an isolated anti-CTLA-4/PD-1 antibody that either alone or in combination with an anti-CTLA-4 antibody (e.g., ipilimumab or tremelimumab), an anti-PD-1 antibody (e.g., nivolumab or pembrolizumab), an anti-TIGIT antibody, an anti-CD137 antibody (e.g., urelumab or utomilumab), or an anti-OX40 antibody (e.g., pogalizumab or tavolixizumab) increases IL-2 production in human peripheral blood mononuclear cells (PBMCs) in response to *Staphylococcus* Enterotoxin A (SEA) stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to IL-2 production without any antibody or with an unrelated antibody (e.g., an antibody that does not specifically bind to CTLA-4 or PD-1).

In certain embodiments, human peripheral blood mononuclear cells (PBMCs) stimulated with *Staphylococcus* Enterotoxin A (SEA) in the presence of an isolated anti-CTLA-4/PD-1 antibody as provided herein, either alone or in combination with an anti-CTLA-4 antibody (e.g., ipilimumab or tremelimumab), an anti-PD-1 antibody (e.g., nivolumab or pembrolizumab), an anti-TIGIT antibody, an anti-CD137 antibody (e.g., urelumab or utomilumab), or an anti-OX40 antibody (e.g., pogalizumab or tavolixizumab), have increased IL-2 production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to PBMCs only stimulated with SEA without any antibody or with an unrelated antibody (e.g., an antibody that does not specifically bind to CTLA-4 or PD-1), as assessed by methods described herein (see the Examples, infra) or known to one of skill in the art.

In specific embodiments, the instant disclosure provides an isolated anti-CTLA-4/PD-1 antibody that increases IFNγ production of a co-culture of human T cells and allogenic dendritic cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to IFNγ production of a co-culture of human T cells and allogenic dendritic cells without any antibody or with an unrelated antibody (e.g., an antibody that does not specifically bind to CTLA-4 or PD-1).

In certain embodiments, a co-culture of human T cells and allogenic dendritic cells in the presence of an isolated anti-CTLA-4/PD-1 antibody as provided herein has increased IFNγ production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to a co-culture of human T cells and allogenic dendritic cells without any antibody or with an unrelated antibody (e.g., an antibody that does not specifically bind to CTLA-4 or PD-1), as assessed by methods described herein (see the Examples, infra) or known to one of skill in the art.

In specific embodiments, the instant disclosure provides an isolated anti-CTLA-4/PD-1 antibody that increases T cell proliferation by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to T cell proliferation without any antibody or with an unrelated antibody (e.g., an antibody that does not specifically bind to CTLA-4 or PD-1). In specific embodiments, the instant disclosure provides an isolated anti-CTLA-4/PD-1 antibody that increases T cell proliferation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to T cell proliferation without any antibody or with an unrelated antibody (e.g., an antibody that does not specifically bind to CTLA-4 or PD-1).

In specific embodiments, the instant disclosure provides an isolated anti-CTLA-4/PD-1 antibody that increases proliferation of anti-CD3-antibody-stimulated CD4+ or CD8+ T cells co-cultured with ovarian cancer ascites fluid by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to proliferation of anti-CD3-antibody-stimulated CD4+ or CD8+ T cells co-cultured with ovarian cancer ascites fluid without any antibody or with an unrelated antibody (e.g., an antibody that does not specifically bind to CTLA-4 or PD-1).

A multispecific antibody, e.g., a bispecific antibody that specifically binds to CTLA-4 (e.g., human CTLA-4) and/or PD-1 (e.g., human PD-1) as provided herein can be prepared by chemically linking two different monoclonal antibodies or by fusing two hybridoma cell lines to produce a hybrid-hybridoma. Other multivalent formats that can be used include, for example, Kλ-bodies, dAbs, diabodies, TandAbs, nanobodies, SMIPs, DNLs, strand-exchange engineered domain bodies (SEEDbodies), Affibodies, Fynomers, Kunitz Domains, Albu-dabs, DARTs, DVD-IG, Covx-bodies, peptibodies, scFv-Igs, SVD-Igs, dAb-Igs, Knobs-in-Holes, and triomAbs. Exemplary bispecific formats are discussed in Garber et al., *Nature Reviews Drug Discovery* 13:799-801 (2014), which is herein incorporated by reference in its entirety.

Exemplary bispecific antibody molecules comprise (i) a single antibody that has two arms comprising different antigen-binding regions, one with a specificity to a first antigen such as CTLA-4 (e.g., human CTLA-4) and one with a specificity to a second antigen such as PD-1 (e.g., human PD-1), (ii) a single antibody that has one antigen-binding region or arm specific to a first antigen such as CTLA-4 (e.g., human CTLA-4) and a second antigen-binding region or arm specific to a second antigen such as PD-1 (e.g., human PD-1), (iii) a single chain antibody that has a first specificity to a first antigen such as CTLA-4 (e.g., human CTLA-4) and a second specificity to a second antigen such as PD-1 (e.g., human PD-1), e.g., via two scFvs linked in tandem by an extra peptide linker; (iv) a dual-variable-domain antibody (DVD-Ig), where each light chain and heavy chain contains two variable regions in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific (Fab')$_2$ fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (ix) a so-called Scorpion molecule, comprising, e.g., two scFvs fused to both termini of a human Fab-arm; and (x) a diabody.

Examples of different classes of bispecific antibodies include but are not limited to IgG-like molecules with complementary CH3 domains to force heterodimerisation; recombinant IgG-like dual targeting molecules, wherein the two sides of the molecule each contain the Fab fragment or part of the Fab fragment of at least two different antibodies; IgG fusion molecules, wherein full length IgG antibodies are fused to extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

Examples of Fab fusion bispecific antibodies include but are not limited to F(ab)$_2$ (Medarex/AMGEN), Dual-Action or Bis-Fab (Genentech), Dock-and-Lock (DNL) (Immuno-Medics), Bivalent Bispecific (Biotecnol) and Fab-Fv (UCB-Celltech). Examples of ScFv-, diabody-based and domain antibodies include but are not limited to Bispecific T Cell Engager (BITE) (Micromet, Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), and dual targeting heavy chain only domain antibodies.

6.2.4 Constant Regions

Any heavy chain or light chain constant region can be used in the antibodies (e.g., monospecific or multispecific antibodies) described herein. In certain embodiments, the antibodies (e.g., monospecific or multispecific antibodies) described herein comprise an Ig region that is a human IgG, IgE, IgM, IgD, IgA, or IgY immunoglobulin molecule, any class (e.g., $IgG_1$, $IgG_2$, $IgG_3$, $IgG_4$, $IgA_1$, and $IgA_2$), or any subclass (e.g., $IgG_{2a}$ and $IgG_{2b}$) of immunoglobulin molecule.

In certain embodiments, the antibodies (e.g., monospecific or multispecific antibodies) described herein comprise a human IgG heavy chain constant region that is a variant of a wild type human IgG heavy chain constant region, wherein the variant human IgG heavy chain constant region binds to human Fc gamma receptors with higher affinity than the wild type human IgG heavy chain constant region binds to the human Fc gamma receptors.

In certain embodiments, the variant human IgG heavy chain constant region comprises one or more of the following amino acid mutations, numbered according to the EU numbering system: S239D, A330L, and I332E. In certain embodiments, the variant human IgG heavy chain constant region comprises the following amino acid mutations, numbered according to the EU numbering system: S239D and I332E. In certain embodiments, the variant human IgG heavy chain constant region is a variant human $IgG_1$ heavy chain constant region comprising the following amino acid mutations, numbered according to the EU numbering system: S239D and I332E. In certain embodiments, the variant human IgG heavy chain constant region comprises the following amino acid mutations, numbered according to the EU numbering system: S239D, A330L, and I332E. In certain embodiments, the variant human IgG heavy chain constant region is a variant human $IgG_1$ heavy chain constant region comprising the following amino acid mutations, numbered according to the EU numbering system: S239D, A330L, and I332E.

In certain embodiments, the variant human IgG heavy chain constant region comprises one or more of the following amino acid mutations, numbered according to the EU numbering system: L235V, F243L, R292P, Y300L, and P396L. In certain embodiments, the variant human IgG heavy chain constant region comprises the following amino acid mutations, numbered according to the EU numbering system: L235V, F243L, R292P, Y300L, and P396L. In certain embodiments, the variant human IgG heavy chain constant region is a variant human $IgG_1$ heavy chain constant region comprising the following amino acid mutations, numbered according to the EU numbering system: L235V, F243L, R292P, Y300L, and P396L.

In certain embodiments, the variant human IgG heavy chain constant region comprises one or more of the following amino acid mutations, numbered according to the EU numbering system: G236A, S239D, F243L, T256A, K290A, R292P, S298A, Y300L, V305I, A330L, I332E, E333A, K334A, A339T, and P396L. In certain embodiments, the variant human IgG heavy chain constant region comprises a set of amino acid mutations selected from the group consisting of: S239D; T256A; K290A; S298A; I332E; E333A; K334A; A339T; S239D and I332E; S239D, A330L, and I332E; S298A, E333A, and K334A; G236A, S239D, and I332E; and F243L, R292P, Y300L, V305I, and P396L, numbered according to the EU numbering system. In certain embodiments, the variant human IgG heavy chain constant region comprises S267E or L328F amino acid mutation, numbered according to the EU numbering system. In certain embodiments, the variant human IgG heavy chain constant region comprises the following amino acid mutations, numbered according to the EU numbering system: S267E and L328F. In certain embodiments, the variant human IgG heavy chain constant region is a variant human $IgG_1$ heavy chain constant region comprising the following amino acid mutations, numbered according to the EU numbering system: S267E and L328F. In certain embodiments, the variant human IgG heavy chain constant region comprises P238D amino acid mutation, numbered according to the EU numbering system. In certain embodiments, the variant human IgG heavy chain constant region is a variant human $IgG_1$ heavy chain constant region comprising P238D amino acid mutation, numbered according to the EU numbering system. In certain embodiments, the variant human IgG heavy chain constant region comprises one or more of the following amino acid mutations, numbered according to the EU numbering system: P238D, E233D, G237D, H268D, P271G, and A330R. In certain embodiments, the variant human IgG heavy chain constant region comprises the following amino acid mutations, numbered according to the EU numbering system: P238D, E233D, G237D, H268D, P271G, and A330R. In certain embodiments, the variant human IgG heavy chain constant region is a variant human $IgG_1$ heavy chain constant region comprising the following amino acid mutations, numbered according to the EU numbering system: P238D, E233D, G237D, H268D, P271G, and A330R. In certain embodiments, the variant human IgG heavy chain constant region comprises C127S amino acid mutation, numbered according to the EU numbering system. In certain embodiments, the variant human IgG heavy chain constant region is a variant human $IgG_2$ heavy chain constant region comprising C127S amino acid mutation, numbered according to the EU numbering system.

In certain embodiments, the antibodies (e.g., monospecific or multispecific antibodies) provided herein comprise an afucosylated Fc region.

In certain embodiments, the antibodies (e.g., monospecific or multispecific antibodies) described herein comprise a human IgG heavy chain constant region that is a variant of a wild type human IgG heavy chain constant region, wherein the variant human IgG heavy chain constant region binds to human Fc gamma receptors with lower affinity than the wild type human IgG heavy chain constant region binds to the human Fc gamma receptors. In certain embodiments, the variant human IgG heavy chain constant region comprises a mutation selected from the group consisting of N297A, N297Q, D265A, and a combination thereof, numbered according to the EU numbering system. In certain embodiments, the variant human IgG heavy chain constant region comprises a mutation selected from the group consisting of D265A, P329A, and a combination thereof, numbered according to the EU numbering system.

In certain embodiments, one, two, or more mutations (e.g., amino acid substitutions) are introduced into the Fc region of an antibody (e.g., a monospecific or multispecific antibody) described herein (e.g., CH2 domain (residues 231-340 of human $IgG_1$) and/or CH3 domain (residues 341-447 of human $IgG_1$) and/or the hinge region numbered according to the EU numbering system to alter one or more functional properties of the antibody (e.g., a monospecific or multispecific antibody), such as serum half-life, complement fixation, Fc receptor binding and/or antigen-dependent cellular cytotoxicity.

In certain embodiments, one, two, or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain may be altered to, e.g., facilitate assembly of the light and heavy chains, or to alter (e.g., increase or decrease) the stability of the antibody (e.g., a monospecific or multispecific antibody).

In some embodiments, one, two, or more mutations (e.g., amino acid substitutions) are introduced into the Fc region of an antibody (e.g., a monospecific or multispecific antibody) described herein (e.g., CH2 domain (residues 231-340 of human $IgG_1$) and/or CH3 domain (residues 341-447 of human $IgG_1$) and/or the hinge region numbered according to the EU numbering system to increase or decrease the affinity of the antibody (e.g., a monospecific or multispecific antibody) for an Fc receptor (e.g., an activated Fc receptor) on the surface of an effector cell. Mutations in the Fc region of an antibody (e.g., a monospecific or multispecific antibody) that decrease or increase the affinity of an antibody (e.g., a monospecific or multispecific antibody) for an Fc receptor and techniques for introducing such mutations into the Fc receptor or fragment thereof are known to one of skill in the art. Examples of mutations in the Fc receptor of an antibody (e.g., a monospecific or multispecific antibody) that can be made to alter the affinity of the antibody (e.g., a monospecific or multispecific antibody) for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In a specific embodiment, one, two, or more amino acid mutations (i.e., substitutions, insertions or deletions) are introduced into an IgG constant domain, or FcRn-binding fragment thereof (for example an Fc or hinge-Fc domain fragment) to alter (e.g., decrease or increase) half-life of an antibody (e.g., a monospecific or multispecific antibody) in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody (e.g., a monospecific or multispecific antibody) in vivo. In some embodiments, one, two or more amino acid mutations (i.e., substitutions, insertions, or deletions) are introduced into an IgG constant domain, or FcRn-binding fragment thereof (for example an Fc or hinge-Fc domain fragment) to decrease the half-life of the antibody (e.g., a monospecific or multispecific antibody) in vivo. In other embodiments, one, two or more amino acid mutations (i.e., substitutions, insertions or deletions) are introduced into an IgG constant domain, or FcRn-binding fragment thereof (for example an Fc or hinge-Fc domain fragment) to increase the half-life of the antibody (e.g., a monospecific or multispecific antibody) in vivo. In a specific embodiment, the antibodies (e.g., monospecific or multispecific antibodies) may have one or more amino acid mutations (e.g., substitutions) in the second constant (CH2) domain (residues 231-340 of human $IgG_1$) and/or the third constant (CH3) domain (residues 341-447 of human $IgG_1$), numbered according to the EU numbering system. In a specific embodiment, the constant region of the $IgG_1$ of an antibody (e.g., a monospecific or multispecific antibody) described herein comprises a methionine (M) to tyrosine (Y) substitution in position 252, a serine (S) to threonine (T) substitution in position 254, and a threonine (T) to glutamic acid (E) substitution in position 256, numbered according to the EU numbering system. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In certain embodiments, an antibody (e.g., a monospecific or multispecific antibody) comprises an IgG constant domain comprising one, two, three or more amino acid substitutions of amino acid residues at positions 251-257, 285-290, 308-314, 385-389, and 428-436, numbered according to the EU numbering system.

In certain embodiments, one or more amino acids selected from amino acid residues 329, 331, and 322 in the constant region of an antibody (e.g., a monospecific or multispecific antibody) described herein, numbered according to the EU numbering system, can be replaced with a different amino acid residue such that the antibody (e.g., a monospecific or multispecific antibody) has altered C1q binding and/or reduced or abolished complement dependent cytotoxicity (CDC). This approach is described in further detail in U.S. Pat. No. 6,194,551 (Idusogie et al). In some embodiments, one or more amino acid residues within amino acid positions 231 to 238 in the N-terminal region of the CH2 domain of an antibody (e.g., a monospecific or multispecific antibody) described herein are altered to thereby alter the ability of the antibody (e.g., a monospecific or multispecific antibody) to fix complement. This approach is described further in International Publication No. WO 94/29351. In certain embodiments, the Fc region of an antibody (e.g., a monospecific or multispecific antibody) described herein is modified to increase the ability of the antibody (e.g., a monospecific or multispecific antibody) to mediate antibody dependent cellular cytotoxicity (ADCC) and/or to increase the affinity of the antibody (e.g., a monospecific or multispecific antibody) for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU numbering system. This approach is described further in International Publication No. WO 00/42072.

In certain embodiments, an antibody (e.g., a monospecific or multispecific antibody) described herein comprises the constant region of an $IgG_4$ antibody and the serine at amino acid residue 228 of the heavy chain, numbered according to the EU numbering system, is substituted for proline.

In certain embodiments, an antibody (e.g., a monospecific or multispecific antibody) described herein comprises the constant region of an $IgG_2$ antibody and the cysteine at amino acid residue 127 of the heavy chain, numbered according to the EU numbering system, is substituted for serine.

Antibodies with reduced fucose content have been reported to have an increased affinity for Fc receptors, such as, e.g., FcγRIIIa. Accordingly, in certain embodiments, the antibodies (e.g., monospecific or multispecific antibodies)

described herein have reduced fucose content or no fucose content. Such antibodies (e.g., monospecific or multispecific antibodies) can be produced using techniques known to one skilled in the art. For example, the antibodies (e.g., monospecific or multispecific antibodies) can be expressed in cells deficient or lacking the ability of fucosylation. In a specific example, cell lines with a knockout of both alleles of α1,6-fucosyltransferase can be used to produce antibodies (e.g., monospecific or multispecific antibodies) with reduced fucose content. The Potelligent® system (Lonza) is an example of such a system that can be used to produce antibodies (e.g., monospecific or multispecific antibodies) with reduced fucose content. Alternatively, antibodies (e.g., monospecific or multispecific antibodies) with reduced fucose content or no fucose content can be produced by, e.g.: (i) culturing cells under conditions which prevent or reduce fucosylation; (ii) posttranslational removal of fucose (e.g., with a fucosidase enzyme); (iii) post-translational addition of the desired carbohydrate, e.g., after recombinant expression of a non-glycosylated glycoprotein; or (iv) purification of the glycoprotein so as to select for antibodies (e.g., monospecific or multispecific antibodies) thereof which are not fucsoylated. See, e.g., Longmore G D & Schachter H (1982) Carbohydr Res 100: 365-92 and Imai-Nishiya H et al., (2007) BMC Biotechnol. 7: 84 for methods for producing antibodies (e.g., monospecific or multispecific antibodies) with no fucose content or reduced fucose content.

Engineered glycoforms may be useful for a variety of purposes, including but not limited to enhancing or reducing effector function. Methods for generating engineered glycoforms in an antibody (e.g., a monospecific or multispecific antibody) described herein include but are not limited to those disclosed, e.g., in Uma5a P et al., (1999) Nat Biotechnol 17: 176-180; Davies J et al., (2001) Biotechnol Bioeng 74: 288-294; Shields R L et al., (2002) J Biol Chem 277: 26733-26740; Shinkawa T et al., (2003) J Biol Chem 278: 3466-3473; Niwa R et al., (2004) Clin Cancer Res 1: 6248-6255; Presta L G et al., (2002) Biochem Soc Trans 30: 487-490; Kanda Y et al., (2007) Glycobiology 17: 104-118; U.S. Pat. Nos. 6,602,684; 6,946,292; and 7,214,775; U.S. Patent Publication Nos. US 2007/0248600; 2007/0178551; 2008/0060092; and 2006/0253928; International Publication Nos. WO 00/61739; WO 01/292246; WO 02/311140; and WO 02/30954; Potillegent™ technology (Biowa, Inc. Princeton, N.J.); and GlycoMAb® glycosylation engineering technology (Glycart biotechnology AG, Zurich, Switzerland). See also, e.g., Ferrara C et al., (2006) Biotechnol Bioeng 93: 851-861; International Publication Nos. WO 07/039818; WO 12/130831; WO 99/054342; WO 03/011878; and WO 04/065540.

In certain embodiments, the technology used to engineer the Fc domain of an antibody (e.g., a monospecific or multispecific antibody) described herein is the Xmab® Technology of Xencor (Monrovia, CA). See, e.g., U.S. Pat. Nos. 8,367,805; 8,039,592; 8,124,731; 8,188,231; U.S. Patent Publication No. 2006/0235208; International Publication Nos. WO 05/077981; WO 11/097527; and Richards J O et al., (2008) Mol Cancer Ther 7: 2517-2527.

In certain embodiments, any of the constant region mutations or modifications described herein can be introduced into one or both heavy chain constant regions of an antibody (e.g., a monospecific or multispecific antibody) described herein having two heavy chain constant regions.

6.3 Pharmaceutical Compositions

Provided herein are compositions comprising an anti-CTLA-4 antibody, an anti-PD-1 antibody, and/or an anti-CTLA-4/PD-1 antibody described herein having the desired degree of purity in a physiologically acceptable carrier, excipient or stabilizer (Remington's Pharmaceutical Sciences (1990) Mack Publishing Co., Easton, PA).

In certain embodiments, the pharmaceutical composition comprises an anti-CTLA-4 antibody described herein and an anti-PD-1 antibody described herein. The pharmaceutical composition can comprise any combination of an anti-CTLA-4 antibody described herein and an anti-PD-1 antibody described herein. In certain embodiments, the pharmaceutical composition comprises a first antibody that specifically binds to CTLA-4 (e.g., human CTLA-4) and a second antibody that specifically binds to PD-1 (e.g., human PD-1), wherein CDRH1, CDRH2, CDRH3, CDRL1, CDRL2, and CDRL3 of the first antibody and CDRH1, CDRH2, CDRH3, CDRL1, CDRL2, and CDRL3 of the second antibody comprise the amino acid sequences listed in a single row of Table 11. In certain embodiments, the pharmaceutical composition comprises a first antibody that specifically binds to CTLA-4 (e.g., human CTLA-4) and a second antibody that specifically binds to PD-1 (e.g., human PD-1), wherein the heavy chain variable region and the light chain variable region of the first antibody and the heavy chain variable region and the light chain variable region of the second antibody comprise the amino acid sequences listed in a single row of Table 12.

In certain embodiments, the pharmaceutical composition comprises an effective amount of an antibody described herein. In certain embodiments, the pharmaceutical composition comprises an effective amount of an anti-CTLA-4/PD-1 antibody described herein. In certain embodiments, the pharmaceutical composition comprises an effective amount of a therapeutic combination comprising an anti-CTLA-4 antibody described herein and an anti-PD-1 antibody described herein. The effective amount of the anti-CTLA-4 antibody in such therapeutic combination can be lower than, equal to, or higher than the effective amounts of the anti-CTLA-4 antibody when administered alone, and the effective amount of the anti-PD-1 antibody in this therapeutic combination can be lower than, equal to, or higher than the effective amounts of the anti-PD-1 antibody when administered alone. In certain embodiments, the effective amount of the anti-CTLA-4 antibody in this therapeutic combination is lower than the effective amount of the anti-CTLA-4 antibody when administered alone. In certain embodiments, the effective amount of the anti-PD-1 antibody in this therapeutic combination is lower than the effective amount of the anti-PD-1 antibody when administered alone. In certain embodiments, the effective amount of the anti-CTLA-4 antibody in this therapeutic combination is lower than the effective amount of the anti-CTLA-4 antibody when administered alone, and the effective amount of the anti-PD-1 antibody in this therapeutic combination is lower than the effective amount of the anti-PD-1 antibody when administered alone.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

A pharmaceutical composition may be formulated for any route of administration to a subject. Specific examples of routes of administration include intranasal, oral, pulmonary, transdermal, intradermal, and parenteral. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

A pharmaceutical composition described herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

A pharmaceutical composition described herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

In certain embodiments, a pharmaceutical composition comprising an antibody or antigen-binding fragment thereof described herein is a lyophilized powder, which can be reconstituted for administration as solutions, emulsions and other mixtures. It may also be reconstituted and formulated as solids or gels. The lyophilized powder is prepared by dissolving an antibody or antigen-binding fragment thereof described herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

A pharmaceutical composition described herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In a specific embodiment, a pharmaceutical composition described herein is targeted to a tumor.

In certain embodiments, pharmaceutical compositions comprise an anti-CTLA-4 antibody, an anti-PD-1 antibody, and/or an anti-CTLA-4/PD-1 antibody described herein described herein, and optionally one or more additional prophylactic or therapeutic agents, in a pharmaceutically acceptable carrier. In some embodiments, the antibody is the only active ingredient included in the pharmaceutical composition.

In certain embodiments, pharmaceutical compositions comprise an effective amount of one or more antibodies described herein, and optionally one or more additional prophylactic or therapeutic agents, in a pharmaceutically acceptable carrier.

The compositions to be used for in vivo administration can be sterile. This is readily accomplished by filtration through, e.g., sterile filtration membranes.

6.4 Methods of Use and Uses

In one aspect, the instant disclosure provides a method of treating a subject using an anti-CTLA-4 antibody, an anti-PD-1 antibody, and/or a multispecific antibody (e.g., an anti-CTLA-4/PD-1 antibody) described herein. In certain embodiments, the instant disclosure provides a method of treating a subject using an anti-CTLA-4/PD-1 antibody described herein. In certain embodiments, the instant disclosure provides a method of treating a subject using a therapeutic combination comprising an anti-CTLA-4 antibody described herein and an anti-PD-1 antibody described herein, optionally in the absence of a concomitant therapy for treating the same disease or disorder. In certain embodiments, the instant disclosure provides a method of treating a subject using an anti-CTLA-4 antibody described herein as a monotherapy. In certain embodiments, the instant disclosure provides a method of treating a subject using an anti-PD-1 antibody described herein as a monotherapy.

The therapeutic combination can comprise any combination of an anti-CTLA-4 antibody described herein and an anti-PD-1 antibody described herein. In certain embodiments, the therapeutic combination comprises a first antibody that specifically binds to CTLA-4 (e.g., human CTLA-4) and a second antibody that specifically binds to PD-1 (e.g., human PD-1), wherein CDRH1, CDRH2, CDRH3, CDRL1, CDRL2, and CDRL3 of the first antibody and CDRH1, CDRH2, CDRH3, CDRL1, CDRL2, and CDRL3 of the second antibody comprise the amino acid sequences listed in a single row of Table 11. In certain embodiments, the therapeutic combination comprises a first antibody that specifically binds to CTLA-4 (e.g., human CTLA-4) and a second antibody that specifically binds to PD-1 (e.g., human PD-1), wherein CDRH1, CDRH2, CDRH3, CDRL1, CDRL2, and CDRL3 of the first antibody and CDRH1, CDRH2, CDRH3, CDRL1, CDRL2, and CDRL3 of the second antibody respectively comprise the amino acid sequences set forth in SEQ ID NOs: 20, 22, 24, 27, 30, 36, 75, 76, 80, 83, 84, and 85; 20, 22, 24, 29, 32, 37, 75, 76, 80, 83, 84, and 85; 20, 22, 24, 29, 33, 38, 75, 76, 80, 83, 84, and 85; 21, 22, 24, 27, 30, 36, 75, 76, 80, 83, 84, and 85; 21, 22, 24, 29, 33, 38, 75, 76, 80, 83, 84, and 85; 20, 22, 24, 28, 31, 36, 75, 76, 80, 83, 84, and 85; 20, 22, 24, 29, 34, 36, 75, 76, 80, 83, 84, and 85; 20, 22, 24, 29, 35, 38, 75, 76, 80, 83, 84, and 85; 21, 22, 26, 27, 30, 36, 75, 76, 80, 83, 84, and 85; 21, 22, 26, 29, 32, 37, 75, 76, 80, 83, 84, and 85; 21, 22, 26, 29, 33, 38, 75, 76, 80, 83, 84, and 85; 21, 22, 26, 29, 35, 38, 75, 76, 80, 83, 84, and 85; 20, 22, 24, 27, 30, 36, 75, 76, 81, 83, 84, and 85; 20, 22, 24, 29, 32, 37, 75, 76, 81, 83, 84, and 85; 20, 22, 24, 29, 33, 38, 75, 76, 81, 83, 84, and 85; 21, 22, 24, 27, 30, 36, 75, 76, 81, 83, 84, and 85; 21, 22, 24, 29, 33, 38, 75, 76, 81, 83, 84, and 85; 20, 22, 24, 28, 31, 36, 75, 76, 81, 83, 84, and 85; 20, 22, 24, 29, 34, 36, 75, 76, 81, 83, 84, and 85; 20, 22, 24, 29, 35, 38, 75, 76, 81, 83, 84, and 85; 21, 22, 26, 27, 30, 36, 75, 76, 81, 83, 84, and 85; 21, 22, 26, 29, 32, 37, 75, 76, 81, 83, 84, and 85; 21, 22, 26, 29, 33, 38, 75, 76, 81, 83, 84, and 85; 21, 22, 26, 29, 35, 38, 75, 76, 81, 83, 84, and 85; 20, 22, 24, 27, 30, 36, 75, 76, 82, 83, 84, and 85; 20, 22, 24, 29, 32, 37, 75, 76, 82, 83, 84, and 85; 20, 22, 24, 29, 33, 38, 75, 76, 82, 83, 84, and 85; 21, 22, 24, 27, 30, 36, 75, 76, 82, 83, 84, and 85; 21, 22, 24, 29, 33, 38, 75, 76, 82, 83, 84, and 85; 20, 22, 24, 28, 31, 36, 75, 76, 82, 83, 84, and 85; 20, 22, 24, 29, 34, 36, 75, 76, 82, 83, 84, and 85; 20, 22, 24, 29, 35, 38, 75, 76, 82, 83, 84, and 85; 21, 22, 26, 27, 30, 36, 75, 76, 82, 83, 84, and 85; 21, 22, 26, 29, 32, 37, 75, 76, 82, 83, 84, and 85; 21, 22, 26, 29, 33, 38, 75, 76, 82, 83, 84, and 85; 21, 22, 26, 29, 35, 38, 75, 76, 82, 83, 84, and 85; 20, 22, 24, 27, 30, 36, 75, 77, 81, 83, 84, and 85; 20, 22, 24, 29, 32, 37, 75, 77, 81, 83, 84, and 85; 20, 22, 24, 29, 33, 38, 75, 77, 81, 83, 84, and 85; 21, 22, 24, 27, 30, 36, 75, 77, 81, 83, 84, and 85; 21, 22, 24, 29, 33, 38, 75, 77, 81, 83, 84, and 85; 20, 22, 24, 28, 31, 36, 75, 77, 81, 83, 84, and 85; 20, 22, 24, 29, 34, 36, 75, 77, 81, 83, 84, and 85; 20, 22, 24, 29, 35, 38, 75, 77, 81, 83, 84, and 85; 21, 22, 26, 27, 30, 36, 75, 77, 81, 83, 84, and 85; 21, 22, 26, 29, 32, 37, 75, 77, 81, 83, 84, and 85; 21, 22, 26, 29, 33, 38, 75, 77, 81, 83, 84, and 85; 21, 22, 26, 29, 35, 38, 75, 77, 81, 83, 84, and 85; 20, 22, 24, 27, 30, 36, 75, 78, 81, 83, 84, and 85; 20, 22, 24, 29, 32, 37, 75, 78, 81, 83, 84, and 85; 20, 22, 24, 29, 33, 38, 75, 78, 81, 83, 84, and 85; 21, 22, 24, 27, 30, 36, 75, 78, 81, 83, 84, and 85; 21, 22, 24, 29, 33, 38, 75, 78, 81, 83, 84, and 85; 20, 22, 24, 28, 31, 36, 75, 78, 81, 83, 84, and 85; 20, 22, 24, 29, 34, 36, 75, 78, 81, 83, 84, and 85; 20, 22, 24, 29, 35, 38, 75, 78, 81, 83, 84, and 85; 21, 22, 26, 27, 30, 36, 75, 78, 81, 83, 84, and 85; 21, 22, 26, 29, 32, 37, 75, 78, 81, 83, 84, and 85; 21, 22, 26, 29, 33, 38, 75, 78, 81, 83, 84, and 85; 21, 22, 26, 29, 35, 38, 75, 78, 81, 83, 84, and 85; 20, 22, 24, 27, 30, 36, 75, 79, 81, 83, 84, and 85; 20, 22, 24, 29, 32, 37, 75, 79, 81, 83, 84, and 85; 20, 22, 24, 29, 33, 38, 75, 79, 81, 83, 84, and 85; 21, 22, 24, 27, 30, 36, 75, 79, 81, 83, 84, and 85; 21, 22, 24, 29, 33, 38, 75, 79, 81, 83, 84, and 85; 20, 22, 24, 28, 31, 36, 75, 79, 81, 83, 84, and 85; 20, 22, 24, 29, 34, 36, 75, 79, 81, 83, 84, and 85; 20, 22, 24, 29, 35, 38, 75, 79, 81, 83, 84, and 85; 21, 22, 26, 27, 30, 36, 75, 79, 81, 83, 84, and 85; 21, 22, 26, 29, 32, 37, 75, 79, 81, 83, 84, and 85; 21, 22, 26, 29, 33, 38, 75, 79, 81, 83, 84, and 85; or 21, 22, 26, 29, 35, 38, 75, 79, 81, 83, 84, and 85.

In certain embodiments, the therapeutic combination comprises a first antibody that specifically binds to CTLA-4 (e.g., human CTLA-4) and a second antibody that specifically binds to PD-1 (e.g., human PD-1), wherein the heavy chain variable region and the light chain variable region of the first antibody and the heavy chain variable region and the light chain variable region of the second antibody comprise the amino acid sequences listed in a single row of Table 12. In certain embodiments, the therapeutic combination comprises a first antibody that specifically binds to CTLA-4 (e.g., human CTLA-4) and a second antibody that specifically binds to PD-1 (e.g., human PD-1), wherein the heavy chain variable region and the light chain variable region of the first antibody and the heavy chain variable region and the light chain variable region of the second antibody respectively comprise the amino acid sequences set forth in SEQ ID NOs: 1, 14, 67, and 74; 1, 16, 67, and 74; 1, 17, 67, and 74; 9, 14, 67, and 74; 9, 17, 67, and 74; 10, 15, 67, and 74; 10, 17, 67, and 74; 10, 18, 67, and 74; 10, 19, 67, and 74; 11, 15, 67, and 74; 11, 14, 67, and 74; 11, 16, 67, and 74; 11, 17, 67, and 74; 12, 14, 67, and 74; 12, 16, 67, and 74; 12, 17, 67, and 74; 12, 19, 67, and 74; 13, 15, 67, and 74; 13, 17, 67, and 74; 1, 14, 66, and 74; 1, 16, 66, and 74; 1, 17, 66, and 74; 9, 14, 66, and 74; 9, 17, 66, and 74; 10, 15, 66, and 74; 10, 17, 66, and 74; 10, 18, 66, and 74; 10, 19, 66, and 74; 11, 15, 66, and 74; 11, 14, 66, and 74; 11, 16, 66, and 74; 11, 17, 66, and 74; 12, 14, 66, and 74; 12, 16, 66, and 74; 12, 17, 66, and 74; 12, 19, 66, and 74; 13, 15, 66, and 74; 13, 17, 66, and 74; 1, 14, 68, and 74; 1, 16, 68, and 74; 1, 17, 68, and 74; 9, 14, 68, and 74; 9, 17, 68, and 74; 10, 15, 68, and 74; 10, 17, 68, and 74; 10, 18, 68, and 74; 10, 19, 68, and 74; 11, 15, 68, and 74; 11, 14, 68, and 74; 11, 16, 68, and 74; 11, 17, 68, and 74; 12, 14, 68, and 74; 12, 16, 68, and 74; 12, 17, 68, and 74; 12, 19, 68, and 74; 13, 15, 68, and 74; 13, 17, 68, and 74; 1, 14, 69, and 74; 1, 16, 69, and 74; 1, 17, 69, and 74; 9, 14, 69, and 74; 9, 17, 69, and 74; 10, 15, 69, and 74; 10, 17, 69, and 74; 10, 18, 69, and 74; 10, 19, 69, and 74; 11, 15, 69, and 74; 11, 14, 69, and 74; 11, 16, 69, and 74; 11, 17, 69, and 74; 12, 14, 69, and 74; 12, 16, 69, and 74; 12, 17, 69, and 74; 12, 19, 69, and 74; 13, 15, 69, and 74; 13, 17, 69, and 74; 1, 14, 70, and 74; 1, 16, 70, and 74; 1, 17, 70, and 74; 9, 14, 70, and 74; 9, 17, 70, and 74; 10, 15, 70, and 74; 10, 17, 70, and 74; 10, 18, 70, and 74; 10, 19, 70, and 74; 11, 15, 70, and 74; 11, 14, 70, and 74; 11, 16, 70, and 74; 11, 17, 70, and 74; 12, 14, 70, and 74; 12, 16, 70, and 74; 12, 17, 70, and 74; 12, 19, 70, and 74; 13, 15, 70, and 74; 13, 17, 70, and 74; 1, 14, 71, and 74; 1, 16, 71, and 74; 1, 17, 71, and 74; 9, 14, 71, and 74; 9, 17, 71, and 74; 10, 15, 71, and 74; 10, 17, 71, and 74; 10, 18, 71, and 74; 10, 19, 71, and 74; 11, 15, 71, and 74; 11, 14, 71, and 74; 11, 16, 71, and 74; 11, 17, 71, and 74; 12, 14, 71, and 74; 12, 16, 71, and 74; 12, 17, 71, and 74; 12, 19, 71, and 74; 13, 15, 71, and 74; 13, 17, 71, and 74; 1, 14, 72, and 74; 1, 16, 72, and 74; 1, 17, 72, and 74; 9, 14, 72, and 74; 9, 17, 72, and 74; 10, 15, 72, and 74; 10, 17, 72, and 74; 10, 18, 72, and 74; 10, 19, 72, and 74; 11, 15, 72, and 74; 11, 14, 72, and 74; 11, 16, 72, and 74; 11, 17, 72, and 74; 12, 14, 72, and 74; 12, 16, 72, and 74; 12, 17, 72, and 74; 12, 19, 72, and 74; 13, 15, 72, and 74; 13, 17, 72, and 74; 1, 14, 73, and 74; 1, 16, 73, and 74; 1, 17, 73, and 74; 9, 14, 73, and 74; 9, 17, 73, and 74; 10, 15, 73, and 74; 10, 17, 73, and 74; 10, 18, 73, and 74; 10, 19, 73, and 74; 11, 15, 73, and 74; 11, 14, 73, and 74; 11, 16, 73, and 74; 11, 17, 73, and 74; 12, 14, 73, and 74; 12, 16, 73, and 74; 12, 17, 73, and 74; 12, 19, 73, and 74; 13, 15, 73, and 74; or 13, 17, 73, and 74.

In certain embodiments, the instant disclosure provides a method of treating a subject using a therapeutic combination comprising an anti-CTLA-4 antibody described herein (e.g., AGEN1884 (IgG$_1$)) and an anti-PD-1 antibody (e.g., an antagonistic anti-PD-1 antibody), optionally in the absence of a concomitant therapy for treating the same disease or disorder. In certain embodiments, the anti-PD-1 antibody is nivolumab, also known as BMS-936558 or MDX1106, developed by Bristol-Myers Squibb. In certain embodiments, the anti-PD-1 antibody is pembrolizumab, also known as lambrolizumab or MK-3475, developed by Merck & Co. In certain embodiments, the anti-PD-1 antibody is pidilizumab, also known as CT-011, developed by CureTech. In certain embodiments, the anti-PD-1 antibody is MEDI0680, also known as AMP-514, developed by Medimmune. In certain embodiments, the anti-PD-1 antibody is PDR001 developed by Novartis Pharmaceuticals. In certain embodiments, the anti-PD-1 antibody is REGN2810 developed by Regeneron Pharmaceuticals. In certain embodiments, the anti-PD-1 antibody is PF-06801591 developed by Pfizer. In certain embodiments, the anti-PD-1 antibody is BGB-A317 developed by BeiGene. In certain embodiments, the anti-PD-1 antibody is TSR-042 developed by AnaptysBio and Tesaro. In certain embodiments, the anti-PD-1 antibody is SHR-1210 developed by Hengrui. In certain embodiments, the anti-CTLA-4 is AGEN1884 (IgG$_1$) and the anti-PD-1 antibody is pembrolizumab.

Further non-limiting examples of anti-PD-1 antibodies that may be used in treatment methods described herein are disclosed in the following patents and patent applications, which are incorporated herein by reference in their entireties for all purposes: U.S. Pat. Nos. 6,808,710; 7,332,582; 7,488,802; 8,008,449; 8,114,845; 8,168,757; 8,354,509; 8,686,119; 8,735,553; 8,747,847; 8,779,105; 8,927,697; 8,993,731; 9,102,727; 9,205,148; U.S. Publication No. US 2013/0202623 A1; U.S. Publication No. US 2013/0291136 A1; U.S. Publication No. US 2014/0044738 A1; U.S. Publication No. US 2014/0356363 A1; U.S. Publication No. US 2016/0075783 A1; and PCT Publication No. WO 2013/033091 A1; PCT Publication No. WO 2015/036394 A1; PCT Publication No. WO 2014/179664 A2; PCT Publication No. WO 2014/209804 A1; PCT Publication No. WO 2014/206107 A1; PCT Publication No. WO 2015/058573 A1; PCT Publication No. WO 2015/085847 A1; PCT Publication No. WO 2015/200119 A1; PCT Publication No. WO 2016/015685 A1; and PCT Publication No. WO 2016/020856 A1.

In certain embodiments, the instant disclosure provides a method of treating a subject using a therapeutic combination comprising an anti-PD-1 antibody described herein (e.g., AGEN2034 (IgG$_4$ S228P)) and an anti-CTLA-4 antibody (e.g., an antagonistic anti-CTLA-4 antibody), optionally in the absence of a concomitant therapy for treating the same disease or disorder. In certain embodiments, the anti-CTLA-4 antibody is ipilimumab. In certain embodiments, the anti-CTLA-4 antibody is tremelimumab.

Any disease or disorder in a subject that would benefit from inhibition of CTLA-4 and/or PD-1 function can be treated using the antibodies, therapeutic combinations, or pharmaceutical composition described herein. The antibodies, or therapeutic combinations or pharmaceutical compositions described herein are particularly useful for inhibiting immune system tolerance to tumors, and accordingly can be used as an immunotherapy for subjects with cancer. For example, in certain embodiments, the instant disclosure provides a method of increasing T-cell activation in response to an antigen in a subject, the method comprising administering to the subject an effective amount of an antibody, therapeutic combination, or pharmaceutical composition as described herein. In certain embodiments, the instant disclosure provides a method of treating cancer in a subject, the method comprising administering to the subject an effective amount of an antibody, therapeutic combination, or pharmaceutical composition as described herein.

Cancers that can be treated with the antibodies, therapeutic combinations, or pharmaceutical compositions described herein include, without limitation, solid cancer (e.g., relapsed or refractory solid cancer, and advanced or metastatic solid cancer), carcinoma, sarcoma, melanoma (e.g., stage III or stage IV melanoma), small cell lung cancer, non-small cell lung cancer, urothelial cancer, ovarian cancer, prostate cancer (e.g., metastatic hormone-refractory prostate cancer and progressive metastatic prostate cancer), pancreatic cancer, breast cancer (e.g., HER2$^+$ breast cancer (e.g., relapsed/refractory HER2$^+$ breast cancer)), head and neck cancer (e.g., relapsed/refractory head and neck squamous cell carcinoma (HNSCC)), glioma, malignant glioma, glioblastoma multiforme, brain metastasis, merkel cancer, gastric cancer, gastroesophageal cancer, renal cell carcinoma, uveal melanoma, colon cancer, cervical cancer, lymphoma (e.g., relapsed or refractory lymphoma), non-Hodgkin's lymphoma, Hodgkin's lymphoma, leukemia, and multiple myeloma. In certain embodiments, the cancer is treated with intratumoral administration of an antibody, therapeutic combination, or pharmaceutical composition described herein. Cancers that can be treated with intratumoral administration of the antibodies, therapeutic combinations, or pharmaceutical compositions described herein include, without limitation, solid tumors (e.g., advanced or metastatic solid tumors), head and neck cancer (e.g., relapsed/refractory head and neck squamous cell carcinoma (HNSCC)), and breast cancer (e.g., HER2$^+$ breast cancer (e.g., relapsed/refractory HER2$^+$ breast cancer)).

In certain embodiments, the cancer treated in accordance with the methods described herein is a metastatic or locally advanced cancer (e.g., solid tumor). In certain embodiments, the cancer is treated in accordance with a method described herein as a first cancer therapy after diagnosis of the metastatic or locally advanced tumor (e.g., within 1, 2, 3, 4, 5, or 6 days; 1, 2, 3, 4, 6, 8, or 12 weeks; or, 1, 2, 3, 4, 6, 8, or 12 months after diagnosis). In certain embodiments, the cancer is treated in accordance with a method described herein as the first cancer therapy after diagnosis of tumor progression (e.g., within 1, 2, 3, 4, 5, or 6 days; 1, 2, 3, 4, 6, 8, or 12 weeks; or, 1, 2, 3, 4, 6, 8, or 12 months after diagnosis of tumor progression) that has occurred despite previous treatment of the tumor with a different cancer therapy, optionally wherein the method described herein is provided as the second cancer therapy administered. In certain embodiments, the cancer is treated in accordance with a method described herein as the first cancer therapy after diagnosis of toxicity of a different cancer therapy (e.g., within 1, 2, 3, 4, 5, or 6 days; 1, 2, 3, 4, 6, 8, or 12 weeks; or, 1, 2, 3, 4, 6, 8, or 12 months after diagnosis of toxicity of the different cancer therapy), optionally wherein the method described herein is provided as the second cancer therapy administered. In certain embodiments, the cancer treated in accordance with the methods described herein is a metastatic or locally advanced cancer (e.g., solid tumor) for which no standard therapy is available. In other embodiments, the cancer treated in accordance with the methods described herein is a metastatic or locally advanced cancer (e.g., solid tumor) for which a standard therapy has failed (i.e., the cancer has progressed after the standard therapy). In certain embodiments, a therapy fails if the cancer is refractory to the therapy. In certain embodiments, a therapy fails if the cancer relapses after responding, fully or partially, to the therapy. In certain embodiments, metastatic or locally advanced cancer (e.g., solid tumor) has been confirmed histologically or cytologically.

In certain embodiments, the cancer is a solid tumor. In certain embodiments, the cancer (e.g., solid tumor) expresses PD-L1. In certain embodiments, the percentage of tumor cells in a sample of the cancer (e.g., solid tumor) that exhibit detectable expression (e.g., partial or complete expression) of PD-L1 is at least 1% (e.g., at least 2%, 3%, 4%, 5%, 10%, 15%, 20%, 25%, 30%, 35%, 40%, 45%, 50%, 60%, 70%, 80%, or 90%). In certain embodiments, the percentage of tumor cells in a sample of the cancer (e.g., solid tumor) that exhibit detectable membrane expression (e.g., partial or complete membrane expression) of PD-L1 is at least 1% (e.g., at least 2%, 3%, 4%, 5%, 10%, 15%, 20%, 25%, 30%, 35%, 40%, 45%, 50%, 60%, 70%, 80%, or 90%). In certain embodiments, the percentage of tumor cells in a sample of the cancer (e.g., solid tumor) that exhibit detectable membrane expression (e.g., partial or complete membrane expression) of PD-L1 is at least 1%. In certain embodiments, the percentage of tumor cells in a sample of the cancer (e.g., solid tumor) that exhibit detectable membrane expression (e.g., partial or complete membrane expression) of PD-L1 is at least 5%. In certain embodiments, the percentage of tumor cells in a sample of the cancer (e.g., solid tumor) that exhibit detectable membrane expression (e.g., partial or complete membrane expression) of PD-L1 is at least 25%. In certain embodiments, the percentage of tumor cells in a sample of the cancer (e.g., solid tumor) that exhibit detectable membrane expression (e.g., partial or complete membrane expression) of PD-L1 is at least 50%. Expression (e.g., membrane expression) of PD-L1 can be detected by any method well known in the art, including but not limited to immunohistochemistry. Exemplary immunohistochemistry assays for measuring PD-L1 expression in tumor cells are provided in Hirsch et al. (2017, J. Thoracic Oncol. 12(2): 208-222), Rimm et al. (2017, JAMA Oncol. 3(8): 1051-1058), and Diggs and Hsueh (2017, Biomarker Res. 5:12), which are incorporated by reference herein in their entirety.

In certain embodiments, the metastatic or locally advanced cancer (e.g., solid tumor) expresses PD-L1. In certain embodiments, the percentage of tumor cells in a sample of the metastatic or locally advanced cancer (e.g., solid tumor) that exhibit detectable expression (e.g., partial or complete expression) of PD-L1 is at least 1% (e.g., at least 2%, 3%, 4%, 5%, 10%, 15%, 20%, 25%, 30%, 35%, 40%, 45%, 50%, 60%, 70%, 80%, or 90%). In certain embodiments, the percentage of tumor cells in a sample of the metastatic or locally advanced cancer (e.g., solid tumor) that exhibit detectable membrane expression (e.g., partial or complete membrane expression) of PD-L1 is at least 1% (e.g., at least 2%, 3%, 4%, 5%, 10%, 15%, 20%, 25%, 30%, 35%, 40%, 45%, 50%, 60%, 70%, 80%, or 90%). In certain embodiments, the percentage of tumor cells in a sample of the metastatic or locally advanced cancer (e.g., solid tumor) that exhibit detectable membrane expression (e.g., partial or complete membrane expression) of PD-L1 is at least 1%. In certain embodiments, the percentage of tumor cells in a sample of the metastatic or locally advanced cancer (e.g., solid tumor) that exhibit detectable membrane expression (e.g., partial or complete membrane expression) of PD-L1 is at least 5%. In certain embodiments, the percentage of tumor cells in a sample of the metastatic or locally advanced cancer (e.g., solid tumor) that exhibit detectable membrane expression (e.g., partial or complete membrane expression) of PD-L1 is at least 25%. In certain embodiments, the percentage of tumor cells in a sample of the metastatic or locally advanced cancer (e.g., solid tumor) that exhibit detectable membrane expression (e.g., partial or complete membrane expression) of PD-L1 is at least 50%. Expression (e.g., membrane expression) of PD-L1 can be detected by any method well known in the art, including but not limited to immunohistochemistry. Exemplary immunohistochemistry assays for measuring PD-L1 expression in tumor cells are provided in Hirsch et al. (2017, J. Thoracic Oncol. 12(2): 208-222), Rimm et al. (2017, JAMA Oncol. 3(8): 1051-1058), and Diggs and Hsueh (2017, Biomarker Res. 5:12), which are incorporated by reference herein in their entirety.

In certain embodiments, the cancer treated in accordance with a method described herein is a non-small cell lung cancer (NSCLC). In certain embodiments, the cancer treated in accordance with a method described herein is a metastatic or locally advanced non-small cell lung cancer (NSCLC). In certain embodiments, the cancer treated in accordance with a method described herein is a Stage IV, metastatic, or locally advanced NSCLC. In certain embodiments, the cancer treated in accordance with a method described herein is a Stage IV NSCLC. In certain embodiments, the method comprises treating a subject using a therapeutic combination comprising (a) an anti-CTLA-4 antibody described herein (e.g., AGEN1884 (IgG$_1$)) or pharmaceutical composition comprising such anti-CTLA-4 antibody; and (b) an anti-PD-1 antibody described herein (e.g., AGEN2034 (IgG$_4$ S228P)) or pharmaceutical composition comprising such anti-PD-1 antibody. In certain embodiments, the anti-CTLA-4 antibody is AGEN1884 (IgG$_1$) and the anti-PD-1 antibody is AGEN2034 (IgG$_4$ S228P). In certain embodiments, the anti-CTLA-4 antibody is AGEN1884 (IgG$_1$) and the anti-PD-1 antibody is pembrolizumab. In certain embodiments, the percentage of tumor cells in a sample of the NSCLC (e.g., the Stage IV, metastatic, or locally advanced NSCLC) that exhibit detectable expression (e.g., partial or complete expression) of PD-L1 is at least 1%, 2%, 3%, 4%, 5%, 10%, 15%, 20%, 25%, 30%, 35%, 40%, 45%, 50%, 60%, 70%, 80%, or 90%. In certain embodiments, the percentage of tumor cells in a sample of the NSCLC (e.g., the Stage IV, metastatic, or locally advanced NSCLC) that exhibit detectable membrane expression (e.g., partial or complete membrane expression) of PD-L1 is at least 1%, 2%, 3%, 4%, 5%, 10%, 15%, 20%, 25%, 30%, 35%, 40%, 45%, 50%, 60%, 70%, 80%, or 90%. In certain embodiments, the percentage of tumor cells in a sample of the NSCLC (e.g., the Stage IV, metastatic, or locally advanced NSCLC) that exhibit detectable membrane expression (e.g., partial or complete membrane expression) of PD-L1 is at least 1%. In certain embodiments, the percentage of tumor cells in a sample of the NSCLC (e.g., the Stage IV, metastatic, or locally advanced NSCLC) that exhibit detectable membrane expression (e.g., partial or complete membrane expression) of PD-L1 is at least 5%. In certain embodiments, the percentage of tumor cells in a sample of the NSCLC (e.g., the Stage IV, metastatic, or locally advanced NSCLC) that exhibit detectable membrane expression (e.g., partial or complete membrane expression) of PD-L1 is at least 25%. In certain embodiments, the percentage of tumor cells in a sample of the NSCLC (e.g., the Stage IV, metastatic, or locally advanced NSCLC) that exhibit detectable membrane expression (e.g., partial or complete membrane expression) of PD-L1 is at least 50%. In certain embodiments, the NSCLC (e.g., the Stage IV, metastatic, or locally advanced NSCLC) has no EGFR or ALK genomic tumor aberrations. In certain embodiments, the NSCLC (e.g., the Stage IV, metastatic, or locally advanced NSCLC) has no EGFR sensitizing mutation (e.g., mutation that is amenable to treatment with a tyrosine kinase inhibitor including erlotinib, gefitinib, or afatanib) or ALK translocation. In certain embodiments, the subject having the NSCLC (e.g., the Stage IV, metastatic, or locally advanced NSCLC) has received no prior systemic chemotherapy treatment for the NSCLC. In certain embodiments, the NSCLC (e.g., the Stage IV, metastatic, or locally advanced NSCLC) is treated in accordance with a method described herein as a first cancer therapy after diagnosis (e.g., within 1, 2, 3, 4, 5, or 6 days; 1, 2, 3, 4, 6, 8, or 12 weeks; or, 1, 2, 3, 4, 6, 8, or 12 months after diagnosis) of the NSCLC. In certain embodiments, the method comprises treating a subject having NSCLC (e.g., Stage IV, metastatic, or locally advanced NSCLC) using a therapeutic combination comprising (a) an anti-CTLA-4 antibody described herein, e.g., AGEN1884 (IgG$_1$), or pharmaceutical composition comprising such anti-CTLA-4 antibody; and (b) an anti-PD-1 antibody described herein, e.g., AGEN2034 (IgG$_4$ S228P), or pharmaceutical composition comprising such anti-PD-1 antibody, wherein the percentage of tumor cells in a sample of the NSCLC that exhibit detectable expression (e.g., membrane expression, partial or complete membrane expression) of PD-L1 is at least 1%, 2%, 3%, 4%, 5%, 10%, 15%, 20%, 25%, 30%, 35%, 40%, 45%, 50%, 60%, 70%, 80%, or 90%, and wherein the method is provided as a first cancer therapy after diagnosis (e.g., within 1, 2, 3, 4, 5, or 6 days; 1, 2, 3, 4, 6, 8, or 12 weeks; or, 1, 2, 3, 4, 6, 8, or 12 months after diagnosis) of the NSCLC. In certain embodiments, the method comprises treating a subject having NSCLC (e.g., Stage IV, metastatic, or locally advanced NSCLC) using a therapeutic combination comprising (a) an anti-CTLA-4 antibody described herein, e.g., AGEN1884 (IgG$_1$), or pharmaceutical composition comprising such anti-CTLA-4 antibody; and (b) pembrolizumab or pharmaceutical composition comprising pembrolizumab, wherein the percentage of tumor cells in a sample of the NSCLC that exhibit detectable expression (e.g., membrane expression, partial or complete membrane expression) of PD-L1 is at least 1%, 2%, 3%, 4%, 5%, 10%, 15%, 20%, 25%, 30%, 35%, 40%, 45%, 50%, 60%, 70%, 80%, or 90%, and wherein the method is provided as a first cancer therapy after diagnosis (e.g., within 1, 2, 3, 4, 5, or 6 days; 1, 2, 3, 4, 6, 8, or 12 weeks; or, 1, 2, 3, 4, 6, 8, or 12 months after diagnosis) of the NSCLC.

In certain embodiments, the cancer treated in accordance with the methods described herein is a cervical cancer. In certain embodiments, the cancer treated in accordance with the methods described herein is a metastatic or locally advanced, unresectable squamous cell carcinoma, adenosquamous carcinoma, or adenocarcinoma of the cervix. In certain embodiments, the cancer treated in accordance with the methods described herein is an unresectable or metastatic cervical cancer. In certain embodiments, the cervical cancer has progressed after a standard therapy (e.g., has relapsed after the standard therapy, or is refractory to the standard therapy). In certain embodiments, the standard therapy comprises a platinum-containing chemotherapy. In certain embodiments, the platinum-containing chemotherapy is selected from the group consisting of cisplatin, carboplatin, oxaliplatin, nedaplatin, satraplatin, picoplatin, triplatin, phenanthriplatin, iproplatin, lobapatin, heptaplatin, lipoplatin, and a combination thereof. In certain embodiments, the standard therapy further comprises a second chemotherapy. In certain embodiments, the second chemotherapy is selected from the group consisting of a nucleotide analog (e.g., gemcitabine), a folate antimetabolite (e.g., pemetrexed), a taxane (e.g., paclitaxel). In certain embodiments, the standard therapy is any platinum-based doublet chemotherapy (PT-DC) (also known as platinum-containing doublet) known in the art. In certain embodiments, the PT-DC comprises cisplatin and gemcitabine, cisplatin and pemetrexed, cisplatin and paclitaxel, carboplatin and paclitaxel, or cisplatin and topotecan. The standard therapy (e.g., one comprising a PT-DC) can optionally further comprise one or more additional therapies, such as bevacizumab. In certain embodiments, the standard therapy comprises paclitaxel and topotecan. In certain embodiments, the cervical cancer is HPV positive. In certain embodiments, the cervical cancer is associated with microsatellite instability. In certain embodiments, the cancer treated in accordance with the methods described herein is a metastatic or locally advanced, unresectable squamous cell carcinoma, adenosquamous carcinoma, or adenocarcinoma of the cervix that has relapsed after a platinum-containing doublet administered for treatment of advanced (recurrent, unresectable, or metastatic) disease. In certain embodiments, the cancer of the cervix is treated in accordance with a method described herein as a first cancer therapy after diagnosis of the cervical cancer (e.g., within 1, 2, 3, 4, 5, or 6 days; 1, 2, 3, 4, 6, 8, or 12 weeks; or, 1, 2, 3, 4, 6, 8, or 12 months after diagnosis). In certain embodiments, the cancer of the cervix is treated in accordance with a method described herein as the first cancer therapy after diagnosis of tumor progression (e.g., within 1, 2, 3, 4, 5, or 6 days; 1, 2, 3, 4, 6, 8, or 12 weeks; or, 1, 2, 3, 4, 6, 8, or 12 months after diagnosis of tumor progression) that has occurred despite previous treatment of the cancer of the cervix with a different cancer therapy, optionally wherein the method described herein is provided as the second cancer therapy administered. In certain embodiments, the cancer of the cervix is treated in accordance with a method described herein as the first cancer therapy after diagnosis of toxicity of a different cancer therapy (e.g., within 1, 2, 3, 4, 5, or 6 days; 1, 2, 3, 4, 6, 8, or 12 weeks; or, 1, 2, 3, 4, 6, 8, or 12 months after diagnosis of toxicity of the different cancer therapy), optionally wherein the method described herein is provided as the second cancer therapy administered. In certain embodiments, the method comprises treating a subject having cervical cancer (e.g., a metastatic or locally advanced, unresectable squamous cell carcinoma, adenosquamous carcinoma, or adenocarcinoma of the cervix) using a therapeutic combination comprising (a) an anti-CTLA-4 antibody described herein, e.g., AGEN1884 (IgG$_1$), or pharmaceutical composition comprising such anti-CTLA-4 antibody; and (b) an anti-PD-1 antibody described herein, e.g., AGEN2034 (IgG$_4$ S228P), or pharmaceutical composition comprising such anti-PD-1 antibody, wherein the method is provided as a first cancer therapy after diagnosis of the cervical cancer (e.g., within 1, 2, 3, 4, 5, or 6 days; 1, 2, 3, 4, 6, 8, or 12 weeks; or, 1, 2, 3, 4, 6, 8, or 12 months after diagnosis). In certain embodiments, the method comprises treating a subject having cervical cancer (e.g., a metastatic or locally advanced, unresectable squamous cell carcinoma, adenosquamous carcinoma, or adenocarcinoma of the cervix) using a therapeutic combination comprising (a) an anti-CTLA-4 antibody described herein, e.g., AGEN1884 (IgG$_1$), or pharmaceutical composition comprising such anti-CTLA-4 antibody; and (b) an anti-PD-1 antibody described herein, e.g., AGEN2034 (IgG$_4$ S228P), or pharmaceutical composition comprising such anti-PD-1 antibody, wherein the method is provided after diagnosis of tumor progression (e.g., within 1, 2, 3, 4, 5, or 6 days; 1, 2, 3, 4, 6, 8, or 12 weeks; or, 1, 2, 3, 4, 6, 8, or 12 months after diagnosis of tumor progression) that has occurred despite previous treatment of the cervical cancer with a different cancer therapy, or provided after diagnosis of toxicity of a different cancer therapy (e.g., within 1, 2, 3, 4, 5, or 6 days; 1, 2, 3, 4, 6, 8, or 12 weeks; or, 1, 2, 3, 4, 6, 8, or 12 months after diagnosis of toxicity of the different cancer therapy), and wherein the method described herein is provided as the second cancer therapy administered. In certain embodiments, the method comprises treating a subject having cervical cancer (e.g., a metastatic or locally advanced, unresectable squamous cell carcinoma, adenosquamous carcinoma, or adenocarcinoma of the cervix) using a therapeutic combination comprising (a) an anti-CTLA-4 antibody described herein, e.g., AGEN1884 (IgG$_1$), or pharmaceutical composition comprising such anti-CTLA-4 antibody, and (b) pembrolizumab or pharmaceutical composition comprising pembrolizumab, wherein the method is provided as a first cancer therapy after diagnosis of the cervical cancer (e.g., within 1, 2, 3, 4, 5, or 6 days; 1, 2, 3, 4, 6, 8, or 12 weeks; or, 1, 2, 3, 4, 6, 8, or 12 months after diagnosis). In certain embodiments, the method comprises treating a subject having cervical cancer (e.g., a metastatic or locally advanced, unresectable squamous cell carcinoma, adenosquamous carcinoma, or adenocarcinoma of the cervix) using a therapeutic combination comprising (a) an anti-CTLA-4 antibody described herein, e.g., AGEN1884 (IgG$_1$), or pharmaceutical composition comprising such anti-CTLA-4 antibody; and (b) pembrolizumab or pharmaceutical composition comprising pembrolizumab, wherein the method is provided after diagnosis of tumor progression (e.g., within 1, 2, 3, 4, 5, or 6 days; 1, 2, 3, 4, 6, 8, or 12 weeks; or, 1, 2, 3, 4, 6, 8, or 12 months after diagnosis of tumor progression) that has occurred despite previous treatment of the cervical cancer with a different cancer therapy, or provided after diagnosis of toxicity of a different cancer therapy (e.g., within 1, 2, 3, 4, 5, or 6 days; 1, 2, 3, 4, 6, 8, or 12 weeks; or, 1, 2, 3, 4, 6, 8, or 12 months after diagnosis of toxicity of the different cancer therapy), and wherein the method described herein is provided as the second cancer therapy administered.

In certain embodiments, the cancer treated in accordance with the methods described herein is a cutaneous squamous-cell carcinoma (cSCC). In certain embodiments, the cancer treated in accordance with the methods described herein is a Stage IV cutaneous squamous-cell carcinoma (cSCC). In certain embodiments, the cSCC (e.g., Stage IV cSCC) is not curable with radiation therapy. In certain embodiments, the Stage IV cSCC is diagnosed histologically or cytologically according to the eighth edition of the American Joint Committee on Cancer staging manual (AJCC-8). In certain embodiments, the method comprises treating a subject using a therapeutic combination comprising (a) an anti-CTLA-4 antibody described herein (e.g., AGEN1884 (IgG$_1$)) or pharmaceutical composition comprising such anti-CTLA-4 antibody; and (b) an anti-PD-1 antibody described herein (e.g., AGEN2034 (IgG$_4$ S228P)) or pharmaceutical composition comprising such anti-PD-1 antibody. In certain embodiments, the method comprises treating a subject using an anti-PD-1 antibody described herein (e.g., AGEN2034 (IgG$_4$ S228P)) or pharmaceutical composition comprising such anti-PD-1 antibody as a monotherapy. In certain embodiments, the cSCC (e.g., Stage IV cSCC) is treated in accordance with a method described herein as a first cancer therapy after diagnosis of the cSCC (e.g., Stage IV cSCC) (e.g., within 1, 2, 3, 4, 5, or 6 days; 1, 2, 3, 4, 6, 8, or 12 weeks; or, 1, 2, 3, 4, 6, 8, or 12 months after diagnosis). In certain embodiments, the cSCC (e.g., Stage IV cSCC) is treated in accordance with a method described herein as the first cancer therapy after diagnosis of tumor progression (e.g., within 1, 2, 3, 4, 5, or 6 days; 1, 2, 3, 4, 6, 8, or 12 weeks; or, 1, 2, 3, 4, 6, 8, or 12 months after diagnosis of tumor progression) that has occurred despite previous treatment of the cSCC (e.g., Stage IV cSCC) with a different cancer therapy, optionally wherein the method described herein is provided as the second cancer therapy administered. In certain embodiments, the cSCC (e.g., Stage IV cSCC) is treated in according with a method described herein as the first cancer therapy after diagnosis of toxicity of a different cancer therapy (e.g., within 1, 2, 3, 4, 5, or 6 days; 1, 2, 3, 4, 6, 8, or 12 weeks; or, 1, 2, 3, 4, 6, 8, or 12 months after diagnosis of toxicity of the different cancer therapy), optionally wherein the method described herein is provided as the second cancer therapy administered. In certain embodiments, the method comprises treating a subject having cSCC (e.g., Stage IV cSCC) using an anti-PD-1 antibody described herein (e.g., AGEN2034 (IgG$_4$ S228P)) or pharmaceutical composition comprising such anti-PD-1 antibody as a monotherapy, wherein the method is provided after diagnosis of tumor progression (e.g., within 1, 2, 3, 4, 5, or 6 days; 1, 2, 3, 4, 6, 8, or 12 weeks; or, 1, 2, 3, 4, 6, 8, or 12 months after diagnosis of tumor progression) that has occurred despite previous treatment of the cervical cancer with a different cancer therapy, or provided after diagnosis of toxicity of a different cancer therapy (e.g., within 1, 2, 3, 4, 5, or 6 days; 1, 2, 3, 4, 6, 8, or 12 weeks; or, 1, 2, 3, 4, 6, 8, or 12 months after diagnosis of toxicity of the different cancer therapy), and wherein the method described herein is provided as the second cancer therapy administered.

In certain embodiments, the cancer treated in accordance with the methods described herein is B cell lymphoma (e.g., B cell chronic lymphocytic leukemia, B cell non-Hodgkin lymphoma, cutaneous B cell lymphoma, diffuse large B cell lymphoma), basal cell carcinoma, bladder cancer, blastoma, brain metastasis, breast cancer, Burkitt lymphoma, carcinoma (e.g., adenocarcinoma (e.g., of the gastroesophageal junction)), cervical cancer, colon cancer, colorectal cancer (colon cancer and rectal cancer), endometrial carcinoma, esophageal cancer, Ewing sarcoma, follicular lymphoma, gastric cancer, gastroesophageal junction carcinoma, gastrointestinal cancer, glioblastoma (e.g., glioblastoma multiforme, e.g., newly diagnosed or recurrent), glioma, head and neck cancer (e.g., head and neck squamous cell carcinoma), hepatic metastasis, Hodgkin's and non-Hodgkin's lymphoma, kidney cancer (e.g., renal cell carcinoma and Wilms' tumors), laryngeal cancer, leukemia (e.g., chronic myelocytic leukemia, hairy cell leukemia), liver cancer (e.g., hepatic carcinoma and hepatoma), lung cancer (e.g., non-small cell lung cancer and small-cell lung cancer), lymphoblastic lymphoma, lymphoma, mantle cell lymphoma, metastatic brain tumor, metastatic cancer, myeloma (e.g., multiple myeloma), neuroblastoma, ocular melanoma, oropharyngeal cancer, osteosarcoma, ovarian cancer, pancreatic cancer (e.g., pancreatic ductal adenocarcinoma), prostate cancer (e.g., hormone refractory (e.g., castration resistant), metastatic, metastatic hormone refractory (e.g., castration resistant, androgen independent)), renal cell carcinoma (e.g., metastatic), salivary gland carcinoma, sarcoma (e.g., rhabdomyosarcoma), skin cancer (e.g., melanoma (e.g., metastatic melanoma)), soft tissue sarcoma, solid tumor, squamous cell carcinoma, synovia sarcoma, testicular cancer, thyroid cancer, transitional cell cancer (urothelial cell cancer), uveal melanoma (e.g., metastatic), verrucous carcinoma, vulval cancer, and Waldenstrom macroglobulinemia.

In certain embodiments, the cancer treated in accordance with the methods described herein is human sarcoma or carcinoma, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma (e.g., metastatic), hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, melanoma, neuroblastoma, or retinoblastoma.

In certain embodiments, the cancer treated in accordance with the methods described herein is an acute lymphocytic leukemia or acute myelocytic leukemia (e.g., myeloblastic, promyelocytic, myelomonocytic, monocytic and erythroleukemia); chronic leukemia (chronic myelocytic (granulocytic) leukemia or chronic lymphocytic leukemia); Hodgkin's disease; non-Hodgkin's disease; acute myeloid leukemia; B-cell lymphoma; T-cell lymphoma; anaplastic large cell lymphoma; intraocular lymphoma; follicular lymphoma; small intestine lymphoma; or splenic marginal zone lymphoma.

In certain embodiments, the cancer treated in accordance with the methods described herein is multiple myeloma, Waldenstrom's macroglobulinemia, heavy chain disease, gastrointestinal stromal tumors, head and/or neck cancer (e.g., squamous cell carcinoma of the hypopharynx, squamous cell carcinoma of the larynx, cell carcinoma of the oropharynx, or verrucous carcinoma of the larynx), endometrial stromal sarcoma, mast cell sarcoma, adult soft tissue sarcoma, uterine sarcoma, merkel cell carcinoma, urothelial carcinoma, melanoma with brain metastases, uveal melanoma, uveal melanoma with liver metastases, non-small cell lung cancer, rectal cancer, or myelodysplastic syndrome. In some embodiments, the cancer treated in accordance with the methods is metastatic.

In certain embodiments, the cancer treated in accordance with the methods described herein is prostate cancer, breast cancer, lung cancer, colorectal cancer, melanoma, bronchial cancer, bladder cancer, brain or central nervous system cancer, peripheral nervous system cancer, uterine or endometrial cancer, cancer of the oral cavity or pharynx, non-Hodgkin's lymphoma, thyroid cancer, kidney cancer, biliary tract cancer, small bowel or appendix cancer, salivary gland cancer, thyroid gland cancer, adrenal gland cancer, squamous cell cancer, mesothelioma, osteocarcinoma, thyoma/thymic carcinoma, glioblastoma, myelodysplastic syndrome, soft tissue sarcoma, DIPG, adenocarcinoma, osteosarcoma, chondrosarcoma, leukemia, or pancreatic cancer. In some embodiments, the cancer treated in accordance with the methods described herein includes a carcinoma (e.g., an adenocarcinoma), lymphoma, blastoma, melanoma, sarcoma, or leukemia.

In certain embodiments, the cancer treated in accordance with the methods described herein is squamous cell cancer, small-cell lung cancer, non-small cell lung cancer, gastrointestinal cancer, Hodgkin's lymphoma, non-Hodgkin's lymphoma, pancreatic cancer, glioblastoma, glioma, cervical cancer, ovarian cancer, liver cancer (e.g., hepatic carcinoma and hepatoma), bladder cancer, breast cancer, inflammatory breast cancer, Merkel cell carcinoma, colon cancer, colorectal cancer, stomach cancer, urinary bladder cancer, endometrial carcinoma, myeloma (e.g., multiple myeloma), salivary gland, carcinoma, kidney cancer (e.g., renal cell carcinoma and Wilms' tumors), basal cell carcinoma, melanoma, prostate cancer, vulval cancer, thyroid cancer, testicular cancer, esophageal cancer, serous adenocarcinoma or various types of head and neck cancer. In certain embodiments, the cancer treated in accordance with the methods described herein includes desmoplastic melanoma, inflammatory breast cancer, thymoma, rectal cancer, anal cancer, or surgically treatable or non-surgically treatable brain stem glioma. In a specific embodiment, the cancer is a solid tumor. In another specific embodiment, the cancer is glioblastoma multiforme. In some embodiments, the glioblastoma multiforme is recurrent. In some embodiments, the glioblastoma multiforme is newly diagnosed. In some embodiments, the glioblastoma multiforme is in a subject having non-methylated MGMT promoters. In some embodiments, the glioblastoma multiforme is refractory to Bevacizumab therapy. In some embodiments, the glioblastoma multiforme is in a subject that has not received Bevacizumab therapy.

In certain embodiments, the cancer treated in accordance with the methods described herein is metastatic melanoma (e.g., resistant metastatic melanoma), metastatic ovarian cancer, or metastatic renal cell carcinoma. In certain embodiments, the cancer treated in accordance with the methods described herein is melanoma that is resistant to ipilimumab. In some embodiments, the cancer treated in accordance with the methods described herein is melanoma that is resistant to nivolumab or pembrolizumab. In some embodiments, the cancer treated in accordance with the methods described herein is melanoma that is resistant to ipilimumab and nivolumab or pembrolizumab.

In certain embodiments, the cancer treated in accordance with the methods described herein is breast cancer (e.g., herceptin resistant breast cancer and trastuzumab-DM1 (T-DM1) resistant breast cancer), prostate cancer, glioblastoma multiforme, colorectal cancer, sarcoma, bladder cancer, cervical cancer, HPV-associated cancers, cancers of the vagina, cancers of the vulva, cancers of the penis, cancer of the anus, cancer of the rectum, cancer of the oropharynx, multiple myeloma, renal cell carcinoma, ovarian cancer, hepatocellular cancer, endometrial cancer, pancreatic cancer, lymphoma, and leukemia (e.g., elderly leukemia, acute myeloid leukemia (AML), and elderly AML).

In certain embodiments, the cancer treated in accordance with the methods described herein is metastatic malignant melanoma (e.g., cutaneous or intraocular malignant melanoma), renal cancer (e.g., clear cell carcinoma), prostate cancer (e.g., hormone refractory prostate adenocarcinoma), breast cancer, colon cancer, lung cancer (e.g., non-small cell lung cancer), bone cancer, pancreatic cancer, skin cancer, cancer of the head or neck, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, glioma, pituitary adenoma, Kaposi's sarcoma, epidermoid cancer, squamous cell cancer, T-cell lymphoma, environmentally induced cancers including those induced by asbestos, esophageal cancer, liver cancer, refractory or recurrent malignancies, metastatic cancers, cancers that express PD-L1, and combinations of said cancers.

In certain embodiments, the subject has previously received an immunotherapy. In certain embodiments, the subject has not previously received any immunotherapy. In certain embodiments, the cancer is an advanced or metastatic cancer.

In certain embodiments, the instant disclosure provides a method of preventing or treating an infectious disease in a subject, the method comprising administering to the subject an effective amount of an antibody, therapeutic combination, or pharmaceutical composition described herein. In one embodiment, provided herein are methods for preventing and/or treating an infection (e.g., a viral infection, a bacterial infection, a fungal infection, a protozoal infection, or a parasitic infection). The infection prevented and/or treated in accordance with the methods can be caused by an infectious agent identified herein. In a specific embodiment, an antibody, therapeutic combination, or pharmaceutical composition described herein is the only active agent administered to a subject. In some embodiments, an antibody, therapeutic combination, or pharmaceutical composition as described herein is used in combination with anti-infective interventions (e.g., antivirals, antibacterials, antifungals, or anti-helminthics) for the treatment of infectious diseases.

Infectious diseases that can be treated and/or prevented by antibodies, therapeutic combinations, or pharmaceutical compositions as described herein are caused by infectious agents including but not limited to bacteria, parasites, fungi, protozoa, and viruses. In a specific embodiment, the infectious disease treated and/or prevented by antibodies, therapeutic combinations, or pharmaceutical compositions as described herein is caused by a virus. Viral diseases or viral infections that can be prevented and/or treated in accordance with the methods described herein include, but are not limited to, those caused by hepatitis type A, hepatitis type B, hepatitis type C, influenza (e.g., influenza A or influenza B), varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial infections that can be prevented and/or treated include infections caused by *Escherichia coli, Klebsiella pneumoniae, Staphylococcus aureus, Enterococcus faecalis, Proteus vulgaris, Staphylococcus viridans*, and *Pseudomonas aeruginosa*. Bacterial diseases caused by bacteria (e.g., *Escherichia coli, Klebsiella pneumoniae, Staphylococcus aureus, Enterococcus faecalis, Proteus vulgaris, Staphylococcus viridans*, and *Pseudomonas aeruginosa*) that can be prevented and/or treated in accordance with the methods described herein include, but are not limited to, Mycobacteria *rickettsia, Mycoplasma, Neisseria, S. pneumonia, Bor-*

*relia burgdorferi* (Lyme disease), *Bacillus antracis* (anthrax), tetanus, *Streptococcus, Staphylococcus, mycobacterium*, pertussis, cholera, plague, diptheria, *chlamydia, S. aureus* and *legionella*.

Protozoal diseases or protozoal infections caused by protozoa that can be prevented and/or treated in accordance with the methods described herein include, but are not limited to, *leishmania*, coccidiosis, *trypanosoma schistosoma* or malaria. Parasitic diseases or parasitic infections caused by parasites that can be prevented and/or treated in accordance with the methods described herein include, but are not limited to, *chlamydia* and *rickettsia*.

Fungal diseases or fungal infections that can be prevented and/or treated in accordance with the methods described herein include, but are not limited to, those caused by *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium keratitis*, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fungal peritonitis, Curvularia *geniculata* infection, staphylococcal endophthalmitis, sporotrichosis, and dermatophytosis.

In certain embodiments, the infectious disease is acute. In certain embodiments, the infectious disease is chronic. In certain embodiments, the infectious disease is caused by flavivirus, e.g., West Nile virus, Saint Louis encephalitis virus, Powassan virus, tick-borne encephalitis virus, dengue virus, zika virus, Kyasanur Forest disease virus, yellow fever virus, and chikungunya virus. In certain embodiments, the infectious disease is caused by Ebola virus. In certain embodiments, the infectious disease is caused by influenza virus. In certain embodiments, the infectious disease is caused by Human Immunodeficiency Virus (HIV), Hepatitis B virus (HBV) or Hepatitis C virus (HCV). In certain embodiments, the antibodies, therapeutic combinations, or pharmaceutical compositions described herein promote viral control. In certain embodiments, the antibodies, therapeutic combinations, or pharmaceutical compositions described herein promote eliminates viral reservoirs.

In certain embodiments, these methods further comprise administering an additional therapeutic agent to the subject. In certain embodiments, the additional therapeutic agent is a chemotherapeutic, radiotherapeutic, or a checkpoint targeting agent. In certain embodiments, the chemotherapeutic agent is a hypomethylating agent (e.g., azacitidine). In certain embodiments, the checkpoint targeting agent is selected from the group consisting of an antagonist anti-CTLA-4 antibody, an antagonist anti-PD-L1 antibody, an antagonist anti-PD-L2 antibody, an antagonist anti-PD-1 antibody, an antagonist anti-TIM-3 antibody, an antagonist anti-LAG-3 antibody, an antagonist anti-CEACAM1 antibody, an agonist anti-GITR antibody, and an agonist anti-OX40 antibody.

In certain embodiments, an anti-PD-1 antibody is used in methods described herein. In certain embodiments, the anti-PD-1 antibody is nivolumab, also known as BMS-936558 or MDX1106, developed by Bristol-Myers Squibb. In certain embodiments, the anti-PD-1 antibody is pembrolizumab, also known as lambrolizumab or MK-3475, developed by Merck & Co. In certain embodiments, the anti-PD-1 antibody is pidilizumab, also known as CT-011, developed by CureTech. In certain embodiments, the anti-PD-1 antibody is MEDI0680, also known as AMP-514, developed by Medimmune. In certain embodiments, the anti-PD-1 antibody is PDR001 developed by Novartis Pharmaceuticals. In certain embodiments, the anti-PD-1 antibody is REGN2810 developed by Regeneron Pharmaceuticals. In certain embodiments, the anti-PD-1 antibody is PF-06801591 developed by Pfizer. In certain embodiments, the anti-PD-1 antibody is BGB-A317 developed by BeiGene. In certain embodiments, the anti-PD-1 antibody is TSR-042 developed by AnaptysBio and Tesaro. In certain embodiments, the anti-PD-1 antibody is SHR-1210 developed by Hengrui.

Further non-limiting examples of anti-PD-1 antibodies that may be used in treatment methods described herein are disclosed in the following patents and patent applications, which are incorporated herein by reference in their entireties for all purposes: U.S. Pat. Nos. 6,808,710; 7,332,582; 7,488,802; 8,008,449; 8,114,845; 8,168,757; 8,354,509; 8,686,119; 8,735,553; 8,747,847; 8,779,105; 8,927,697; 8,993,731; 9,102,727; 9,205,148; U.S. Publication No. US 2013/0202623 A1; U.S. Publication No. US 2013/0291136 A1; U.S. Publication No. US 2014/0044738 A1; U.S. Publication No. US 2014/0356363 A1; U.S. Publication No. US 2016/0075783 A1; and PCT Publication No. WO 2013/033091 A1; PCT Publication No. WO 2015/036394 A1; PCT Publication No. WO 2014/179664 A2; PCT Publication No. WO 2014/209804 A1; PCT Publication No. WO 2014/206107 A1; PCT Publication No. WO 2015/058573 A1; PCT Publication No. WO 2015/085847 A1; PCT Publication No. WO 2015/200119 A1; PCT Publication No. WO 2016/015685 A1; and PCT Publication No. WO 2016/020856 A1.

In certain embodiments, an anti-PD-L1 antibody is used in methods described herein. In certain embodiments, the anti-PD-L1 antibody is atezolizumab developed by Genentech. In certain embodiments, the anti-PD-L1 antibody is durvalumab developed by AstraZeneca, Celgene and Medimmune. In certain embodiments, the anti-PD-L1 antibody is avelumab, also known as MSB0010718C, developed by Merck Serono and Pfizer. In certain embodiments, the anti-PD-L1 antibody is MDX-1105 developed by Bristol-Myers Squibb. In certain embodiments, the anti-PD-L1 antibody is AMP-224 developed by Amplimmune and GSK.

Non-limiting examples of anti-PD-L1 antibodies that may be used in treatment methods described herein are disclosed in the following patents and patent applications, which are incorporated herein by reference in their entireties for all purposes: U.S. Pat. Nos. 7,943,743; 8,168,179; 8,217,149; 8,552,154; 8,779,108; 8,981,063; 9,175,082; U.S. Publication No. US 2010/0203056 A1; U.S. Publication No. US 2003/0232323 A1; U.S. Publication No. US 2013/0323249 A1; U.S. Publication No. US 2014/0341917 A1; U.S. Publication No. US 2014/0044738 A1; U.S. Publication No. US 2015/0203580 A1; U.S. Publication No. US 2015/0225483 A1; U.S. Publication No. US 2015/0346208 A1; U.S. Publication No. US 2015/0355184 A1; and PCT Publication No. WO 2014/100079 A1; PCT Publication No. WO 2014/022758 A1; PCT Publication No. WO 2014/055897 A2; PCT Publication No. WO 2015/061668 A1; PCT Publication No. WO 2015/109124 A1; PCT Publication No. WO 2015/195163 A1; PCT Publication No. WO 2016/000619 A1; and PCT Publication No. WO 2016/030350 A1.

In certain embodiments, an antibody, therapeutic combination, or pharmaceutical composition described herein is administered to a subject in combination with a compound that targets an immunomodulatory enzyme(s) such as IDO (indoleamine-(2,3)-dioxygenase) and/or TDO (tryptophan 2,3-dioxygenase). In certain embodiments, such compound is selected from the group consisting of epacadostat (Incyte Corp; see, e.g., WO 2010/005958 which is incorporated by reference herein in its entirety), F001287 (Flexus Biosciences/Bristol-Myers Squibb), indoximod (NewLink Genetics), and NLG919 (NewLink Genetics). In one embodiment, the compound is epacadostat. In another embodiment, the compound is F001287. In another embodiment, the compound is indoximod. In another embodiment, the compound is NLG919. In a specific embodiment, an antibody, therapeutic combination, or pharmaceutical composition described herein is administered to a subject in combination with an IDO inhibitor for treating cancer. The IDO inhibitor as described herein for use in treating cancer is present in a solid dosage form of a pharmaceutical composition such as a tablet, a pill or a capsule, wherein the pharmaceutical composition includes an IDO inhibitor and a pharmaceutically acceptable excipient. As such, the antibody as described herein and the IDO inhibitor as described herein can be administered separately, sequentially or concurrently as separate dosage forms. In one embodiment, the antibody is administered parenterally, and the IDO inhibitor is administered orally. In particular embodiments, the inhibitor is selected from the group consisting of epacadostat (Incyte Corporation), F001287 (Flexus Biosciences/Bristol-Myers Squibb), indoximod (NewLink Genetics), and NLG919 (NewLink Genetics). Epacadostat has been described in PCT Publication No. WO 2010/005958, which is incorporated herein by reference in its entirety for all purposes. In one embodiment, the inhibitor is epacadostat. In another embodiment, the inhibitor is F001287. In another embodiment, the inhibitor is indoximod. In another embodiment, the inhibitor is NLG919.

In certain embodiments, an antibody, therapeutic combination, or pharmaceutical composition described herein is administered to a subject in combination with a vaccine. In certain embodiments, the vaccine is a heat shock protein based tumor vaccine or a heat shock protein based pathogen vaccine. In a specific embodiment, an antibody, therapeutic combination, or pharmaceutical composition described herein is administered to a subject in combination with a heat shock protein based tumor-vaccine. Heat shock proteins (HSPs) are a family of highly conserved proteins found ubiquitously across all species. Their expression can be powerfully induced to much higher levels as a result of heat shock or other forms of stress, including exposure to toxins, oxidative stress or glucose deprivation. Five families have been classified according to molecular weight: HSP-110, -90, -70, -60 and -28. HSPs deliver immunogenic peptides through the cross-presentation pathway in antigen presenting cells (APCs) such as macrophages and dendritic cells (DCs), leading to T cell activation. HSPs function as chaperone carriers of tumor-associated antigenic peptides forming complexes able to induce tumor-specific immunity. Upon release from dying tumor cells, the HSP-antigen complexes are taken up by antigen-presenting cells (APCs) wherein the antigens are processed into peptides that bind MHC class I and class II molecules leading to the activation of anti-tumor CD8+ and CD4+ T cells. The immunity elicited by HSP complexes derived from tumor preparations is specifically directed against the unique antigenic peptide repertoire expressed by the cancer of each subject.

A heat shock protein peptide complex (HSPPC) is a protein peptide complex consisting of a heat shock protein non-covalently complexed with antigenic peptides. HSPPCs elicit both innate and adaptive immune responses. In a specific embodiment, the antigenic peptide(s) displays antigenicity for the cancer being treated. HSPPCs are efficiently seized by APCs via membrane receptors (mainly CD91) or by binding to Toll-like receptors. HSPPC internalization results in functional maturation of the APCs with chemokine and cytokine production leading to activation of natural killer cells (NK), monocytes and Th1 and Th-2-mediated immune responses. In certain embodiments, HSPPCs used in methods described herein comprise one or more heat shock proteins from the hsp60, hsp70, or hsp90 family of stress proteins complexed with antigenic peptides. In certain embodiments, HSPPCs comprise hsc70, hsp70, hsp90, hsp110, grp170, gp96, calreticulin, or combinations of two or more thereof.

In a specific embodiment, an antibody, therapeutic combination, or pharmaceutical composition described herein is administered to a subject in combination with a heat shock protein peptide complex (HSPPC), e.g., heat shock protein peptide complex-96 (HSPPC-96), to treat cancer. HSPPC-96 comprises a 96 kDa heat shock protein (Hsp), gp96, complexed to antigenic peptides. HSPPC-96 is a cancer immunotherapy manufactured from a subject's tumor and contains the cancer's antigenic "fingerprint." In certain embodiments, this fingerprint contains unique antigens that are present only in that particular subject's specific cancer cells and injection of the vaccine is intended to stimulate the subject's immune system to recognize and attack any cells with the specific cancer fingerprint.

In certain embodiments, the HSPPC, e.g., HSPPC-96, is produced from the tumor tissue of a subject. In a specific embodiment, the HSPPC (e.g., HSPPC-96) is produced from a tumor of the type of cancer or metastasis thereof being treated. In another specific embodiment, the HSPPC (e.g., HSPPC-96) is autologous to the subject being treated. In certain embodiments, the tumor tissue is non-necrotic tumor tissue. In certain embodiments, at least 1 gram (e.g., at least 1, at least 2, at least 3, at least 4, at least 5, at least 6, at least 7, at least 8, at least 9, or at least 10 grams) of non-necrotic tumor tissue is used to produce a vaccine regimen. In certain embodiments, after surgical resection, non-necrotic tumor tissue is frozen prior to use in vaccine preparation. In some embodiments, the HSPPC, e.g., HSPPC-96, is isolated from the tumor tissue by purification techniques, filtered and prepared for an injectable vaccine. In certain embodiments, a subject is administered 6-12 doses of the HSPPC, e.g., HSPCC-96. In such embodiments, the HSPPC, e.g., HSPPC-96, doses may be administered weekly for the first 4 doses and then biweekly for the 2-8 additional doses.

Further examples of HSPPCs that may be used in accordance with the methods described herein are disclosed in the following patents and patent applications, which are incorporated herein by reference herein in their entireties, U.S. Pat. Nos. 6,391,306, 6,383,492, 6,403,095, 6,410,026, 6,436,404, 6,447,780, 6,447,781 and 6,610,659.

The antibody, therapeutic combination, or pharmaceutical composition and the additional therapeutic agent (e.g., chemotherapeutic, radiotherapeutic, checkpoint targeting agent, IDO inhibitor, and/or vaccine) can be administered separately, sequentially or concurrently as separate dosage forms. In one embodiment, an antibody, therapeutic combination, or pharmaceutical composition described herein is administered parenterally, and an IDO inhibitor is administered orally.

An antibody, therapeutic combination, or pharmaceutical composition described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival and subcutaneous routes. Pulmonary administration can also be employed, e.g., by use of an inhaler or nebulizer, and formulation with an aerosolizing agent for use as a spray. In certain embodiments, the antibody, therapeutic combination, or pharmaceutical composition described herein is delivered subcutaneously or intravenously. In certain embodiments, the antibody, therapeutic combination, or pharmaceutical composition described herein is delivered intratumorally. In certain embodiments, the antibody, therapeutic combination, or pharmaceutical composition described herein is delivered into a tumor draining lymph node. In certain embodiments, the antibody, therapeutic combination, or pharmaceutical composition described herein is delivered via a localized administration (e.g., subcutaneous administration). In certain embodiments, the antibody, therapeutic combination, or pharmaceutical composition described herein is delivered systemically. In certain embodiments, the antibody, therapeutic combination, or pharmaceutical composition described herein is delivered locally. In certain embodiments, the therapeutic combination comprises a first antibody and a second antibody, wherein the first antibody and the second antibody are delivered via the same route (e.g., intravenously, subcutaneously, or intratumorally). In certain embodiments, the therapeutic combination comprises a first antibody and a second antibody, wherein the first antibody and the second antibody are delivered via different routes.

The amount of an antibody, therapeutic combination, or pharmaceutical composition which will be effective in the treatment and/or prevention of a condition will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human but non-human mammals including transgenic mammals can also be treated. Treatment dosages are optimally titrated to optimize safety and efficacy.

In certain embodiments, an anti-CTLA-4 antibody, an anti-PD-1 antibody, an anti-CTLA-4/PD-1 antibody, and/or a pharmaceutical composition described herein is administered to a subject (e.g., intravenously, intratumorally, or subcutaneously) at 0.01 mg/kg, 0.03 mg/kg, 0.1 mg/kg, 0.3 mg/kg, 1 mg/kg, 3 mg/kg, 6 mg/kg, 10 mg/kg, about 0.01 mg/kg, about 0.03 mg/kg, about 0.1 mg/kg, about 0.3 mg/kg, about 1 mg/kg, about 3 mg/kg, about 6 mg/kg, or about 10 mg/kg, optionally every one, two or three weeks.

In one aspect, provided herein is an anti-CTLA-4 antibody, an anti-PD-1 antibody, an anti-CTLA-4/PD-1 antibody, and/or a pharmaceutical composition, and optionally an additional therapeutic agent, for use in a method for treating cancer, for enhancing or inducing an immune response, or for treating an infectious disease, wherein the antibody and/or pharmaceutical composition is administered to a subject at 0.01 mg/kg, 0.03 mg/kg, 0.1 mg/kg, 0.3 mg/kg, 1 mg/kg, 3 mg/kg, 6 mg/kg, 10 mg/kg, about 0.1 mg/kg, about 0.3 mg/kg, about 1 mg/kg, about 3 mg/kg, about 6 mg/kg, or about 10 mg/kg, optionally every one, two or three weeks.

In one aspect, provided herein is a use of a therapeutic combination, a multispecific antibody, a kit, and/or a pharmaceutical composition described herein in the preparation of a medicament, for treating cancer, for enhancing or inducing an immune response, or for treating an infectious disease. Alternatively, the use of a therapeutic combination and/or a multispecific antibody for preparing a medicament, pharmaceutical composition or kit is provided. For example, the use of an anti-CTLA-4 antibody, an anti-PD-1 antibody, an anti-CTLA-4/PD-1 antibody, and optionally an additional therapeutic agent, for preparing a pharmaceutical composition, medicament or kit for treating cancer, for enhancing or inducing an immune response, or for treating an infectious disease is provided herein.

In certain embodiments, an antibody or pharmaceutical composition described herein is administered to a subject (e.g., via intravenous injection or via intratumoral injection) at 0.01 mg/kg or about 0.01 mg/kg, optionally every one, two or three weeks. In certain embodiments, an antibody or pharmaceutical composition described herein is administered to a subject (e.g., intravenously, intratumorally, or subcutaneously) at 0.03 mg/kg or about 0.03 mg/kg, optionally every one, two or three weeks. In certain embodiments, an antibody or pharmaceutical composition described herein is administered to a subject (e.g., intravenously, intratumorally, or subcutaneously) at 0.1 mg/kg or about 0.1 mg/kg, optionally every one, two or three weeks. In certain embodiments, an antibody or pharmaceutical composition described herein is administered to a subject (e.g., intravenously, intratumorally, or subcutaneously) at 0.3 mg/kg or about 0.3 mg/kg, optionally every one, two or three weeks. In certain embodiments, an antibody or pharmaceutical composition described herein is administered to a subject (e.g., intravenously, intratumorally, or subcutaneously) at 1 mg/kg or about 1 mg/kg, optionally every one, two or three weeks. In certain embodiments, an antibody or pharmaceutical composition described herein is administered to a subject (e.g., intravenously, intratumorally, or subcutaneously) at 3 mg/kg or about 3 mg/kg, optionally every one, two or three weeks. In certain embodiments, an antibody or pharmaceutical composition described herein is administered to a subject (e.g., intravenously, intratumorally, or subcutaneously) at 6 mg/kg or about 6 mg/kg, optionally every one, two or three weeks. In certain embodiments, an antibody or pharmaceutical composition described herein is administered to a subject (e.g., intravenously, intratumorally, or subcutaneously) at 10 mg/kg or about 10 mg/kg, optionally every one, two or three weeks.

The effective amount of a therapeutic combination of a first therapy and a second therapy includes a first amount of the first therapy and a second amount of the second therapy, wherein the administration of the therapeutic combination achieves a desired prophylactic or therapeutic effect. The first amount can be lower than, equal to, or higher than the effective amount of the first therapy when administered alone, and the second amount can be lower than, equal to, or higher than the effective amount of the second therapy when administered alone. In certain embodiments, the first amount is lower than the effective amount of the first therapy when administered alone. In certain embodiments, the second amount is lower than the effective amount of second first therapy when administered alone. In certain embodiments, the first amount is lower than the effective amount of the first therapy when administered alone, and the second amount is lower than the effective amount of the second therapy when administered alone.

For example, where a therapeutic combination comprises an anti-CTLA-4 antibody described herein and an anti-PD-1 antibody described herein, the effective amount of the anti-CTLA-4 antibody in this therapeutic combination can be lower than, equal to, or higher than the effective amounts of the anti-CTLA-4 antibody when administered alone, and/or the effective amount of the anti-PD-1 antibody in this therapeutic combination can be lower than, equal to, or higher than the effective amounts of the anti-PD-1 antibody when administered alone. In certain embodiments, the effective amount of the anti-CTLA-4 antibody in this therapeutic combination is lower than the effective amount of the anti-CTLA-4 antibody when administered alone. In certain embodiments, the effective amount of the anti-PD-1 antibody in this therapeutic combination is lower than the effective amount of the anti-PD-1 antibody when administered alone. In certain embodiments, the effective amount of the anti-CTLA-4 antibody in this therapeutic combination is lower than the effective amount of the anti-CTLA-4 antibody when administered alone, and the effective amount of the anti-PD-1 antibody in this therapeutic combination is lower than the effective amount of the anti-PD-1 antibody when administered alone.

In certain embodiments, the therapeutic combination comprises an anti-CTLA-4 antibody described herein administered at a first frequency and an anti-PD-1 antibody described herein administered at a second frequency. The first and second frequencies can be independently selected from every week, every two weeks, every three weeks, every four weeks, every six weeks, every eight weeks, every twelve weeks, every month, every two months, every three months, every four months, every five months, every six months, every eight months, and every year. In certain embodiments, the first and second frequencies are the same. In certain embodiments, the first and second frequencies are different. In certain embodiments, the anti-CTLA-4 antibody described is administered every three weeks and the anti-PD-1 antibody is administered every two weeks.

The anti-CTLA-4 antibody and the anti-PD-1 antibody in a therapeutic combination can be administered simultaneously or sequentially. In certain embodiments, the anti-CTLA-4 antibody and the anti-PD-1 antibody are administered simultaneously. In certain embodiments, the anti-CTLA-4 antibody and the anti-PD-1 antibody are administered in the same pharmaceutical composition (e.g., provided as one pharmaceutical composition, or provided as separate pharmaceutical compositions and mixed completely or partially right before or during administration). In certain embodiments, the anti-CTLA-4 antibody and the anti-PD-1 antibody are administered sequentially. In certain embodiments, the anti-CTLA-4 antibody and the anti-PD-1 antibody are administered in separate pharmaceutical compositions, wherein the anti-CTLA-4 antibody is administered after (e.g., about 1 day, 2 days, 3 days, 4 days, 5 days, 6 days, 7 days, 10 days, or 14 days after) the administration of the anti-PD-1 antibody. In certain embodiments, the anti-CTLA-4 antibody and the anti-PD-1 antibody are administered in separate pharmaceutical compositions, wherein the anti-PD-1 antibody is administered after (e.g., about 1 day, 2 days, 3 days, 4 days, 5 days, 6 days, 7 days, 10 days, or 14 days after) the administration of the anti-CTLA-4 antibody.

In certain embodiments, the therapeutic combination comprises an anti-CTLA-4 antibody described herein administered (e.g., intravenously) about every six weeks, and an anti-PD-1 antibody described herein administered (e.g., intravenously) about every two weeks. In certain embodiments, the therapeutic combination comprises an anti-CTLA-4 antibody described herein administered (e.g., intravenously) every six weeks, and an anti-PD-1 antibody described herein administered (e.g., intravenously) every two weeks. In certain embodiments, the therapeutic combination comprises an anti-CTLA-4 antibody described herein administered (e.g., intravenously) about every six weeks, and an anti-PD-1 antibody described herein administered (e.g., intravenously) about every three weeks. In certain embodiments, the therapeutic combination comprises an anti-CTLA-4 antibody described herein administered (e.g., intravenously) every six weeks, and an anti-PD-1 antibody described herein administered (e.g., intravenously) every three weeks. In certain embodiments, the anti-CTLA-4 antibody is administered on the same day as the anti-PD-1 antibody. In certain embodiments, each administration of the anti-CTLA-4 antibody is conducted on the same day as the anti-PD-1 antibody. In certain embodiments, the anti-CTLA-4 antibody is administered within 30 minutes or 1 hour after the completion of administration of the anti-PD-1 antibody.

In certain embodiments, the anti-CTLA-4 antibody is administered at 0.01 mg/kg or about 0.01 mg/kg and the anti-PD-1 antibody is administered at 0.01 mg/kg, 0.03 mg/kg, 0.1 mg/kg, 0.3 mg/kg, 1 mg/kg, 3 mg/kg, 6 mg/kg, 10 mg/kg, about 0.1 mg/kg, about 0.3 mg/kg, about 1 mg/kg, about 3 mg/kg, about 6 mg/kg, or about 10 mg/kg, optionally every one, two or three weeks. In certain embodiments, the anti-CTLA-4 antibody is administered at 0.03 mg/kg or about 0.03 mg/kg and the anti-PD-1 antibody is administered at 0.01 mg/kg, 0.03 mg/kg, 0.1 mg/kg, 0.3 mg/kg, 1 mg/kg, 3 mg/kg, 6 mg/kg, 10 mg/kg, about 0.1 mg/kg, about 0.3 mg/kg, about 1 mg/kg, about 3 mg/kg, about 6 mg/kg, or about 10 mg/kg, optionally every one, two or three weeks. In certain embodiments, the anti-CTLA-4 antibody is administered at 0.1 mg/kg or about 0.1 mg/kg and the anti-PD-1 antibody is administered at 0.01 mg/kg, 0.03 mg/kg, 0.1 mg/kg, 0.3 mg/kg, 1 mg/kg, 3 mg/kg, 6 mg/kg, 10 mg/kg, about 0.1 mg/kg, about 0.3 mg/kg, about 1 mg/kg, about 3 mg/kg, about 6 mg/kg, or about 10 mg/kg, optionally every one, two or three weeks. In certain embodiments, the anti-CTLA-4 antibody is administered at 0.3 mg/kg or about 0.3 mg/kg and the anti-PD-1 antibody is administered at 0.01 mg/kg, 0.03 mg/kg, 0.1 mg/kg, 0.3 mg/kg, 1 mg/kg, 3 mg/kg, 6 mg/kg, 10 mg/kg, about 0.1 mg/kg, about 0.3 mg/kg, about 1 mg/kg, about 3 mg/kg, about 6 mg/kg, or about 10 mg/kg, optionally every one, two or three weeks. In certain embodiments, the anti-CTLA-4 antibody is administered at 1 mg/kg or about 1 mg/kg and the anti-PD-1 antibody is administered at 0.01 mg/kg, 0.03 mg/kg, 0.1 mg/kg, 0.3 mg/kg, 1 mg/kg, 3 mg/kg, 6 mg/kg, 10 mg/kg, about 0.1 mg/kg, about 0.3 mg/kg, about 1 mg/kg, about 3 mg/kg, about 6 mg/kg, or about 10 mg/kg, optionally every one, two or three weeks. In certain embodiments, the anti-CTLA-4 antibody is administered at 3 mg/kg or about 3 mg/kg and the anti-PD-1 antibody is administered at 0.01 mg/kg, 0.03 mg/kg, 0.1 mg/kg, 0.3 mg/kg, 1 mg/kg, 3 mg/kg, 6 mg/kg, 10 mg/kg, about 0.1 mg/kg, about 0.3 mg/kg, about 1 mg/kg, about 3 mg/kg, about 6 mg/kg, or about 10 mg/kg, optionally every one, two or three weeks. In certain embodiments, the anti-CTLA-4 antibody is administered at 6 mg/kg or about 6 mg/kg and the anti-PD-1 antibody is administered at 0.01 mg/kg, 0.03 mg/kg, 0.1 mg/kg, 0.3 mg/kg, 1 mg/kg, 3 mg/kg, 6 mg/kg, 10 mg/kg, about 0.1 mg/kg, about 0.3 mg/kg, about 1 mg/kg, about 3 mg/kg, about 6 mg/kg, or about 10 mg/kg, optionally every one, two or three weeks. In certain embodiments, the anti-CTLA-4 antibody is administered at 10 mg/kg or about 10 mg/kg and the anti-PD-1 antibody is administered at 0.01 mg/kg, 0.03 mg/kg, 0.1 mg/kg, 0.3 mg/kg, 1 mg/kg, 3 mg/kg, 6 mg/kg, 10 mg/kg, about 0.1 mg/kg, about 0.3 mg/kg, about 1 mg/kg, about 3 mg/kg, about 6 mg/kg, or about 10 mg/kg, optionally every one, two or three weeks. The anti-CTLA-4 antibody and the anti-PD-1 antibody can be administered simultaneously or sequentially by the same or different routes of administration (e.g., as described herein). In certain embodiments, the anti-CTLA-4 antibody and the anti-PD-1 antibody are administered simultaneously via intravenous injection (e.g., intravenous infusion). In certain embodiments, the anti-CTLA-4 antibody and the anti-PD-1 antibody are both administered sequentially via intravenous injection (e.g., intravenous infusion). In certain embodiments, the anti-CTLA-4 antibody is administered intravenously at 0.1 mg/kg and the anti-PD-1 antibody is administered intravenously at 3 mg/kg, optionally every one, two or three weeks. In certain embodiments, the anti-CTLA-4 antibody is administered every three weeks and the anti-PD-1 antibody is administered every two weeks.

In certain embodiments, the anti-CTLA-4 antibody is administered (e.g., intravenously) at about 0.3 mg/kg or 1 mg/kg, and the anti-PD-1 antibody is administered (e.g., intravenously) at about 1 mg/kg, 3 mg/kg, 6 mg/kg, or 10 mg/kg. In certain embodiments, the anti-CTLA-4 antibody is administered (e.g., intravenously) at about 0.3 mg/kg and the anti-PD-1 antibody is administered (e.g., intravenously) at about 1 mg/kg. In certain embodiments, the anti-CTLA-4 antibody is administered (e.g., intravenously) at about 1 mg/kg and the anti-PD-1 antibody is administered (e.g., intravenously) at about 1 mg/kg. In certain embodiments, the anti-CTLA-4 antibody is administered (e.g., intravenously) at about 1 mg/kg and the anti-PD-1 antibody is administered (e.g., intravenously) at about 3 mg/kg. In certain embodiments, the anti-CTLA-4 antibody is administered (e.g., intravenously) at about 1 mg/kg and the anti-PD-1 antibody is administered (e.g., intravenously) at about 6 mg/kg. In certain embodiments, the anti-CTLA-4 antibody is administered (e.g., intravenously) at 0.3 mg/kg or 1 mg/kg, and the anti-PD-1 antibody is administered (e.g., intravenously) at 1 mg/kg or 3 mg/kg. In certain embodiments, the anti-CTLA-4 antibody is administered (e.g., intravenously) at 0.3 mg/kg and the anti-PD-1 antibody is administered (e.g., intravenously) at 1 mg/kg. In certain embodiments, the anti-CTLA-4 antibody is administered (e.g., intravenously) at 1 mg/kg and the anti-PD-1 antibody is administered (e.g., intravenously) at 1 mg/kg. In certain embodiments, the anti-CTLA-4 antibody is administered (e.g., intravenously) at 1 mg/kg and the anti-PD-1 antibody is administered (e.g., intravenously) at 3 mg/kg. In certain embodiments, the anti-CTLA-4 antibody is administered (e.g., intravenously) at 1 mg/kg and the anti-PD-1 antibody is administered (e.g., intravenously) at 6 mg/kg. In certain embodiments, the anti-CTLA-4 antibody is administered on the same day as the anti-PD-1 antibody. In certain embodiments, each administration of the anti-CTLA-4 antibody is conducted on the same day as the anti-PD-1 antibody. In certain embodiments, the anti-CTLA-4 antibody is administered within 30 minutes or 1 hour after the completion of administration of the anti-PD-1 antibody.

In certain embodiments, the anti-CTLA-4 antibody, e.g., AGEN1884 (IgG$_1$), and the anti-PD-1 antibody, e.g., AGEN2034 (IgG$_4$ S228P), are each administered at the dosage and at the frequency shown in a single row of Table 13 below. In certain embodiments, the anti-CTLA-4 antibody, e.g., AGEN1884 (IgG$_1$), and the anti-PD-1 antibody, e.g., AGEN2034 (IgG$_4$ S228P), are each administered at about the dosage and at the frequency shown in a single row of Table 13 below. In certain embodiments, the anti-CTLA-4 antibody, e.g., AGEN1884 (IgG$_1$), and the anti-PD-1 antibody, e.g., AGEN2034 (IgG$_4$ S228P), are each administered at the dosage and at about the frequency shown in a single row of Table 13 below. In certain embodiments, the anti-CTLA-4 antibody, e.g., AGEN1884 (IgG$_1$), and the anti-PD-1 antibody, e.g., AGEN2034 (IgG$_4$ S228P), are each administered at about the dosage and at about the frequency shown in a single row of Table 13 below. In certain embodiments, the anti-CTLA-4 antibody is administered (e.g., intravenously) at about 0.3 mg/kg or 1 mg/kg about every six weeks, and the anti-PD-1 antibody is administered (e.g., intravenously) at about 1 mg/kg, 3 mg/kg, 6 mg/kg, or 10 mg/kg about every two weeks. In certain embodiments, the anti-CTLA-4 antibody is administered (e.g., intravenously) at about 0.3 mg/kg or 1 mg/kg about every six weeks, and the anti-PD-1 antibody is administered (e.g., intravenously) at about 1 mg/kg, 3 mg/kg, 6 mg/kg, or 10 mg/kg about every three weeks. In certain embodiments, the anti-CTLA-4 antibody is administered (e.g., intravenously) at about 0.3 mg/kg about every six weeks and the anti-PD-1 antibody is administered (e.g., intravenously) at about 1 mg/kg about every two weeks. In certain embodiments, the anti-CTLA-4 antibody is administered (e.g., intravenously) at about 1 mg/kg about every six weeks and the anti-PD-1 antibody is administered (e.g., intravenously) at about 1 mg/kg about every two weeks. In certain embodiments, the anti-CTLA-4 antibody is administered (e.g., intravenously) at about 1 mg/kg about every six weeks and the anti-PD-1 antibody is administered (e.g., intravenously) at about 3 mg/kg about every two weeks. In certain embodiments, the anti-CTLA-4 antibody is administered (e.g., intravenously) at about 1 mg/kg about every six weeks and the anti-PD-1 antibody is administered (e.g., intravenously) at about 6 mg/kg about every three weeks. In certain embodiments, the anti-CTLA-4 antibody is administered (e.g., intravenously) at 0.3 mg/kg or 1 mg/kg every six weeks, and the anti-PD-1 antibody is administered (e.g., intravenously) at 1 mg/kg or 3 mg/kg every two weeks. In certain embodiments, the anti-CTLA-4 antibody is administered (e.g., intravenously) at 0.3 mg/kg every six weeks and the anti-PD-1 antibody is administered (e.g., intravenously) at 1 mg/kg every two weeks. In certain embodiments, the anti-CTLA-4 is administered (e.g., intravenously) at antibody 1 mg/kg every six weeks and the anti-PD-1 antibody is administered (e.g., intravenously) at 1 mg/kg about every two weeks. In certain embodiments, the anti-CTLA-4 antibody is administered (e.g., intravenously) at 1 mg/kg every six weeks and the anti-PD-1 antibody is administered (e.g., intravenously) at 3 mg/kg every two weeks. In certain embodiments, the anti-CTLA-4 antibody is administered (e.g., intravenously) at 1 mg/kg about every six weeks and the anti-PD-1 antibody is administered (e.g., intravenously) at 6 mg/kg about every three weeks. In certain embodiments, the anti-CTLA-4 antibody is administered (e.g., intravenously) on the same day as the anti-PD-1 antibody. In certain embodiments, each administration of the anti-CTLA-4 antibody is conducted on the same day as the anti-PD-1 antibody. In certain embodiments, the anti-CTLA-4 antibody is administered within 30 minutes or 1 hour after the completion of administration of the anti-PD-1 antibody. In certain embodiments, the anti-CTLA-4 antibody is administered on the same day as the anti-PD-1 antibody. In certain embodiments, each administration of the anti-CTLA-4 antibody is conducted on the same day as the anti-PD-1 antibody. In certain embodiments, the anti-CTLA-4 antibody is administered within 30 minutes or 1 hour after the completion of administration of the anti-PD-1 antibody. In certain embodiments, the therapeutic combination is administered to a subject for at least 3, 6, 9, 12, 18, or 24 months. In certain embodiments, the therapeutic combination is administered to a subject for up to 3, 6, 9, 12, 18, or 24 months.

TABLE 13

Dosage and frequency of administration of an anti-CTLA-4 antibody and an anti-PD-1 antibody in combination.

| Anti-CTLA-4 antibody | | Anti-PD-1 antibody | |
|---|---|---|---|
| Dosage (mg/kg) | Frequency | Dosage (mg/kg) | Frequency |
| 0.3 | every 4 weeks | 1 | every 2 weeks |
| 0.3 | every 4 weeks | 1 | every 3 weeks |
| 0.3 | every 4 weeks | 3 | every 2 weeks |
| 0.3 | every 4 weeks | 3 | every 3 weeks |
| 0.3 | every 4 weeks | 6 | every 2 weeks |
| 0.3 | every 4 weeks | 6 | every 3 weeks |
| 0.3 | every 4 weeks | 10 | every 2 weeks |
| 0.3 | every 4 weeks | 10 | every 3 weeks |
| 0.3 | every 6 weeks | 1 | every 2 weeks |
| 0.3 | every 6 weeks | 1 | every 3 weeks |
| 0.3 | every 6 weeks | 3 | every 2 weeks |
| 0.3 | every 6 weeks | 3 | every 3 weeks |
| 0.3 | every 6 weeks | 6 | every 2 weeks |
| 0.3 | every 6 weeks | 6 | every 3 weeks |
| 0.3 | every 6 weeks | 10 | every 2 weeks |
| 0.3 | every 6 weeks | 10 | every 3 weeks |
| 0.3 | every 12 weeks | 1 | every 2 weeks |
| 0.3 | every 12 weeks | 1 | every 3 weeks |
| 0.3 | every 12 weeks | 3 | every 2 weeks |
| 0.3 | every 12 weeks | 3 | every 3 weeks |
| 0.3 | every 12 weeks | 6 | every 2 weeks |
| 0.3 | every 12 weeks | 6 | every 3 weeks |
| 0.3 | every 12 weeks | 10 | every 2 weeks |
| 0.3 | every 12 weeks | 10 | every 3 weeks |
| 1 | every 4 weeks | 1 | every 2 weeks |
| 1 | every 4 weeks | 1 | every 3 weeks |
| 1 | every 4 weeks | 3 | every 2 weeks |
| 1 | every 4 weeks | 3 | every 3 weeks |
| 1 | every 4 weeks | 6 | every 2 weeks |
| 1 | every 4 weeks | 6 | every 3 weeks |
| 1 | every 4 weeks | 10 | every 2 weeks |
| 1 | every 4 weeks | 10 | every 3 weeks |
| 1 | every 6 weeks | 1 | every 2 weeks |
| 1 | every 6 weeks | 1 | every 3 weeks |
| 1 | every 6 weeks | 3 | every 2 weeks |
| 1 | every 6 weeks | 3 | every 3 weeks |
| 1 | every 6 weeks | 6 | every 2 weeks |
| 1 | every 6 weeks | 6 | every 3 weeks |
| 1 | every 6 weeks | 10 | every 2 weeks |
| 1 | every 6 weeks | 10 | every 3 weeks |
| 1 | every 12 weeks | 1 | every 2 weeks |
| 1 | every 12 weeks | 1 | every 3 weeks |
| 1 | every 12 weeks | 3 | every 2 weeks |
| 1 | every 12 weeks | 3 | every 3 weeks |
| 1 | every 12 weeks | 6 | every 2 weeks |
| 1 | every 12 weeks | 6 | every 3 weeks |
| 1 | every 12 weeks | 10 | every 2 weeks |
| 1 | every 12 weeks | 10 | every 3 weeks |
| 3 | every 4 weeks | 1 | every 2 weeks |
| 3 | every 4 weeks | 1 | every 3 weeks |
| 3 | every 4 weeks | 3 | every 2 weeks |
| 3 | every 4 weeks | 3 | every 3 weeks |
| 3 | every 4 weeks | 6 | every 2 weeks |
| 3 | every 4 weeks | 6 | every 3 weeks |
| 3 | every 4 weeks | 10 | every 2 weeks |
| 3 | every 4 weeks | 10 | every 3 weeks |
| 3 | every 6 weeks | 1 | every 2 weeks |
| 3 | every 6 weeks | 1 | every 3 weeks |
| 3 | every 6 weeks | 3 | every 2 weeks |
| 3 | every 6 weeks | 3 | every 3 weeks |
| 3 | every 6 weeks | 6 | every 2 weeks |
| 3 | every 6 weeks | 6 | every 3 weeks |
| 3 | every 6 weeks | 10 | every 2 weeks |
| 3 | every 6 weeks | 10 | every 3 weeks |
| 3 | every 12 weeks | 1 | every 2 weeks |
| 3 | every 12 weeks | 1 | every 3 weeks |
| 3 | every 12 weeks | 3 | every 2 weeks |
| 3 | every 12 weeks | 3 | every 3 weeks |
| 3 | every 12 weeks | 6 | every 2 weeks |
| 3 | every 12 weeks | 6 | every 3 weeks |
| 3 | every 12 weeks | 10 | every 2 weeks |
| 3 | every 12 weeks | 10 | every 3 weeks |

In certain embodiments, the anti-CTLA-4 antibody, e.g., AGEN1884 (IgG$_1$), is administered, optionally as a monotherapy, at the dosage and at the frequency shown in a single row of Table 13. In certain embodiments, the anti-CTLA-4 antibody, e.g., AGEN1884 (IgG$_1$), is administered, optionally as a monotherapy, at about the dosage and at the frequency shown in a single row of Table 13. In certain embodiments, the anti-CTLA-4 antibody, e.g., AGEN1884 (IgG$_1$), is administered, optionally as a monotherapy, at the dosage and at about the frequency shown in a single row of Table 13. In certain embodiments, the anti-CTLA-4 antibody, e.g., AGEN1884 (IgG$_1$), is administered, optionally as a monotherapy, at about the dosage and at about the frequency shown in a single row of Table 13. In certain embodiments, the anti-CTLA-4 antibody is administered (e.g., intravenously), optionally as a monotherapy, at about 0.3 mg/kg, 1 mg/kg, or 3 mg/kg about every four weeks. In certain embodiments, the anti-CTLA-4 antibody is administered (e.g., intravenously), optionally as a monotherapy, at about 0.3 mg/kg, 1 mg/kg, or 3 mg/kg about every six weeks. In certain embodiments, the anti-CTLA-4 antibody is administered (e.g., intravenously), optionally as a monotherapy, at about 0.3 mg/kg, 1 mg/kg, or 3 mg/kg about every twelve weeks. In certain embodiments, the anti-CTLA-4 antibody is administered (e.g., intravenously), optionally as a monotherapy, at 0.3 mg/kg, 1 mg/kg, or 3 mg/kg every four weeks. In certain embodiments, the anti-CTLA-4 antibody is administered (e.g., intravenously), optionally as a monotherapy, at 0.3 mg/kg, 1 mg/kg, or 3 mg/kg every six weeks. In certain embodiments, the anti-CTLA-4 antibody is administered (e.g., intravenously), optionally as a monotherapy, at 0.3 mg/kg, 1 mg/kg, or 3 mg/kg every twelve weeks. In certain embodiments, the anti-CTLA-4 antibody is administered to a subject for at least 3, 6, 9, 12, 18, or 24 months. In certain embodiments, the anti-CTLA-4 antibody is administered to a subject for up to 3, 6, 9, 12, 18, or 24 months.

In certain embodiments, the anti-CTLA-4 antibody, e.g., AGEN1884 (IgG$_1$), is administered at the dosage and at the frequency shown in a single row of Table 13, in combination with pembrolizumab administered at 200 mg every three weeks. In certain embodiments, the anti-CTLA-4 antibody, e.g., AGEN1884 (IgG$_1$), is administered at about the dosage and at the frequency shown in a single row of Table 13, in combination with pembrolizumab administered at about 200 mg every three weeks. In certain embodiments, the anti-CTLA-4 antibody, e.g., AGEN1884 (IgG$_1$), is administered at the dosage and at about the frequency shown in a single row of Table 13, in combination with pembrolizumab administered at 200 mg about every three weeks. In certain embodiments, the anti-CTLA-4 antibody, e.g., AGEN1884 (IgG$_1$), is administered at about the dosage and at about the frequency shown in a single row of Table 13, in combination with pembrolizumab administered at about 200 mg about every three weeks. In certain embodiments, the anti-CTLA-4 antibody is administered (e.g., intravenously) at about 0.3 mg/kg, 1 mg/kg, or 3 mg/kg about every four weeks, in combination with pembrolizumab administered (e.g., intravenously) at about 200 mg about every three weeks. In certain embodiments, the anti-CTLA-4 antibody is administered (e.g., intravenously) at about 0.3 mg/kg, 1 mg/kg, or 3 mg/kg about every six weeks, in combination with pembrolizumab administered (e.g., intravenously) at about 200 mg about every three weeks. In certain embodiments, the anti-CTLA-4 antibody is administered (e.g., intravenously) at about 0.3 mg/kg, 1 mg/kg, or 3 mg/kg about every twelve weeks, in combination with pembrolizumab administered (e.g., intravenously) at about 200 mg about every three weeks. In certain embodiments, the anti-CTLA-4 antibody is administered (e.g., intravenously) at 0.3 mg/kg, 1 mg/kg, or 3 mg/kg every four weeks, in combination with pembrolizumab administered (e.g., intravenously) at 200 mg every three weeks. In certain embodiments, the anti-CTLA-4 antibody is administered (e.g., intravenously) at 0.3 mg/kg, 1 mg/kg, or 3 mg/kg every six weeks, in combination with pembrolizumab administered (e.g., intravenously) at 200 mg every three weeks. In certain embodiments, the anti-CTLA-4 antibody is administered (e.g., intravenously) at 0.3 mg/kg, 1 mg/kg, or 3 mg/kg every twelve weeks, in combination with pembrolizumab administered (e.g., intravenously) at 200 mg every three weeks. In certain embodiments, the anti-CTLA-4 antibody and pembrolizumab are administered to a subject for at least 3, 6, 9, 12, 18, or 24 months. In certain embodiments, the anti-CTLA-4 antibody and pembrolizumab are administered to a subject for up to 3, 6, 9, 12, 18, or 24 months.

In certain embodiments, the anti-PD-1 antibody, e.g., AGEN2034 (IgG$_4$ S228P), is administered, optionally as a monotherapy, at the dosage and at the frequency shown in a single row of Table 13. In certain embodiments, the anti-PD-1 antibody, e.g., AGEN2034 (IgG$_4$ S228P), is administered, optionally as a monotherapy, at about the dosage and at the frequency shown in a single row of Table 13. In certain embodiments, the anti-PD-1 antibody, e.g., AGEN2034 (IgG$_4$ S228P), is administered, optionally as a monotherapy, at the dosage and at about the frequency shown in a single row of Table 13. In certain embodiments, the anti-PD-1 antibody, e.g., AGEN2034 (IgG$_4$ S228P), is administered, optionally as a monotherapy, at about the dosage and at about the frequency shown in a single row of Table 13. In certain embodiments, the anti-PD-1 antibody is administered (e.g., intravenously), optionally as a monotherapy, at about 1 mg/kg, 3 mg/kg, 6 mg/kg, or 10 mg/kg about every two weeks. In certain embodiments, the anti-PD-1 antibody is administered (e.g., intravenously), optionally as a monotherapy, at about 1 mg/kg, 3 mg/kg, 6 mg/kg, or 10 mg/kg about every three weeks. In certain embodiments, the anti-PD-1 antibody is administered (e.g., intravenously), optionally as a monotherapy, at 1 mg/kg, 3 mg/kg, 6 mg/kg, or 10 mg/kg every two weeks. In certain embodiments, the anti-PD-1 antibody is administered (e.g., intravenously), optionally as a monotherapy, at 1 mg/kg, 3 mg/kg, 6 mg/kg, or 10 mg/kg every three weeks. In certain embodiments, the anti-PD-1 antibody is administered to a subject for at least 3, 6, 9, 12, 18, or 24 months. In certain embodiments, the anti-PD-1 antibody is administered to a subject for up to 3, 6, 9, 12, 18, or 24 months.

In certain embodiments, the instant disclosure provides a method of treating a subject having angiosarcoma, the method comprising administering to the subject (e.g., intravenously, intratumorally, or subcutaneously) an effective amount of a therapeutic combination and/or multispecific antibody as described herein. In certain embodiments, the subject is administered a therapeutic combination comprising an anti-CTLA-4 antibody described herein and an anti-PD-1 antibody described herein. In certain embodiments, the effective amount of the anti-CTLA-4 antibody in this therapeutic combination is lower than the effective amount of the anti-CTLA-4 antibody when administered alone. In certain embodiments, the anti-CTLA-4 antibody is administered (e.g., intravenously, intratumorally, or subcutaneously) at 0.1 mg/kg and the anti-PD-1 antibody is administered (e.g., intravenously, intratumorally, or subcutaneously) at 0.01 mg/kg, 0.03 mg/kg, 0.1 mg/kg, 0.3 mg/kg, 1 mg/kg, 3 mg/kg, 6 mg/kg, 10 mg/kg, about 0.1 mg/kg, about 0.3 mg/kg, about 1 mg/kg, about 3 mg/kg, about 6 mg/kg, or about 10 mg/kg, optionally every one, two or three weeks. In certain embodiments, the anti-CTLA-4 antibody is administered (e.g., intravenously) at 0.1 mg/kg and the anti-PD-1 antibody is administered (e.g., intravenously) at 3 mg/kg, optionally every one, two or three weeks.

6.5 Antibody Production

Antibodies, including monospecific or multispecific (e.g., bispecific) antibodies, that specifically bind to CTLA-4 and/or PD-1, (e.g., human CTLA-4 and/or PD-1) can be produced by any method known in the art for the synthesis of antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, NY; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a specific embodiment, an antibody described herein is an antibody (e.g., a recombinant antibody) prepared, expressed, created or isolated by any means that involves creation, e.g., via synthesis, genetic engineering of DNA sequences. In certain embodiments, such antibody comprises sequences (e.g., DNA sequences or amino acid sequences) that do not naturally exist within the antibody germline repertoire of an animal or mammal (e.g., human) in vivo.

In a certain aspect, provided herein is a method of making an antibody which specifically binds to CTLA-4 and/or PD-1 (including, e.g., monospecific or multispecific antibodies that bind to human CTLA-4 and/or human PD-1) comprising culturing a cell or host cell described herein. In a certain aspect, provided herein is a method of making an antibody which specifically binds to CTLA-4 and/or PD-1 (including, e.g., monospecific or multispecific antibodies that bind to human CTLA-4 and/or PD-1) comprising expressing (e.g., recombinantly expressing) the antibody using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981). The term "monoclonal antibody" as used herein is not limited to antibodies produced through hybridoma technology. For example, monoclonal antibodies can be produced recombinantly from host cells exogenously expressing an antibody described herein.

In specific embodiments, a "monoclonal antibody," as used herein, is an antibody produced by a single cell (e.g., hybridoma or host cell producing a recombinant antibody), wherein the antibody specifically binds to CTLA-4 and/or PD-1 (including, e.g., monospecific or multispecific antibodies that bind to human CTLA-4 and/or PD-1) as determined, e.g., by ELISA or other antigen-binding or competitive binding assay known in the art or in the Examples provided herein. In particular embodiments, a monoclonal antibody can be a chimeric antibody or a humanized antibody. In certain embodiments, a monoclonal antibody is a monovalent antibody or multivalent (e.g., bivalent) antibody. In certain embodiments, a monoclonal antibody can be a Fab fragment or a F(ab')$_2$ fragment. Monoclonal antibodies described herein can, for example, be made by the hybridoma method as described in Kohler G & Milstein C (1975) Nature 256: 495 or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., CTLA-4 or PD-1 (e.g., human CTLA-4 or PD-1)) used for immunization. Alternatively, lymphocytes can be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986)). Additionally, a RIMMS (repetitive immunization multiple sites) technique can be used to immunize an animal (Kilpatrick K E et al., (1997) Hybridoma 16:381-9, incorporated by reference in its entirety).

In some embodiments, mice (or other animals, such as rats, monkeys, donkeys, pigs, sheep, hamster, or dogs) can be immunized with an antigen (e.g., CTLA-4 or PD-1 (e.g., human CTLA-4 or PD-1)) and once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the American Type Culture Collection (ATCC©) (Manassas, VA), to form hybridomas. Hybridomas are selected and cloned by limited dilution. In certain embodiments, lymph nodes of the immunized mice are harvested and fused with NSO myeloma cells.

The hybridoma cells thus prepared are seeded and grown in a suitable culture medium that optionally contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as NSO cell line or those derived from MOPC-21 and MPC-11 mouse tumors available from the Salk Institute Cell Distribution Center, San Diego, CA, USA, and SP-2 or $X_{63}$-Ag8.653 cells available from the American Type Culture Collection, Rockville, MD, USA. Human myeloma and mouse-human heteromyeloma cell lines also have been described for the production of human monoclonal antibodies (Kozbor D (1984) J Immunol 133: 3001-5; Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against CTLA-4 and/or PD-1 (e.g., human CTLA-4 and/or PD-1). The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')2 fragments). A Fab fragment corresponds to one of the two identical arms of a tetrameric antibody molecule and contains the complete light chain paired with the VH and CH1 domains of the heavy chain. A F(ab')$_2$ fragment contains the two antigen-binding arms of a tetrameric antibody molecule linked by disulfide bonds in the hinge region.

Further, the antibodies or antigen-binding fragments described herein can also be generated using various phage display methods known in the art. In phage display methods, proteins are displayed on the surface of phage particles which carry the polynucleotide sequences encoding them. In particular, DNA sequences encoding heavy and light chain variable regions are amplified from animal cDNA libraries (e.g., human or murine cDNA libraries of affected tissues). The DNA encoding the heavy and light chain variable regions are recombined together with a scFv linker by PCR and cloned into a phagemid vector. The vector is electroporated in E. coli and the E. coli is infected with helper phage. Phage used in these methods are typically filamentous phage including fd and M13, and the heavy and light chain variable regions are usually recombinantly fused to either the phage gene III or gene VIII. Phage expressing an antibody that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton DR & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108.

As described in the above references, after phage selection, the antibody coding regions from the phage can be isolated and used to generate antibodies, including human antibodies, and expressed in any desired host, including mammalian cells, insect cells, plant cells, yeast, and bacteria, e.g., as described below. Techniques to recombinantly produce antibodies such as Fab, Fab' and F(ab')$_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043.

In one aspect, to generate antibodies, PCR primers including heavy or light chain variable region nucleotide sequences, a restriction site, and a flanking sequence to protect the restriction site can be used to amplify the heavy or light chain variable region sequences from a template, e.g., scFv clones. Utilizing cloning techniques known to those of skill in the art, the PCR amplified heavy chain variable regions can be cloned into vectors expressing a heavy chain constant region, and the PCR amplified light chain variable regions can be cloned into vectors expressing a light chain constant region, e.g., human kappa or lambda constant regions. The heavy and light chain variable regions can also be cloned into one vector expressing the necessary constant regions. The heavy chain conversion vectors and light chain conversion vectors are then co-transfected into cell lines to generate stable or transient cell lines that express antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including $IgG_1$, $IgG_2$, $IgG_3$ and $IgG_4$. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10 and Pedersen J T et al., (1994) J Mol Biol 235(3): 959-73. See also U.S. Application Publication No. US 2005/0042664 A1 (Feb. 24, 2005), which is incorporated by reference herein in its entirety.

Single domain antibodies, for example, antibodies lacking the light chains, can be produced by methods well known in the art. See Riechmann L & Muyldermans S (1999) J Immunol 231: 25-38; Nuttall S D et al., (2000) Curr Pharm Biotechnol 1(3): 253-263; Muyldermans S, (2001) J Biotechnol 74(4): 277-302; U.S. Pat. No. 6,005,079; and International Publication Nos. WO 94/04678, WO 94/25591 and WO 01/44301.

Further, antibodies that specifically bind to a CTLA-4 and/or PD-1 antigen can, in turn, be utilized to generate anti-idiotype antibodies that "mimic" an antigen using techniques well known to those skilled in the art. (See, e.g., Greenspan N S & Bona C A (1989) FASEB J 7(5): 437-444; and Nissinoff A (1991) J Immunol 147(8): 2429-2438).

In particular embodiments, an antibody or antigen-binding fragment thereof described herein, which binds to the same epitope of CTLA-4 and/or PD-1 (e.g., human CTLA-4 and/or PD-1) as an anti-CTLA-4 or anti-PD-1 antibody or antigen-binding fragment thereof described herein, is a human antibody. In particular embodiments, an antibody described herein, which competitively blocks (e.g., in a dose-dependent manner) any one of the antibodies described herein, from binding to CTLA-4 or PD-1 (e.g., human CTLA-4 or PD-1), is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., CTLA-4 or PD-1). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13:65-93. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598. Examples of mice capable of producing human antibodies include the Xenomouse™ (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569,825), the Trans Chromo Mousem (Kirin) and the KM Mouse™ (Medarex/Kirin).

Human antibodies or antigen-binding fragments which specifically bind to CTLA-4 and/or PD-1 (including, e.g., monospecific or multispecific antibodies that bind to human CTLA-4 and/or PD-1) can be made by a variety of methods known in the art including phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that specifically bind to a target antigen (e.g., CTLA-4 or PD-1, e.g., human CTLA-4 or PD-1). Such methods are known and are described in the art, see, e.g., Shinmoto H et al., (2004) Cytotechnology 46: 19-23; Naganawa Y et al., (2005) Human Antibodies 14: 27-31.

Bispecific, bivalent antibodies, and methods of making them, are described, for instance in U.S. Pat. Nos. 5,731,168, 5,807,706, 5,821,333, and U.S. Appl. Publ. Nos. 2003/020734 and 2002/0155537; each of which is herein incorporated by reference in its entirety. Bispecific tetravalent antibodies, and methods of making them are described, for instance, in Int. Appl. Publ. Nos. WO02/096948 and WO00/44788, the disclosures of both of which are herein incorporated by reference in its entirety. See generally, Int. Appl. Publ. Nos. WO93/17715, WO92/08802, WO91/00360, and WO92/05793; Tutt et al., J. Immunol. 147:60-69 (1991); U.S. Pat. Nos. 4,474,893; 4,714,681; 4,925,648; 5,573,920; and 5,601,819; and Kostelny et al., J. Immunol. 148:1547-1553 (1992); each of which is herein incorporated by reference in its entirety.

One method for generating bispecific antibodies has been termed the "knobs-into-holes" strategy (see, e.g., Intl. Publ. WO2006/028936). The mispairing of Ig heavy chains is reduced in this technology by mutating selected amino acids forming the interface of the CH3 domains in IgG. At positions within the CH3 domain at which the two heavy chains interact directly, an amino acid with a small side chain (hole) is introduced into the sequence of one heavy chain and an amino acid with a large side chain (knob) into the counterpart interacting residue location on the other heavy chain. In some embodiments, the compositions described herein have immunoglobulin chains in which the CH3 domains have been modified by mutating selected amino acids that interact at the interface between two polypeptides to form a bispecific antibody. The bispecific antibodies can be composed of immunoglobulin chains of the same subclass (e.g., IgG1 or IgG3) or different subclasses (e.g., IgG1 and IgG3, or IgG3 and IgG4)

In one embodiment, a bispecific antibody that binds to CTLA-4 and/or PD-1 comprises a T366W mutation in the "knobs chain" and T366S, L368A, Y407V mutations in the "hole chain," and optionally an additional interchain disulfide bridge between the CH3 domains by, e.g., introducing a Y349C mutation into the "knobs chain" and a E356C mutation or a S354C mutation into the "hole chain;" R409D, K370E mutations in the "knobs chain" and D399K, E357K mutations in the "hole chain;" R409D, K370E mutations in the "knobs chain" and D399K, E357K mutations in the "hole chain;" a T366W mutation in the "knobs chain" and T366S, L368A, Y407V mutations in the "hole chain;" R409D, K370E mutations in the "knobs chain" and D399K, E357K mutations in the "hole chain;" Y349C, T366W mutations in one of the chains and E356C, T366S, L368A, Y407V mutations in the counterpart chain; Y349C, T366W mutations in one chain and S354C, T366S, L368A, Y407V mutations in the counterpart chain; Y349C, T366W mutations in one chain and S354C, T366S, L368A, Y407V mutations in the counterpart chain; and Y349C, T366W mutations in one chain and S354C, T366S, L368A, Y407V mutations in the counterpart chain, numbering according to the EU numbering system.

Bispecific antibodies that bind to CTLA-4 and/or PD-1 can, in some instances contain, IgG4 and IgG1, IgG4 and IgG2, IgG4 and IgG2, IgG4 and IgG3, or IgG1 and IgG3 chain heterodimers. Such heterodimeric heavy chain antibodies, can routinely be engineered by, for example, modifying selected amino acids forming the interface of the CH3 domains in human IgG4 and the IgG1 or IgG3 so as to favor heterodimeric heavy chain formation.

In particular embodiments, a multispecific (e.g., bispecific) antibody can be a chimeric antibody or a humanized antibody. In certain embodiments, a multispecific (e.g., bispecific) antibody can be a F(ab')$_2$ fragment. A F(ab')$_2$ fragment contains the two antigen-binding arms of a tetrameric antibody molecule linked by disulfide bonds in the hinge region.

Multispecific (e.g., bispecific) antibodies described herein can be generated by any technique known to those of skill in the art. For example, F(ab')$_2$ fragments described herein can be produced by proteolytic cleavage of immunoglobulin molecules, using enzymes such as pepsin.

6.6 Kits

Also provided are kits comprising one or more antibodies described herein, or therapeutic combination, pharmaceutical composition, or conjugates thereof. In a specific embodiment, provided herein is a pharmaceutical pack or kit comprising one or more containers filled with one or more of the ingredients of the pharmaceutical compositions described herein, such as one or more antibodies provided herein. In some embodiments, the kits contain one or more pharmaceutical compositions described herein and any prophylactic or therapeutic agent, such as those described herein. In certain embodiments, the kits may contain a T cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

In certain embodiments, the kit comprises a container filled with a pharmaceutical composition comprising an anti-CTLA-4/PD-1 antibody described herein. In certain embodiments, the kit comprises a container filled with a pharmaceutical composition comprising an effective amount of an anti-CTLA-4/PD-1 antibody described herein.

In certain embodiments, the kit comprises a first container filled with a pharmaceutical composition comprising an anti-CTLA-4 antibody and a second container filled with a pharmaceutical composition comprising an anti-PD-1 antibody. The combination of the anti-CTLA-4 antibody and anti-PD-1 antibody can be any combination of an anti-CTLA-4 antibody described herein and an anti-PD-1 antibody described herein. In certain embodiments, the kit comprises a first container filled with a pharmaceutical composition comprising a first antibody that specifically binds to CTLA-4 (e.g., human CTLA-4), and a second container filled with a pharmaceutical composition comprising a second antibody that specifically binds to PD-1 (e.g., human PD-1), wherein CDRH1, CDRH2, CDRH3, CDRL1, CDRL2, and CDRL3 of the first antibody and CDRH1, CDRH2, CDRH3, CDRL1, CDRL2, and CDRL3 of the second antibody comprise the amino acid sequences listed in a single row of Table 11. In certain embodiments, the kit comprises a first container filled with a pharmaceutical composition comprising a first antibody that specifically binds to CTLA-4 (e.g., human CTLA-4), and a second container filled with a pharmaceutical composition comprising a second antibody that specifically binds to PD-1 (e.g., human PD-1), wherein CDRH1, CDRH2, CDRH3, CDRL1, CDRL2, and CDRL3 of the first antibody and CDRH1, CDRH2, CDRH3, CDRL1, CDRL2, and CDRL3 of the second antibody respectively comprise the amino acid sequences set forth in SEQ ID NOs: 20, 22, 24, 27, 30, 36, 75, 76, 80, 83, 84, and 85; 20, 22, 24, 29, 32, 37, 75, 76, 80, 83, 84, and 85; 20, 22, 24, 29, 33, 38, 75, 76, 80, 83, 84, and 85; 21, 22, 24, 27, 30, 36, 75, 76, 80, 83, 84, and 85; 21, 22, 24, 29, 33, 38, 75, 76, 80, 83, 84, and 85; 20, 22, 24, 28, 31, 36, 75, 76, 80, 83, 84, and 85; 20, 22, 24, 29, 34, 36, 75, 76, 80, 83, 84, and 85; 20, 22, 24, 29, 35, 38, 75, 76, 80, 83, 84, and 85; 21, 22, 26, 27, 30, 36, 75, 76, 80, 83, 84, and 85; 21, 22, 26, 29, 32, 37, 75, 76, 80, 83, 84, and 85; 21, 22, 26, 29, 33, 38, 75, 76, 80, 83, 84, and 85; 21, 22, 26, 29, 35, 38, 75, 76, 80, 83, 84, and 85; 20, 22, 24, 27, 30, 36, 75, 76, 81, 83, 84, and 85; 20, 22, 24, 29, 32, 37, 75, 76, 81, 83, 84, and 85; 20, 22, 24, 29, 33, 38, 75, 76, 81, 83, 84, and 85; 21, 22, 24, 27, 30, 36, 75, 76, 81, 83, 84, and 85; 21, 22, 24, 29, 33, 38, 75, 76, 81, 83, 84, and 85; 20, 22, 24, 28, 31, 36, 75, 76, 81, 83, 84, and 85; 20, 22, 24, 29, 34, 36, 75, 76, 81, 83, 84, and 85; 20, 22, 24, 29, 35, 38, 75, 76, 81, 83, 84, and 85; 21, 22, 26, 27, 30, 36, 75, 76, 81, 83, 84, and 85; 21, 22, 26, 29, 32, 37, 75, 76, 81, 83, 84, and 85; 21, 22, 26, 29, 33, 38, 75, 76, 81, 83, 84, and 85; 21, 22, 26, 29, 35, 38, 75, 76, 81, 83, 84, and 85; 20, 22, 24, 27, 30, 36, 75, 76, 82, 83, 84, and 85; 20, 22, 24, 29, 32, 37, 75, 76, 82, 83, 84, and 85; 20, 22, 24, 29, 33, 38, 75, 76, 82, 83, 84, and 85; 21, 22, 24, 27, 30, 36, 75, 76, 82, 83, 84, and 85; 21, 22, 24, 29, 33, 38, 75, 76, 82, 83, 84, and 85; 20, 22, 24, 28, 31, 36, 75, 76, 82, 83, 84, and 85; 20, 22, 24, 29, 34, 36, 75, 76, 82, 83, 84, and 85; 20, 22, 24, 29, 35, 38, 75, 76, 82, 83, 84, and 85; 21, 22, 26, 27, 30, 36, 75, 76, 82, 83, 84, and 85; 21, 22, 26, 29, 32, 37, 75, 76, 82, 83, 84, and 85; 21, 22, 26, 29, 33, 38, 75, 76, 82, 83, 84, and 85; 21, 22, 26, 29, 35, 38, 75, 76, 82, 83, 84, and 85; 20, 22, 24, 27, 30, 36, 75, 77, 81, 83, 84, and 85; 20, 22, 24, 29, 32, 37, 75, 77, 81, 83, 84, and 85; 20, 22, 24, 29, 33, 38, 75, 77, 81, 83, 84, and 85; 21, 22, 24, 27, 30, 36, 75, 77, 81, 83, 84, and 85; 21, 22, 24, 29, 33, 38, 75, 77, 81, 83, 84, and 85; 20, 22, 24, 28, 31, 36, 75, 77, 81, 83, 84, and 85; 20, 22, 24, 29, 34, 36, 75, 77, 81, 83, 84, and 85; 20, 22, 24, 29, 35, 38, 75, 77, 81, 83, 84, and 85; 21, 22, 26, 27, 30, 36, 75, 77, 81, 83, 84, and 85; 21, 22, 26, 29, 32, 37, 75, 77, 81, 83, 84, and 85; 21, 22, 26, 29, 33, 38, 75, 77, 81, 83, 84, and 85; 21, 22, 26, 29, 35, 38, 75, 77, 81, 83, 84, and 85; 20, 22, 24, 27, 30, 36, 75, 78, 81, 83, 84, and 85; 20, 22, 24, 29, 32, 37, 75, 78, 81, 83, 84, and 85; 20, 22, 24, 29, 33, 38, 75, 78, 81, 83, 84, and 85; 21, 22, 24, 27, 30, 36, 75, 78, 81, 83, 84, and 85; 21, 22, 24, 29, 33, 38, 75, 78, 81, 83, 84, and 85; 20, 22, 24, 28, 31, 36, 75, 78, 81, 83, 84, and 85; 20, 22, 24, 29, 34, 36, 75, 78, 81, 83, 84, and 85; 20, 22, 24, 29, 35, 38, 75, 78, 81, 83, 84, and 85; 21, 22, 26, 27, 30, 36, 75, 78, 81, 83, 84, and 85; 21, 22, 26, 29, 32, 37, 75, 78, 81, 83, 84, and 85; 21, 22, 26, 29, 33, 38, 75, 78, 81, 83, 84, and 85; 21, 22, 26, 29, 35, 38, 75, 78, 81, 83, 84, and 85; 20, 22, 24, 27, 30, 36, 75, 79, 81, 83, 84, and 85; 20, 22, 24, 29, 32, 37, 75, 79, 81, 83, 84, and 85; 20, 22, 24, 29, 33, 38, 75, 79, 81, 83, 84, and 85; 21, 22, 24, 27, 30, 36, 75, 79, 81, 83, 84, and 85; 21, 22, 24, 29, 33, 38, 75, 79, 81, 83, 84, and 85; 20, 22, 24, 28, 31, 36, 75, 79, 81, 83, 84, and 85; 20, 22, 24, 29, 34, 36, 75, 79, 81, 83, 84, and 85; 20, 22, 24, 29, 35, 38, 75, 79, 81, 83, 84, and 85; 21, 22, 26, 27, 30, 36, 75, 79, 81, 83, 84, and 85; 21, 22, 26, 29, 32, 37, 75, 79, 81, 83, 84, and 85; 21, 22, 26, 29, 33, 38, 75, 79, 81, 83, 84, and 85; or 21, 22, 26, 29, 35, 38, 75, 79, 81, 83, 84, and 85.

In certain embodiments, the kit comprises a first container filled with a pharmaceutical composition comprising a first antibody that specifically binds to CTLA-4 (e.g., human CTLA-4), and a second container filled with a pharmaceutical composition comprising a second antibody that specifically binds to PD-1 (e.g., human PD-1), wherein the heavy chain variable region and the light chain variable region of the first antibody and the heavy chain variable region and the light chain variable region of the second antibody comprise the amino acid sequences listed in a single row of Table 12. In certain embodiments, the kit comprises a first container filled with a pharmaceutical composition comprising a first antibody that specifically binds to CTLA-4 (e.g., human CTLA-4), and a second container filled with a pharmaceutical composition comprising a second antibody that specifically binds to PD-1 (e.g., human PD-1), wherein the heavy chain variable region and the light chain variable region of the first antibody and the heavy chain variable region and the light chain variable region of the second antibody respectively comprise the amino acid sequences set forth in SEQ ID NOs: 1, 14, 67, and 74; 1, 16, 67, and 74; 1, 17, 67, and 74; 9, 14, 67, and 74; 9, 17, 67, and 74; 10, 15, 67, and 74; 10, 17, 67, and 74; 10, 18, 67, and 74; 10, 19, 67, and 74; 11, 15, 67, and 74; 11, 14, 67, and 74; 11, 16, 67, and 74; 11, 17, 67, and 74; 12, 14, 67, and 74; 12, 16, 67, and 74; 12, 17, 67, and 74; 12, 19, 67, and 74; 13, 15, 67, and 74; 13, 17, 67, and 74; 1, 14, 66, and 74; 1, 16, 66, and 74; 1, 17, 66, and 74; 9, 14, 66, and 74; 9, 17, 66, and 74; 10, 15, 66, and 74; 10, 17, 66, and 74; 10, 18, 66, and 74; 10, 19, 66, and 74; 11, 15, 66, and 74; 11, 14, 66, and 74; 11, 16, 66, and 74; 11, 17, 66, and 74; 12, 14, 66, and 74; 12, 16, 66, and 74; 12, 17, 66, and 74; 12, 19, 66, and 74; 13, 15, 66, and 74; 13, 17, 66, and 74; 1, 14, 68, and 74; 1, 16, 68, and 74; 1, 17, 68, and 74; 9, 14, 68, and 74; 9, 17, 68, and 74; 10, 15, 68, and 74; 10, 17, 68, and 74; 10, 18, 68, and 74; 10, 19, 68, and 74; 11, 15, 68, and 74; 11, 14, 68, and 74; 11, 16, 68, and 74; 11, 17, 68, and 74; 12, 14, 68, and 74; 12, 16, 68, and 74; 12, 17, 68, and 74; 12, 19, 68, and 74; 13, 15, 68, and 74; 13, 17, 68, and 74; 1, 14, 69, and 74; 1, 16, 69, and 74; 1, 17, 69, and 74; 9, 14, 69, and 74; 9, 17, 69, and 74; 10, 15, 69, and 74; 10, 17, 69, and 74; 10, 18, 69, and 74; 10, 19, 69, and 74; 11, 15, 69, and 74; 11, 14, 69, and 74; 11, 16, 69, and 74; 11, 17, 69, and 74; 12, 14, 69, and 74; 12, 16, 69, and 74; 12, 17, 69, and 74; 12, 19, 69, and 74; 13, 15, 69, and 74; 13, 17, 69, and 74; 1, 14, 70, and 74; 1, 16, 70, and 74; 1, 17, 70, and 74; 9, 14, 70, and 74; 9, 17, 70, and 74; 10, 15, 70, and 74; 10, 17, 70, and 74; 10, 18, 70, and 74; 10, 19, 70, and 74; 11, 15, 70, and 74; 11, 14, 70, and 74; 11, 16, 70, and 74; 11, 17, 70, and 74; 12, 14, 70, and 74; 12, 16, 70, and 74; 12, 17, 70, and 74; 12, 19, 70, and 74; 13, 15, 70, and 74; 13, 17, 70, and 74; 1, 14, 71, and 74; 1, 16, 71, and 74; 1, 17, 71, and 74; 9, 14, 71, and 74; 9, 17, 71, and 74; 10, 15, 71, and 74; 10, 17, 71, and 74; 10, 18, 71, and 74; 10, 19, 71, and 74; 11, 15, 71, and 74; 11, 14, 71, and 74; 11, 16, 71, and 74; 11, 17, 71, and 74; 12, 14, 71, and 74; 12, 16, 71, and 74; 12, 17, 71, and 74; 12, 19, 71, and 74; 13, 15, 71, and 74; 13, 17, 71, and 74; 1, 14, 72, and 74; 1, 16, 72, and 74; 1, 17, 72, and 74; 9, 14, 72, and 74; 9, 17, 72, and 74; 10, 15, 72, and 74; 10, 17, 72, and 74; 10, 18, 72, and 74; 10, 19, 72, and 74; 11, 15, 72, and 74; 11, 14, 72, and 74; 11, 16, 72, and 74; 11, 17, 72, and 74; 12, 14, 72, and 74; 12, 16, 72, and 74; 12, 17, 72, and 74; 12, 19, 72, and 74; 13, 15, 72, and 74; 13, 17, 72, and 74; 1, 14, 73, and 74; 1, 16, 73, and 74; 1, 17, 73, and 74; 9, 14, 73, and 74; 9, 17, 73, and 74; 10, 15, 73, and 74; 10, 17, 73, and 74; 10, 18, 73, and 74; 10, 19, 73, and 74; 11, 15, 73, and 74; 11, 14, 73, and 74; 11, 16, 73, and 74; 11, 17, 73, and 74; 12, 14, 73, and 74; 12, 16, 73, and 74; 12, 17, 73, and 74; 12, 19, 73, and 74; 13, 15, 73, and 74; or 13, 17, 73, and 74.

In certain embodiments, the kit comprises a first container filled with a pharmaceutical composition comprising a first antibody that specifically binds to CTLA-4 (e.g., human CTLA-4) described herein, and a second container filled with a pharmaceutical composition comprising a second antibody that specifically binds to PD-1 (e.g., human PD-1) described herein, wherein a therapeutic combination of the first antibody and the second antibody is in an effective amount. The amount of the anti-CTLA-4 antibody in this kit can be lower than, equal to, or higher than the effective amounts of the anti-CTLA-4 antibody when administered alone, and the amount of the anti-PD-1 antibody in this kit can be lower than, equal to, or higher than the effective amounts of the anti-PD-1 antibody when administered alone. In certain embodiments, the amount of the anti-CTLA-4 antibody in this kit is lower than the effective amount of the anti-CTLA-4 antibody when administered alone. In certain embodiments, the amount of the anti-PD-1 antibody in this kit is lower than the effective amount of the anti-PD-1 antibody when administered alone. In certain embodiments, the amount of the anti-CTLA-4 antibody in this kit is lower than the effective amount of the anti-CTLA-4 antibody when administered alone, and the amount of the anti-PD-1 antibody in this kit is lower than the effective amount of the anti-PD-1 antibody alone.

7. EXAMPLES

The examples in this Section (i.e., Section 6) are offered by way of illustration, and not by way of limitation.

7.1 Example 1: Combination of Anti-CTLA-4 Antibody and Anti-PD-1 Antibody

This example characterizes the functional activity of combining an anti-CTLA-4 antagonist antibody with an anti-PD-1 antagonist antibody. The full length sequences of the antibodies tested are shown in Table 14.

TABLE 14

Full length sequences of anti-CTLA-4 antibody and anti-PD-1 antibody.

| Antibody | Heavy chain SEQ ID NO | Light chain SEQ ID NO |
| --- | --- | --- |
| AGEN1884 (IgG$_1$) | 51 | 59 |
| AGEN2034 (IgG$_4$ S228P) | 91 | 93 |

7.1.1 Dosage Titrations of Anti-CTLA-4 Antibody in Combination with Anti-PD-1 Antibody In a series of experiments, the functional activity of the anti-CTLA-4 antibody AGEN1884 (IgG$_1$) administered at varying concentrations, in combination with a fixed concentration of the anti-PD-1 antibody AGEN2034 (IgG$_4$ S228P), was tested in human peripheral blood mononuclear cells (PBMCs).

In a first experiment, human peripheral blood mononuclear cells (PBMCs) were stimulated with a sub-optimal concentration (100 ng/ml) of the Staphylococcal Enterotoxin A (SEA) superantigen (Toxin Technologies, Cat #at101red) in the presence of a dose titration of an anti-CTLA-4 antibody AGEN1884 (IgG$_1$) or an isotype control antibody (IgG$_1$) in combination with 10 μg/ml of an anti-PD-1 antibody AGEN2034 (IgG$_4$ S228P) or an isotype control antibody (IgG$_4$ S228P) for 5 days at 37° C. and 5% CO$_2$. IL-2 concentrations in the culture supernatant were analyzed by AlphaLISA (Perkin Elmer, Cat #AL221F). PBMCs from two different donors were tested.

As shown in FIGS. 1A and 1B, the anti-CTLA-4 antibody AGEN1884 (IgG$_1$) stimulated IL-2 production in a dose dependent manner. Combination with the anti-PD-1 antibody AGEN2034 (IgG$_4$ S228P) further enhanced the secretion of IL-2 induced by the anti-CTLA-4 antibody alone.

In a second experiment, cryopreserved human PBMCs were plated at 10$^5$ cells/well in medium (RPMI1640 supplemented with Normocin™ (Invivogen #ant-nr) and 10% heat-inactivated FBS (Gibco, Invitrogen Corporation)). Cells were stimulated with a sub-optimal concentration (100 ng/ml) of the SEA superantigen (Toxin Technologies, Cat #at 101red) in the presence of a dose range (100-0.001 μg/mL) of anti-CTLA-4 antibody AGEN1884 (IgG$_1$) in combination with a fixed antibody concentration of 20 μg/ml of either (i) anti-PD-1 antibody AGEN2034 (IgG$_4$ S228P), or (ii) an isotype control antibody (IgG$_4$ S228P). Cells were then incubated for 5 days at 37° C. in 5% CO$_2$. IL-2 concentrations in the culture supernatant were analyzed by AlphaLISA (Perkin Elmer, Cat #AL221F). PBMCs from two different donors were tested.

As shown in FIGS. 2A and 2B, the combination of AGEN1884 (IgG$_1$) and AGEN2034 (IgG$_4$ S228P) enhanced the secretion of IL-2 by stimulated PBMCs relative to AGEN1884 (IgG$_1$) and isotype control. This effect was observed in PBMCs from both donors.

7.1.2 Functional Activity of Anti-CTLA-4 Antibody and Anti-PD-1 Antibody at Fixed Concentrations In each of two experiments, the functional activity of fixed concentrations of the anti-CTLA-4 antibody AGEN1884 (IgG$_1$) and the anti-PD-1 antibody AGEN2034 (IgG$_4$ S228P) was tested in PBMCs from six different human donors. Five of the six donors were the same between the two experiments (donors 5, 7, 8, 9, and 10). The remaining donors were different between the two experiments (donors 6 and 11, as shown in FIGS. 3 and 4, respectively).

In each experiment, cryopreserved human PBMCs from six healthy donors were plated at 10$^5$ cells/well in medium (RPMI1640 supplemented with Normocin™ (Invivogen #ant-nr) and 10% heat-inactivated FBS (Gibco, Invitrogen Corporation)). PBMCs were stimulated with a sub-optimal concentration (100 ng/ml) of the SEA superantigen (Toxin Technologies, Cat #at101red) in the presence of 10 μg/mL of either (i) anti-CTLA-4 antibody AGEN1884 (IgG$_1$) or (ii) an isotype control antibody (IgG$_1$), in combination with 10 μg/ml of either (i) anti-PD-1 antibody AGEN2034 (IgG$_4$ S228P) or (ii) an isotype control antibody (IgG$_4$ S228P). Cells were then incubated for 5 days at 37° C. in 5% CO$_2$. Clarified supernatants were collected and stored at −80° C. until analysis. IL-2 concentrations in the culture supernatant were analyzed by AlphaLISA (Perkin Elmer, Cat #AL221F).

As shown in FIGS. 3 and 4, anti-PD-1 AGEN2034 antibody (IgG$_4$ S228P) and anti-CTLA-4 antibody AGEN1884 (IgG$_1$) consistently combined to enhance IL-2 secretion in cultures of activated human PBMCs above levels observed for each of these antibodies alone. This enhancement was observed in PBMCs obtained from seven different human donors.

7.1.3 Anti-CTLA-4 Antibody and Anti-PD-1 Antibody Combine to Enhance Central Memory T Cell Activation and Proliferation in a Non-Human Primate In this example, cynomolgus monkeys were administered anti-CTLA-4 antibody AGEN1884 (IgG$_1$) in combination with anti-PD-1 antibody AGEN2034 (IgG$_4$ S228P) and assessed for change in central memory T cell activation and proliferation three days after treatment.

Four cynomolgus monkeys were treated with AGEN1884 (IgG$_1$) in combination with AGEN2034 (IgG$_4$ S228P). For each monkey, 10 mg/kg of AGEN1884 (IgG$_1$) was administered first intravenously (slow bolus) with an unprimed stopcock, immediately followed by 3 mg/kg AGEN2034 (IgG$_4$ S228P) administered in the same fashion. Following antibody administration, a 3 mL saline flush was run through the bolus and stopcock to ensure that the correct and full amount of test material was administered. The dose volume for each animal was based on its most recent body weight measurement. Animals were temporarily restrained for dose administration and were not sedated. The first day of dosing was designated as Day 1. Blood samples (2 mL) were collected for PBMC isolation and flow cytometry analysis prior to dosing on Day −14 (3 animals) or Day −7 (1 animal), as well as three days after dosing. FIG. 5A shows the gating strategy for defining each of the T cell populations measured—i.e., CD4 naïve T cells (CD3+, CD4+, CD28+, CD95−), CD8 naïve T cells (CD3+, CD8+, CD28+, CD95−), CD4 central memory T cells (CD3+, CD4+, CD28+, CD95+), CD8 central memory T cells (CD3+, CD8+, CD28+, CD95+), CD4 effector memory T cells (CD3+, CD4+, CD28−, CD95+), and CD8 effector memory T cells (CD3+, CD8+, CD28−, CD95+). Shown in FIGS. 5B and 5C are representative flow cytometry data for Ki67 and ICOS expression in CD4+ and CD8+ central memory T cells, in pre-dose samples (Day −14) and at three days after antibody administration for one animal in the study. T cell activation and proliferation were found to be elevated in both CD4+ and CD8+ central memory T cell populations three days after antibody treatment, relative to pre-dose levels.

As shown in FIGS. 6A-6D, cynomolgus monkeys administered the anti-CTLA-4 antibody AGEN1884 (IgG$_1$) and anti-PD-1 antibody AGEN2034 (IgG$_4$ S228P) exhibited a substantial increase in ICOS+ and Ki67+ central memory T cells three days after antibody administration, relative to pre-dose samples. These results include the data shown in FIG. 5 for one of the animals in the study. A statistically significant increase in activated and proliferating populations was observed for CD8+ central memory T cells (FIGS. 6C and 6D). These data show that AGEN1884 (IgG$_1$) and AGEN2034 (IgG$_4$ S228P) combination treatment increased central memory T cell activation and proliferation.

7.2 Example 2: Epitope Mapping of Anti-CTLA-4 Antibody

The interaction of the Fab fragment of AGEN1884 (AGEN1884-Fab) with the extracellular domain of human CTLA-4 was studied by hydrogen-deuterium exchange (HDX) mass spectrometry. CTLA-4 extracellular domain alone or in combination with AGEN1884-Fab, in phosphate buffered saline solution at pH 7.4, was diluted with a ten-fold volume of deuterium oxide labeling buffer and incubated for varying periods of time (0, 60, 300, 1800, and 7200 seconds) at room temperature. Exchange of deuterium for hydrogen was quenched by adding one volume of 4 M guanidine hydrochloride, 0.85 M TCEP (tris(2-carboxyethyl)phosphine) buffer and the final pH was 2.5. Samples were then subjected to on-column pepsin/protease type XIII digestion and LC-MS analysis. Mass spectra were recorded in MS only mode. For the calculation of deuterium incorporation, the mass spectra for a given peptide were combined across the extracted ion chromatogram peak and the weighted average m/z was calculated. The mass increase from the mass of the native peptide (0 minute) to the weighted averaged mass corresponds to the level of deuterium incorporation. The deuterium buildup curves over exchange time for all the peptides were plotted for further analysis and were compared with HDExaminer software.

Most of the CTLA-4 peptides displayed identical or similar deuterium levels with and without the anti-human CTLA-4 Fab present. Several peptide segments, however, were found to have significantly decreased deuterium incorporation upon Fab binding. All the residues in this paragraph are numbered according to SEQ ID NO: 96. Two regions, residues 80-82 (QVT, SEQ ID NO: 102) and residues 135-149 (YPPPYYLGIGNGTQI, SEQ ID NO: 100), experienced strong deuterium protection when human CTLA-4 was bound to Fab. The strongest decrease in deuterium uptake was observed at residues 140-141 (YL) which thus appeared to be a main feature of the epitope of AGEN1884 on CTLA-4. Inspection of the sequences of human and cynomolgus monkey CTLA-4, both of which AGEN1884 binds strongly (data not shown), reveals almost complete sequence identity in the two regions described above, except for a methionine substitution for leucine at position 141 (FIG. 7A). In contrast, AGEN1884 does not bind to any significant extent to either mouse or rat CTLA-4 (data not shown) which differ from human CTLA-4 at residues 140-143 (YLGI, SEQ ID NO: 97) at three out of four positions (FIG. 7A). Further selectivity data show that AGEN1884 binds with high specificity to human and cynolmolgus monkey CTLA-4 and not to other related CD28 family members including CD28, ICOS, BTLA, and PD-1 (data not shown). Sequence comparison among these related proteins shows that the non-CTLA-4 proteins all differ at residues 140-143 (YLGI, SEQ ID NO: 97) (FIG. 7B), further supporting the importance of this epitope to the binding of AGEN1884.

7.3 Example 3: Epitope Mapping of Anti-PD-1 Antibody

The epitope of the anti-PD-1 antibody AGEN2034 was characterized using hydrogen-deuterium exchange (HDX) mass spectrometry and a Pepscan analysis.

7.3.1 Epitope Mapping of Anti-PD-1 Fab Using Hydrogen-Deuterium Exchange (HDX) Mass Spectrometry The interaction of a Fab fragment of AGEN2034 (AGEN2034-Fab) with the extracellular domain of human PD-1 was studied by hydrogen-deuterium exchange (HDX) mass spectrometry.

Recombinant His-tagged human PD-1 was obtained from Sino Biological Inc (Cat #10377-H08H). When used, deglycosylated PD-1 was prepared from 300 µg of recombinant His-tagged human PD-1 protein incubated with 6 µl of PNGase F at 37° C. for 4 hours. Fab fragment of an anti-PD-1 antibody was prepared from AGEN2034 by protease treatment.

For pepsin/protease XVIII digestion, 4.0 µg of native or deglycosylated human PD-1 in 125 µl control buffer (50 mM phosphate, 100 mM sodium chloride at pH 7.4) was denatured by adding 135 µl of 4 M guanidine hydrochloride, 0.85 M TCEP buffer (final pH is 2.5), and incubating the mixture for 3 minutes at 11° C. Then, the mixture was subjected to on-column pepsin/protease XVIII digestion using an in-house packed pepsin/protease XVIII column and the resultant peptides were analyzed using a UPLC-MS system comprised of a Waters Acquity UPLC coupled to a Q Exactive™ Hybrid Quadrupole-Orbitrap Mass Spectrometer (Thermo). The peptides were separated on a 50 mm×1 mm C8 column with a 19 min gradient from 2-27% solvent B (0.2% formic acid in acetonitrile). Peptide identification was done through searching MS/MS data against the human PD-1 sequence with Mascot. The mass tolerance for the precursor and product ions was 10 ppm and 0.05 Da, respectively.

10 µl human PD-1 (4.0 µg) or 10 µl human PD-1 and Fab mixture (4.0 µg: 4.0 µg) was incubated with 125 µl deuterium oxide labeling buffer (50 mM sodium phosphate, 100 mM sodium chloride at pD 7.4) for 0 second, 60 seconds, 600 seconds, and 3600 seconds at 11° C. Hydrogen/deuterium exchange was quenched by adding 135 µl of 4 M guanidine hydrochloride, 0.85 M TCEP buffer and the final pH was 2.5. Subsequently, the quenched samples were subjected to on column pepsin/protease XVIII digestion and LC-MS analysis as described above. The mass spectra were recorded in MS only mode.

Raw MS data was processed using HDX WorkBench, software for the analysis of H/D exchange MS data (J. Am. Soc. Mass Spectrom. 2012, 23 (9), 1512-1521, incorporated herein by reference in its entirety). The deuterium levels were calculated using the average mass difference between the deuteriated peptide and its native form (to).

Sequence coverage of 85.4% was achieved for deglycosylated human PD-1 without His-tag. Most PD-1 peptides displayed identical or similar deuterium levels with and without the anti-human PD-1 Fab present. Several peptide segments, however, were found to have significantly decreased deuterium incorporation upon Fab binding. All the residues in this paragraph are numbered according to SEQ ID NO: 96. Deglycosylated human PD-1 showed strong reduction in deuterium uptake upon binding to anti-human PD-1 Fab at residues 127-142 (SLAPKAQIKESL-RAEL, SEQ ID NO: 103). In addition, a decrease in deuterium uptake was observed at residues 25-42 (LD-SPDRPWNPPTFSPALL) (SEQ ID NO: 104) upon binding to anti-human PD-1 Fab.

7.3.2 Epitope Mapping of Anti-PD-1 Antibody Using a Pepscan Analysis

The binding of the anti-PD-1 antibody AGEN2034 was measured against synthesized PD-1 peptide fragments prepared as a chip-bound peptide array. Analysis was performed by Pepscan Presto BV, Lelystad, the Netherlands. Briefly, to reconstruct epitopes of human PD-1, a library of peptides was synthesized. An amino functionalized polypropylene support was obtained by grafting with a proprietary hydrophilic polymer formulation, followed by reaction with t-butyloxycarbonyl-hexamethylenediamine (BocHMDA)

using dicyclohexylcarbodiimide (DCC) with Nhydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer). Synthesis of structural mimics was conducted using Pepscan's proprietary Chemically Linked Peptides on Scaffolds (CLIPS) technology. CLIPS technology allows to structure peptides into single loops, double loops, triple loops, sheet-like folds, helix-like folds and combinations thereof. The binding of antibody to each of the synthesized peptides was tested in a PEPSCAN-based ELISA. The peptide arrays were incubated with primary antibody solution overnight at 4° C. After washing, the peptide arrays were incubated with a goat anti-human HRP conjugate (Southern Biotech, Cat #2010-05) for one hour at 25° C. After washing, the peroxidase substrate 2,2'-azino-di-3-ethylbenzthiazoline sulfonate (ABTS) and 20 µl/ml of 3% $H_2O_2$ were added. After one hour, the color development was measured and quantified with a charge coupled device (CCD)—camera and an image processing system.

The Pepscan study showed that the anti-PD-1 antibody AGEN2034 recognized stretches of human PD-1 including residues 26-35 (DSPDRPWNPP, SEQ ID NO: 105), residues 150-158 (EVPTAHPSP, SEQ ID NO: 106), and residues 126-133 (ISLAPKAQ, SEQ ID NO: 107), numbered according to SEQ ID NO: 96.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entireties and for all purposes to the same extent as if each individual reference (e.g., publication or patent or patent application) was specifically and individually indicated to be incorporated by reference in its entirety for all purposes.

Other embodiments are within the following claims.

What is claimed:

1. A method of increasing T cell activation in a subject that has cancer, the method comprising administering to the subject an effective amount of a therapeutic combination comprising a first isolated antibody that specifically binds to human CTLA-4 and a second isolated antibody that specifically binds to human PD-1, wherein:
    (a) the first isolated antibody comprises a heavy chain variable region (VH) comprising the complementarity determining regions CDRH1, CDRH2, and CDRH3 of the VH amino acid sequence of SEQ ID NO: 1 and a light chain variable region (VL) comprising the complementarity determining regions CDRL1, CDRL2, and CDRL3 of the VL amino acid sequence of SEQ ID NO: 14, and
    (b) the second isolated antibody comprises a heavy chain variable region (VH) comprising the complementarity determining regions CDRH1, CDRH2 and CDRH3 of the VH amino acid sequence of SEQ ID NO: 66 and a light chain variable region (VL) comprising the complementarity determining regions CDRL1, CDRL2 and CDRL3 of the VL amino acid sequence of SEQ ID NO: 74.

2. The method of claim 1, wherein CDRH1, CDRH2, CDRH3, CDRL1, CDRL2, and CDRL3 of the first isolated antibody comprise the amino acid sequences set forth in SEQ ID NOs: 20, 22, 24, 27, 30, and 36, respectively.

3. The method of claim 1, wherein the first isolated antibody comprises
    a heavy chain variable region and a light chain variable region comprising the amino acid sequences set forth in SEQ ID NOs: 1 and 14, respectively.

4. The method of claim 1, wherein the first isolated antibody comprises a heavy chain comprising the amino acid sequence of SEQ ID NO: 51, and a light chain comprising the amino acid sequence of SEQ ID NO: 59.

5. The method of claim 1, wherein the first isolated antibody comprises:
    (a) a heavy chain constant region selected from the group consisting of human IgG1, IgG2, IgG3, IgG4, IgA1, and IgA2;
    (b) a heavy chain constant region comprising the amino acid sequence of SEQ ID NO: 60;
    (c) an IgG1 heavy chain constant region comprising S239D/I332E mutations, numbered according to the EU numbering system;
    (d) a heavy chain constant region comprising the amino acid sequence of SEQ ID NO: 61;
    (e) an IgG1 heavy chain constant region comprising S239D/A330L/I332E mutations, numbered according to the EU numbering system;
    (f) a heavy chain constant region comprising the amino acid sequence of SEQ ID NO: 62;
    (g) an IgG1 heavy chain constant region comprising L235V/F243L/R292P/Y300L/P396L mutations, numbered according to the EU numbering system;
    (h) a heavy chain constant region comprising the amino acid sequence of SEQ ID NO: 63;
    (i) an IgG1 heavy chain constant region, wherein the IgG1 heavy chain constant region is non-fucosylated;
    (j) a light chain constant region selected from the group consisting of human Igκ and Igλ; or
    (k) a light chain constant region comprising the amino acid sequence of SEQ ID NO: 64.

6. The method of claim 1, wherein CDRH1, CDRH2, CDRH3, CDRL1, CDRL2, and CDRL3 of the second isolated antibody comprise the amino acid sequences set forth in SEQ ID NOs: 75, 76, 81, 83, 84, and 85, respectively.

7. The method of claim 1, wherein the second isolated antibody comprises a heavy chain variable region and a light chain variable region comprising the amino acid sequences set forth in SEQ ID NOs: 66 and 74, respectively.

8. The method of claim 1, wherein the second isolated antibody comprises a heavy chain comprising the amino acid sequence of SEQ ID NO: 91 and a light chain comprising the amino acid sequence of SEQ ID NO: 93.

9. The method of claim 1, wherein:
   (a) the first isolated antibody comprises a heavy chain variable region and a light chain variable region comprising the amino acid sequences set forth in SEQ ID NOs: 1 and 14, respectively; and
   (b) the second isolated antibody comprises a heavy chain variable region and a light chain variable region comprising the amino acid sequences set forth in SEQ ID NOs: 66 and 74, respectively.

10. The method of claim 1, wherein:
    (a) the first isolated antibody comprises a heavy chain comprising the amino acid sequence of SEQ ID NO: 51 and a light chain comprising the amino acid sequence of SEQ ID NO: 59; and
    (b) the second isolated antibody comprises a heavy chain comprising the amino acid sequence of SEQ ID NO: 91 and a light chain comprising the amino acid sequence of SEQ ID NO: 93.

11. The method of claim 1, wherein the second isolated antibody comprises:
    (a) a heavy chain constant region selected from the group consisting of human IgG1, IgG2, IgG3, IgG4, IgA1, and IgA2;
    (b) an IgG1 heavy chain constant region comprising an N297A mutation, numbered according to the EU numbering system;
    (c) a heavy chain constant region comprising the amino acid sequence of SEQ ID NO: 94;
    (d) an IgG4 heavy chain constant region comprising an S228P mutation, numbered according to the EU numbering system;
    (e) a heavy chain constant region comprising the amino acid sequence of SEQ ID NO: 95;
    (f) a light chain constant region selected from the group consisting of human Igκ and Igλ; or
    (g) a light chain constant region comprising the amino acid sequence of SEQ ID NO: 64.

12. The method of claim 1, wherein:
    (a) the first isolated antibody is administered at 0.3 mg/kg or 1 mg/kg;
    (b) the second isolated antibody is administered at 1 mg/kg, 3 mg/kg, or 6 mg/kg;
    (c) the second isolated antibody is administered at a dose of 200 mg;
    (d) the first isolated antibody is administered at 0.3 mg/kg, and the second isolated antibody is administered at 1 mg/kg;
    (e) the first isolated antibody is administered at 1 mg/kg, and the second isolated antibody is administered at 1 mg/kg;
    (f) the first isolated antibody is administered at 1 mg/kg, and the second isolated antibody is administered at 3 mg/kg;
    (g) the first isolated antibody is administered at 1 mg/kg, and the second isolated antibody is administered at 6 mg/kg;
    (h) the first isolated antibody is administered every six weeks;
    (i) the second isolated antibody is administered every two weeks or every three weeks;
    (j) the first isolated antibody is administered at 0.3 mg/kg every six weeks, and the second isolated antibody is administered at 1 mg/kg every two weeks;
    (k) the first isolated antibody is administered at 1 mg/kg every six weeks, and the second isolated antibody is administered at 1 mg/kg every two weeks;
    (l) the first isolated antibody is administered at 1 mg/kg every six weeks, and the second isolated antibody is administered at 3 mg/kg every two weeks; or
    (m) the first isolated antibody is administered at 1 mg/kg every six weeks, and the second isolated antibody is administered at 6 mg/kg every three weeks.

13. The method of claim 1, wherein:
    (a) the cancer is a metastatic or locally advanced solid tumor;
    (b) the cancer is a metastatic or locally advanced, unresectable squamous cell carcinoma, adenosquamous carcinoma, or adenocarcinoma of the cervix,
    (c) no standard therapy is available for the cancer;
    (d) the cancer is refractory to a standard therapy,
    (e) the cancer has relapsed after a standard therapy;
    (f) the cancer is HPV positive;
    (g) the cancer is a non-small cell lung cancer (NSCLC);
    (h) the cancer is a Stage IV, metastatic, or locally advanced NSCLC;
    (i) the cancer is a non-small cell lung cancer (NSCLC), and wherein the NSCLC has no EGFR or ALK genomic tumor aberrations;
    (j) the cancer is a non-small cell lung cancer (NSCLC), and wherein the subject has received no prior systemic chemotherapy treatment for the NSCLC;
    (k) the cancer is a cutaneous squamous-cell carcinoma (cSCC);
    (l) the cancer is a cutaneous squamous-cell carcinoma (cSCC), and wherein is not curable with radiation therapy; or
    (m) the percentage of tumor cells in a sample of the cancer that exhibit detectable membrane expression of PD-L1 is at least 1%, 2%, 3%, 4%, 5%, 10%, 15%, 20%, 25%, 30%, 35%, 40%, 45%, 50%, 60%, 70%, 80%, or 90%.

14. The method of claim 13, wherein:
    (a) the first and second isolated antibodies are administered as a first cancer therapy after diagnosis of the cancer;
    (b) the first and second isolated antibodies are administered as a first cancer therapy after diagnosis of tumor progression that has occurred despite previous treatment of the cancer with a different cancer therapy; or
    (c) the first and second isolated antibodies are administered as a first cancer therapy after diagnosis of toxicity of a different cancer therapy.

15. A method of increasing T cell activation in a subject that has cervical cancer, the method comprising administering to the subject an effective amount of a therapeutic combination comprising a first isolated antibody that specifically binds to human CTLA-4 and a second isolated antibody that specifically binds to human PD-1, wherein:
    (a) the first isolated antibody comprises a heavy chain variable region (VH) comprising the complementarity determining regions CDRH1, CDRH2, and CDRH3 of the VH amino acid sequence of SEQ ID NO: 1 and a light chain variable region (VL) comprising the complementarity determining regions CDRL1, CDRL2, and CDRL3 of the VL amino acid sequence of SEQ ID NO: 14, and
    (b) the second isolated antibody comprises a heavy chain variable region (VH) comprising the complementarity determining regions CDRH1, CDRH2 and CDRH3 of the VH amino acid sequence of SEQ ID NO: 66 and a light chain variable region (VL) comprising the complementarity determining regions CDRL1, CDRL2 and CDRL3 of the VL amino acid sequence of SEQ ID NO: 74.

16. The method of claim 15, wherein the cancer has relapsed after platinum-based chemotherapy.

17. The method of claim 15, wherein the cancer is advanced or metastatic.

18. The method of claim 15, wherein:
(a) the first isolated antibody comprises a heavy chain variable region and a light chain variable region comprising the amino acid sequences set forth in SEQ ID NOs: 1 and 14, respectively; and
(b) the second isolated antibody comprises a heavy chain variable region and a light chain variable region comprising the amino acid sequences set forth in SEQ ID NOs: 66 and 74, respectively.

19. The method of claim 15, wherein:
(a) the first isolated antibody comprises a heavy chain comprising the amino acid sequence of SEQ ID NO: 51 and a light chain comprising the amino acid sequence of SEQ ID NO: 59; and
(b) the second isolated antibody comprises a heavy chain comprising the amino acid sequence of SEQ ID NO: 91 and a light chain comprising the amino acid sequence of SEQ ID NO: 93.

* * * * *

SEQUENCE LISTING

```
<160> NUMBER OF SEQ ID NOS: 120

<210> SEQ ID NO 1
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 1

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser
        115

<210> SEQ ID NO 2

<400> SEQUENCE: 2

000

<210> SEQ ID NO 3

<400> SEQUENCE: 3

000
```

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Val Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser
        115
```

<210> SEQ ID NO 10
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser
        115

<210> SEQ ID NO 11
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser
        115

<210> SEQ ID NO 12
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Val Trp Val
        35                  40                  45

Ser Ser Ile Ser Ser Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asn Ile Trp Gly Gln Gly Thr
            100                 105                 110

Met Val Thr Val Ser Ser
        115
```

<210> SEQ ID NO 13
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

```
Glu Val Gln Leu Val Glu Ser Gly Gly Gly Leu Val Gln Pro Gly Gly
1               5                   10                  15

Ser Leu Thr Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser
        115
```

<210> SEQ ID NO 14
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Gly Trp Tyr Gln Gln Lys Pro Gly Gln Ala Pro Arg Leu Leu Ile
        35                  40                  45
```

Tyr Gly Ala Ser Thr Arg Ala Thr Gly Ile Pro Asp Arg Phe Ser Gly
        50                  55                  60

Ser Gly Ser Gly Thr Asp Phe Thr Leu Thr Ile Thr Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys
            100                 105

<210> SEQ ID NO 15
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Thr Tyr
            20                  25                  30

Leu Ala Trp Tyr Gln His Lys Val Gly Gln Ala Pro Arg Leu Leu Ile
        35                  40                  45

Tyr Gly Ala Ser Arg Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys
            100                 105

<210> SEQ ID NO 16
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Ser Leu Leu Ile
        35                  40                  45

Tyr Ala Thr Ser Ser Arg Ala Thr Gly Ile Pro Asp Arg Phe Ser Gly
    50                  55                  60

Ser Val Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys
            100                 105

-continued

```
<210> SEQ ID NO 17
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Glu Ile Val Leu Thr Gln Ser Pro Ala Thr Leu Ser Phe Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
50                  55                  60

Ser Gly Ser Gly Thr Asp Phe Thr Phe Thr Ile Ser Arg Leu Glu Pro
65                  70                  75                  80

Glu Asp Phe Ala Val Tyr Tyr Cys Gln Gln Tyr Gly Ser Ser Pro Phe
                85                  90                  95

Thr Phe Gly Pro Gly Thr Lys Val Asp Ile Lys
            100                 105

<210> SEQ ID NO 18
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Ala Ala Ser Thr Arg Ala Thr Gly Ile Pro Asp Arg Phe Ser Gly
50                  55                  60

Ser Ala Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys
            100                 105

<210> SEQ ID NO 19
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Gly Ser Ser Pro Phe
                85                  90                  95

Thr Phe Gly Pro Gly Thr Lys Val Asp Ile Lys
                100                 105

<210> SEQ ID NO 20
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ser Tyr Ser Met Asn
1               5

<210> SEQ ID NO 21
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ser Tyr Ala Met Ser
1               5

<210> SEQ ID NO 22
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ser Ile Ser Ser Ser Ser Tyr Ile Tyr Tyr Ala Asp Ser Val Lys
1               5                   10                  15

Gly

<210> SEQ ID NO 23

<400> SEQUENCE: 23

000

<210> SEQ ID NO 24
<211> LENGTH: 9
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 24

Val Gly Leu Met Gly Pro Phe Asp Ile
1               5

<210> SEQ ID NO 25

<400> SEQUENCE: 25

000

<210> SEQ ID NO 26
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Val Gly Leu Met Gly Pro Phe Asn Ile
1               5

<210> SEQ ID NO 27
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Arg Ala Ser Gln Ser Val Ser Arg Tyr Leu Gly
1               5                   10

<210> SEQ ID NO 28
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Arg Ala Ser Gln Ser Val Gly Thr Tyr Leu Ala
1               5                   10

<210> SEQ ID NO 29
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Arg Ala Ser Gln Ser Val Ser Ser Tyr Leu Ala
1               5                   10

<210> SEQ ID NO 30
<211> LENGTH: 7
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gly Ala Ser Thr Arg Ala Thr
1               5

<210> SEQ ID NO 31
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Gly Ala Ser Arg Arg Ala Thr
1               5

<210> SEQ ID NO 32
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Ala Thr Ser Ser Arg Ala Thr
1               5

<210> SEQ ID NO 33
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Gly Ala Ser Ser Arg Ala Thr
1               5

<210> SEQ ID NO 34
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ala Ala Ser Thr Arg Ala Thr
1               5

<210> SEQ ID NO 35
<211> LENGTH: 7
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 35

Gly Ala Ser Asn Arg Ala Thr
1               5

<210> SEQ ID NO 36
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Gln Gln Tyr Gly Ser Ser Pro Trp Thr
1               5

<210> SEQ ID NO 37
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Gln Gln Tyr Gly Thr Ser Pro Trp Thr
1               5

<210> SEQ ID NO 38
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Gln Gln Tyr Gly Ser Ser Pro Phe Thr
1               5

<210> SEQ ID NO 39
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Ser"
<220> FEATURE:
<221> NAME/KEY: MISC_FEATURE
<222> LOCATION: (1)..(5)
<223> OTHER INFORMATION: /note="Variant residues given in the sequence
      have no preference with respect to those in the annotations
      for variant positions"

<400> SEQUENCE: 39
```

```
Ser Tyr Ser Met Asn
1               5

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (7)..(7)
<223> OTHER INFORMATION: /replace="Gly"
<220> FEATURE:
<221> NAME/KEY: VARIANT
<222> LOCATION: (8)..(8)
<223> OTHER INFORMATION: /replace="Ser" or "Thr"
<220> FEATURE:
<221> NAME/KEY: VARIANT
<222> LOCATION: (11)..(11)
<223> OTHER INFORMATION: /replace="Ala"
<220> FEATURE:
<221> NAME/KEY: MISC_FEATURE
<222> LOCATION: (1)..(11)
<223> OTHER INFORMATION: /note="Variant residues given in the sequence
      have no preference with respect to those in the annotations
      for variant positions"

<400> SEQUENCE: 43

Arg Ala Ser Gln Ser Val Ser Arg Tyr Leu Gly
1               5                   10

<210> SEQ ID NO 44
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Ala"
<220> FEATURE:
<221> NAME/KEY: VARIANT
<222> LOCATION: (2)..(2)
<223> OTHER INFORMATION: /replace="Thr"
<220> FEATURE:
<221> NAME/KEY: VARIANT
<222> LOCATION: (4)..(4)
<223> OTHER INFORMATION: /replace="Ser" or "Arg" or "Asn"
<220> FEATURE:
```

```
<221> NAME/KEY: MISC_FEATURE
<222> LOCATION: (1)..(7)
<223> OTHER INFORMATION: /note="Variant residues given in the sequence
      have no preference with respect to those in the annotations
      for variant positions"

<400> SEQUENCE: 44

Gly Ala Ser Thr Arg Ala Thr
1               5

<210> SEQ ID NO 45
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="Thr"
<220> FEATURE:
<221> NAME/KEY: VARIANT
<222> LOCATION: (8)..(8)
<223> OTHER INFORMATION: /replace="Phe"
<220> FEATURE:
<221> NAME/KEY: MISC_FEATURE
<222> LOCATION: (1)..(9)
<223> OTHER INFORMATION: /note="Variant residues given in the sequence
      have no preference with respect to those in the annotations
      for variant positions"

<400> SEQUENCE: 45

Gln Gln Tyr Gly Ser Ser Pro Trp Thr
1               5

<210> SEQ ID NO 46

<400> SEQUENCE: 46

000

<210> SEQ ID NO 47
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (9)..(9)
<223> OTHER INFORMATION: /replace="Ala"
<220> FEATURE:
<221> NAME/KEY: VARIANT
<222> LOCATION: (13)..(13)
<223> OTHER INFORMATION: /replace="Val" or "Phe"
<220> FEATURE:
<221> NAME/KEY: VARIANT
<222> LOCATION: (30)..(30)
<223> OTHER INFORMATION: /replace="Gly"
<220> FEATURE:
<221> NAME/KEY: VARIANT
<222> LOCATION: (31)..(31)
<223> OTHER INFORMATION: /replace="Thr" or "Ser"
<220> FEATURE:
<221> NAME/KEY: VARIANT
<222> LOCATION: (34)..(34)
<223> OTHER INFORMATION: /replace="Ala"
<220> FEATURE:
<221> NAME/KEY: VARIANT
<222> LOCATION: (38)..(38)
```

```
<223> OTHER INFORMATION: /replace="His"
<220> FEATURE:
<221> NAME/KEY: VARIANT
<222> LOCATION: (40)..(40)
<223> OTHER INFORMATION: /replace="Val"
<220> FEATURE:
<221> NAME/KEY: VARIANT
<222> LOCATION: (45)..(45)
<223> OTHER INFORMATION: /replace="Ser"
<220> FEATURE:
<221> NAME/KEY: VARIANT
<222> LOCATION: (50)..(50)
<223> OTHER INFORMATION: /replace="Ala"
<220> FEATURE:
<221> NAME/KEY: VARIANT
<222> LOCATION: (51)..(51)
<223> OTHER INFORMATION: /replace="Thr"
<220> FEATURE:
<221> NAME/KEY: VARIANT
<222> LOCATION: (53)..(53)
<223> OTHER INFORMATION: /replace="Arg" or "Ser" or "Asn"
<220> FEATURE:
<221> NAME/KEY: VARIANT
<222> LOCATION: (60)..(60)
<223> OTHER INFORMATION: /replace="Ala"
<220> FEATURE:
<221> NAME/KEY: VARIANT
<222> LOCATION: (66)..(66)
<223> OTHER INFORMATION: /replace="Val" or "Ala"
<220> FEATURE:
<221> NAME/KEY: VARIANT
<222> LOCATION: (73)..(73)
<223> OTHER INFORMATION: /replace="Phe"
<220> FEATURE:
<221> NAME/KEY: VARIANT
<222> LOCATION: (76)..(76)
<223> OTHER INFORMATION: /replace="Ser"
<220> FEATURE:
<221> NAME/KEY: VARIANT
<222> LOCATION: (77)..(77)
<223> OTHER INFORMATION: /replace="Ser"
<220> FEATURE:
<221> NAME/KEY: VARIANT
<222> LOCATION: (93)..(93)
<223> OTHER INFORMATION: /replace="Thr"
<220> FEATURE:
<221> NAME/KEY: VARIANT
<222> LOCATION: (96)..(96)
<223> OTHER INFORMATION: /replace="Phe"
<220> FEATURE:
<221> NAME/KEY: VARIANT
<222> LOCATION: (100)..(100)
<223> OTHER INFORMATION: /replace="Pro"
<220> FEATURE:
<221> NAME/KEY: VARIANT
<222> LOCATION: (105)..(105)
<223> OTHER INFORMATION: /replace="Asp"
<220> FEATURE:
<221> NAME/KEY: MISC_FEATURE
<222> LOCATION: (1)..(107)
<223> OTHER INFORMATION: /note="Variant residues given in the sequence
      have no preference with respect to those in the annotations
      for variant positions"

<400> SEQUENCE: 47

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Gly Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Ser Gly
    50                  55                  60

Ser Gly Ser Gly Thr Asp Phe Thr Leu Thr Ile Thr Arg Leu Glu Pro
```

-continued

```
                65                  70                  75                  80
Glu Asp Phe Ala Val Tyr Tyr Cys Gln Gln Tyr Gly Ser Ser Pro Trp
                    85                  90                  95
Thr Phe Gly Gln Gly Thr Lys Val Glu Ile Lys
                    100                 105

<210> SEQ ID NO 48
<211> LENGTH: 98
<212> TYPE: PRT
<213> ORGANISM: Homo sapiens

<400> SEQUENCE: 48

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Ser Tyr
                20                  25                  30
Ser Met Asn Trp Val Arg Gln Ala Pro Gly Lys Gly Leu Glu Trp Val
            35                  40                  45
Ser Ser Ile Ser Ser Ser Ser Tyr Ile Tyr Tyr Ala Asp Ser Val
        50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                    85                  90                  95
Ala Arg

<210> SEQ ID NO 49
<211> LENGTH: 96
<212> TYPE: PRT
<213> ORGANISM: Homo sapiens

<400> SEQUENCE: 49

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
                20                  25                  30
Tyr Leu Ala Trp Tyr Gln Gln Lys Pro Gly Gln Ala Pro Arg Leu Leu
            35                  40                  45
Ile Tyr Gly Ala Ser Ser Arg Ala Thr Gly Ile Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                    85                  90                  95

<210> SEQ ID NO 50
<211> LENGTH: 96
<212> TYPE: PRT
<213> ORGANISM: Homo sapiens

<400> SEQUENCE: 50

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
                20                  25                  30
Leu Ala Trp Tyr Gln Gln Lys Pro Gly Gln Ala Pro Arg Leu Leu Ile
            35                  40                  45
```

Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

<210> SEQ ID NO 51
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr

```
305                 310                 315                 320
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 52
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
                35                  40                  45

Ser Ser Ile Ser Ser Ser Ser Tyr Ile Tyr Tyr Ala Asp Ser Val
                50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
                100                 105                 110

Met Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Arg Val Glu Pro Lys Ser Cys Asp Lys Thr
                210                 215                 220
```

```
His Thr Cys Pro Pro Cys Pro Ala Pro Glu Leu Leu Gly Gly Pro Asp
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Glu Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 53
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Val Gly Leu Met Gly Pro Phe Asp Ile Trp Gly Gln Gly Thr
        100                 105                 110

Met Val Thr Val Ser Ser Ala Ser Thr Lys Gly Pro Ser Val Phe Pro
    115                 120                 125
```

```
Leu Ala Pro Ser Ser Lys Ser Thr Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Asp
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Leu Pro Glu Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 54
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
```

```
            35                  40                  45
Ser Ser Ile Ser Ser Ser Ser Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Val Gly Leu Met Gly Pro Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Val Gly Gly Pro Ser
225                 230                 235                 240

Val Phe Leu Leu Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Pro Glu Glu Gln Tyr Asn Ser Thr Leu Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Leu Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 55
```

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Gly Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Ser Gly
    50                  55                  60

Ser Gly Ser Gly Thr Asp Phe Thr Leu Thr Ile Thr Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 60
<211> LENGTH: 329
<212> TYPE: PRT
<213> ORGANISM: Homo sapiens

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 61
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Glu Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 62
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 62

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Leu Pro Glu Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 63
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 63

```
Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Val Gly Gly Pro Ser Val Phe Leu Leu Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Leu Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Leu Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 64
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
```

35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 65
<211> LENGTH: 223
<212> TYPE: PRT
<213> ORGANISM: Homo sapiens

<400> SEQUENCE: 65

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
                35                  40                  45

Ser Ser Arg Gly Ile Ala Ser Phe Val Cys Glu Tyr Ala Ser Pro Gly
 50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Tyr Leu Gly Ile Gly
        130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 66
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Gln Val Gln Leu Val Glu Ser Gly Gly Gly Val Val Gln Pro Gly Arg
1               5                   10                  15

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ser Asn Gly Asp His Trp Gly Gln Gly Thr Leu Val Thr Val Ser
            100                 105                 110

Ser

<210> SEQ ID NO 67
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ser Asn Val Asp Tyr Trp Gly Gln Gly Thr Leu Val Thr Val Ser
            100                 105                 110

Ser

<210> SEQ ID NO 68
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
 50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Asn Gly Asp Tyr Trp Gly Gln Gly Thr Leu Val Thr Val Ser
            100                 105                 110

Ser
```

```
<210> SEQ ID NO 69
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Asn Gly Asp Tyr Trp Gly Gln Gly Thr Leu Val Thr Val Ser
            100                 105                 110

Ser
```

```
<210> SEQ ID NO 70
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Glu Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Asn Gly Asp His Trp Gly Gln Gly Thr Leu Val Thr Val Ser
            100                 105                 110
```

Ser

<210> SEQ ID NO 71
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

```
Gln Val Gln Leu Val Glu Ser Gly Gly Met Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Phe Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Gly Asp His Trp Gly Gln Gly Thr Leu Val Thr Val Ser
            100                 105                 110

Ser
```

<210> SEQ ID NO 72
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Gly Asp His Trp Gly His Gly Thr Leu Val Thr Val Ser
            100                 105                 110

Ser
```

<210> SEQ ID NO 73
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Met Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Gly Asp His Trp Gly Gln Gly Thr Leu Val Thr Val Ser
            100                 105                 110

Ser
```

<210> SEQ ID NO 74
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
                85                  90                  95

Thr Phe Gly Gln Gly Thr Lys Val Glu Ile Lys
            100                 105
```

<210> SEQ ID NO 75
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

```
Ser Tyr Gly Met His
1               5
```

<210> SEQ ID NO 76
<211> LENGTH: 17

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Val Ile Trp Tyr Asp Gly Ser Asn Lys Tyr Tyr Ala Asp Ser Val Lys
1               5                   10                  15
Gly

<210> SEQ ID NO 77
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Val Ile Trp Tyr Asp Gly Ser Asn Glu Tyr Tyr Ala Asp Ser Val Lys
1               5                   10                  15
Gly

<210> SEQ ID NO 78
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Val Ile Trp Phe Asp Gly Ser Asn Lys Tyr Tyr Ala Asp Ser Val Lys
1               5                   10                  15
Gly

<210> SEQ ID NO 79
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Val Ile Trp Tyr Asp Gly Ser Asn Lys Tyr Tyr Ala Asp Ser Val Met
1               5                   10                  15
Gly

<210> SEQ ID NO 80
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Asn Val Asp Tyr
1
```

```
<210> SEQ ID NO 81
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Asn Gly Asp His
1

<210> SEQ ID NO 82
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Asn Gly Asp Tyr
1

<210> SEQ ID NO 83
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Arg Ala Ser Gln Ser Val Ser Ser Asn Leu Ala
1               5                   10

<210> SEQ ID NO 84
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Gly Ala Ser Thr Arg Ala Thr
1               5

<210> SEQ ID NO 85
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Gln Gln Tyr Asn Asn Trp Pro Arg Thr
1               5

<210> SEQ ID NO 86
<211> LENGTH: 17
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="Phe"
<220> FEATURE:
<221> NAME/KEY: VARIANT
<222> LOCATION: (9)..(9)
<223> OTHER INFORMATION: /replace="Glu"
<220> FEATURE:
<221> NAME/KEY: VARIANT
<222> LOCATION: (16)..(16)
<223> OTHER INFORMATION: /replace="Met"
<220> FEATURE:
<221> NAME/KEY: MISC_FEATURE
<222> LOCATION: (1)..(17)
<223> OTHER INFORMATION: /note="Variant residues given in the sequence
      have no preference with respect to those in the annotations
      for variant positions"

<400> SEQUENCE: 86

Val Ile Trp Tyr Asp Gly Ser Asn Lys Tyr Tyr Ala Asp Ser Val Lys
1               5                   10                  15

Gly

<210> SEQ ID NO 87
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Val"
<220> FEATURE:
<221> NAME/KEY: VARIANT
<222> LOCATION: (4)..(4)
<223> OTHER INFORMATION: /replace="Tyr"
<220> FEATURE:
<221> NAME/KEY: MISC_FEATURE
<222> LOCATION: (1)..(4)
<223> OTHER INFORMATION: /note="Variant residues given in the sequence
      have no preference with respect to those in the annotations
      for variant positions"

<400> SEQUENCE: 87

Asn Gly Asp His
1

<210> SEQ ID NO 88
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (11)..(11)
<223> OTHER INFORMATION: /replace="Met"
<220> FEATURE:
<221> NAME/KEY: VARIANT
<222> LOCATION: (53)..(53)
<223> OTHER INFORMATION: /replace="Phe"
<220> FEATURE:
```

```
<221> NAME/KEY: VARIANT
<222> LOCATION: (58)..(58)
<223> OTHER INFORMATION: /replace="Glu"
<220> FEATURE:
<221> NAME/KEY: VARIANT
<222> LOCATION: (65)..(65)
<223> OTHER INFORMATION: /replace="Met"
<220> FEATURE:
<221> NAME/KEY: VARIANT
<222> LOCATION: (98)..(98)
<223> OTHER INFORMATION: /replace="Thr"
<220> FEATURE:
<221> NAME/KEY: VARIANT
<222> LOCATION: (100)..(100)
<223> OTHER INFORMATION: /replace="Val"
<220> FEATURE:
<221> NAME/KEY: VARIANT
<222> LOCATION: (102)..(102)
<223> OTHER INFORMATION: /replace="Tyr"
<220> FEATURE:
<221> NAME/KEY: VARIANT
<222> LOCATION: (105)..(105)
<223> OTHER INFORMATION: /replace="His"
<220> FEATURE:
<221> NAME/KEY: MISC_FEATURE
<222> LOCATION: (1)..(113)
<223> OTHER INFORMATION: /note="Variant residues given in the sequence
      have no preference with respect to those in the annotations
      for variant positions"

<400> SEQUENCE: 88

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Gly Asp His Trp Gly Gln Gly Thr Leu Val Thr Val Ser
            100                 105                 110

Ser

<210> SEQ ID NO 89
<211> LENGTH: 98
<212> TYPE: PRT
<213> ORGANISM: Homo sapiens

<400> SEQUENCE: 89

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

Ala Arg

<210> SEQ ID NO 90
<211> LENGTH: 95
<212> TYPE: PRT
<213> ORGANISM: Homo sapiens

<400> SEQUENCE: 90

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95
```

<210> SEQ ID NO 91
<211> LENGTH: 439
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Gly Asp His Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
```

```
            195                 200                 205
Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Gln Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly
        435

<210> SEQ ID NO 92
<211> LENGTH: 442
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Gly Asp His Trp Gly Gln Gly Thr Leu Val Thr Val Ser
            100                 105                 110
```

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Ala Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440

<210> SEQ ID NO 93
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 94
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp

```
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 95
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 96
<211> LENGTH: 288
<212> TYPE: PRT
<213> ORGANISM: Homo sapiens

<400> SEQUENCE: 96

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
```

```
              210                 215                 220
Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 97
<211> LENGTH: 4
<212> TYPE: PRT
<213> ORGANISM: Homo sapiens

<400> SEQUENCE: 97

Tyr Leu Gly Ile
1

<210> SEQ ID NO 98
<211> LENGTH: 9
<212> TYPE: PRT
<213> ORGANISM: Homo sapiens

<400> SEQUENCE: 98

Tyr Pro Pro Pro Tyr Tyr Leu Gly Ile
1               5

<210> SEQ ID NO 99
<211> LENGTH: 10
<212> TYPE: PRT
<213> ORGANISM: Homo sapiens

<400> SEQUENCE: 99

Tyr Leu Gly Ile Gly Asn Gly Thr Gln Ile
1               5                   10

<210> SEQ ID NO 100
<211> LENGTH: 15
<212> TYPE: PRT
<213> ORGANISM: Homo sapiens

<400> SEQUENCE: 100

Tyr Pro Pro Pro Tyr Tyr Leu Gly Ile Gly Asn Gly Thr Gln Ile
1               5                   10                  15

<210> SEQ ID NO 101
<211> LENGTH: 7
<212> TYPE: PRT
<213> ORGANISM: Homo sapiens

<400> SEQUENCE: 101

Met Tyr Pro Pro Pro Tyr Tyr
1               5

<210> SEQ ID NO 102
<211> LENGTH: 3
<212> TYPE: PRT
<213> ORGANISM: Homo sapiens

<400> SEQUENCE: 102

Gln Val Thr
1

<210> SEQ ID NO 103
<211> LENGTH: 16
<212> TYPE: PRT
<213> ORGANISM: Homo sapiens

<400> SEQUENCE: 103

Ser Leu Ala Pro Lys Ala Gln Ile Lys Glu Ser Leu Arg Ala Glu Leu
1               5                   10                  15

<210> SEQ ID NO 104
<211> LENGTH: 18
<212> TYPE: PRT
<213> ORGANISM: Homo sapiens

<400> SEQUENCE: 104

Leu Asp Ser Pro Asp Arg Pro Trp Asn Pro Thr Phe Ser Pro Ala
1               5                   10                  15

Leu Leu

<210> SEQ ID NO 105
<211> LENGTH: 10
<212> TYPE: PRT
<213> ORGANISM: Homo sapiens

<400> SEQUENCE: 105

Asp Ser Pro Asp Arg Pro Trp Asn Pro Pro
1               5                   10

<210> SEQ ID NO 106
<211> LENGTH: 9
<212> TYPE: PRT
<213> ORGANISM: Homo sapiens

<400> SEQUENCE: 106

Glu Val Pro Thr Ala His Pro Ser Pro
1               5

<210> SEQ ID NO 107
<211> LENGTH: 8
<212> TYPE: PRT
<213> ORGANISM: Homo sapiens

<400> SEQUENCE: 107

Ile Ser Leu Ala Pro Lys Ala Gln
1               5

<210> SEQ ID NO 108
<211> LENGTH: 223
<212> TYPE: PRT
<213> ORGANISM: Macaca fascicularis

<400> SEQUENCE: 108

Met Ala Cys Leu Gly Phe Gln Arg His Lys Ala Arg Leu Asn Leu Ala
1               5                   10                  15

Thr Arg Thr Arg Pro Tyr Thr Leu Leu Phe Ser Leu Leu Phe Ile Pro
                20                  25                  30

Val Phe Ser Lys Ala Met His Val Ala Gln Pro Ala Val Val Leu Ala
            35                  40                  45

Asn Ser Arg Gly Ile Ala Ser Phe Val Cys Glu Tyr Ala Ser Pro Gly
        50                  55                  60

Lys Ala Thr Glu Val Arg Val Thr Val Leu Arg Gln Ala Asp Ser Gln

```
65                  70                  75                  80
Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Tyr Tyr Met Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
            195                 200                 205

Pro Glu Cys Glu Lys Gln Phe Gln Pro Tyr Phe Ile Pro Ile Asn
    210                 215                 220

<210> SEQ ID NO 109
<211> LENGTH: 223
<212> TYPE: PRT
<213> ORGANISM: Mus musculus

<400> SEQUENCE: 109

Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
            20                  25                  30

Val Phe Ser Glu Ala Ile Gln Val Thr Gln Pro Ser Val Val Leu Ala
        35                  40                  45

Ser Ser His Gly Val Ala Ser Phe Pro Cys Glu Tyr Ser Pro Ser His
    50                  55                  60

Asn Thr Asp Glu Val Arg Val Thr Val Leu Arg Gln Thr Asn Asp Gln
65                  70                  75                  80

Met Thr Glu Val Cys Ala Thr Thr Phe Thr Glu Lys Asn Thr Val Gly
                85                  90                  95

Phe Leu Asp Tyr Pro Phe Cys Ser Gly Thr Phe Asn Glu Ser Arg Val
            100                 105                 110

Asn Leu Thr Ile Gln Gly Leu Arg Ala Val Asp Thr Gly Leu Tyr Leu
        115                 120                 125

Cys Lys Val Glu Leu Met Tyr Pro Pro Tyr Phe Val Gly Met Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Val Ala Val Ser Leu Gly Leu Phe Phe
                165                 170                 175

Tyr Ser Phe Leu Val Ser Ala Val Ser Leu Ser Lys Met Leu Lys Lys
                180                 185                 190

Arg Ser Pro Leu Thr Thr Gly Val Tyr Val Lys Met Pro Pro Thr Glu
            195                 200                 205

Pro Glu Cys Glu Lys Gln Phe Gln Pro Tyr Phe Ile Pro Ile Asn
    210                 215                 220
```

```
<210> SEQ ID NO 110
<211> LENGTH: 223
<212> TYPE: PRT
<213> ORGANISM: Rattus norvegicus

<400> SEQUENCE: 110

Met Ala Cys Leu Gly Leu Gln Arg Tyr Lys Thr His Leu Gln Leu Pro
1               5                   10                  15

Ser Arg Thr Trp Pro Phe Gly Val Leu Leu Ser Leu Leu Phe Ile Pro
            20                  25                  30

Ile Phe Ser Glu Ala Ile Gln Val Thr Gln Pro Ser Val Val Leu Ala
        35                  40                  45

Ser Ser His Gly Val Ala Ser Phe Pro Cys Glu Tyr Ala Ser Ser His
    50                  55                  60

Asn Thr Asp Glu Val Arg Val Thr Val Leu Arg Gln Thr Asn Asp Gln
65                  70                  75                  80

Val Thr Glu Val Cys Ala Thr Thr Phe Thr Val Lys Asn Thr Leu Gly
                85                  90                  95

Phe Leu Asp Asp Pro Phe Cys Ser Gly Thr Phe Asn Glu Ser Arg Val
            100                 105                 110

Asn Leu Thr Ile Gln Gly Leu Arg Ala Ala Asp Thr Gly Leu Tyr Phe
        115                 120                 125

Cys Lys Val Glu Leu Met Tyr Pro Pro Pro Tyr Phe Val Gly Met Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Val Thr Ala Val Ser Leu Asn Arg Thr Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 111
<211> LENGTH: 220
<212> TYPE: PRT
<213> ORGANISM: Homo sapiens

<400> SEQUENCE: 111

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110
```

```
Lys Ile Glu Val Met Tyr Pro Pro Tyr Leu Asp Asn Glu Lys Ser
            115                 120                 125

Asn Gly Thr Ile Ile His Val Lys Gly Lys His Leu Cys Pro Ser Pro
        130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
                180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
        210                 215                 220

<210> SEQ ID NO 112
<211> LENGTH: 199
<212> TYPE: PRT
<213> ORGANISM: Homo sapiens

<400> SEQUENCE: 112

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195

<210> SEQ ID NO 113
<211> LENGTH: 289
<212> TYPE: PRT
<213> ORGANISM: Homo sapiens

<400> SEQUENCE: 113

Met Lys Thr Leu Pro Ala Met Leu Gly Thr Gly Lys Leu Phe Trp Val
1               5                   10                  15
```

```
Phe Phe Leu Ile Pro Tyr Leu Asp Ile Trp Asn Ile His Gly Lys Glu
                20                  25                  30

Ser Cys Asp Val Gln Leu Tyr Ile Lys Arg Gln Ser Glu His Ser Ile
            35                  40                  45

Leu Ala Gly Asp Pro Phe Glu Leu Glu Cys Pro Val Lys Tyr Cys Ala
50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Lys Asn Ile Ser
                85                  90                  95

Phe Phe Ile Leu His Phe Glu Pro Val Leu Pro Asn Asp Asn Gly Ser
                100                 105                 110

Tyr Arg Cys Ser Ala Asn Phe Gln Ser Asn Leu Ile Glu Ser His Ser
            115                 120                 125

Thr Thr Leu Tyr Val Thr Asp Val Lys Ser Ala Ser Glu Arg Pro Ser
        130                 135                 140

Lys Asp Glu Met Ala Ser Arg Pro Trp Leu Leu Tyr Arg Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Thr Gly
210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
            245                 250                 255

Tyr Ala Ser Leu Asn His Ser Val Ile Gly Pro Asn Ser Arg Leu Ala
        260                 265                 270

Arg Asn Val Lys Glu Ala Pro Thr Glu Tyr Ala Ser Ile Cys Val Arg
            275                 280                 285

Ser

<210> SEQ ID NO 114

<400> SEQUENCE: 114

000

<210> SEQ ID NO 115
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (8)..(8)
<223> OTHER INFORMATION: /replace="Asn"
<220> FEATURE:
<221> NAME/KEY: MISC_FEATURE
<222> LOCATION: (1)..(9)
<223> OTHER INFORMATION: /note="Variant residues given in the sequence
      have no preference with respect to those in the annotations
      for variant positions"
```

```
<400> SEQUENCE: 115

Val Gly Leu Met Gly Pro Phe Asp Ile
1               5

<210> SEQ ID NO 116
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (5)..(5)
<223> OTHER INFORMATION: /replace="Leu"
<220> FEATURE:
<221> NAME/KEY: VARIANT
<222> LOCATION: (13)..(13)
<223> OTHER INFORMATION: /replace="Gln"
<220> FEATURE:
<221> NAME/KEY: VARIANT
<222> LOCATION: (19)..(19)
<223> OTHER INFORMATION: /replace="Thr"
<220> FEATURE:
<221> NAME/KEY: VARIANT
<222> LOCATION: (33)..(33)
<223> OTHER INFORMATION: /replace="Ala"
<220> FEATURE:
<221> NAME/KEY: VARIANT
<222> LOCATION: (35)..(35)
<223> OTHER INFORMATION: /replace="Ser"
<220> FEATURE:
<221> NAME/KEY: VARIANT
<222> LOCATION: (46)..(46)
<223> OTHER INFORMATION: /replace="Val"
<220> FEATURE:
<221> NAME/KEY: VARIANT
<222> LOCATION: (78)..(78)
<223> OTHER INFORMATION: /replace="Thr"
<220> FEATURE:
<221> NAME/KEY: VARIANT
<222> LOCATION: (106)..(106)
<223> OTHER INFORMATION: /replace="Asn"
<220> FEATURE:
<221> NAME/KEY: MISC_FEATURE
<222> LOCATION: (1)..(118)
<223> OTHER INFORMATION: /note="Variant residues given in the sequence
      have no preference with respect to those in the annotations
      for variant positions"

<400> SEQUENCE: 116

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser
        115
```

<210> SEQ ID NO 117
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 117

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

```
Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly
            435                 440

<210> SEQ ID NO 118
<211> LENGTH: 325
<212> TYPE: PRT
<213> ORGANISM: Homo sapiens

<400> SEQUENCE: 118

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285
```

```
Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 119

<400> SEQUENCE: 119

000

<210> SEQ ID NO 120
<211> LENGTH: 439
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Val Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270
```

-continued

```
Asp Gly Val Glu Val His Asn Ala Lys Thr Lys Pro Arg Glu Glu Gln
        275                 280                 285
Phe Asn Ser Thr Tyr Arg Val Val Ser Val Leu Thr Val Leu His Gln
        290                 295                 300
Asp Trp Leu Asn Gly Lys Glu Tyr Lys Cys Lys Val Ser Asn Lys Gly
305                 310                 315                 320
Leu Pro Ser Ser Ile Glu Lys Thr Ile Ser Lys Ala Lys Gly Gln Pro
            325                 330                 335
Arg Glu Pro Gln Val Tyr Thr Leu Pro Pro Ser Gln Glu Glu Met Thr
            340                 345                 350
Lys Asn Gln Val Ser Leu Thr Cys Leu Val Lys Gly Phe Tyr Pro Ser
            355                 360                 365
Asp Ile Ala Val Glu Trp Glu Ser Asn Gly Gln Pro Glu Asn Asn Tyr
        370                 375                 380
Lys Thr Thr Pro Pro Val Leu Asp Ser Asp Gly Ser Phe Phe Leu Tyr
385                 390                 395                 400
Ser Arg Leu Thr Val Asp Lys Ser Arg Trp Gln Glu Gly Asn Val Phe
                405                 410                 415
Ser Cys Ser Val Met His Glu Ala Leu His Asn His Tyr Thr Gln Lys
            420                 425                 430
Ser Leu Ser Leu Ser Leu Gly
            435
```